US012760301B2

(12) United States Patent
Pfeiffer et al.

(10) Patent No.: US 12,760,301 B2
(45) Date of Patent: Oct. 13, 2026

(54) PROBE-BASED ANALYSIS OF NUCLEIC ACIDS AND PROTEINS

(71) Applicant: 10x Genomics, Inc., Pleasanton, CA (US)

(72) Inventors: Katherine Pfeiffer, San Francisco, CA (US); Andrew Scott Kohlway, Dublin, CA (US); Andrew John Hill, Seattle, WA (US); Paul Eugene Lund, San Leandro, CA (US); Jawad N. Abousoud, Pleasanton, CA (US); Sharmila Chatterjee Bhattacharjee, San Jose, CA (US); Ryan Stott, Oakland, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 19/039,632

(22) Filed: Jan. 28, 2025

(65) Prior Publication Data

US 2025/0179474 A1 Jun. 5, 2025

Related U.S. Application Data

(63) Continuation of application No. 18/810,294, filed on Aug. 20, 2024, now abandoned, which is a continuation-in-part of application No. 18/412,111, filed on Jan. 12, 2024, now abandoned, which is a continuation of application No. 18/370,826, filed on Sep. 20, 2023, now abandoned, which is a continuation of application No. 18/217,310, filed on Jun. 30, 2023, now abandoned, which is a continuation of application No. PCT/US2023/026504, filed on Jun. 28, 2023.

(60) Provisional application No. 63/386,135, filed on Dec. 5, 2022, provisional application No. 63/356,887, filed on Jun. 29, 2022.

(51) Int. Cl.
*C12N 15/10* (2006.01)

(52) U.S. Cl.
CPC ................................ *C12N 15/1065* (2013.01)

(58) Field of Classification Search
None
See application file for complete search history.

(56) References Cited

U.S. PATENT DOCUMENTS

| | | | |
|---|---|---|---|
| 4,124,638 | A | 11/1978 | Hansen |
| 5,185,099 | A | 2/1993 | Delpuech et al. |
| 5,270,183 | A | 12/1993 | Corbett et al. |
| 5,478,893 | A | 12/1995 | Ghosh et al. |
| 5,736,330 | A | 4/1998 | Fulton |
| 5,756,334 | A | 5/1998 | Perler et al. |
| 5,846,719 | A | 12/1998 | Brenner et al. |
| 5,900,481 | A | 5/1999 | Lough et al. |
| 5,942,609 | A | 8/1999 | Hunkapiller et al. |
| 5,994,056 | A | 11/1999 | Higuchi |
| 6,033,880 | A | 3/2000 | Haff et al. |
| 6,057,149 | A | 5/2000 | Burns et al. |
| 6,123,798 | A | 9/2000 | Gandhi et al. |
| 6,171,850 | B1 | 1/2001 | Nagle et al. |
| 6,172,218 | B1 | 1/2001 | Brenner |
| 6,176,962 | B1 | 1/2001 | Soane et al. |
| 6,265,552 | B1 | 7/2001 | Schatz |
| 6,306,590 | B1 | 10/2001 | Mehta et al. |
| 6,327,410 | B1 | 12/2001 | Walt et al. |
| 6,379,929 | B1 | 4/2002 | Burns et al. |
| 6,406,848 | B1 | 6/2002 | Bridgham et al. |
| 6,409,832 | B2 | 6/2002 | Weigl et al. |
| 6,444,661 | B1 | 9/2002 | Barton et al. |
| 6,492,118 | B1 | 12/2002 | Abrams et al. |

(Continued)

FOREIGN PATENT DOCUMENTS

| | | | |
|---|---|---|---|
| CN | 106460033 | A | 2/2017 |
| CN | 109983126 | A | 7/2019 |

(Continued)

OTHER PUBLICATIONS

Bolognesi et al. "Digital Sorting of Pure Cell Populations Enables Unambiguous Genetic Analysis of Heterogeneous Formalin-Fixed Paraffin-Embedded Tumors by Next Generation Sequencing", Scientific Reports 6, 20944, published Feb. 11, 2016 (Year: 2016).*

(Continued)

*Primary Examiner* — Heather Calamita
*Assistant Examiner* — Jessica D Parisi
(74) *Attorney, Agent, or Firm* — WILSON SONSINI GOODRICH & ROSATI

(57) ABSTRACT

Provided herein are systems and methods for processing biomolecules (e.g., nucleic acid molecules, proteins) from a sample. A method for processing biomolecules may comprise hybridizing a probe molecule to a target region of a nucleic acid molecule (e.g., a ribonucleic acid (RNA) molecule) and barcoding the probe-nucleic acid molecule complex or derivatives thereof. Such a method can comprise performing a nucleic acid reaction, e.g., extension, denaturation, and amplification. A method for processing a sample may comprise hybridizing probes to (i) target regions of a nucleic acid molecule (e.g., RNA molecule) and (ii) a reporter oligonucleotide of a feature binding group, and barcoding the probe-associated molecules. One or more processes of the methods described herein may be performed within a partition, such as a droplet or well.

29 Claims, 65 Drawing Sheets

Specification includes a Sequence Listing.

(56) References Cited

U.S. PATENT DOCUMENTS

| | | | |
|---|---|---|---|
| 6,524,456 | B1 | 2/2003 | Ramsey et al. |
| 6,586,176 | B1 | 7/2003 | Trnovsky et al. |
| 6,632,655 | B1 | 10/2003 | Mehta et al. |
| 6,828,098 | B2 | 12/2004 | Langmore et al. |
| 6,915,679 | B2 | 7/2005 | Chien et al. |
| 6,964,847 | B1 | 11/2005 | Englert |
| 7,041,481 | B2 | 5/2006 | Anderson et al. |
| 7,115,400 | B1 | 10/2006 | Adessi et al. |
| 7,129,091 | B2 | 10/2006 | Ismagilov et al. |
| 7,268,167 | B2 | 9/2007 | Higuchi et al. |
| 7,282,370 | B2 | 10/2007 | Bridgham et al. |
| 7,294,503 | B2 | 11/2007 | Quake et al. |
| 7,323,305 | B2 | 1/2008 | Leamon et al. |
| 7,544,473 | B2 | 6/2009 | Brenner |
| 7,622,076 | B2 | 11/2009 | Davies et al. |
| 7,622,280 | B2 | 11/2009 | Holliger et al. |
| 7,645,596 | B2 | 1/2010 | Williams et al. |
| 7,708,949 | B2 | 5/2010 | Stone et al. |
| 7,709,197 | B2 | 5/2010 | Drmanac |
| 7,772,287 | B2 | 8/2010 | Higuchi et al. |
| 7,776,927 | B2 | 8/2010 | Chu et al. |
| 7,838,270 | B2 | 11/2010 | Davydova et al. |
| 7,842,457 | B2 | 11/2010 | Berka et al. |
| 7,910,354 | B2 | 3/2011 | Drmanac et al. |
| 7,927,797 | B2 | 4/2011 | Nobile et al. |
| 7,960,104 | B2 | 6/2011 | Drmanac et al. |
| 7,968,287 | B2 | 6/2011 | Griffiths et al. |
| 8,053,192 | B2 | 11/2011 | Bignell et al. |
| 8,133,719 | B2 | 3/2012 | Drmanac et al. |
| 8,168,385 | B2 | 5/2012 | Brenner |
| 8,268,564 | B2 | 9/2012 | Roth et al. |
| 8,273,573 | B2 | 9/2012 | Ismagilov et al. |
| 8,298,767 | B2 | 10/2012 | Brenner et al. |
| 8,304,193 | B2 | 11/2012 | Ismagilov et al. |
| 8,318,433 | B2 | 11/2012 | Brenner |
| 8,329,407 | B2 | 12/2012 | Ismagilov et al. |
| 8,460,866 | B2 | 6/2013 | Van Eijk et al. |
| 8,574,847 | B2 | 11/2013 | Becker et al. |
| 8,592,150 | B2 | 11/2013 | Drmanac et al. |
| 8,658,430 | B2 | 2/2014 | Miller et al. |
| 8,822,148 | B2 | 9/2014 | Ismagliov et al. |
| 8,835,358 | B2 | 9/2014 | Fodor et al. |
| 8,871,444 | B2 | 10/2014 | Griffiths et al. |
| 8,889,083 | B2 | 11/2014 | Ismagilov et al. |
| 8,975,302 | B2 | 3/2015 | Light et al. |
| 9,012,370 | B2 | 4/2015 | Hong |
| 9,012,390 | B2 | 4/2015 | Holtze et al. |
| 9,029,083 | B2 | 5/2015 | Griffiths et al. |
| 9,029,085 | B2 | 5/2015 | Agresti et al. |
| 9,085,798 | B2 | 7/2015 | Chee |
| 9,089,844 | B2 | 7/2015 | Hiddessen et al. |
| 9,126,160 | B2 | 9/2015 | Ness et al. |
| 9,156,010 | B2 | 10/2015 | Colston et al. |
| 9,194,861 | B2 | 11/2015 | Hindson et al. |
| 9,216,392 | B2 | 12/2015 | Hindson et al. |
| 9,238,206 | B2 | 1/2016 | Rotem et al. |
| 9,266,104 | B2 | 2/2016 | Link |
| 9,290,808 | B2 | 3/2016 | Fodor et al. |
| 9,328,382 | B2 | 5/2016 | Drmanac et al. |
| 9,347,059 | B2 | 5/2016 | Saxonov |
| 9,371,598 | B2 | 6/2016 | Chee |
| 9,388,465 | B2 | 7/2016 | Hindson et al. |
| 9,417,190 | B2 | 8/2016 | Hindson et al. |
| 9,486,757 | B2 | 11/2016 | Romanowsky et al. |
| 9,498,761 | B2 | 11/2016 | Holtze et al. |
| 9,500,664 | B2 | 11/2016 | Ness et al. |
| 9,567,631 | B2 | 2/2017 | Hindson et al. |
| 9,593,365 | B2 | 3/2017 | Frisen et al. |
| 9,623,384 | B2 | 4/2017 | Hindson et al. |
| 9,637,799 | B2 | 5/2017 | Fan et al. |
| 9,644,204 | B2 | 5/2017 | Hindson et al. |
| 9,689,024 | B2 | 6/2017 | Hindson et al. |
| 9,694,361 | B2 | 7/2017 | Bharadwaj et al. |
| 9,701,998 | B2 | 7/2017 | Hindson et al. |
| 9,758,814 | B2 | 9/2017 | Fehr et al. |
| 9,764,322 | B2 | 9/2017 | Hiddessen et al. |
| 9,824,068 | B2 | 11/2017 | Wong |
| 9,834,765 | B2 | 12/2017 | Bergmann et al. |
| 9,868,979 | B2 | 1/2018 | Chee et al. |
| 9,879,313 | B2 | 1/2018 | Chee et al. |
| 9,946,577 | B1 | 4/2018 | Stafford et al. |
| 9,951,386 | B2 | 4/2018 | Hindson et al. |
| 9,957,558 | B2 | 5/2018 | Leamon et al. |
| 9,975,122 | B2 | 5/2018 | Masquelier et al. |
| 10,011,872 | B1 | 7/2018 | Belgrader et al. |
| 10,017,759 | B2 | 7/2018 | Kaper et al. |
| 10,030,261 | B2 | 7/2018 | Frisen et al. |
| 10,041,116 | B2 | 8/2018 | Hindson et al. |
| 10,059,989 | B2 | 8/2018 | Giresi et al. |
| 10,144,950 | B2 | 12/2018 | Nolan |
| 10,174,310 | B2 | 1/2019 | Nolan |
| 10,221,436 | B2 | 3/2019 | Hardenbol et al. |
| 10,221,442 | B2 | 3/2019 | Hindson et al. |
| 10,253,364 | B2 | 4/2019 | Hindson et al. |
| 10,273,541 | B2 | 4/2019 | Hindson et al. |
| 10,323,279 | B2 | 6/2019 | Hindson et al. |
| 10,344,329 | B2 | 7/2019 | Hindson et al. |
| 10,347,365 | B2 | 7/2019 | Wong et al. |
| 10,357,771 | B2 | 7/2019 | Bharadwaj et al. |
| 10,395,758 | B2 | 8/2019 | Schnall-Levin |
| 10,400,280 | B2 | 9/2019 | Hindson et al. |
| 10,428,326 | B2 | 10/2019 | Belhocine et al. |
| 10,450,607 | B2 | 10/2019 | Hindson et al. |
| 10,457,986 | B2 | 10/2019 | Hindson et al. |
| 10,533,221 | B2 | 1/2020 | Hindson et al. |
| 10,544,413 | B2 | 1/2020 | Bharadwaj et al. |
| 10,549,279 | B2 | 2/2020 | Bharadwaj et al. |
| 10,550,429 | B2 | 2/2020 | Harada et al. |
| 10,557,158 | B2 | 2/2020 | Hardenbol et al. |
| 10,590,244 | B2 | 3/2020 | Delaney et al. |
| 10,745,742 | B2 | 8/2020 | Bent et al. |
| 10,752,949 | B2 | 8/2020 | Hindson et al. |
| 10,774,374 | B2 | 9/2020 | Frisen et al. |
| 10,815,525 | B2 | 10/2020 | Lucero et al. |
| 10,829,815 | B2 | 11/2020 | Bharadwaj et al. |
| 10,837,047 | B2 | 11/2020 | Delaney et al. |
| 10,874,997 | B2 | 12/2020 | Weitz et al. |
| 10,995,333 | B2 | 5/2021 | Pfeiffer |
| 11,371,094 | B2 | 6/2022 | Ryvkin et al. |
| 11,459,607 | B1 | 10/2022 | Terry et al. |
| 11,467,153 | B2 | 10/2022 | Belhocine et al. |
| 11,639,928 | B2 | 5/2023 | Mikkelsen et al. |
| 11,655,499 | B1 | 5/2023 | Pfeiffer |
| 11,845,983 | B1 | 12/2023 | Belhocine et al. |
| 11,851,683 | B1 | 12/2023 | Maheshwari et al. |
| 11,851,700 | B1 | 12/2023 | Bava et al. |
| 11,852,628 | B2 | 12/2023 | Mikkelsen et al. |
| 11,920,183 | B2 | 3/2024 | Bharadwaj et al. |
| 11,952,626 | B2 | 4/2024 | Pfeiffer et al. |
| 12,065,688 | B2 | 8/2024 | Bell |
| 12,084,715 | B1 | 9/2024 | Lund |
| 12,092,635 | B2 | 9/2024 | Mikkelsen et al. |
| 12,163,179 | B2 | 12/2024 | Bell et al. |
| 12,169,198 | B2 | 12/2024 | Price et al. |
| 12,188,014 | B1 | 1/2025 | Price et al. |
| 12,235,262 | B1 | 2/2025 | Giresi |
| 12,398,262 | B1 | 8/2025 | Gibbons |
| 2002/0005354 | A1 | 1/2002 | Spence et al. |
| 2002/0051971 | A1 | 5/2002 | Stuelpnagel et al. |
| 2002/0092767 | A1 | 7/2002 | Bjornson et al. |
| 2002/0119455 | A1 | 8/2002 | Chan |
| 2002/0127736 | A1 | 9/2002 | Chou et al. |
| 2003/0036206 | A1 | 2/2003 | Chien et al. |
| 2003/0075446 | A1 | 4/2003 | Culbertson et al. |
| 2003/0124509 | A1 | 7/2003 | Kenis et al. |
| 2003/0198980 | A1 | 10/2003 | Greenfield et al. |
| 2003/0215862 | A1 | 11/2003 | Parce et al. |
| 2004/0086892 | A1 | 5/2004 | Crothers et al. |
| 2005/0130188 | A1 | 6/2005 | Walt et al. |
| 2005/0250147 | A1 | 11/2005 | Macevicz |
| 2005/0266582 | A1 | 12/2005 | Modlin et al. |
| 2005/0287572 | A1 | 12/2005 | Mathies et al. |
| 2006/0177832 | A1 | 8/2006 | Brenner |
| 2006/0275782 | A1 | 12/2006 | Gunderson et al. |

(56) References Cited

U.S. PATENT DOCUMENTS

| | | | |
|---|---|---|---|
| 2007/0020640 | A1 | 1/2007 | McCloskey et al. |
| 2007/0042419 | A1 | 2/2007 | Barany et al. |
| 2007/0111241 | A1 | 5/2007 | Cereb et al. |
| 2007/0172873 | A1 | 7/2007 | Brenner et al. |
| 2007/0190543 | A1 | 8/2007 | Livak |
| 2007/0196397 | A1 | 8/2007 | Torii et al. |
| 2007/0264320 | A1 | 11/2007 | Lee et al. |
| 2007/0275415 | A1 | 11/2007 | Srinivasan et al. |
| 2008/0056948 | A1 | 3/2008 | Dale et al. |
| 2008/0166720 | A1 | 7/2008 | Hsieh et al. |
| 2008/0242560 | A1 | 10/2008 | Gunderson et al. |
| 2009/0011943 | A1 | 1/2009 | Drmanac et al. |
| 2009/0047713 | A1 | 2/2009 | Handique |
| 2009/0099041 | A1 | 4/2009 | Church et al. |
| 2009/0131543 | A1 | 5/2009 | Weitz et al. |
| 2009/0148961 | A1 | 6/2009 | Luchini et al. |
| 2009/0155563 | A1 | 6/2009 | Petsev et al. |
| 2009/0202984 | A1 | 8/2009 | Cantor |
| 2009/0235990 | A1 | 9/2009 | Beer |
| 2009/0269248 | A1 | 10/2009 | Falb et al. |
| 2009/0286687 | A1 | 11/2009 | Dressman et al. |
| 2010/0035254 | A1 | 2/2010 | Williams |
| 2010/0069263 | A1 | 3/2010 | Shendure et al. |
| 2010/0086914 | A1 | 4/2010 | Bentley et al. |
| 2010/0105866 | A1 | 4/2010 | Fraden et al. |
| 2010/0184928 | A1 | 7/2010 | Kumacheva |
| 2010/0216153 | A1 | 8/2010 | Lapidus et al. |
| 2010/0248991 | A1 | 9/2010 | Roesler et al. |
| 2010/0304982 | A1 | 12/2010 | Hinz et al. |
| 2011/0027862 | A1 | 2/2011 | Bates et al. |
| 2011/0217736 | A1 | 9/2011 | Hindson |
| 2011/0257889 | A1 | 10/2011 | Klammer et al. |
| 2011/0305761 | A1 | 12/2011 | Shum et al. |
| 2012/0034603 | A1 | 2/2012 | Oliphant et al. |
| 2012/0041727 | A1 | 2/2012 | Mishra et al. |
| 2012/0071331 | A1 | 3/2012 | Casbon et al. |
| 2012/0172259 | A1 | 7/2012 | Rigatti et al. |
| 2012/0196288 | A1 | 8/2012 | Beer |
| 2012/0219947 | A1 | 8/2012 | Yurkovetsky et al. |
| 2012/0220494 | A1 | 8/2012 | Samuels et al. |
| 2012/0230338 | A1 | 9/2012 | Ganeshalingam et al. |
| 2013/0028812 | A1 | 1/2013 | Prieto et al. |
| 2013/0109575 | A1 | 5/2013 | Kleinschmidt et al. |
| 2013/0203605 | A1 | 8/2013 | Shendure et al. |
| 2013/0210079 | A1 | 8/2013 | Stanojevic et al. |
| 2013/0261196 | A1 | 10/2013 | Diamond et al. |
| 2013/0268206 | A1 | 10/2013 | Porreca et al. |
| 2013/0296172 | A1 | 11/2013 | Fu et al. |
| 2013/0311106 | A1 | 11/2013 | White et al. |
| 2014/0065234 | A1 | 3/2014 | Shum et al. |
| 2014/0155295 | A1 | 6/2014 | Hindson et al. |
| 2014/0170653 | A1 | 6/2014 | Ying |
| 2014/0200166 | A1 | 7/2014 | Van Rooyen et al. |
| 2014/0214334 | A1 | 7/2014 | Plattner et al. |
| 2014/0221217 | A1 | 8/2014 | Van Eijk et al. |
| 2014/0221239 | A1 | 8/2014 | Carman et al. |
| 2014/0272996 | A1 | 9/2014 | Bemis |
| 2014/0274740 | A1 | 9/2014 | Srinivasan et al. |
| 2014/0274756 | A1 | 9/2014 | Nguyen et al. |
| 2014/0302503 | A1 | 10/2014 | Lowe et al. |
| 2014/0338753 | A1 | 11/2014 | Sperling et al. |
| 2014/0378345 | A1 | 12/2014 | Hindson et al. |
| 2015/0133344 | A1 | 5/2015 | Shendure et al. |
| 2015/0265995 | A1 | 9/2015 | Head et al. |
| 2015/0267191 | A1 | 9/2015 | Steelman et al. |
| 2015/0284786 | A1 | 10/2015 | Shapero et al. |
| 2015/0361418 | A1 | 12/2015 | Reed |
| 2015/0376605 | A1 | 12/2015 | Jarosz et al. |
| 2015/0376609 | A1 | 12/2015 | Hindson et al. |
| 2015/0376700 | A1 | 12/2015 | Schnall-Levin et al. |
| 2015/0379196 | A1 | 12/2015 | Schnall-Levin et al. |
| 2016/0008778 | A1 | 1/2016 | Weitz et al. |
| 2016/0024558 | A1 | 1/2016 | Hardenbol et al. |
| 2016/0024572 | A1 | 1/2016 | Shishkin et al. |
| 2016/0053253 | A1 | 2/2016 | Salathia et al. |
| 2016/0059204 | A1 | 3/2016 | Hindson et al. |
| 2016/0060621 | A1 | 3/2016 | Agresti et al. |
| 2016/0122753 | A1 | 5/2016 | Mikkelsen et al. |
| 2016/0122817 | A1 | 5/2016 | Jarosz et al. |
| 2016/0138086 | A1 | 5/2016 | Seelig et al. |
| 2016/0203196 | A1 | 7/2016 | Schnall-Levin et al. |
| 2016/0232291 | A1 | 8/2016 | Kyriazopoulou-Panagiotopoulou et al. |
| 2016/0244809 | A1 | 8/2016 | Belgrader et al. |
| 2016/0281160 | A1 | 9/2016 | Jarosz et al. |
| 2016/0289769 | A1 | 10/2016 | Schwartz et al. |
| 2016/0314242 | A1 | 10/2016 | Schnall-Levin et al. |
| 2016/0348093 | A1 | 12/2016 | Price et al. |
| 2016/0350478 | A1 | 12/2016 | Chin et al. |
| 2017/0016041 | A1 | 1/2017 | Greenfield et al. |
| 2017/0128937 | A1 | 5/2017 | Hung et al. |
| 2017/0144161 | A1 | 5/2017 | Hindson et al. |
| 2017/0145476 | A1 | 5/2017 | Ryvkin et al. |
| 2017/0159109 | A1 | 6/2017 | Zheng et al. |
| 2017/0191113 | A1 | 7/2017 | Barany |
| 2017/0235876 | A1 | 8/2017 | Jaffe et al. |
| 2017/0260584 | A1 | 9/2017 | Zheng et al. |
| 2018/0023119 | A1 | 1/2018 | Adey et al. |
| 2018/0023138 | A1 | 1/2018 | Collins et al. |
| 2018/0030515 | A1 | 2/2018 | Regev et al. |
| 2018/0073073 | A1 | 3/2018 | Fu et al. |
| 2018/0080075 | A1 | 3/2018 | Brenner et al. |
| 2018/0105808 | A1 | 4/2018 | Mikkelsen et al. |
| 2018/0127816 | A1 | 5/2018 | Teo et al. |
| 2018/0179591 | A1 | 6/2018 | Belgrader et al. |
| 2018/0251825 | A1 | 9/2018 | Stoeckius et al. |
| 2018/0265917 | A1 | 9/2018 | Barany et al. |
| 2018/0273933 | A1 | 9/2018 | Gunderson et al. |
| 2018/0312822 | A1 | 11/2018 | Lee et al. |
| 2018/0312873 | A1 | 11/2018 | Zheng |
| 2018/0320241 | A1 | 11/2018 | Nolan |
| 2018/0340169 | A1 | 11/2018 | Belhocine et al. |
| 2018/0340939 | A1 | 11/2018 | Gaublomme et al. |
| 2018/0346969 | A1 | 12/2018 | Chang et al. |
| 2018/0355348 | A1 | 12/2018 | Adey et al. |
| 2018/0371545 | A1 | 12/2018 | Wong et al. |
| 2019/0002971 | A1 | 1/2019 | Koslover et al. |
| 2019/0040382 | A1 | 2/2019 | Steemers et al. |
| 2019/0060890 | A1 | 2/2019 | Bharadwaj et al. |
| 2019/0060905 | A1 | 2/2019 | Bharadwaj et al. |
| 2019/0064173 | A1 | 2/2019 | Bharadwaj et al. |
| 2019/0071656 | A1 | 3/2019 | Chang et al. |
| 2019/0127731 | A1 | 5/2019 | Mcdermott |
| 2019/0134633 | A1 | 5/2019 | Bharadwaj et al. |
| 2019/0153532 | A1 | 5/2019 | Bharadwaj et al. |
| 2019/0176152 | A1 | 6/2019 | Bharadwaj et al. |
| 2019/0177800 | A1 | 6/2019 | Boutet et al. |
| 2019/0256547 | A1 | 8/2019 | Routh et al. |
| 2019/0323088 | A1 | 10/2019 | Boutet et al. |
| 2019/0345636 | A1 | 11/2019 | McDermott et al. |
| 2019/0352717 | A1 | 11/2019 | Schnall-Levin |
| 2019/0361010 | A1 | 11/2019 | Pfeiffer et al. |
| 2019/0367969 | A1 | 12/2019 | Belhocine et al. |
| 2019/0367997 | A1 | 12/2019 | Bent et al. |
| 2019/0376118 | A1 | 12/2019 | Belhocine et al. |
| 2020/0002764 | A1 | 1/2020 | Belgrader et al. |
| 2020/0005902 | A1 | 1/2020 | Mellen et al. |
| 2020/0032335 | A1 | 1/2020 | Martinez |
| 2020/0033237 | A1 | 1/2020 | Hindson et al. |
| 2020/0033366 | A1 | 1/2020 | Alvarado Martinez |
| 2020/0056223 | A1 | 2/2020 | Bell |
| 2020/0199669 | A1 | 6/2020 | Hindson et al. |
| 2020/0224243 | A1 | 7/2020 | Desai et al. |
| 2020/0224244 | A1 | 7/2020 | Nilsson et al. |
| 2020/0239874 | A1 | 7/2020 | Mikkelsen et al. |
| 2020/0263232 | A1 | 8/2020 | Bell et al. |
| 2020/0291454 | A1 | 9/2020 | Belhocine et al. |
| 2021/0040551 | A1 | 2/2021 | Mikkelsen et al. |
| 2021/0140969 | A1 | 5/2021 | Boutet et al. |
| 2021/0190770 | A1 | 6/2021 | Delaney et al. |
| 2021/0230584 | A1 | 7/2021 | Mikkelsen et al. |
| 2021/0262018 | A1 * | 8/2021 | Bava .................... C12Q 1/6844 |
| 2021/0270703 | A1 | 9/2021 | Abousoud |
| 2021/0389325 | A1 | 12/2021 | Norris et al. |

(56) References Cited

U.S. PATENT DOCUMENTS

| | | | |
|---|---|---|---|
| 2022/0039874 | A1 | 2/2022 | Choi |
| 2022/0145370 | A1 | 5/2022 | Alvarado Martinez et al. |
| 2022/0162671 | A1 | 5/2022 | Pfeiffer et al. |
| 2022/0276229 | A1 | 9/2022 | Mikkelsen et al. |
| 2022/0325357 | A1 | 10/2022 | Dhingra et al. |
| 2022/0340968 | A1 | 10/2022 | Hindson et al. |
| 2022/0403375 | A1 | 12/2022 | Alvarado Martinez |
| 2022/0403452 | A1 | 12/2022 | Lance et al. |
| 2023/0167496 | A1 | 6/2023 | Bava |
| 2023/0236176 | A1 | 7/2023 | Mikkelsen et al. |
| 2023/0399691 | A1 | 12/2023 | Pfeiffer et al. |
| 2024/0002914 | A1 | 1/2024 | Pfeiffer et al. |
| 2024/0019422 | A1 | 1/2024 | Pfeiffer et al. |
| 2024/0044877 | A1 | 2/2024 | Price et al. |
| 2024/0060968 | A1 | 2/2024 | Mikkelsen et al. |
| 2024/0247303 | A1 | 7/2024 | Pfeiffer et al. |
| 2024/0254474 | A1 | 8/2024 | Nemec |
| 2024/0254552 | A1 | 8/2024 | Pfeiffer et al. |
| 2024/0272044 | A1 | 8/2024 | Bava |
| 2024/0309448 | A1 | 9/2024 | Pfeiffer et al. |
| 2024/0401028 | A1 | 12/2024 | McDermott et al. |
| 2025/0171845 | A1 | 5/2025 | Pfeiffer et al. |
| 2025/0250612 | A1 | 8/2025 | Smibert et al. |
| 2025/0257396 | A1 | 8/2025 | Belgrader et al. |

FOREIGN PATENT DOCUMENTS

| | | | |
|---|---|---|---|
| CN | 112074610 | A | 12/2020 |
| EP | 1019496 | B1 | 9/2004 |
| EP | 1841879 | A2 | 10/2007 |
| EP | 1967592 | B1 | 4/2010 |
| EP | 2540389 | A1 | 1/2013 |
| EP | 2635679 | B1 | 4/2017 |
| GB | 2097692 | A | 11/1982 |
| GB | 2097692 | B | 5/1985 |
| RU | 2321638 | C2 | 4/2008 |
| WO | WO-8402000 | A1 | 5/1984 |
| WO | WO-9530782 | A1 | 11/1995 |
| WO | WO-9952708 | A1 | 10/1999 |
| WO | WO-2000008212 | A1 | 2/2000 |
| WO | WO-2001002850 | A1 | 1/2001 |
| WO | WO-0114589 | A2 | 3/2001 |
| WO | WO-0190418 | A1 | 11/2001 |
| WO | WO-2001089787 | A2 | 11/2001 |
| WO | WO-2004002627 | A2 | 1/2004 |
| WO | WO-2004065617 | A2 | 8/2004 |
| WO | WO-2004069849 | A2 | 8/2004 |
| WO | WO-2004091763 | A2 | 10/2004 |
| WO | WO-2005021151 | A1 | 3/2005 |
| WO | WO-2005021794 | A2 | 3/2005 |
| WO | WO-2005049787 | A9 | 6/2005 |
| WO | WO-2005082098 | A2 | 9/2005 |
| WO | WO-2006040551 | A2 | 4/2006 |
| WO | WO-2006078841 | A1 | 7/2006 |
| WO | WO-2006096571 | A2 | 9/2006 |
| WO | WO-2007081385 | A2 | 7/2007 |
| WO | WO-2007081387 | A1 | 7/2007 |
| WO | WO-2007089541 | A2 | 8/2007 |
| WO | WO-2007133710 | A2 | 11/2007 |
| WO | WO-2007140015 | A2 | 12/2007 |
| WO | WO-2007147079 | A2 | 12/2007 |
| WO | WO-2008021123 | A1 | 2/2008 |
| WO | WO-2008109176 | A2 | 9/2008 |
| WO | WO-2008121342 | A2 | 10/2008 |
| WO | WO-2008134153 | A1 | 11/2008 |
| WO | WO-2008150432 | A1 | 12/2008 |
| WO | WO-2009011808 | A1 | 1/2009 |
| WO | WO-2009015296 | A1 | 1/2009 |
| WO | WO-2009023821 | A1 | 2/2009 |
| WO | WO-2009085215 | A1 | 7/2009 |
| WO | WO-2009152928 | A2 | 12/2009 |
| WO | WO-2010033200 | A2 | 3/2010 |
| WO | WO-2010104604 | A1 | 9/2010 |
| WO | WO-2010117620 | A2 | 10/2010 |
| WO | WO-2010148039 | A2 | 12/2010 |
| WO | WO-2011028539 | A1 | 3/2011 |
| WO | WO-2011047870 | A1 | 4/2011 |
| WO | WO-2011056546 | A1 | 5/2011 |
| WO | WO-2011066476 | A1 | 6/2011 |
| WO | WO-2012048341 | A1 | 4/2012 |
| WO | WO-2012061832 | A1 | 5/2012 |
| WO | WO-2012083225 | A2 | 6/2012 |
| WO | WO-2012100216 | A2 | 7/2012 |
| WO | WO-2012106385 | A2 | 8/2012 |
| WO | WO-2012106546 | A2 | 8/2012 |
| WO | WO-2012112804 | A1 | 8/2012 |
| WO | WO-2012112970 | A2 | 8/2012 |
| WO | WO-2012116331 | A2 | 8/2012 |
| WO | WO-2012142531 | A2 | 10/2012 |
| WO | WO-2012142611 | A2 | 10/2012 |
| WO | WO-2012149042 | A2 | 11/2012 |
| WO | WO-2012166425 | A2 | 12/2012 |
| WO | WO-2012167142 | A2 | 12/2012 |
| WO | WO-2013019751 | A1 | 2/2013 |
| WO | WO-2013036929 | A1 | 3/2013 |
| WO | WO-2013055955 | A1 | 4/2013 |
| WO | WO-2013096643 | A1 | 6/2013 |
| WO | WO-2013123220 | A1 | 8/2013 |
| WO | WO-2013126741 | A1 | 8/2013 |
| WO | WO-2013134261 | A1 | 9/2013 |
| WO | WO-2013192292 | A1 | 12/2013 |
| WO | WO-2014026032 | A2 | 2/2014 |
| WO | WO-2014028378 | A2 | 2/2014 |
| WO | WO-2014108810 | A2 | 7/2014 |
| WO | WO-2014165559 | A2 | 10/2014 |
| WO | WO-2015015199 | A2 | 2/2015 |
| WO | WO-2015044428 | A1 | 4/2015 |
| WO | WO-2015164212 | A1 | 10/2015 |
| WO | WO-2016040476 | A1 | 3/2016 |
| WO | WO-2016061517 | A2 | 4/2016 |
| WO | WO-2016100976 | A2 | 6/2016 |
| WO | WO-2016126871 | A2 | 8/2016 |
| WO | WO-2016135800 | A1 | 9/2016 |
| WO | WO-2016168584 | A1 | 10/2016 |
| WO | WO-2017015075 | A1 | 1/2017 |
| WO | WO-2017044993 | A2 | 3/2017 |
| WO | WO-2017066231 | A1 | 4/2017 |
| WO | WO-2017075265 | A1 | 5/2017 |
| WO | WO-2017180949 | A1 | 10/2017 |
| WO | WO-2017184707 | A1 | 10/2017 |
| WO | WO-2017197343 | A2 | 11/2017 |
| WO | WO-2018039338 | A1 | 3/2018 |
| WO | WO-2018075693 | A1 | 4/2018 |
| WO | WO-2018091676 | A1 | 5/2018 |
| WO | WO-2018119301 | A1 | 6/2018 |
| WO | WO-2018119447 | A2 | 6/2018 |
| WO | WO-2018138237 | A1 | 8/2018 |
| WO | WO-2018172726 | A1 | 9/2018 |
| WO | WO-2018191701 | A1 | 10/2018 |
| WO | WO-2018213643 | A1 | 11/2018 |
| WO | WO-2018226546 | A1 | 12/2018 |
| WO | WO-2018236615 | A1 | 12/2018 |
| WO | WO-2019028166 | A1 | 2/2019 |
| WO | WO-2019038372 | A1 | 2/2019 |
| WO | WO-2019040637 | A1 | 2/2019 |
| WO | WO-2019071039 | A1 | 4/2019 |
| WO | WO-2019083852 | A1 | 5/2019 |
| WO | WO-2019084043 | A1 | 5/2019 |
| WO | WO-2019084165 | A1 | 5/2019 |
| WO | WO-2019108851 | A1 | 6/2019 |
| WO | WO-2019113235 | A1 | 6/2019 |
| WO | WO-2019118355 | A1 | 6/2019 |
| WO | WO-2019126789 | A1 | 6/2019 |
| WO | WO-2019148042 | A1 | 8/2019 |
| WO | WO-2019152108 | A1 | 8/2019 |
| WO | WO-2019157529 | A1 | 8/2019 |
| WO | WO-2019165318 | A1 | 8/2019 |
| WO | WO-2019169028 | A1 | 9/2019 |
| WO | WO-2019169347 | A1 | 9/2019 |
| WO | WO-2019173638 | A1 | 9/2019 |
| WO | WO-2019191321 | A1 | 10/2019 |
| WO | WO-2019217758 | A1 | 11/2019 |
| WO | WO-2019236599 | A2 | 12/2019 |
| WO | WO-2020028882 | A1 | 2/2020 |

(56) References Cited

FOREIGN PATENT DOCUMENTS

| | | | | |
|---|---|---|---|---|
| WO | WO-2020041148 | A1 | 2/2020 | |
| WO | WO-2020077236 | A1 * | 4/2020 | ............ A61K 31/00 |
| WO | WO-2020142779 | A1 | 7/2020 | |
| WO | WO-2020167862 | A1 | 8/2020 | |
| WO | WO-2020167866 | A1 | 8/2020 | |
| WO | WO-2020168013 | A1 | 8/2020 | |
| WO | WO-2020176788 | A1 | 9/2020 | |
| WO | WO-2020198532 | A1 | 10/2020 | |
| WO | WO-2021041974 | A1 | 3/2021 | |
| WO | WO-2021046475 | A1 | 3/2021 | |
| WO | WO-2021133845 | A1 | 7/2021 | |
| WO | WO-2021133849 | A1 | 7/2021 | |
| WO | WO-2021207610 | A1 | 10/2021 | |
| WO | WO-2021212042 | A1 | 10/2021 | |
| WO | WO-2021222301 | A1 | 11/2021 | |
| WO | WO-2021222302 | A1 | 11/2021 | |
| WO | WO-2021237087 | A1 | 11/2021 | |
| WO | WO-2022103712 | A1 | 5/2022 | |
| WO | WO-2022182682 | A1 | 9/2022 | |
| WO | WO-2022182785 | A1 | 9/2022 | |
| WO | WO-2022216688 | A1 | 10/2022 | |
| WO | WO-2022271908 | A1 | 12/2022 | |
| WO | WO-2023076528 | A2 | 5/2023 | |
| WO | WO-2024006392 | A1 | 1/2024 | |
| WO | WO-2024243444 | A1 | 11/2024 | |

OTHER PUBLICATIONS

Co-pending U.S. Appl. No. 18/593,799, inventors Pfeiffer; Katherine et al., filed Mar. 1, 2024.
Co-pending U.S. Appl. No. 18/743,583, inventor Nagendran; Monica, filed Jun. 14, 2024.
Co-pending U.S. Appl. No. 18/795,976, inventors Meer; Elliott et al., filed Aug. 6, 2024.
Co-pending U.S. Appl. No. 18/824,258, inventor Stott; Ryan Timothy, filed Sep. 4, 2024.
Co-pending U.S. Appl. No. 18/959,351, inventor Schnalll-Levin; Michael, filed Nov. 25, 2024.
Co-pending U.S. Appl. No. 19/044,383, inventors Smibert; Peter et al., filed Feb. 3, 2025.
Rosenberg et al., Supplementary Materials for Single cell profiling of the developing mouse brain and spinal cord with split pool barcoding, Published Mar. 15, 2018 on Science First Release DOI: 10.1126/science.aam8999, 55 pages.
10X Genomics, Inc. CG000153 Rev A. Chromium Single Cell DNA Reagent Kits User Guide. 2018. 62 pages.
10X Genomics, Inc. CG000184 Rev A. Chromium Single Cell 3' Reagent Kits v3 User Guide with Feature Barcoding Technology for CRISPR Screening. 2018. 70 pages.
10X Genomics, Inc. CG000185 Rev B. Chromium Single Cell 3' Reagent Kits User Guide with Feature Barcoding Technology for Cell Surface Protein. 2018. 66 pages.
10X Genomics, Inc. CG000208 Rev E. Chromium Next GEM Single Cell V(D)J reagent Kits v1.1 User Guide with Feature Barcode Technology for Cell Surface Protein. 2020. 88 pages.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Abate, A.R. et al. "Beating Poisson encapsulation statistics using close-packed ordering" Lab on a Chip (Sep. 21, 2009) 9(18):2628-2631.
Adamson et al., "Production of arrays of chemically distinct nanolitre plugs via repeated splitting in microfluidic devices", Lab Chip 6(9): 1178-1186 (Sep. 2006).
Adey, et al. Rapid, low-input, low-bias construction of shotgun fragment libraries by high-density in vitro transposition. Genome Biology 11:R119 (2010).
Agasti, S.S. et al. "Photocleavable DNA barcode-antibody conjugates allow sensitive and multiplexed protein analysis in single cell" J Am Chem Soc (2012) 134(45):18499-18502.
"Algae," Wikipedia.com, accessed Mar. 4, 2016. (Year: 2016).
Altemose et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
"Archaea". Wikipedia.com; accessed Sep. 8, 2023. 22 pages.
Bansal et al. "An MCMC algorithm for haplotype assembly from whole-genome sequence data," (2008) Genome Res 18:1336-1346.
Bansal et al. "HapCUT: an efficient and accurate algorithm for the haplotype assembly problem," Bioinformatics (2008) 24:1153-i159.
Baret, "Surfactants in droplet-based microfluidics" Lab Chip (12(3):422-433 (2012).
Bedtools: General Usage, http://bedtools.readthedocs.io/en/latest/content/generalusage .html; Retrieved from the Internet Jul. 8, 2016.
Beer et al. On-Chip, Real-Time, Single-Copy Polymerase Chain Reaction in Picoliter Droplets. Anal Chem 79:8471-8475 (2007).
Boulanger, et al, "Massively parallel haplotyping on microscopic beads for the high-throughput phase analysis of single molecules", PLoS One, vol. 7:1-10, 2012.
Braeckmans et al., Scanning the Code. Modern Drug Discovery. 2003:28-32.
Bray, "The JavaScript Object Notation (JSON) Data Interchange Format," Mar. 2014, retrieved from the Internet Feb. 15, 2015; https://tools.ietf.org/html/rfc7159.
Brenner, Sydney. et al. In Vitro Cloning of Complex Mixtures of DNA on Microbeads: Physical Separation of Differentially Expressed cDNAs. Proceedings of the National Academy of Sciences of the United States of America 97(4):1665-1670 (2000).
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Cao, et al. Joint profiling of chromatin accessibility and gene expression in thousands of single cells. Science. Sep. 28, 2018;361(6409):1380-1385. doi: 10.1126/science.aau0730. Epub Aug. 30, 2018.
Cao, Junyue et al. Comprehensive single-cell transcriptional profiling of a multicellular organism. Science vol. 357,6352 : pp. 661-667 (2017).
Cao, Junyue et al. The Single-cell Transcriptional Landscape of Mammalian Organogenesis. Nature vol. 566,7745: pp. 1-31 (2019).
Chen et al. BreakDancer: an algorithm for high-resolution mapping of genomic structural variation. Nature Methods (2009) 6(9):677-681.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).

(56) References Cited

OTHER PUBLICATIONS

Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Cleary et al. "Joint variant and de novo mutation identification on pedigrees from highthroughput sequencing data," J Comput Biol (2014) 21:405-419.
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/737,762, inventors Price; Andrew D. et al., filed Jan. 8, 2020.
Co-pending U.S. Appl. No. 17/148,942, inventors Mcdermott; Geoffrey et al., filed Jan. 14, 2021.
Co-pending U.S. Appl. No. 17/166,982, inventors Mcdermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/512,241, inventors Hill; Andrew John et al., filed Oct. 27, 2021.
Co-pending U.S. Appl. No. 17/517,408, inventors Salmanzadeh; Alireza et al., filed Nov. 2, 2021.
Co-pending U.S. Appl. No. 17/522,741, inventors Zheng; Xinying et al., filed Nov. 9, 2021.
Co-pending U.S. Appl. No. 17/538,783, inventors Hindson; Benjamin et al., filed Nov. 30, 2021.
Co-pending U.S. Appl. No. 17/545,862, inventor Katherine; Pfeiffer, filed Dec. 8, 2021.
Co-pending U.S. Appl. No. 17/573,350, inventor Nemec; Corey M., filed Jan. 11, 2022.
Co-pending U.S. Appl. No. 17/580,947, inventor Gibbons; Michael, filed Jan. 21, 2022.
Co-pending U.S. Appl. No. 18/046,843, inventor Toh; Mckenzi, filed Oct. 14, 2022.
Co-pending U.S. Appl. No. 18/152,650, inventor Shastry; Shankar, filed Jan. 10, 2023.
Co-pending U.S. Appl. No. 18/223,996, inventors Mikkelsen; Tarjei Sigurd et al., filed Jul. 19, 2023.
Co-pending U.S. Appl. No. 18/392,684, inventors Fernandes; Sunjay Jude et al., filed Dec. 21, 2023.
Cusanovich, et al. Multiplex single-cell profiling of chromatin accessibility by combinatorial cellular indexing. Science, May 22, 2015;348(6237):910-14.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Datlinger, et al. Ultra-high throughput single-cell RNA sequencing by combinatorial fluidic indexing. bioRxiv preprint first posted online Dec. 18, 2019; doi: https://doi.org/10.1101/2019.12.17.879304.
Depristo et al. A framework for variation discovery and genotyping using next-generation DNA sequencing data. Nature Genet 43:491-498 (2011).
Dostie, Josee et al. Chromosome Conformation Capture Carbon Copy (5C): A Massively Parallel Solution for Mapping Interaction between Genomic Elements. Genome Research 16(10):1299-1309 (2006).
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Ekblom, R. et al. "A field guide to whole-genome sequencing, assembly and annotation" Evolutionary Apps (Jun. 24, 2014) 7(9):1026-1042.
Esser-Kahn, et al. Triggered release from polymer capsules. Macromolecules. 2011; 44:5539-5553.
Fan et al., Noninvasive diagnosis of fetal aneuploidy by shotgun sequencing DNA from maternal blood. Proc Natl Acad Sci U S A :105(42):16266-71 (2008).
Fan, et al. Whole-genome molecular haplotyping of single cells. Nature Biotechnology, vol. 29, No. 1. Jan. 1, 2011. pp. 51-59.
Fang, Shiyue et al. Fluoride-cleavable Biotinylation Phosphoramidite for 5'-end-labeling and Affinity Purification of Synthetic Oligonucleotides. Nucleic Acids Research 31(2):708-715 (2008).
"Fish". Wikipedia.com; accessed Sep. 8, 2023. 19 pages.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
"Fungus" (Redirected from Fungi). Wikipedia.com; accessed Sep. 8, 2023. 26 pages.
Gehring, et al. Highly Multiplexed Single-Cell RNA-seq for Defining Cell Population and Transcriptional Spaces. bioRxiv (2018): 315333.
Gericke, et al. Functional cellulose beads: preparation, characterization, and applications. Chemical reviews 113.7 (2013): 4812-4836.
Gordon et al. "Consed: A Graphical Tool for Sequence Finishing," Genome Research (1998) 8:198-202.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, Tamar et al., CEL-Seq: Single-Cell RNA-Seq by Multiplexed Linear Amplification. Cell Reports 2(3):666-673 (2012).
Hiatt, et al. Parallel, tag-directed assembly of locally derived short sequence reads. Nat Methods. Feb. 2010;7(2):119-22. Epub Jan. 17, 2010.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
"How many species of bacteria are there" (wisegeek.com; accessed Jan. 21, 2014).
Huang et al. EagleView: A genome assembly viewer for next-generation sequencing technologies, Genome Research (2008) 18:1538-1543.
Hug, et al. Measurement of the number of molecules of a single mRNA species in a complex mRNA preparation. J Theor Biol. Apr. 21, 2003;221(4):615-24.
Hughes, et al. Choose Your Label Wisely: Water-Soluble Fluorophores Often Interact with Lipid Bilayers. Dept. of Chem. 2014. Plos One. Feb. 4; 9(2):e87649.
Hwang, et al. SCITO-seq: single-cell combinatorial indexed cytometry sequencing. bioRxiv. Jan. 1, 2020.
Insect. Wikipedia, Sep. 10, 2020. Available at URL:https://en.wikipedia.org/wiki/Insect pp. 1-21.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, Diego Adhemar, et al., Massively Parallel single-cell RNA-seq for Marker-free Decomposition of Tissues into cell types. Science 343(6172):776-779 (2014).
Jarosz, M. et al. "Using 1ng of DNA to detect haplotype phasing and gene fusions from whole exome sequencing of cancer cell lines" Cancer Res (2015) 75(supp15):4742.

(56) References Cited

OTHER PUBLICATIONS

Kanehisa et al. KEGG: Kyoto Encyclopedia of Genes and Genomes. Nucleic Acids Res 28:27-30 (2000).
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kim et al. "HapEdit: an accuracy assessment viewer for haplotype assembly using massively parallel DNA-sequencing technologies," Nucleic Acids Research (2011) pp. W557-W561.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioja, Teemu. et al. Counting Absolute Numbers Of Molecules Using Unique Molecular Identifiers. Nature Methods 9(1):72-74 (2012).
Klein, Allon M, et al., Droplet Barcoding for Single-cell Transcriptomics Applied to Embryonic Stem Cells. Cell 161(5):1187-1201 (2015).
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chern. 8: 1110-1115 (2008).
Kvastad et al., Single cell analysis of cancer cells using an improved RT-MLPA method has potential for cancer diagnosis and monitoring, Scientific Reports 5:16519; Nov. 12, 2015.
Lagally, et al. Single-Molecular DNA Amplification and Analysis in an Integrated Microfluidic Device. Anal Chem. Feb. 1, 2001;73(3):565-70.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Layer et al. "LUMPY: A probabilistic framework for structural variant discovery," Genome Biology (2014) 15(6):R84.
Lennon et al. A scalable, fully automated process for construction of sequence-ready barcoded libraries for 454. Genome Biology 11:R15 (2010).
Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Li, et al. Fast and accurate long-read alignment with Burrows-Wheeler transform. Bioinformatics 26.5 (2010): 589-595.
Lippert et al. "" Algorithmic strategies for the single nucleotide polymorphism haplotype assembly problem, Brief. Bionform (2002) 3:23-31.
Lundin, et al, "Hierarchical molecular tagging to resolve long continuous sequences by massively parallel sequencing", Sci Rep., 3:1186, 2013.
Macosko, Evan Z. et al. Highly Parallel Genome-wide Expression Profiling of Individual Cells Using Nanoliter Droplets. Cell 161(5):1202-1214 (2015).
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
"Mammal". Wikipedia.com; accessed Sep. 8, 2023. 50 pages.
Mccoy, R. et al. "Illumina TruSeq Synthetic Long-Reads Empower De Novo Assembly and Resolve Complex, Highly-Repetitive Transposable Elements" PLOS (2014) 9(9):e1016689.
Mckenna, Aaron et al. "The Genome Analysis Toolkit: A MapReduce Framework for Analyzing next-Generation DNA Sequencing Data." Genome Research 20.9 (2010): 1297-1303. PMC. Web. Feb. 2, 2017.
Microfluidic ChipShop. Microfluidic product catalogue. Oct. 2009. 48 pages.
Miller et al. "Assembly Algorithms for next-generation sequencing data," Genomics, 95 (2010), pp. 315-327.
Mulqueen, et al. Scalable and efficient single-cell DNA methylation sequencing by combinatorial indexing. bioRxiv. Jun. 28, 2017.
"Murinae". Wikipedia.com; accessed Sep. 8, 2023. 12 pages.
Myllykangas et al. "Efficient targeted resequencing of human germline and cancer genomes by oligonucleotide-selective sequencing," Nat Biotechnol, (2011) 29:1024-1027.
Myllykangas et al., Targeted Sequencing Library Preparation By Genomic DNA Circularization, BMC Biotechnology, 2011, 11(122), 1-12.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, Richard, et al., Single-Cell Multiplex Gene Detection and Sequencing with Microfluidically Generated Agarose Emulsions. Angewandte Chemie 50(2): 390-395 (2011).
Oligonucleotide. Merriam-webster, Aug. 23, 2017. Available at URL:https://www.merriam-webster.com/dictionary/oligonucleotide p. 1.
Oligonucleotide. Wikipedia, Feb. 17, 2019. Available at URL:https://en.wikipedia.org/wiki/Oligonucleotide pp. 1-3.
Orakdogen, N. "Novel responsive poly(N,N-dimethylaminoethyl methacrylate) gel beads: preparation, mechanical properties and pH-dependent swelling behavior" J Polym Res (2012) 19:9914.
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 2012).
"Plant". Wikipedia.com; accessed Sep. 8, 2023. 25 pages.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
"Protozoa," Wikipedia.com, accessed May 11, 2016. (Year: 2016).
Pushkarev et al. "Single-molecule sequencing of an individual human genome," Nature Biotech (2009) 27:847-850.
Ramani, et al. Massively multiplex single-cell Hi-C. Nat Methods 14(3):263-266 (2017).
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ritz, A. et al. "Characterization of structural variants with single molecule and hybrid sequencing approaches" Bioinformatics (2014) 30(24):3458-3466.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11.

(56) References Cited

OTHER PUBLICATIONS

Rodrigue, S. et al. "Whole genome amplification and de novo assembly of single bacterial cells" PLoS One. Sep. 2, 2009;4(9):e6864. doi: 10.1371/journal.pone.0006864.
Rosenberg, et al. SPLiT-seq reveals cell types and lineages in the developing brain and spinal cord. Science (New York, NY) 360. 6385 (2018): 176-182.
Rotem, A. et al., "High-throughput single-cell labeling (Hi-SCL) for RNA-Seq using drop-based microfluidics" PLOS One (May 22, 2015) 0116328 (14 pages).
Rotem, A. et al. "Single Cell Chip-Seq Using Drop-Based Microfluidics" Abstract #50. Frontiers of Single Cell Analysis, Stanford University Sep. 5-7, 2013.
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. Polymer. vol. 51, Issue 25, Nov. 26, 2010, pp. 5883-5889.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shembekar, et al. "Droplet-based microfluidics in drug discovery, transcriptomics and high-throughput molecular genetics" LabChip (2016) 16(8):1314-1331.
Shendure, Jay. et al. Accurate Multiplex Polony Sequencing Of An Evolved Bacterial Genome. Science 309(5741):1728-1732 (2005).
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
SSH Tunnel—Local and Remote Port Forwarding Explained With Examples, Trackets Blog, http://blog.trackets.com/2014/05/17/ssh-tunnel-local-and-remote-port-forwarding-explained-with-examples.html; Retrieved from the Internet Jul. 7, 2016.
Tewhey et al. The importance of phase information for human genomics, Nat Rev Genet (2011) 12:215-223.
Thaxton, C.S. et al. "A Bio-Bar-Code Assay Based Upon Dithiothreitol Oligonucleotide Release" Anal Chem (2005) 77:8174-8178.
The SAM/BAM Format Specificatio Working Group, "Sequence Alignment/ Map Format Specification," Sep. 6, 2016.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1) 107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Turner, et al. Assaying chromosomal inversions by single-molecule haplotyping. Nat Methods. Jun. 2006;3(6):439-45.
Turner, et al., "High-throughput haplotype determination over long distances by haplotype fusion PCR and ligation haplotyping", Nat Protoc., 4:1771-83, 2009.
U.S. Appl. No. 18/412,111 Office Action dated Jul. 8, 2024.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
"Virus", Wikipedia.com, accessed Sep. 8, 2023. 43 pages.
Vitak, et al. Sequencing thousands of single-cell genomes with combinatorial indexing. Nature methods 14.3 (2017): 302-308.
Voskoboynik, A. et al. The genome sequence of the colonial chordate, Botryllus schlosseri. eLife 2:e00569 (2013).
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. Efficient and unique cobarcoding of second-generation sequencing reads from long DNA molecules enabling cost-effective and accurate sequencing, haplotyping, and de novo assembly. Genome Research 29.5 (2019): 798-808.
Weigl, et al. Microfluidic Diffusion-Based Separation and Detection. Science. 1999; pp. 346-347.
Wheeler et al., "Database resources of the National Center for Biotechnology Information," Nucleic Acids Res. (2007) 35 (Database issue): D5-12.
Williams, et al. Amplification of complex gene libraries by emulsion PCR. Nature Methods. 3(7):545-50 (2006).
Wu, L. et al. "Detection DNA Point Mutation with Rolling-Circle Amplification Chip" Bioinformatics & Biomed Eng Conference (2010) Piscataway, NJ pp. 1-4.
Xi, et al. New library construction method for single-cell genomes. PLoS One. Jul. 19, 2017;12(7):e0181163. doi: 10.1371/journal.pone.0181163. eCollection 2017.
Xiao, et al, "Determination of haplotypes from single DNA molecules: a method for single-molecule barcoding", Hum Mutat., 28:913-21, 2007.
Zerbino, D.R. "Using the Velvet de novo assembler for short-read sequencing technologies" Curr Protoc Bioinformatics. Sep. 2010;Chapter 11:Unit 11.5. doi: 10.1002/0471250953.bi1105s31.
Zerbino et al. "Velvet: Algorithms for de novo short read assembly using de Bruijn graphs," Genome Research (2008) 18:821-829.
Zhang, et al. One-step fabrication of supramolecular microcapsules from microfluidic droplets. Science. Feb. 10, 2012;335(6069):690-4. doi: 10.1126/science.1215416.
Zhang, et al. Reconstruction of DNA sequencing by hybridization. Bioinformatics 19(1):14-21 (2003).
Zhang, Lei, and Anubhav Tripathi. Archaeal RNA Ligase From Thermoccocus Kodakarensis For Template Dependent Ligation. RNA Biology 14(1):36-44 (2017). Published online Oct. 7, 2016.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu et al., Reverse transcriptase template switching: a SMART approach for full-length cDNA library construction. Biotechniques 30(4):892-7 (2001).
Zilionis et al., Single-cell barcoding and sequencing using droplet microfluidics. Nat Protoc. 12(1):44-73 (2017).
Co-pending U.S. Appl. No. 19/047,506, inventor Pfeiffer; Katherine, filed Feb. 6, 2025.
Co-pending U.S. Appl. No. 19/047,512, inventors Pfeiffer; Katherine et al., filed Feb. 6, 2025.
Co-pending U.S. Appl. No. 19/093,986, inventors Bloju; Octavian Marian et al., filed Mar. 28, 2025.
Jaitin, Diego Adhemar, et al., Supplemental Figures Massively Parallel single-cell RNA-seq for Marker-free Decomposition of Tissues into cell types. Science 343(6172):776-779 (2014 (17 pages).
Co-pending U.S. Appl. No. 19/342,226, inventor Rahimi Lenji; Mohammad, filed Sep. 26, 2025.
Co-pending U.S. Appl. No. 19/342,369, inventor Paul; Eugene Lund et al., filed Sep. 26, 2025.
Co-pending U.S. Appl. No. 19/343,385, inventor Schnall-Levin; Michael, filed Sep. 29, 2025.

* cited by examiner

2500 to 60000 cells
7nM to 70nM Libraries
[21 cycles]

1000 to 24000 cells
9nM to 90nM Libraries
[21 cycles]

Cell recovery (single GEM lane, 16-plex)

| | Donor 1 | Donor 2 |
|---|---|---|
| 0 min control | 4360 | 4442 |
| 120 min control | 6919 | 4285 |
| 5 min | 2946 | 3909 |
| 15 min | 2953 | 3676 |
| 30 min | 3369 | 4558 |
| 60 min | 4064 | 4069 |
| 90 min | 3615 | 3706 |
| 120 min | 2661 | 4746 |

| Metric | DIR | FIG. 44 | FIG. 45 | FIG. 46 |
|---|---|---|---|---|
| Cell Yield (2x 25uM scrolls) | >400k | 80% | 95% | 85% |
| Expected Cells Recovered | >0.5 | 15% | 70% | 65% |
| Reads mapped to filtered probe set | >0.8 | 30% | 60% | 75% |
| Fraction reads in cells | >0.6 | 55% | 80% | 85% |
| Fraction reads usable | >0.4 | 50% | 90% | 85% |
| Valid barcodes | >0.9 | 100% | 100% | 100% |
| **Comparison to Cytassist** | - | - | - | - |
| Pseudobulk cell-UMI R^2 | >0.7 | 97% | 97% | 98% |
| obs. targeted gene cell-UMI recovery median | >0.8 | 98% | 99% | 99% |

*FIG. 47*

Tissue Scrolls gentleMACS Program 37C_FFPE_1

| | |
|---|---|
| 1 | temp ON |
| 2 | spin -20 rpm, 5' 0" *(counterclock)* |
| 3 | loop 3X |
| 4 | spin 20 rpm, 14' 0" |
| 5 | spin 1700 rpm, 7" |
| 6 | spin 1700 rpm, 1" |
| 7 | spin -1700 rpm, 2" *(counterclock)* |
| 8 | spin 1700 rpm, 1" |
| 9 | spin 1700 rpm, 4" |
| 10 | end loop |
| 11 | end |

*FIG. 51*

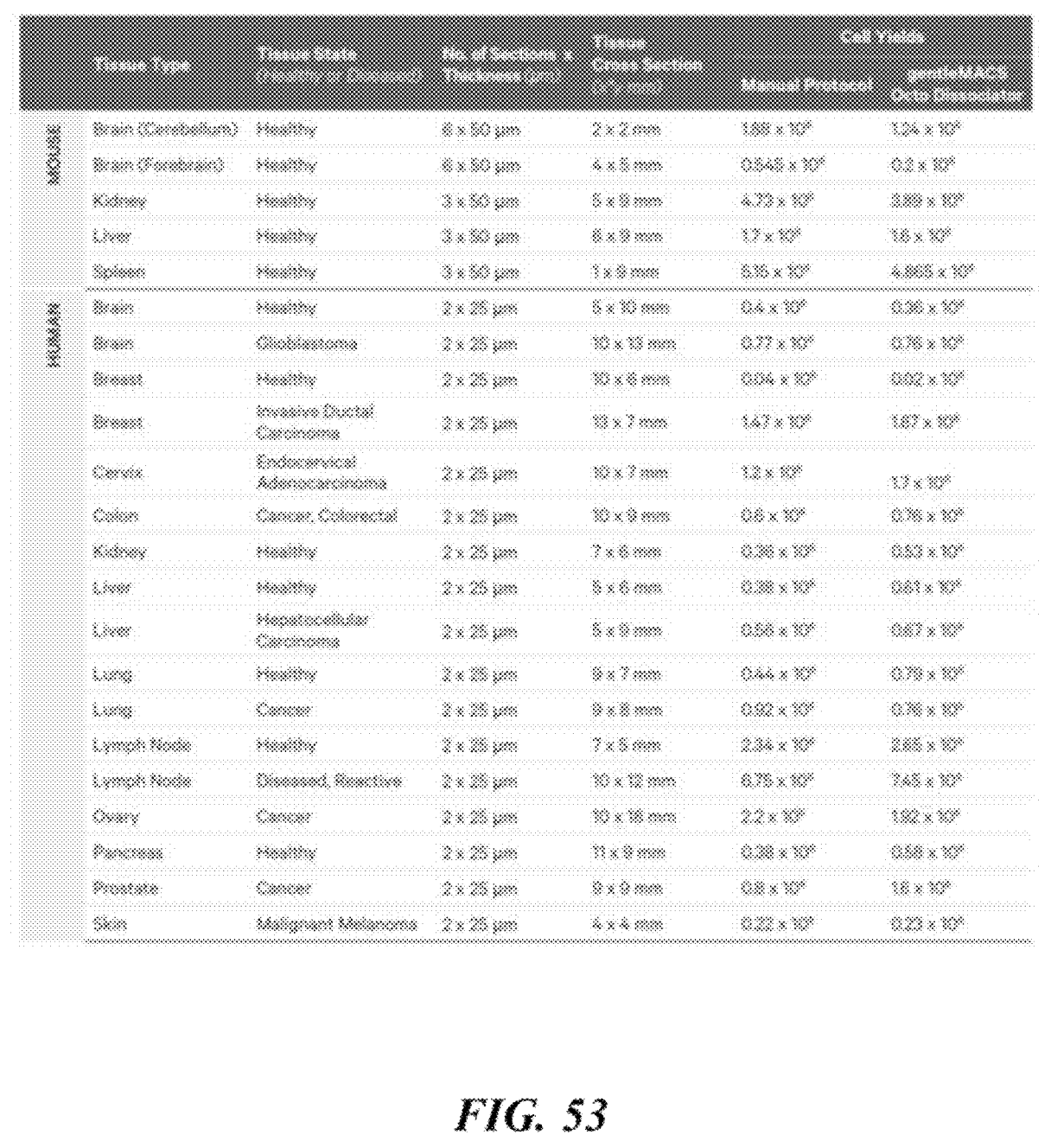

| | Tissue Type | Tissue State | No of Sections x Thickness (µm) | Tissue Cross Section | Cell Yields | |
|---|---|---|---|---|---|---|
| | | | | | Manual Protocol | gentleMACS Octo Dissociator |
| MOUSE | Brain (Cerebellum) | Healthy | 6 x 50 µm | 2 x 2 mm | 1.88 x 10^[illegible] | 1.24 x 10^[illegible] |
| | Brain (Forebrain) | Healthy | 6 x 50 µm | 4 x 5 mm | 0.545 x 10^[illegible] | 0.2 x 10^[illegible] |
| | Kidney | Healthy | 3 x 50 µm | 5 x 9 mm | 4.73 x 10^[illegible] | 3.89 x 10^[illegible] |
| | Liver | Healthy | 3 x 50 µm | 6 x 9 mm | 1.7 x 10^[illegible] | 1.6 x 10^[illegible] |
| | Spleen | Healthy | 3 x 50 µm | 1 x 9 mm | 5.15 x 10^[illegible] | 4.865 x 10^[illegible] |
| HUMAN | Brain | Healthy | 2 x 25 µm | 5 x 10 mm | 0.4 x 10^[illegible] | 0.36 x 10^[illegible] |
| | Brain | Glioblastoma | 2 x 25 µm | 10 x 13 mm | 0.77 x 10^[illegible] | 0.76 x 10^[illegible] |
| | Breast | Healthy | 2 x 25 µm | 10 x 6 mm | 0.04 x 10^[illegible] | 0.02 x 10^[illegible] |
| | Breast | Invasive Ductal Carcinoma | 2 x 25 µm | 13 x 7 mm | 1.47 x 10^[illegible] | 1.87 x 10^[illegible] |
| | Cervix | Endocervical Adenocarcinoma | 2 x 25 µm | 10 x 7 mm | 1.2 x 10^[illegible] | 1.7 x 10^[illegible] |
| | Colon | Cancer, Colorectal | 2 x 25 µm | 10 x 9 mm | 0.6 x 10^[illegible] | 0.76 x 10^[illegible] |
| | Kidney | Healthy | 2 x 25 µm | 7 x 6 mm | 0.36 x 10^[illegible] | 0.53 x 10^[illegible] |
| | Liver | Healthy | 2 x 25 µm | 5 x 6 mm | 0.38 x 10^[illegible] | 0.61 x 10^[illegible] |
| | Liver | Hepatocellular Carcinoma | 2 x 25 µm | 5 x 9 mm | 0.56 x 10^[illegible] | 0.67 x 10^[illegible] |
| | Lung | Healthy | 2 x 25 µm | 9 x 7 mm | 0.44 x 10^[illegible] | 0.79 x 10^[illegible] |
| | Lung | Cancer | 2 x 25 µm | 9 x 8 mm | 0.92 x 10^[illegible] | 0.76 x 10^[illegible] |
| | Lymph Node | Healthy | 2 x 25 µm | 7 x 5 mm | 2.34 x 10^[illegible] | 2.65 x 10^[illegible] |
| | Lymph Node | Diseased, Reactive | 2 x 25 µm | 10 x 12 mm | 6.75 x 10^[illegible] | 7.45 x 10^[illegible] |
| | Ovary | Cancer | 2 x 25 µm | 10 x 18 mm | 2.2 x 10^[illegible] | 1.92 x 10^[illegible] |
| | Pancreas | Healthy | 2 x 25 µm | 11 x 9 mm | 0.38 x 10^[illegible] | 0.58 x 10^[illegible] |
| | Prostate | Cancer | 2 x 25 µm | 9 x 9 mm | 0.8 x 10^[illegible] | 1.6 x 10^[illegible] |
| | Skin | Malignant Melanoma | 2 x 25 µm | 4 x 4 mm | 0.22 x 10^[illegible] | 0.23 x 10^[illegible] |

*FIG. 53*

SEQUENCE LISTING

```
Sequence total quantity: 15
SEQ ID NO: 1            moltype = RNA  length = 11
FEATURE                 Location/Qualifiers
source                  1..11
                        mol_type = other RNA
                        organism = synthetic construct
SEQUENCE: 1
aaaaaaaaaa a                                                       11

SEQ ID NO: 2            moltype = DNA  length = 13
FEATURE                 Location/Qualifiers
source                  1..13
                        mol_type = other DNA
                        organism = synthetic construct
SEQUENCE: 2
tttttttttt ttt                                                     13

SEQ ID NO: 3            moltype = DNA  length = 37
FEATURE                 Location/Qualifiers
source                  1..37
                        mol_type = other DNA
                        organism = synthetic construct
SEQUENCE: 3
atcttcaata gacacatcgg ccacacggtc ctagcaa                           37

SEQ ID NO: 4            moltype = DNA  length = 33
FEATURE                 Location/Qualifiers
source                  1..33
                        mol_type = other DNA
                        organism = synthetic construct
SEQUENCE: 4
atcgttcggg tctcctgaga gtgagatcac aga                               33

SEQ ID NO: 5            moltype = DNA  length = 37
FEATURE                 Location/Qualifiers
source                  1..37
                        mol_type = other DNA
                        organism = synthetic construct
misc_difference         22
                        note = a, c, t, or g
misc_difference         23
                        note = a, c, t, or g
misc_difference         24
                        note = a, c, t, or g
misc_difference         25
                        note = a, c, t, or g
misc_difference         26
                        note = a, c, t, or g
misc_difference         27
                        note = a, c, t, or g
misc_difference         28
                        note = a, c, t, or g
misc_difference         29
                        note = a, c, t, or g
SEQUENCE: 5
ccttggcacc cgagaattcc annnnnnnna gcacgta                           37

SEQ ID NO: 6            moltype = DNA  length = 12
FEATURE                 Location/Qualifiers
source                  1..12
                        mol_type = other DNA
                        organism = synthetic construct
SEQUENCE: 6
ttgctaggac cg                                                      12

SEQ ID NO: 7            moltype = DNA  length = 88
FEATURE                 Location/Qualifiers
```

```
source                  1..88
                        mol_type = unassigned DNA
                        organism = unidentified
SEQUENCE: 7
gtgactgctg acaaagatgg tgtggccgat gtgtctattg aagattctgt gatctcactc  60
tcaggagacc attgcatcat tggccgca                                     88

SEQ ID NO: 8            moltype = DNA  length = 16
FEATURE                 Location/Qualifiers
source                  1..16
                        mol_type = other DNA
                        organism = synthetic construct
SEQUENCE: 8
cgaacgatta cgtgct                                                  16

SEQ ID NO: 9            moltype = DNA  length = 28
FEATURE                 Location/Qualifiers
source                  1..28
                        mol_type = other DNA
                        organism = synthetic construct
misc_difference         9
                        note = a, c, t, or g
misc_difference         10
                        note = a, c, t, or g
misc_difference         11
                        note = a, c, t, or g
misc_difference         12
                        note = a, c, t, or g
misc_difference         13
                        note = a, c, t, or g
misc_difference         14
                        note = a, c, t, or g
misc_difference         15
                        note = a, c, t, or g
misc_difference         16
                        note = a, c, t, or g
SEQUENCE: 9
attcaggtnn nnnnnncggt cctagcaa                                     28

SEQ ID NO: 10           moltype = DNA  length = 33
FEATURE                 Location/Qualifiers
source                  1..33
                        mol_type = other DNA
                        organism = synthetic construct
SEQUENCE: 10
atcttcaata gacacatcgg ccacaaaccg cgt                               33

SEQ ID NO: 11           moltype = DNA  length = 46
FEATURE                 Location/Qualifiers
source                  1..46
                        mol_type = other DNA
                        organism = synthetic construct
SEQUENCE: 11
ccttggcacc cgagaattcc aggtctcctg agagtgagat cacaga                 46

SEQ ID NO: 12           moltype = DNA  length = 16
FEATURE                 Location/Qualifiers
source                  1..16
                        mol_type = other DNA
                        organism = synthetic construct
SEQUENCE: 12
acctgaatac gcggtt                                                  16

SEQ ID NO: 13           moltype = DNA  length = 88
FEATURE                 Location/Qualifiers
source                  1..88
                        mol_type = other DNA
                        organism = synthetic construct
SEQUENCE: 13
gtgactgctg acaaagatgg tgtggccgat gtgtctattg aagattctgt gatctcactc  60
tcaggagacc attgcatcat tggccgca                                     88

SEQ ID NO: 14           moltype = DNA  length = 29
FEATURE                 Location/Qualifiers
source                  1..29
                        mol_type = other DNA
                        organism = synthetic construct
misc_difference         1
                        note = a, c, t, or g
```

-continued

```
misc_difference        2
                       note = a, c, t, or g
misc_difference        3
                       note = a, c, t, or g
misc_difference        4
                       note = a, c, t, or g
misc_difference        5
                       note = a, c, t, or g
misc_difference        6
                       note = a, c, t, or g
misc_difference        7
                       note = a, c, t, or g
misc_difference        8
                       note = a, c, t, or g
SEQUENCE: 14
nnnnnnnngg aaccgtgggc tcttaaggt                                            29

SEQ ID NO: 15          moltype = RNA  length = 10
FEATURE                Location/Qualifiers
source                 1..10
                       mol_type = other RNA
                       organism = synthetic construct
SEQUENCE: 15
aaaaaaaaaa                                                                 10
```

PROBE-BASED ANALYSIS OF NUCLEIC ACIDS AND PROTEINS

CROSS REFERENCE

This application is a continuation of U.S. application Ser. No. 18/810,294, filed Aug. 20, 2024, which is a continuation-in-part of U.S. application Ser. No. 18/412,111, filed Jan. 12, 2024, which is a continuation of U.S. application Ser. No. 18/370,826, filed Sep. 20, 2023, which is a continuation of U.S. application Ser. No. 18/217,310, filed Jun. 30, 2023, which is a continuation of International Application No. PCT/US2023/026504, filed Jun. 28, 2023, which claims the benefit of U.S. Provisional Application No. 63/356,887, filed Jun. 29, 2022, and U.S. Provisional Application No. 63/386,135, filed Dec. 5, 2022; each of which applications is incorporated by reference herein in its entirety for all purposes.

SEQUENCE LISTING

The instant application contains a Sequence Listing which has been submitted electronically in XML format and is hereby incorporated by reference in its entirety. Said XML copy, created on Jan. 28, 2025, is named 43487-890_502_SL.xml and is 23,450 bytes in size.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

Biological molecules, such as nucleic acids and proteins, within biological samples may be probed and/or processed for quantitative or qualitative assessment.

SUMMARY

The present disclosure provides methods for use in sample processing and analysis. The methods provided herein may involve hybridizing a probe to a molecule of interest (e.g., target protein, target nucleic acid molecule) and processing the probe-molecule complex. Such processing can include barcoding the probe, the probe-molecule complex, or the molecule, and/or performing a nucleic acid reaction. The probe may comprise a nucleic acid molecule, and further processing can include extension, denaturation, and amplification processes to provide nucleic acid molecules comprising a sequence the same or substantially the same as or complementary to that of a target region of a nucleic acid molecule of interest (e.g., target nucleic acid molecule). A method may comprise hybridizing a first probe and a second probe to first and second target regions of the nucleic acid molecule, linking the first and second probes to provide a probe-linked nucleic acid molecule, and barcoding the probe-linked nucleic acid molecule. A method may comprise hybridizing a first probe to a first target region of a nucleic acid molecule, barcoding the probe, and hybridizing a second probe to a second target region of the nucleic acid molecule to generate a barcoded, probe-linked nucleic acid molecule. In some aspects, the method may comprise hybridizing a probe to a nucleic acid molecule attached to a feature-binding moiety to provide a probe-binding moiety complex and barcoding the probe. One or more processes of the methods provided herein may be performed within a partition such as a droplet or well. The methods of the present disclosure be useful, for example, in controlled analysis and processing of analytes such as biological particles, nucleic acids, and proteins. One or more of the methods described herein may allow for genomic, transcriptomic, or exomic profiling with higher sensitivity. The methods of the present disclosure may be useful in detecting variants and characterizing nucleic acid molecules, e.g., for assessment of single nucleotide polymorphisms (SNPs), alternative splice junctions, insertions, deletions, V (D) J rearrangements, etc. The methods of the present disclosure may be useful for multiplexed analysis of nucleic acids and proteins while minimizing reagent usage, e.g., by decreasing the number of unoccupied partitions for analysis.

In an aspect, disclosed herein is a method for multiplexed nucleic acid assays, comprising: (a) contacting a cell, nucleus, or cell bead with a first probe, a second probe, and a third probe under conditions sufficient to generate a first probe-associated molecule and a second probe-associated molecule, wherein the cell, nucleus, or cell bead comprises (i) a nucleic acid molecule comprising a first target region and a second target region and (ii) a feature coupled to a feature binding group, wherein the feature binding group comprises (i) a reporter oligonucleotide associated with the feature and (ii) a feature probe binding sequence, wherein the first probe comprises (i) a first probe sequence complementary to the first target region and (ii) a probe capture sequence, wherein the second probe comprises a second probe sequence complementary to the second target region, wherein the third probe comprises a (i) third probe sequence complementary to the feature probe binding sequence and (ii) the probe capture sequence; (b) in a first partition of a first set of partitions, contacting the first probe-associated molecule and the second probe-associated molecule to probe binding molecules and barcode molecules under conditions sufficient to generate a first barcoded nucleic acid molecule and a second barcoded nucleic acid molecule, wherein the barcode molecules comprise (i) a common sequence common to a plurality of barcode molecules comprising the barcode molecules and (ii) a first barcode sequence common to the first partition of the first set of partitions, wherein the probe binding molecule comprises (i) a probe binding sequence complementary to the probe capture sequence and (ii) a barcode binding sequence complementary to the common sequence; and (c) in a second partition of a second set of partitions, (i) contacting the first barcoded nucleic acid molecule, or derivative thereof, to a first capture molecule of a plurality of capture molecules under conditions sufficient to generate a third barcoded nucleic acid molecule, and (ii) contacting the second barcoded nucleic acid molecule, or derivative thereof, to a second capture molecule of the plurality of capture molecules under conditions sufficient to generate a fourth barcoded nucleic acid molecule, wherein the plurality of capture molecules comprise a second barcode sequence, wherein each of the third barcoded nucleic acid molecule and the fourth barcoded molecule comprises a sequence corresponding to the first barcode sequence and a sequence corresponding to the second barcode sequence.

In some embodiments, the first target region and the second target region are on a same strand of the nucleic acid molecule. In some embodiments, the probe capture sequence is common to a plurality of first probes including the first probe, wherein one or more additional partitions of the first set of partitions comprise one or more additional probe-associated nucleic acid molecules, wherein each of the one or more additional probe-associated nucleic acid molecules comprises the probe capture sequence. In some embodiments, the second probe comprises a second probe capture sequence complementary to a capture sequence of the plurality of capture molecules, and wherein (c) comprises hybridizing the second probe capture sequence to the capture sequence. In some embodiments, the barcode molecules comprise a capture binding sequence complementary to a capture sequence of the plurality of capture molecules, and wherein (c) comprises hybridizing the capture binding sequence to the capture sequence. In some embodiments, the first set of partitions are a plurality of wells. In some embodiments, the second set of partitions are a plurality of droplets. In some embodiments, the second set of partitions are a plurality of wells. In some embodiments, the plurality of capture molecules is coupled to a particle. In some embodiments, the particle is a bead. In some embodiments, the bead is a gel bead. In some embodiments, each capture molecule of the plurality of capture molecules coupled to the gel bead comprises the second barcode sequence. In some embodiments, one or more additional partitions of the second set of partitions comprise one or more additional gel beads of a plurality of gel beads, and wherein the second barcode sequence is unique to the gel bead among the plurality of gel beads. In some embodiments, a capture molecule of the plurality of capture molecules comprises a third barcode sequence unique to the capture molecule among the plurality of capture molecules. In some embodiments, one or more additional partitions of the second set of partitions comprise one or more additional capture molecules, and wherein the second barcode sequence is unique to the second partition among the second set of partitions. In some embodiments, (a) comprises hybridizing the first probe and the second probe to the first target region and the second target region, respectively. In some embodiments, the method further comprises subjecting the first probe-associated molecule to conditions sufficient to yield a probe-linked nucleic acid molecule comprising the first probe linked to the second probe. In some embodiments, the probe-linked nucleic acid molecule is generated via chemical or enzymatic ligation of the first probe and the second probe. In some embodiments, the chemical or enzymatic ligation occurs subsequent to (b). In some embodiments, the first target region and the second target region are adjacent. In some embodiments, the first target region and the second target region are non-adjacent, and the method further comprises (i) extending the first probe or the second probe annealed to the first target region or the second target region, respectively, towards the second target region or the first target region, respectively, to generate an extended probe, and (ii) ligating the extended probe to the second probe or the first probe, respectively. In some embodiments, (a) comprises contacting the first probe and the second probe to the nucleic acid molecule inside the cell or nucleus. In some embodiments, the first partition comprises a plurality of cells, cell beads, or nuclei. In some embodiments, the cell or nucleus is permeabilized. In some embodiments, the cell or nucleus is fixed. In some embodiments, the method further comprises releasing the first probe-associated molecule, or derivative thereof, from the cell, nucleus, or cell bead. In some embodiments, the releasing comprises lysing the cell. In some embodiments, the reporter oligonucleotide comprises the feature probe binding sequence. In some embodiments, the method further comprises, subsequent to (b) and prior to (c), pooling the first barcoded nucleic acid molecule, the second barcoded nucleic acid molecule, additional first barcoded nucleic acid molecules from the first set of partitions, and additional second barcoded nucleic acid molecules form the first set of partitions. In some embodiments, the method further comprises subsequent to (c) and prior to sequencing, pooling the third barcoded nucleic acid molecule, the fourth barcoded nucleic acid molecule, additional third barcoded nucleic acid molecules from the second set of partitions, and additional fourth barcoded nucleic acid molecules from the second set of partitions. In some embodiments, the probe capture sequence is from 8 to 50 bp.

In another aspect of the present disclosure, provided herein is a method, comprising: (a) contacting a nucleic acid molecule with a first probe to generate a probe-associated nucleic acid molecule, wherein the nucleic acid molecule comprises a first target region and a second target region not adjacent to the first target region, wherein the first probe comprises a first probe sequence complementary to the first target region; (b) extending the first probe under conditions sufficient to generate an extended probe molecule comprising a sequence complementary to the second target region; (c) in a partition of a plurality of partitions, providing the extended probe molecule, a second probe, and a barcode molecule and a probe binding molecule, under conditions sufficient to generate a barcoded molecule, wherein the second probe comprises a second probe sequence corresponding to the second target region, wherein the first probe or the second probe comprises a probe capture sequence, wherein the barcode molecule comprises (i) a barcode capture sequence and (ii) a barcode sequence, wherein the probe binding molecule comprises (i) a probe binding sequence complementary to the probe capture sequence and (ii) a barcode binding sequence complementary to the barcode capture sequence, wherein the barcoded molecule comprises a sequence corresponding to the first target region, a sequence corresponding to the second target region, a sequence corresponding to the probe capture sequence, and a sequence corresponding to the barcode sequence.

In some embodiments, (c) comprises ligating the second probe and the barcode molecule. In some embodiments, the ligating comprises chemical or enzymatic ligation. In some embodiments, the particle is a bead. In some embodiments, the bead is a gel bead. In some embodiments, the cell or nucleus is permeabilized. In some embodiments, the cell or nucleus is fixed. In some embodiments, the first probe comprises the probe capture sequence. In some embodiments, the method further comprises, subsequent to (b), releasing the extended probe molecule from the nucleic acid molecule. In some embodiments, the releasing comprises freeing a ribonucleic acid (RNA) strand using RNase. In some embodiments, the releasing comprises heat cycling. In some embodiments, (c) comprises (i) hybridizing the second probe sequence of the second probe to the sequence complementary to the second target region and (ii) extending the second probe. In some embodiments, in (c) the barcode molecule and the probe binding molecule are provided as a pre-annealed complex, wherein the barcode capture sequence is annealed to the barcode binding sequence in the pre-annealed complex. In some embodiments, the first probe comprises the probe capture sequence, wherein (c) comprises (i) annealing the probe binding sequence and the barcode binding sequence to the probe capture sequence and the barcode capture sequence, respectively (ii) ligating the barcode molecule and the extended probe molecule, to generate a first barcoded molecule and (iii) annealing the second probe to the first barcoded molecule and initiating an extension reaction to generate the barcoded molecule. In some embodiments, (ii) and (iii) are preformed outside the partition. In some embodiments, the second probe comprises the probe capture sequence, wherein (c) comprises (i) annealing the second probe to the extended probe molecule and initiating an extension reaction to generate an extension molecule, (ii) annealing the probe binding sequence and the barcode binding sequence to the probe capture sequence and the barcode capture sequence, and (iii) ligating the barcode molecule and the extension molecule.

In another aspect, provided herein is a method of analyzing a sample, comprising: (a) providing: (i) a feature-binding group bound to at least a portion of the sample, wherein the feature-binding group comprises a reporter oligonucleotide, wherein the reporter oligonucleotide comprises a reporter barcode sequence, a first target region and a second target region, wherein the first target region and the second target region are disposed on a same strand of the reporter oligonucleotide; (ii) a first probe comprising a first probe sequence, wherein the first probe sequence of the first probe is complementary to the first target region of the reporter oligonucleotide; and (iii) a second probe comprising a second probe sequence, wherein the second probe sequence of the second probe is complementary to the second target region of the reporter oligonucleotide; (b) subjecting the sample to conditions sufficient to (i) hybridize the first probe sequence of the first probe to the first target region of the reporter oligonucleotide, and (ii) hybridize the second probe sequence of the second probe to the second target region of the reporter oligonucleotide to yield a probe-associated reporter oligonucleotide complex; and (c) subjecting the probe-associated reporter oligonucleotide complex to conditions sufficient to yield a probe-linked nucleic acid molecule comprising the first probe linked to the second probe.

In some embodiments, the method further comprises (d) attaching a barcode molecule to the probe-linked nucleic acid molecule. In some embodiments, (d) occurs in a partition. In some embodiments, the partition is a droplet or a well. In some embodiments, the sample comprises a nucleic acid molecule, and wherein (d) further comprises attaching an additional barcode molecule to the nucleic acid molecule or derivative thereof. In some embodiments, the feature-binding group is an antibody. In some embodiments, the first probe or the second probe comprises an additional probe sequence. In some embodiments, the method further comprises attaching a barcode sequence to the additional probe sequence. In some embodiments, the method further comprises (d) providing a barcode molecule and a probe binding molecule comprising (i) a first sequence complementary to the additional probe sequence and (ii) a second sequence complementary to a capture sequence of the barcode molecule. In some embodiments, the method further comprises providing conditions sufficient to hybridize the first sequence to the additional probe sequence and the second sequence to the capture sequence of the barcode molecule, thereby generating a barcoded probe-associated complex. In some embodiments, (d) occurs in a partition among a plurality of partitions. In some embodiments, the method further comprises pooling the barcoded probe-associated complex from the partition with other barcoded probe-associated complexes from other partitions of the plurality of partitions to generate a pooled set of barcoded probe-associated complexes. In some embodiments, the method further comprises (i) partitioning the pooled set of barcoded probe-associated complexes into a plurality of additional partitions, wherein an additional partition of the plurality of additional partitions comprises the barcoded probe-associated complex and an additional barcode molecule comprising an additional barcode sequence and (ii) attaching the additional barcode molecule to the barcoded probe-associated complex. In some embodiments, the additional barcode molecule is coupled to a bead. In some embodiments, the bead is a gel bead. In some embodiments, the additional barcode molecule is releasably coupled to the bead. In some embodiments, (d) occurs prior to (c). In some embodiments, (d) occurs subsequent to (c). In some embodiments, the at least the portion of the sample comprises a feature. In some embodiments, the feature is a protein. In some embodiments, the protein is a cell surface receptor or an intracellular protein. In some embodiments, the sample comprises a cell or cell bead. In some embodiments, the cell is a formalin fixed, paraffin-embedded cell. In some embodiments, (c) occurs in a partition. In some embodiments, the partition is among a plurality of partitions. In some embodiments, (c) comprises enzymatic or chemical ligation. In some embodiments, the ligation is performed in the absence of adenosine triphosphate. In some embodiments, the first probe or the second probe comprises an adenylated end, a phosphorylated end, a ribonucleotide, a dideoxynucleotide, or a flap sequence. In some embodiments, the first target region and the second target region are separated by a gap region disposed between the first target region and the second target region. In some embodiments, (c) comprises performing an extension reaction to fill the gap region to yield the probe-linked nucleic acid molecule. In some embodiments, (c) comprises providing a third probe comprising a third probe sequence complementary to the gap region, hybridizing the third probe sequence to the gap region, and providing conditions sufficient to yield the probe-linked nucleic acid molecule comprising the first probe linked to the second probe via the third probe.

In another aspect, the present disclosure provides a method for analyzing a nucleic acid molecule of an embedded, fixed tissue, comprising: (a) providing the embedded, fixed tissue, wherein: (i) the embedded, fixed tissue comprises a plurality of cells, (ii) a cell of the plurality of cells comprises the nucleic acid molecule, and (iii) the embedded, fixed tissue is embedded in a solid medium; (b) removing at least a portion of the solid medium from the embedded, fixed tissue, thereby obtaining a fixed tissue comprising the plurality of cells; (c) dissociating the fixed tissue into cells of the plurality of cells, wherein the cells comprise the cell comprising the nucleic acid molecule; and (d) in the cell, using a barcode sequence to generate a barcoded nucleic acid molecule comprising a barcode sequence and a sequence corresponding to the nucleic acid molecule.

In some embodiments, the fixed tissue is fixed at least about 1 year prior to (a). In some embodiments, the fixed tissue is fixed at least about 5 years prior to (a). In some embodiments, the method further comprises, in (b), adding a first solvent to the embedded, fixed tissue, thereby dissolving the solid medium, thereby obtaining a fixed tissue.

In some embodiments, the first solvent is a non-polar solvent. In some embodiments, the non-polar solvent comprises xylene. In some embodiments, the non-polar solvent comprises neo-Clear® xylene alternative. In some embodiments, the method further comprises removing the first solvent from the fixed tissue. In some embodiments, the method further comprises adding a second solvent to the fixed tissue. In some embodiments, the second solvent is a polar solvent. In some embodiments, the polar solvent comprises ethanol. In some embodiments, the method further comprises removing the second solvent from the fixed tissue. In some embodiments, the method further comprises adding a rehydration agent to the fixed tissue. In some embodiments, the rehydration agent comprises water. In some embodiments, the method further comprises removing the rehydration agent from the tissue. In some embodiments, the method further comprises adding buffer to the fixed tissue. In some embodiments, the method further comprises removing the buffer from the fixed tissue. In some embodiments, the method further comprises, in (c), dissociating the tissue. In some embodiments, the method further comprises resuspending the tissue in a supernatant. In some embodiments, the method further comprises filtering the tissue. In some embodiments, the method further comprises washing the tissue. In some embodiments, the method further comprises resuspending the tissue. In some embodiments, the dissociating the tissue is performed using an automated dissociator. In some embodiments, said automated dissociator is a gentleMACS™ Octo Dissociator. In some embodiments, the dissociating the tissue is performed using a manual pulverizer. In some embodiments, (b) and (c) provide a yield of cells of at least about $1\times10^5$ cells per two 25 micrometer sections of the fixed tissue. In some embodiments, the fixed tissue comprises fixed human tissue. In some embodiments, the fixed tissue comprises one or more of fixed connective tissue, fixed epithelial tissue, fixed organ tissue, fixed muscle tissue, fixed ligaments, fixed tendons, fixed a skin tissue, fixed breast tissue, fixed bladder, fixed kidney tissue, fixed liver tissue, fixed colon tissue, fixed thyroid tissue, fixed cervical tissue, fixed prostate tissue, fixed lung tissue, fixed cardiac tissue, fixed heart tissue, fixed muscle tissue, fixed pancreas tissue, fixed anal tissue, fixed bile duct tissue, fixed a bone tissue, fixed bone marrow, fixed uterine tissue, fixed ovarian tissue, fixed endometrial tissue, fixed vaginal tissue, fixed vulvar tissue, fixed stomach tissue, fixed ocular tissue, fixed nasal tissue, fixed sinus tissue, fixed penile tissue, fixed salivary gland tissue, fixed gut tissue, fixed gallbladder tissue, fixed gastrointestinal tissue, fixed bladder tissue, fixed brain tissue, fixed spinal tissue, fixed neurons, fixed cells representative of a blood-brain barrier, fixed blood, fixed hair, fixed nails, fixed keratin, or fixed collagen. In some embodiments, (d) comprises hybridizing the barcode sequence to the nucleic acid molecule. In some embodiments, the method further comprises extending the barcode to form the barcoding nucleic acid molecule. In some embodiments, the extending comprises the use of an enzyme. In some embodiments, the extending comprises ligating the barcode sequence to a probe. In some embodiments, the probe comprises a portion at least partially complementary to the nucleic acid molecule. In some embodiments, the method further comprises, prior to (d), partitioning the nucleic acid molecule into a partition. In some embodiments, the partition is a well of a plurality of wells. In some embodiments, the partition is a droplet of a plurality of droplets. In some embodiments, the plurality of droplets comprises an oil droplet. In some embodiments, the partition comprises a support. In some embodiments, the support comprises a bead. In some embodiments, the barcode sequence is attached to the support. In some embodiments, the solid medium comprises paraffin. In some embodiments, the fixed tissue comprises a formalin fixed tissue embedded in the paraffin. In some embodiments, the nucleic acid molecule comprises a ribonucleic acid (RNA) molecule. In some embodiments, the nucleic acid molecule comprises a messenger RNA molecule.

In an aspect, the present disclosure provides a method for analyzing a nucleic acid molecule of an embedded, fixed tissue, comprising: (a) providing the embedded, fixed tissue, wherein: (i) the embedded, fixed tissue comprises a plurality of cells, (ii) a cell of the plurality of cells comprises the nucleic acid molecule, and (iii) the embedded, fixed tissue is embedded in a solid medium; (b) removing at least a portion of the solid medium from the embedded, fixed tissue, by adding a first solvent to the embedded, fixed tissue, thereby dissolving the solid medium thereby obtaining a fixed tissue comprising the plurality of cells; (c) removing the first solvent from the fixed tissue; (d) adding a second solvent to the fixed tissue; (e) removing the second solvent from the fixed tissue; (f) adding a rehydrated agent to the fixed tissue; (g) removing the rehydration agent from the fixed tissue; (h) adding buffer to the fixed tissue; (i) removing the buffer from the fixed tissue; (j) dissociating the fixed tissue into cells of the plurality of cells, wherein the cells comprise the cell comprising the nucleic acid molecule; and (l) in the cell, using a barcode sequence to generate a barcoded nucleic acid molecule comprising a barcode sequence and a sequence corresponding to the nucleic acid molecule.

In some embodiments, the solid medium comprises paraffin. In some embodiments, the first solvent comprises xylene. In some embodiments, the second solvent comprises ethanol. In some embodiments, the rehydration agent comprises water. In some embodiments, the buffer comprises phosphate buffered saline. In some embodiments, dissociating the tissue is performed using an automated dissociator or a manual pulverizer. In some embodiments, the strainer has a pore size of about 70 micrometers.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 12B shows "AAAAAAAAAAA" (SEQ ID NO: 1) and "TTTTTTTTTTTTT" (SEQ ID NO: 2).

FIG. 12C shows "AAAAAAAAAAA" (SEQ ID NO: 1).

FIG. 15A shows 1506 (SEQ ID NO: 3), 1516 (SEQ ID NO: 4), 1519 (SEQ ID NO: 5), 1520 (SEQ ID NO: 6), 1500 (SEQ ID NO: 7), and 1517 (SEQ ID NO: 8). FIG. 15B shows 1520 (SEQ ID NO: 6), 1519 (SEQ ID NO: 9), 1506 (SEQ ID NO: 10), 1516 (SEQ ID NO: 11), 1517 (SEQ ID NO: 12), and 1500 (SEQ ID NO: 13). FIG. 15C discloses 1506 (SEQ ID NO: 3), 1520 (SEQ ID NO: 6), 1500 (SEQ ID NO: 7), 1516 (SEQ ID NO: 11), 1517 (SEQ ID NO: 14).

FIG. 17 shows 1719 (SEQ ID NO: 5) and 1717 (SEQ ID NO: 8).

FIG. 27 shows "AAAAAAAAAA" (SEQ ID NO: 15).

FIG. 32A shows example data showing different immune cell clusters. FIG. 32B shows example data of gene expression of GZMB gene. FIG. 32C shows example data of protein expression resulting from antibody staining.

FIG. 33A shows example data showing different immune cell clusters. FIG. 33B shows example data of gene expression of GZMB gene. FIG. 33C shows example data of protein expression resulting from antibody staining.

FIG. 34A shows example data showing different immune cell clusters. FIG. 34B shows example data of gene expression of GZMB gene. FIG. 34C shows example data of protein expression resulting from antibody staining.

FIG. 35A shows example data showing different immune cell clusters. FIG. 35B shows example data of gene expression of GZMB gene. FIG. 35C shows example data of protein expression resulting from antibody staining.

FIG. 35A shows example data showing different immune cell clusters. FIG.

36B shows example data of gene expression of GZMB gene. FIG. 36C shows example data of protein expression resulting from antibody staining.

FIG. 37A shows example data showing different immune cell clusters. FIG. 37B shows example data of gene expression of GZMB gene. FIG. 37C shows example data of protein expression resulting from antibody staining.

FIG. 47 provides a table of the pass percentages and other properties for the various procedures of the present example, according to some embodiments.

FIG. 51 shows an example gentleMACS™ program for tissue dissociation.

FIG. 53 shows example cell yield from fixed tissue sections.

DETAILED DESCRIPTION

Figure 1:
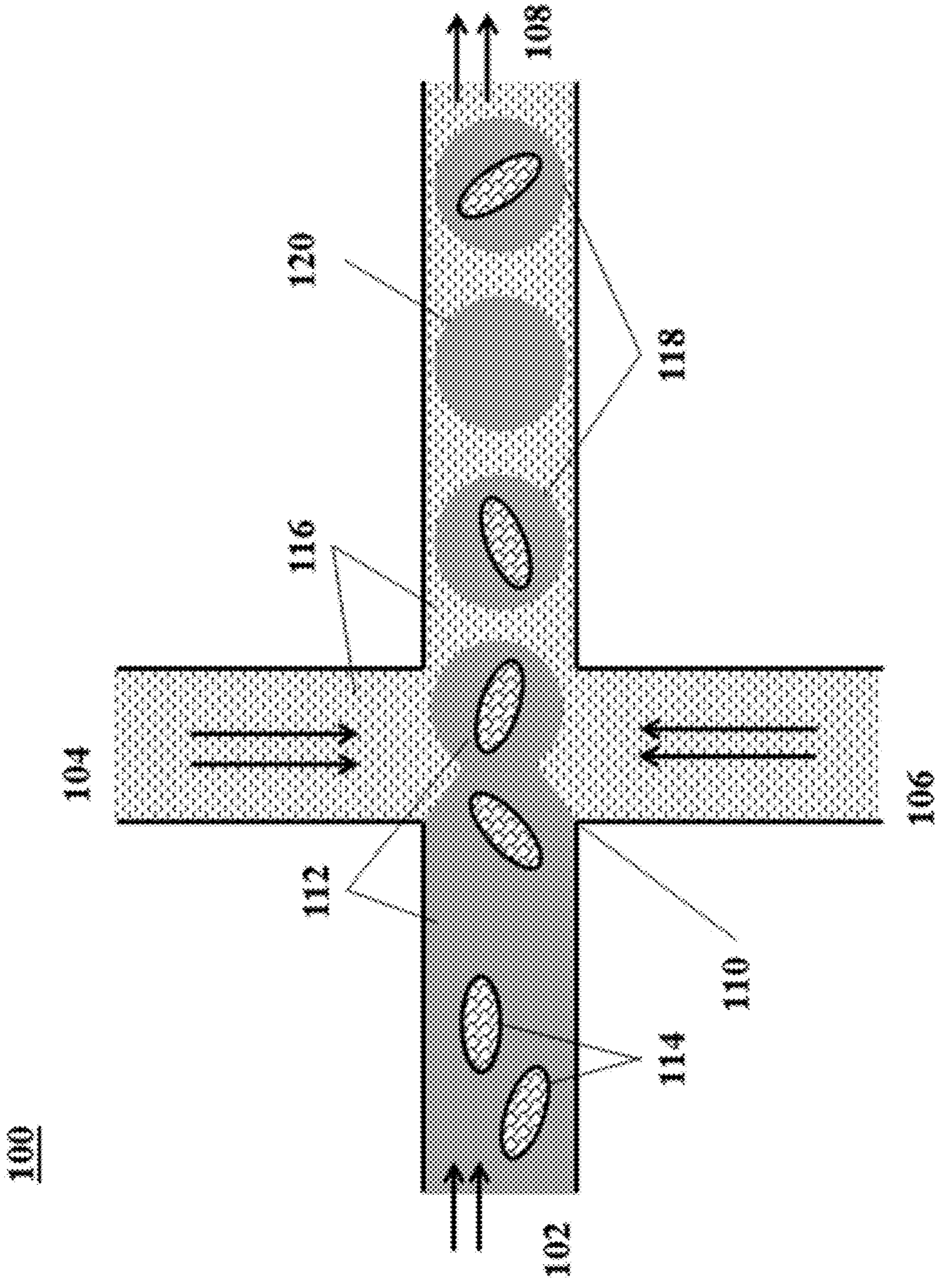
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The terms "about" and "approximately," as used herein, when preceding a numerical value indicates the value plus or minus a range of 10%. For example, about 10 may be reasonably understood to convey 9, 10, or 11, or a range of numerical values spanning from 9 to 11. Whenever "about" or "approximately" precedes the first numerical value in a series of two or more numerical values, the term "about" or "approximately" applies to each of the numerical values in that series of numerical values.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human, mouse, rat) or avian (e.g., bird), or other organism, such as a plant. For example, the subject can be a vertebrate, such as a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence or a non-targeted sequence. For example, in the methods and systems described herein, hybridization and reverse transcription of a nucleic acid molecule (e.g., a messenger RNA (mRNA) molecule) of a cell or nucleus with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells or nuclei. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The tissue sample may be a fresh tissue sample, a frozen tissue sample (e.g., flash frozen, lyophilized, cryo-sectioned, etc.), or a fixed tissue sample (e.g., a formalin-fixed and paraffin-embedded tissue sample). The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. Examples of an organelle from a cell include, without limitation, a nucleus, a ribosome, a Golgi apparatus, an endoplasmic reticulum, a chloroplast, an endocytic vesicle, an exocytic vesicle, a vacuole, and a lysosome. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject (e.g., a human, a mouse, a rat, or other mammal). The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The term "solid medium," as used herein, generally refers to a non-gaseous or non-liquid material. The solid medium may comprise a long chain hydrophobic compound, glycerin, gels, hydrogels, epoxy, resin, or any combination thereof. A long chain hydrophobic compound may include a wax, such as paraffin wax.

Provided herein are methods for sample processing and/or analysis. A method of the present disclosure may comprise barcoding one or more types of biomolecules (e.g., a nucleic acid molecule, a protein, a lipid, a carbohydrate, or a combination thereof). The biomolecule may be, for instance, a nucleic acid molecule (e.g., a ribonucleic acid (RNA) molecule) or a protein. Such a method may involve attaching one or more probes (e.g., nucleic acid probes) to the biomolecules and subsequently attaching a nucleic acid barcode molecule comprising a barcode sequence to the one or more probes. For example, the nucleic acid barcode molecule may attach to an overhanging sequence of a probe or to the end of a probe. Extension from an end of the probe to an end of the nucleic acid barcode molecule may form an extended nucleic acid molecule comprising both a sequence complementary to the barcode sequence and a sequence complementary to a target region of the nucleic acid molecule. The extended nucleic acid molecule may then be denatured from the nucleic acid barcode molecule and the nucleic acid molecule may be duplicated. One or more processes of the method may be carried out within a partition such as a droplet or well.

The present disclosure also provides a method of processing a sample (e.g., a cell sample or a tissue sample) that provides a barcoded nucleic acid molecule having linked probe molecules attached thereto. The method may comprise providing a sample comprising a nucleic acid molecule (e.g., an RNA molecule) having a first and second target region; a first probe having a (i) first probe sequence that is complementary to the first target region and (ii) an additional probe sequence; and a second probe having a second probe sequence that is complementary to the second target region. In some instances, the first target region and the second target region are adjacent. The first and second probe sequences may also comprise first and second reactive moieties, respectively. Upon hybridization of the first probe sequence of the first probe to the first target region of the nucleic acid molecule, and hybridization of the second probe sequence of the second probe to the second target region of the nucleic acid molecule, the reactive moieties may be adjacent to one another. Subsequent reaction between the adjacent reactive moieties under sufficient conditions may link the first and second probes to yield a probe-linked nucleic acid molecule. The probe-linked nucleic acid molecule may also be referred to as a probe-ligated nucleic acid molecule. In other instances, the first target region and the second target region are not adjacent, and a nucleic acid reaction (e.g., a nucleic acid extension reaction, a gap-filling reaction) may be performed to yield a probe-linked nucleic acid molecule.

The probe-linked nucleic acid molecule may be barcoded with a barcode sequence of a nucleic acid barcode molecule to provide a barcoded probe-linked nucleic acid molecule. Barcoding may be achieved by hybridizing a binding sequence of the nucleic acid barcode molecule to the additional probe sequence of the first probe of the probe-linked nucleic acid molecule. The barcoded probe linked-nucleic acid molecule may be subjected to amplification reactions to yield an amplified product comprising the first and second target regions and the barcode sequence or sequences complementary to these sequences. Accordingly, the method may provide amplified products without the use of reverse transcription. One or more processes may be performed within a partition such as a droplet or well.

The present disclosure also provides a method of generating barcoded, probe-linked nucleic acid molecules. The method may comprise providing a sample comprising a nucleic acid molecule (e.g., an RNA molecule) having a first target region and a second target region; a first probe having a first probe sequence that is complementary to the first target region and optionally an additional probe sequence;

and a second probe having a second probe sequence that is complementary to the second target region. The additional probe sequence of the first probe may comprise a probe capture sequence. Alternatively or in addition to, the second probe may comprise a probe capture sequence. The first probe sequence of the first probe may hybridize to the first target region of the nucleic acid molecule, generating a probe-associated nucleic acid molecule, and a nucleic acid reaction (e.g., a nucleic acid extension reaction using a polymerase or reverse transcriptase) may be performed to generate an extended nucleic acid molecule comprising a sequence complementary to the second target region. Prior to, during, or subsequent to the nucleic acid extension reaction, the second probe may hybridize to the nucleic acid molecule (or extended nucleic acid molecule, or complement thereof), and optionally, a nucleic acid extension reaction may be performed. The extended nucleic acid molecule may be barcoded, such as by (a) hybridization of a barcode binding sequence of the nucleic acid barcode molecule to the first probe (e.g., the additional probe sequence of the first probe) or the second probe (e.g., a probe capture sequence of the second probe), or (b) via a probe binding molecule (also referred to herein as a "splint molecule" or "splint oligonucleotide"), in which the probe binding molecule comprises (i) a probe binding sequence complementary to the additional probe sequence of the first probe (which may comprise the probe capture sequence) and/or a capture sequence of the second probe and a (ii) barcode binding sequence complementary to a sequence (e.g., a common sequence) of the barcode molecule. In some instances, the barcoding may be performed prior to hybridization of the second probe to the second target region. In such cases, the barcoded nucleic acid molecule may be subjected to conditions sufficient for hybridization of the second probe sequence of the second probe to the second target region of the nucleic acid molecule (or barcoded nucleic acid molecule). A nucleic acid reaction (e.g., nucleic acid extension) may be performed, thereby generating a barcoded, probe-linked nucleic acid molecule.

Another aspect of the present disclosure provides a method of barcoding multiple analytes, such as the probe-linked nucleic acid molecules described herein, as well as other types of biomolecules (e.g., proteins). The method may comprise providing (i) a sample comprising a nucleic acid molecule (e.g., an RNA molecule) having first and second target regions and (ii) a feature-binding moiety comprising a reporter oligonucleotide comprising a capture sequence; (iii) a first probe having a first probe sequence that is complementary to the first target region and an additional probe sequence; (iv) a second probe having a second probe sequence that is complementary to the second target region; and (v) a third probe having a third probe sequence that is complementary to a sequence of the reporter oligonucleotide. The first probe and the second probe may be subjected to conditions sufficient to hybridize to the first target region and the second target region, respectively, and to generate a probe-linked nucleic acid molecule. The third probe sequence of the third probe may be subjected to conditions sufficient to hybridize to the capture sequence of the reporter oligonucleotide, generating a probe-binding moiety complex. The probe-linked nucleic acid molecule and the probe-binding moiety complex may be subjected to conditions sufficient for barcoding, thereby generating a barcoded probe-linked nucleic acid molecule and a barcoded probe-binding moiety complex. The barcoded probe-linked molecule may be subjected to amplification reactions to yield an amplified product comprising the first and second target regions and the barcode sequence or sequences complementary to these sequences. The barcoded probe-binding moiety complex may similarly be subjected to amplification reactions to yield an amplified product comprising the fourth probe sequence and the barcode sequence. One or more processes may be performed within a cell bead and/or a partition, such as a droplet or well. Beneficially, the methods described herein may be useful in indexing cells, nuclei, or cell beads to partitions; such indexing may be useful in partitions occupied by more than one cell and identifying the cell, nucleus, cell bead or partition from which an analyte was derived.

Fixed Samples

A sample may be a fixed sample. For example, a sample may comprise a plurality of fixed samples, such as a plurality of fixed cells or fixed nuclei. Alternatively or in addition, a sample may comprise a fixed tissue. Fixation of cell or cellular constituent, or a tissue comprising a plurality of cells or nuclei, may comprise application of a chemical species or chemical stimulus. The term "fixed" as used herein with regard to biological samples generally refers to the state of being preserved from decay and/or degradation. "Fixation" generally refers to a process that results in a fixed sample, and in some instances can include contacting the biomolecules within a biological sample with a fixative (or fixation reagent) for some amount of time, whereby the fixative results in covalent bonding interactions such as crosslinks between biomolecules in the sample. A "fixed biological sample" may generally refer to a biological sample that has been contacted with a fixation reagent or fixative. For example, a formaldehyde-fixed biological sample has been contacted with the fixation reagent formaldehyde. "Fixed cells", "fixed nuclei" or "fixed tissues" refer to cells/nuclei or tissues that have been in contact with a fixative under conditions sufficient to allow or result in the formation of intra- and inter-molecular covalent crosslinks between biomolecules in the biological sample. Generally, contact of biological sample (e.g., a cell or nucleus) with a fixation reagent (e.g., paraformaldehyde or PFA) results in the formation of intra- and inter-molecular covalent crosslinks between biomolecules in the biological sample. In some cases, the fixation reagent, formaldehyde, may result in covalent aminal crosslinks within RNA, DNA, and/or protein molecules. For example, the widely used fixative reagent, paraformaldehyde or PFA, fixes tissue samples by catalyzing crosslink formation between basic amino acids in proteins, such as lysine and glutamine. Both intra-molecular and inter-molecular crosslinks can form in the protein. These crosslinks can preserve protein secondary structure and also eliminate enzymatic activity in the preserved tissue sample. Examples of fixation reagents include but are not limited to aldehyde fixatives (e.g., formaldehyde, also commonly referred to as "paraformaldehyde," "PFA," and "formalin"; glutaraldehyde; etc.), imidoesters, NHS (N-Hydroxysuccinimide) esters, and the like.

In some embodiments, the fixative or fixation reagent useful for fixing samples is formaldehyde. The term "formaldehyde" when used in the context of a fixative may also refer to "paraformaldehyde" (or "PFA") and "formalin", both of which are terms with specific meanings related to the formaldehyde composition (e.g., formalin is a mixture of formaldehyde and methanol). Thus, a formaldehyde-fixed biological sample may also be referred to as formalin-fixed or PFA-fixed. Protocols and methods for the use of formaldehyde as a fixation reagent to prepare fixed biological samples are well known in the art and can be used in the methods and compositions of the present disclosure. For example, suitable ranges of formaldehyde concentrations for use in preparing a fixed biological sample is 0.1 to 10%, 1-8%, 1-4%, 1-2%, 3-5%, or 3.5-4.5%. In some embodiments of the present disclosure the biological sample is fixed using a final concentration of 1% formaldehyde, 4% formaldehyde, or 10% formaldehyde. The formaldehyde can be diluted from a more concentrated stock solution—e.g., a 35%, 25%, 15%, 10%, 5% PFA stock solution.

Other examples of fixatives include, for example, organic solvents such as alcohols (e.g., methanol or ethanol), ketones (e.g., acetone), and aldehydes (e.g., paraformaldehyde, formaldehyde (e.g., formalin), or glutaraldehyde). As described herein, cross-linking agents may also be used for fixation including, without limitation, disuccinimidyl suberate (DSS), dimethylsuberimidate (DMS), formalin, and dimethyladipimidate (DMA), dithio-bis(succinimidyl propionate) (DSP), disuccinimidyl tartrate (DST), and ethylene glycol bis(succinimidyl succinate) (EGS). In some cases, a cross-linking agent may be a cleavable cross-linking agent (e.g., thermally cleavable, photocleavable, etc.).

In some cases, more than one fixation reagent can be used in combination when preparing a fixed biological sample. For example, a first fixation agent, such as an organic solvent, may be used in combination with a second fixation agent, such as a cross-linking agent. The organic solvent may be an alcohol (e.g., ethanol or methanol), ketone (e.g., acetone), or aldehyde (e.g., paraformaldehyde, formaldehyde, or glutaraldehyde). The cross-linking agent may be selected from the group consisting of disuccinimidyl suberate (DSS), dimethylsuberimidate (DMS), formalin, and dimethyladipimidate (DMA), dithio-bis(succinimidyl propionate) (DSP), disuccinimidyl tartrate (DST), and ethylene glycol bis(succinimidyl succinate) (EGS). In some cases, a first fixation agent may be provided to or brought into contact with the cell or nucleus to bring about a change in a first characteristic or set of characteristics of the cell/nucleus, and a fixation agent may be provided to or brought into contact with the cell or nucleus to bring about a change in a second characteristic or set of characteristics of the cell or nucleus. For example, a first fixation agent may be provided to or brought into contact with a cell or nucleus to bring about a change in a dimension of the cell (e.g., a reduction in cross-sectional diameter, see, e.g., U.S. Pat. Pub. No. 2020/0033237, which is incorporated herein by reference in its entirety), and a second fixation agent may be provided to or brought into contact with a cell or nucleus to bring about a change in a second characteristic or set of characteristics of the cell (e.g., forming crosslinks within and/or surrounding the cell or nucleus). The first and second fixation agents may be provided to or brought into contact with the cell or nucleus at the same or different times. Other suitable fixing agents include those disclosed in, e.g., International PCT App. No. PCT/US2020/066705, which is incorporated herein by reference in its entirety.

In an example, a first fixation agent that is an organic solvent may be provided to a cell to change a first characteristic (e.g., cell size) and a second fixation agent that is a cross-linking agent may be provided to a cell to change a second characteristic (e.g., cell fluidity or rigidity). The first fixation agent may be provided to the cell before the second fixation agent.

In another embodiment, biomolecules (e.g., biological samples such as tissue specimens) are contacted with a fixation reagent containing both formaldehyde and glutaraldehyde, and thus the contacted biomolecules can include fixation crosslinks resulting both from formaldehyde induced fixation and glutaraldehyde induced fixation. A suitable concentration of glutaraldehyde can be used for use as a fixation reagent can be 0.1 to 1%. Fixation and wash reagents may also include commercially available products, e.g., BioLegend® Fixation Buffer (420801) and Permeabilization Wash Buffer (421002).

Changes to a characteristic or a set of characteristics of a cell or cellular constituents (e.g., incurred upon interaction with one or more fixation agents) may be at least partially reversible (e.g., via rehydration or de-crosslinking). Alternatively, changes to a characteristic or set of characteristics of a cell or cellular constituents (e.g., incurred upon interaction with one or more fixation agents) may be substantially irreversible.

A sample (e.g., a cell sample) may be subjected to a fixation process at any useful point in time. For example, cells, nuclei and/or cellular/nuclear constituents of a sample may be subjected to a fixation process involving one or more fixation agents (e.g., as described herein) prior to commencement of any subsequent processing, such as for storage. Cells, nuclei and/or cellular/nuclear constituents, such as cells, nuclei and/or cellular/nuclear constituents of a tissue sample, subjected to a fixation process prior to storage, may be stored in an aqueous solution, optionally in combination with one or more preserving agents configured to preserve morphology, size, or other features of the cells and/or cellular components. Fixed cells, nuclei and/or cellular/nuclear constituents may be stored below room temperature, such as in a freezer. Alternatively, cells, nuclei and/or cellular/nuclear constituents of a sample may be subjected to a fixation process involving one or more fixation agents subsequent to one or more other processes, such as filtration, centrifugation, agitation, selective precipitation, purification, permeabilization, isolation, heating, etc. For example, cells, nuclei, and/or cellular/nuclear constituents of a given type from a sample may be subjected to a fixation process following a separation and/or enrichment procedure (e.g., as described herein). In an example, a sample comprising a plurality of cells including a plurality of cells of a given type may be subjected to a positive separation process to provide a sample enriched in the plurality of cells of the given type. The enriched sample may then be subjected to a fixation process involving one or more fixation agents (e.g., as described herein) to provide an enriched sample comprising a plurality of fixed cells. A fixation process may be performed in a bulk solution. In some cases, fixed samples (e.g., fixed cells, fixed nuclei, and/or cellular/nuclear constituents) may be partitioned amongst a plurality of partitions (e.g., droplets or wells) and subjected to processing as described elsewhere herein. In some cases, fixed samples may undergo additional processing, such as partial or complete reversal of a fixation process by, for example, rehydration or de-crosslinking, prior to partitioning and any subsequent processing. In some cases, fixed samples may undergo partial or complete reversal of a fixation process within a plurality of partitions (e.g., prior to or concurrent with additional processing described elsewhere herein).

In some cases, a tissue specimen comprising a plurality of cells, nuclei and/or cellular/nuclear constituents may be processed to provide formalin-fixed paraffin-embedded (FFPE) tissue. A tissue specimen may be contacted (e.g., saturated) with formalin and then embedded in a solid medium. In an example, the solid medium may be paraffin wax. FFPE processing may facilitate preservation of a tissue sample (e.g., prior to subsequent processing and analysis). A tissue sample, including an FFPE tissue sample, may additionally or alternatively be subjected to storage in a low-temperature freezer. Cells, nuclei and/or cellular/nuclear constituents may be dissociated from a tissue sample (e.g., FFPE tissue sample) prior to undergoing subsequent processing. In some cases, individual cells, nuclei and/or cellular/nuclear constituents of a tissue sample such as an FFPE tissue sample may be optically detected, labeled, or otherwise processed prior to any such dissociation. Such detection, labeling, or other processing may be performed according to a 2- or 3-dimensional array and optionally according to a pre-determined pattern. In some cases, a tissue specimen may be embedded in other materials such as, for example, optimal cutting temperature (OCT) compound, crosslinking-based supports (e.g., polymers), or the like.

The tissue specimen may have been fixed at least about 1 day (d), 2 d, 3 d, 4 d, 5 d, 6 d, 1 week (wk), 2 wk, 3 wk, 1 month (m), 2 m, 3 m, 4 m, 5 m, 6 m, 7 m, 8 m, 9 m, 10 m, 11 m, 1 year (y), 2 y, 3 y, 4 y, 5 y, 6 y, 7 y, 8 y, 9 y, 10 y, 15 y, 20 y, 25 y, 30 y, 35 y, 40 y, 45 y, 50 y, or longer before use in the methods and systems described elsewhere herein.

In some cases, preparation of a fixed sample may comprise securing and sectioning at least a portion of a fixed sample (e.g., via microtomy, ultramicrotomy, etc.). The fixed sample may be sectioned into one or more (e.g., a plurality) of scrolls. The fixed tissue (e.g., a scroll) may be at least about 1, 5, 10, 20, 30, 40, 50, 60, 70, 80, 90, 100, or more micrometers in thickness. The sectioning and/or securing may be performed at ambient temperature. The sectioning and/or securing may be performed at temperatures above or below ambient temperature. The fixed tissue (e.g., a scroll) may have a mass of at least about 100 micrograms (μg), 150 μg, 200 μg 250 μg, 300 μg, 350 μg, 400 μg, 450 μg, 500 μg, 550 μg, 600 μg, 650 μg, 700 μg, 750 μg, 800 μg, 850 μg, 900 μg, 950 μg, 1 milligram (mg), 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 gram (g), 1.25 g, 1.5 g, 1.75 g, 2 g, 2.25 g, 2.5 g, 2.75 g, 3 g, 3.25 g, 3.5 g, 3.75 g, 4 g, 4.25 g, 4.5 g, 4.75 g, 5 g, 10 g, 15 g, 20 g, 25 g, 30 g, 35 g, 40 g, 45 g, 50 g, or more. The fixed tissue (e.g., a scroll) may have a mass of at most about 50 g, 45 g, 40 g, 35 g, 30 g, 25 g, 20 g, 15 g, 10 g, 5 g, 4.75 g, 4.5 g, 4.25 g, 4 g, 3.75 g, 3.5 g, 3.25 g, 3 g, 2.75 g, 2.5 g, 2.25 g, 2 g, 1.75 g, 1.5 g, 1.25 g, 1 g, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, 9 mg, 8 mg, 7 mg, 6 mg, 5 mg, 4 mg, 3 mg, 2 mg, 1 mg, 950 μg, 900 μg, 850 μg, 800 μg, 750 μg, 700 μg, 650 μg, 600 μg, 550 μg, 500 μg, 450 μg, 400 μg, 350 μg, 300 μg, 250 μg, 200 μg, 150 μg, 100 μg, or less. The fixed tissue (e.g., a scroll) may have a mass in a range as defined by any two of the preceding values. For example, a fixed tissue or a scroll can have a mass from about 100 micrograms to about 5 grams.

In some cases, the scroll can be mechanically and/or enzymatically dissociated. The mechanical dissociation may comprise sonication (e.g., sonication at below ambient temperatures). The sonication may comprise a sonication at a power of at least about 5, 10, 15, 20, 25, 30, 35, 40, 45, 50, 55, 60, 65, 70, 65, 80, 85, 90, 95, or 100 percent power. The sonication may comprise sonication at a power of at most about 100, 95, 90, 85, 80, 75, 70, 65, 60, 55, 50, 45, 40, 35, 30, 25, 20, 15, 10, 5, or less percent power. The sonication may be for at least about 1, 2, 3, 4, 5, 6, 7, 8, 9, 10, 15, 30, 45, 60, or more minutes. The sonication may be for at most about 60, 45, 30, 15, 10, 9, 8, 7, 6, 5, 4, 3, 2, 1, or fewer minutes. The mechanical dissociation may comprise use of a shake plate. For example, the sample can be placed in a sample tube, and the sample tube can be shaken on a shake plate. The mechanical dissociation may comprise stirring the sample.

In some optional cases, the fixed sample may be processed to remove one or more fixatives and/or supports (e.g., solid medium). For example, the fixed sample can be deparaffinized. In some cases, the fixed sample may not be processed to remove the one or more fixatives and/or supports (e.g., solid medium). For example, a fixed sample can be used as sectioned (e.g., a scroll). Examples of processes include use of one or more non-polar solvents (e.g., linear alkanes, cyclic alkanes, benzene, xylenes, neoclear, orange oil, other substituted or non-substituted alkanes, or the like, or any combination thereof). In an example, the non-polar solvent is xylene. The removal of the one or more fixatives and/or supports (e.g., solid medium) may be repeated (e.g., for more complete removal of the one or more fixatives and/or supports). In some optional cases, the sample may be rehydrated (e.g., via water addition, ethanol rehydration, gaseous rehydration, or the like, or any combination thereof). For example, ethanolic solutions of water with increasing water concentration can be used to rehydrate the sample. In some cases, the sample can be analyzed without rehydration. The sample may be washed using a polar (e.g., aqueous) solution to remove additional impurities. For example, an aqueous solution of phosphate buffered saline can be used to remove impurities from a sample.

One or more dissociation solutions comprising, for example, liberase with low thermolysis (TL), liberase with medium thermolysis (TM), liberase with high thermolysis (TH), collagenases, or the like, or any combination thereof may be added to process a sample. The dissociation sample may be added at ambient (e.g., room) temperature. The dissociation solution be heated prior to the addition. The dissociation solution may be cooled prior to the addition. The dissociation sample may be at a temperature of at least about 20, 21, 22, 23, 24, 25, 26, 27, 28, 29, 30, 31, 32, 33, 34, 34, 36, 37, 38, 39, 40, or more degrees Celsius when added. The dissociation solution may be at a temperature of at most about 40, 39, 38, 37, 36, 35, 34, 33, 32, 31, 30, 29, 28, 27, 26, 25, 24, 23, 22, 21, or fewer degrees Celsius when added. The dissociation solution may be added at a temperature in a range as defined by any two of the proceeding values. The sample may be titrated at least about 5, 10, 15, 20, 25, 30, 35, 40, 45, 50, or more times to form a cellular suspension. In some cases, impurities (e.g., paraffin) can be removed by allowing the suspension to rest, and the impurities can precipitate from the solution, and the purified solution can be removed and further processed.

A liberase can comprise one or more enzymes configured to degrade at least a portion of a biological molecule. For example, the liberase can comprise one or more collagenases. The collagenases can comprise one or more isoforms of collagenase, collagenase I, collagenase II, or the like, or any combination thereof. The collagenase isoforms may be present in ratios between the various isoforms of at least about 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, or more. In some cases, a composition comprising the one or more enzymes can comprise a dispase. The dispase may be a protease (e.g., a neutral protease, etc.). The dispase may be a non-clostridial dispase. A composition comprising the one or more enzymes may comprise thermoysin. The thermoysin can be a protease (e.g., a neutral protease, etc.). The thermolysin can be a non-clostridial thermoysin. A composition comprising the one or more enzymes may comprise a plurality of additional components as described elsewhere herein (e.g., a dispase, a thermoysin, etc.).

The sample may be filtered one or more (e.g., 1, 2, 3, 4, 5, 6, 7, 8, 9, 10, or more) times. The filtration may comprise use of one or more different sizes (e.g., pore sizes) of filter. The filter may comprise a pore size of at most about 500, 400, 300, 200, 100, 90, 80, 70, 60, 50, 40, 30, 20, 10, 5, 1, or less micrometers. For example, a first filtration with a 70 micrometer pore size filter can be performed. In this example, a second filtration with a 30 micrometer filtration can be performed, which can reduce debris (e.g., undissolved paraffin or other support) without reducing cellular recovery from the sample. The filtrate and the cellular suspension may be combined and subsequently centrifuged. The centrifugation may occur at a value of at least about 100, 200, 300, 400, 500, 600, 700, 850, 900, 950, 1,000, 1,100, 1,200, 1,300, 1,400, 1,500, 1,600, 1,700, 1,800, 1,900, 2,000, 2,100, 2,200, 2,300, 2,400, 2,500, 3,000, or more reciprocal centrifugal force (rcf). The centrifugation may occur at a value of at most about 3,000, 2,500, 2,400, 2,300, 2,200, 2,100, 2,000, 1,900, 1,800, 1,700, 1,600, 1,500, 1,400, 1,300, 1,200, 1,100, 1,000, 950, 900, 850, 800, 700, 600,500, 400, 300, 200, 100, or fewer rcf. The centrifugation may be performed at a value within a range as defined by any two of the proceeding values. For example, the centrifugation may be performed at a value of about 850 to about 2,000 rcf.

In some cases, the solution can be removed from the centrifuged pellet (e.g., without disturbing the pellet). In some cases, the pellet can be resuspended into solution. For example, the pellet can be resuspended into a buffer solution.

The resuspended solution can then be analyzed (e.g., to determine cellular concentration). Examples of cellular concentration determination systems include, but are not limited to the Countess II FL Automated Cell Counter, Cellaca MX High-Throughput Automated Cell Counter, or the like using a fluorescent dye (e.g., ethidium homodimer-1, ect.) or AO/PI staining solution, or the like. The resuspended solution may then be used as a sample for the methods and systems described elsewhere herein (e.g., RNA profiling, etc.).

In some cases, use of a fixed sample (e.g., an FFPE sample) with the methods and systems described elsewhere herein may provide different information as compared to use of a fresh sample. For example, the fixation process may capture ephemeral states of the cells of the sample and/or ephemeral types of cells in the sample that may not be captured in fresh samples. In this way, cellular processes can be investigated in different ways by use of fixed samples. In some cases, use of the methods and systems described elsewhere herein on fixed samples may provide unexpected improvements to the analysis of the fixed samples, such as improved sensitivity versus other analysis methods as well as the aforementioned analysis of different ephemeral states/types within the sample. In some cases, the use of fixed samples may permit time series analysis of samples (e.g., samples can be fixed at different times and later analyzed). Such a time series analysis may provide information related to the evolution of states and/or cell types within the samples.

Methods of Nucleic Acid Analysis

In an aspect, the present disclosure provides a method for barcoding nucleic acid molecules. The method may generally comprise contacting a nucleic acid molecule with a pair of probes and a barcode molecule to generate a barcoded molecule (e.g., a barcoded probe-linked molecule). The nucleic acid molecule may comprise a sequence corresponding to a target sequence or a template sequence. One or more nucleic acid reactions (e.g., a ligation, a nucleic acid extension reaction, amplification, etc.) may be performed to generate the barcoded molecule. In some aspects, the method comprises: contacting a nucleic acid molecule with a first probe to generate a probe-associated nucleic acid molecule, wherein the nucleic acid molecule comprises a first target region and a second target region, wherein the first probe comprises a first probe sequence complementary to the first target region; performing a nucleic acid reaction (e.g., a nucleic acid extension reaction, e.g., by using a polymerase or reverse transcriptase, etc.) to generate an extended probe molecule comprising a sequence complementary to the second target region; providing (i) a second probe comprising a second probe sequence corresponding to or complementary to the second target region and (ii) a nucleic acid barcode molecule; and subjecting the extended probe molecule or derivative thereof to conditions sufficient to generate a barcoded molecule. The first target region and the second target region may be disposed adjacent to one another or may be separate from one another (e.g., disposed on opposite ends of a gap region). In some instances, barcoding may be facilitated by providing a probe binding molecule (also referred to herein as a “splint molecule” or in some instances, a “splint oligonucleotide”). For example, the first probe and/or the second probe may comprise a probe capture sequence, and the probe-binding molecule may comprise a probe-binding sequence complementary to the probe capture sequence. In addition to or alternatively, the nucleic acid barcode molecule may comprise a barcode sequence and a barcode capture sequence, and the probe-binding molecule may comprise a barcode binding sequence complementary to the barcode capture sequence. In some instances, the probe-binding molecule may be pre-annealed to the nucleic acid barcode molecule. Barcoding may comprise hybridization of the probe binding molecule to the probe capture sequence (or complement thereof) of the first probe and/or second probe and to the barcode capture sequence of the nucleic acid barcode molecule. Accordingly, the barcoded molecule may comprise a sequence corresponding to the first target region, a sequence corresponding to the second target region, a sequence corresponding to the probe capture sequence, and a sequence corresponding to the barcode sequence. One or more operations may be performed within a partition (e.g., droplet or well).

The methods described herein may facilitate gene expression profiling with single-cell, single-nucleus or single-cell bead resolution using, for example, nucleic acid extension reactions, probe hybridization, chemical or enzymatic ligation, barcoding, amplification, and sequencing. The methods described herein may allow for gene expression analysis while avoiding the use of specialized imaging equipment and, in certain instances, reverse transcription, which may be highly error prone and inefficient. In some instances, the methods may be used to analyze a pre-determined panel of target genes in a population of single cells, nuclei, or cell beads in a sensitive and accurate manner. The methods described herein may also be useful in detecting or characterizing genetic variants, for example, in instances where the sequence of a region disposed between the target regions (e.g., a gap region) is not known. In some cases, the methods described herein may be useful in analyzing a single nucleotide polymorphism (SNP), an alternative-spliced junction, an insertion, a mutation, a deletion, a gene rearrangement (e.g., V (D) J rearrangements), a transposon, or other genetic element or variants. In some cases, the nucleic acid molecule analyzed by the methods described herein may comprise a fusion gene (e.g., a hybrid gene generated via translocation, interstitial deletion, or chromosomal inversion). In some cases, the methods described herein may be useful in analyzing genomic, transcriptomic, exomic and/or proteomic elements in cells, nuclei, cell beads, tissue samples, spatial arrays of cells, nuclei or tissues, etc.

The nucleic acid molecule analyzed by the methods described herein may be a single-stranded or a double-stranded nucleic acid molecule. A double-stranded nucleic acid molecule may be completely or partially denatured to provide access to a target region (e.g., a target sequence) of a strand of the nucleic acid molecule. Denaturation may be achieved by, for example, adjusting the temperature or pH of a solution comprising the nucleic acid molecule; using a chemical agent such as formamide, guanidine, sodium salicylate, dimethyl sulfoxide, propylene glycol, urea, or an alkaline agent (e.g., NaOH); or using mechanical agitation (e.g., centrifuging or vortexing a solution including the nucleic acid molecule).

The nucleic acid molecule may be a target nucleic acid molecule. The target nucleic acid molecule may be an RNA molecule. The RNA molecule may be, for example, a transfer RNA (tRNA) molecule, ribosomal RNA (rRNA) molecule, mitochondrial RNA (mtRNA) molecule, messenger RNA (mRNA) molecule, non-coding RNA molecule, synthetic RNA molecule, or another type of RNA molecule. For example, the RNA molecule may be an mRNA molecule. In some cases, the nucleic acid molecule may be a viral or pathogenic RNA. In some cases, the nucleic acid molecule may be a synthetic nucleic acid molecule previously introduced into or onto a cell. For example, the nucleic acid molecule may comprise a plurality of barcode sequences, and two or more barcode sequences may be target regions of the nucleic acid molecule. In some instances, the nucleic acid molecule is a guide RNA (gRNA), which may be exogenously introduced in a cell or cell bead. In some instances, the nucleic acid molecule is an RNA molecule derived from an exogenously introduced nucleic acid molecule, e.g., an RNA derived from a plasmid, an integrated DNA sequence (e.g. using viral transduction in a cell), a gRNA from a CRISPR genetic element, etc.

The nucleic acid molecule (e.g., RNA molecule) may comprise one or more features selected from the group consisting of a 5' cap structure, an untranslated region (UTR), a 5' triphosphate moiety, a 5' hydroxyl moiety, a Kozak sequence, a Shine-Dalgarno sequence, a coding sequence, a codon, an intron, an exon, an open reading frame, a regulatory sequence, an enhancer sequence, a silencer sequence, a promoter sequence, and a poly(A) sequence (e.g., a poly(A) tail). For example, the nucleic acid molecule may comprise one or more features selected from the group consisting of a 5' cap structure, an untranslated region (UTR), a Kozak sequence, a Shine-Dalgarno sequence, a coding sequence, and a poly(A) sequence (e.g., a poly(A) tail).

Features of the nucleic acid molecule may have any useful characteristics. A 5' cap structure may comprise one or more nucleoside moieties joined by a linker such as a triphosphate (ppp) linker. A 5' cap structure may comprise naturally occurring nucleoside and/or non-naturally occurring (e.g., modified) nucleosides. For example, a 5' cap structure may comprise a guanine moiety or a modified (e.g., alkylated, reduced, or oxidized) guanine moiety such as a 7-methylguanylate ($m^7G$) cap. Examples of 5' cap structures include, but are not limited to, $m^7GpppG$, $m^7Gpppm^7G$, $m^7GpppA$, $m^7GpppC$, GpppG, $m^{2,7}GpppG$, $m^{2,2,7}GpppG$, and anti-reverse cap analogs such as $m^{7,2'Ome}GpppG$, $m^{7,2'd}GpppG$, $m^{7,3'Ome}GpppG$, and $m^{7,3'd}GpppG$. An untranslated region (UTR) may be a 5' UTR or a 3' UTR. A UTR may include any number of nucleotides. For example, a UTR may comprise at least 3, 5, 7, 10, 20, 30, 40, 50, 60, 70, 80, 90, 100, or more nucleotides. In some cases, a UTR may comprise fewer than 20 nucleotides. In other cases, a UTR may comprise at least 100 nucleotides, such as more than 200, 300, 400, 500, 600, 700, 800, 900, or 1000 nucleotides. Similarly, a coding sequence may include any number of nucleotides, such as at least 3, 5, 10, 20, 30, 40, 50, 60, 70, 80, 90, 100, or more nucleotides. A UTR, coding sequence, or other sequence of a nucleic acid molecule may have any nucleotide or base content or arrangement. For example, a sequence of a nucleic acid molecule may comprise any number or concentration of guanine, cytosine, uracil, and adenine bases. A nucleic acid molecule may also include non-naturally occurring (e.g., modified) nucleosides. A modified nucleoside may comprise one or more modifications (e.g., alkylations, hydroxylation, oxidation, or other modification) in its nucleobase and/or sugar moieties.

The nucleic acid molecule may comprise one or more target regions. In some cases, a target region may correspond to a gene or a portion thereof. Each region may have the same or different sequences. For example, the nucleic acid molecule may comprise two target regions having the same sequence located at different positions along a strand of the nucleic acid molecule. Alternatively, the nucleic acid molecule may comprise two or more target regions having different sequences. Different target regions may be interrogated by different probes. Target regions may be located adjacent to one another or may be spatially separated along a strand of the nucleic acid molecule. The target regions may be located on the same strand or different strands. As used herein with regard to two entities, "adjacent," may mean that the entities directly next to one other (e.g., contiguous) or in proximity to one another. For example, a first target region may be directly next to a second target region (e.g., having no other entity disposed between the first and second target regions) or in proximity to a second target region (e.g., having an intervening sequence or molecule between the first and second target regions). In some cases, a double-stranded nucleic acid molecule may comprise a target region in each strand that may be the same or different. For a nucleic acid molecule comprising multiple target regions, the methods described herein may be performed for one or more target regions at a time. For example, a single target region of the multiple target regions may be analyzed (e.g., as described herein) or two or more target regions may be analyzed at the same time. Analyzing two or more target regions may involve providing two or more probes, where a first probe has a sequence that is complementary to the first target region, a second probe has a sequence that is complementary to the second target region, etc.

Each probe (e.g., the first probe and the second probe) may further comprise one or more additional sequences (e.g., additional probe sequences, unique molecular identifiers (UMIs), a barcode sequence, a primer sequence, a capture sequence, or other functional sequence). For example, in some instances, the first probe and/or the second probe may comprise the same or different barcode sequences. In some examples, the first probe and the second probe may be configured to hybridize to one or more nucleic acid barcode molecules. For example, the first probe and/or the second probe may comprise a probe capture sequence, which may be configured to hybridize to a nucleic acid barcode molecule or to a probe binding molecule (e.g., a splint oligonucleotide) that is configured to hybridize to a nucleic acid barcode molecule (e.g., via a barcode binding sequence that is complementary to a capture sequence of the nucleic acid barcode molecule). The probe capture sequence may be any useful length; for example, the probe capture sequence may be about 1, about 2, about 3, about 4, about 5, about 6, about 7, about 8, about 9, about 10, about 20, about 30, about 40, about 50, about 60, about 70, about 80, about 90, about 100 or more nucleotides in length. The probe capture sequence may be at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100 or more nucleotides in length. The probe capture sequence may be at most 100, at most 90, at most 80, at most 70, at most 60, at most 50, at most 40, at most 30, at most 20, at most 10, at most 9, at most 8, at most 7, at most 6, at most 5, at most 4, at most 3, at most 2, or at most 1 nucleotide in length. A range of lengths of the probe capture sequence, such as from about 8 to about 50 nucleotides in length, etc. In some instances, the probe capture sequence length may be varied based on any useful application and properties, e.g., melting temperature, annealing temperature, annealing strength (e.g., GC content), hybridization stringency, etc.

Similarly, the probe binding molecule and nucleic acid barcode molecule may further comprise one or more additional sequences (e.g., unique molecular identifiers (UMIs), a barcode sequence, a primer sequence, a capture sequence, or other functional sequence). For example, in some instances, the probe binding molecule or barcode molecule may comprise a functional sequence, a primer sequence (e.g., sequencing primer sequence or partial sequencing primer sequence), a UMI, etc. The probe binding molecule and the nucleic acid barcode molecule may be any useful length; for example, either or both may be about 1, about 2, about 3, about 4, about 5, about 6, about 7, about 8, about 9, about 10, about 20, about 30, about 40, about 50, about 60, about 70, about 80, about 90, about 100 or more nucleotides in length. The probe binding molecule or the barcode molecule may be at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100 or more nucleotides in length. The probe capture binding molecule or the barcode molecule may be at most 100, at most 90, at most 80, at most 70, at most 60, at most 50, at most 40, at most 30, at most 20, at most 10, at most 9, at most 8, at most 7, at most 6, at most 5, at most 4, at most 3, at most 2, or at most 1 nucleotide in length. A range of lengths of the probe binding molecule or barcode molecule may be used, such as from about 16 to about 100 nucleotides in length, etc. In some instances, the probe binding molecule or barcode molecule length may be varied based on any useful application and properties, e.g., melting temperature, annealing temperature, etc. In some instances, the first target region and the second target region of the nucleic acid molecule are not adjacent. For instance, the first target region and the second target region may be separated by one or more gap regions disposed between the first target region and the second target region. The gap region may comprise, for example, at least one nucleotide base, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, at least about 200, at least about 300, at least about 400, at least about 500, or more bases. The gap region may comprise at most about 1000, at most about 500, at most about 400, at most about 300, at most about 200, at most about 100, at most about 90, at most about 80, at most about 70, at most about 60, at most about 50, at most about 40, at most about 30, at most about 20, at most about 10, or at most about 5 bases. The gap region may comprise a range of number of bases, such as between about 1 and 30 bases.

A target region of the nucleic acid molecule may have one or more useful characteristics. For example, a target region may have any useful length, base content, sequence, melting point, or other characteristic. A target region may comprise, for example, at least 10 bases, such as at least about 20, 25, 30, 35, 40, 45, 50, 60, 65, 70, 75, 80, 85, 90, 95, 100, 110, 120, 130, 140, 150, 160, 170, 180, 190, 200, 250, 300, 350, 400, 450, 500, or more bases. A target region may have any useful base content and any useful sequence and combination of bases. For example, a target region may comprise one or more adenine, thymine, uracil, cytosine, and/or guanine bases (e.g., natural or canonical bases). A target region may also comprise one or more derivatives or modified versions of a natural or canonical base, such as an oxidized, alkylated (e.g., methylated), hydroxylated, or otherwise modified base. Similarly, a target region may comprise ribose or deoxyribose moieties and phosphate moieties or derivatives or modified versions thereof.

A target region of the nucleic acid molecule may comprise one or more sequences or features, or portions thereof, of the nucleic acid molecule. For example, a target region may comprise all or a portion of a UTR (e.g., a 3' UTR or a 5' UTR), a Kozak sequence, a Shine-Dalgarno sequence, a coding sequence, a poly A sequence, a cap structure, an intron, an exon, or any other sequence or feature of the nucleic acid molecule.

The nucleic acid molecule (e.g., RNA molecule, such as an mRNA molecule) of a sample may be included within a cell, nucleus or cell bead. For example, the sample may comprise a cell or nucleus comprising the nucleic acid molecule. The cell, nucleus, or cell bead may comprise additional nucleic acid molecules that may be the same as or different from the nucleic acid molecule of interest. In some cases, the sample may comprise a plurality of cells, and each cell may contain one or more nucleic acid molecules. The cell may be, for example, a human cell, an animal cell, or a plant cell. In some cases, the cell may be derived from a tissue or fluid, as described herein. The cell may be a prokaryotic cell or a eukaryotic cell. The cell may be a lymphocyte such as a B cell or T cell. The cell may be comprised within a bead, such as those disclosed in U.S. Pat. No. 10,428,326, which is incorporated by reference herein in its entirety. In some instances, the cell is comprised within a tissue sample and may be fixed to a substrate. For example, the cell may be a cell of a formalin-fixed, paraffin-embedded (FFPE) sample, as described above. In such instances, the method may comprise additional operations for preparing the cell or nucleic acid molecule comprised therein, e.g., deparaffinization, staining (e.g., using immunological agents) or destaining, decrosslinking, washing, enzymatic treatment, etc. Additional examples of treating FFPE samples prior to and following hybridization of probes are included in PCT/US2020/066720, which is included by reference herein in its entirety.

Access to a nucleic acid molecule included in a cell, nucleus or cell bead may be provided by lysing or permeabilizing the cell or nucleus. Lysing the cell, nucleus or cell bead may release the nucleic acid molecule contained therein from the cell, nucleus or cell bead. A cell or nucleus may be lysed using a lysis agent such as a bioactive agent. A bioactive agent useful for lysing a cell or nucleus may be, for example, an enzyme (e.g., as described herein). An enzyme used to lyse a cell or nucleus may or may not be capable of carrying out additional functions such as degrading, extending, reverse transcribing, or otherwise altering a nucleic acid molecule. Alternatively, an ionic or non-ionic surfactant such as Triton® X-100 (t-Octylphenoxypolyethoxyethanol), Tween® 20 (polysorbate 20), Sarcosyl® (sodium lauroyl sarcosinate), or sodium dodecyl sulfate may be used to lyse a cell or nucleus. Cell/nucleus lysis may also be achieved using a cellular disruption method such as an electroporation or a thermal, acoustic, or mechanical disruption method. Alternatively, a cell or nucleus may be permeabilized to provide access to a nucleic acid molecule included therein. Permeabilization may involve partially or completely dissolving or disrupting a cell/nuclear membrane or a portion thereof. Permeabilization may be achieved by, for example, contacting a cell membrane with an organic solvent (e.g., methanol) or a detergent such as Triton® X-100 (t-Octylphenoxypolyethoxyethanol) or NP-40 (octylphenoxypolyethoxyethanol). The cell, nucleus or cell bead may be fixed, as described elsewhere herein.

In some cases, the cell may be lysed within the cell bead, and a subset of the intracellular contents may associate with the bead. In some cases, the cell bead may comprise thioacrydite-modified nucleic acid molecules that can hybridize with nucleic acids from the cell. For example, a poly-T nucleic acid sequence may be thioacrydite-modified and bound to the cell bead matrix. Upon cell or nucleus lysis, the cellular nucleic acids (e.g., mRNA) may hybridize with the poly-T sequence. The retained intracellular/intranuclear contents may be released, for example, by addition of a reducing agent, e.g., DTT, TCEP, etc. The release may occur at any convenient step, such as before or after partitioning.

The nucleic acid molecule or probe-associated nucleic acid molecule may be subjected to conditions sufficient to generate a probe-linked molecule. For instance, the first target region may be adjacent to the second target region, and the first probe and the second probe may hybridize to the first target region and the second target region, respectively. The first probe may comprise a first reactive moiety, and the second probe may comprise a second reactive moiety. In some instances, the first reactive moiety of the first probe is adjacent to the second reactive moiety of the second probe. The reactive moieties may then be subjected to conditions sufficient to cause them to react to yield a probe-linked nucleic acid molecule comprising the first probe linked to the second probe. For example, the reactive moieties may be joined together via click chemistry or enzymatic ligation, such as those disclosed in in U.S. Pat. Pub. No. 2020/0239874, International Pub. No. WO 2019/165318, and International Pat. Pub. No. WO2021/237087, each of which is incorporated by reference herein in its entirety. In some examples, the first probe or the second probe may comprise an adenylated oligonucleotide or moiety (e.g., an adenylated phosphate group), which may be useful in reducing non-specific ligation reactions. In some instances, the linking of the probes (e.g., via ligation) may be performed in substantially ATP-free conditions, optionally using an enzyme (e.g., ligase) that does not require ATP (e.g., truncated T4 RNA ligase) or that is pre-activated (e.g., a preactivated T4 DNA ligase). Additional examples of such ligation schemes can be found in PCT/US2020/066720 and International Pat. App. No. PCT/US2021/33649, filed May 21, 2021, which is incorporated by reference herein in its entirety.

In some instances, the first target region of the nucleic acid molecule (e.g., RNA molecule) may not be adjacent to the second target region. In such cases, the nucleic acid molecule may be subjected to conditions sufficient for hybridization of the first probe sequence of the first probe to the first target region to generate a probe-associated nucleic acid molecule. The probe-associated nucleic acid molecule may be subjected to a nucleic acid reaction (e.g., a nucleic acid extension reaction, reverse transcription, etc.) to generate an extended probe molecule comprising a sequence complementary to the second target region. A second probe comprising a second probe sequence may hybridize to the extended probe molecule (or complement thereof) and subjected to conditions sufficient (e.g., nucleic acid extension, amplification, hybridization of additional probe molecules, ligation, etc.) to generate a probe-linked molecule comprising a sequence corresponding to the first target region and a sequence corresponding to the second target region. Alternatively or in addition to, the first probe and the second probe may be provided simultaneously, and following hybridization of the first probe sequence and the second probe sequence to the first target region and the second target region, respectively, to generate a dual-probe-associated nucleic acid molecule, the gap (e.g., the region disposed between the first target region and the second region) may be filled (e.g., via a nucleic acid extension or gap-fill reaction and/or hybridization of additional probe molecules that hybridize to at least a portion of the gap region). In some instances, one or both probes may comprise an overhang or flap sequence (e.g., at a 5' end) that is recognizable or cleavable by an enzyme (e.g., an endonuclease such as FEN1 endonuclease). For example, the second probe may comprise a 5' flap sequence that is cleaved by FEN1 endonuclease if at least a specific portion of the second probe hybridizes to the nucleic acid molecule (e.g., target molecule). Subsequent to hybridization of the second probe to the second target sequence of the nucleic acid molecule, an endonuclease (e.g., FEN1) may be used to cleave the flap sequence and leave a ligatable end (e.g., a phosphorylated end) of the second probe. In instances in which the first target region is not adjacent to the second target region, the gap region may be filled, followed by cleavage of the flap sequence. In some instances, the first probe or the second probe and the gap-filled region may be ligated, e.g., chemically or enzymatically. Additional examples of systems and methods for generating probe-linked nucleic acid molecules and gap-filling reactions can be found, for example in U.S. Pat. Pub. No. 2020/0239874, International Pub. No. WO 2019/165318, and International Pat. Pub. No. WO2021/237087, each of which is incorporated by reference herein in its entirety.

The probe-linked nucleic acid molecule may be barcoded to provide a barcoded probe-linked nucleic acid molecule, or barcoding may occur prior to generation of the probe-linked nucleic acid molecule. Barcoding may be performed using a variety of techniques. For example, the first probe or the second probe may comprise a probe capture sequence. The nucleic acid barcode molecule may comprise a barcode capture sequence capable of hybridizing to the probe capture sequence. Alternatively, barcoding may be mediated by a probe binding molecule (e.g., a splint oligonucleotide) comprising (i) a probe binding sequence, which may be complementary to the probe capture sequence of the first probe or the second probe, and (ii) a barcode binding sequence, which may be complementary to the barcode capture sequence of the nucleic acid barcode molecule. In some instances, the barcoding may be followed by ligation, e.g., chemically or enzyme-mediated, to covalently link the nucleic acid barcode molecule to the probe (or to the probe binding sequence, and the probe binding sequence may be ligated to the probe). Examples of chemical ligation of nucleic acid molecules may include "click chemistry" approaches, e.g., reaction of azide and alkyne moieties, as described in U.S. Pat. Pub. No. 2020/0239874, which is incorporated by reference herein in its entirety.

By way of example, the first probe may comprise a first probe sequence and a probe capture sequence, and the first probe may be subjected to conditions sufficient to hybridize the first probe sequence to the first target region, thereby generating a probe-associated nucleic acid molecule. In some instances, the probe-associated nucleic acid molecule may be subjected to washing or other conditions to remove unannealed probes from a mixture. The probe-associated nucleic acid molecule may be extended from an end of the first probe towards an end of the nucleic acid molecule to which it is hybridized (towards the end which is proximal to the second target region) to provide an extended nucleic acid molecule. The extended nucleic acid barcode molecule may comprise the first probe sequence and a complement to the second target region. In some instances, the extended nucleic acid molecule may be barcoded, e.g., by hybridizing the barcode capture sequence of the nucleic acid barcode molecule to the probe capture sequence, or by hybridizing (i) a probe-binding molecule comprising a probe binding sequence and a barcode binding sequence to the probe capture sequence and (ii) the barcode capture sequence of the nucleic acid barcode molecule to the barcode binding sequence of the probe binding molecule. In some instances, the probe-binding molecule may be provided pre-annealed to the nucleic acid barcode molecule. Subsequently, a second probe comprising a second probe sequence may be provided. The barcoded, extended nucleic acid molecule may be subjected to conditions sufficient to hybridize the second probe sequence to the second target region or complement thereof. A nucleic acid extension reaction may be performed, thereby generating a barcoded molecule (e.g., barcoded probe-linked molecule) comprising a sequence corresponding to the first target region, a sequence corresponding to the second target region, a sequence corresponding to the probe capture sequence, and a sequence corresponding to the barcode sequence.

Figure 7:
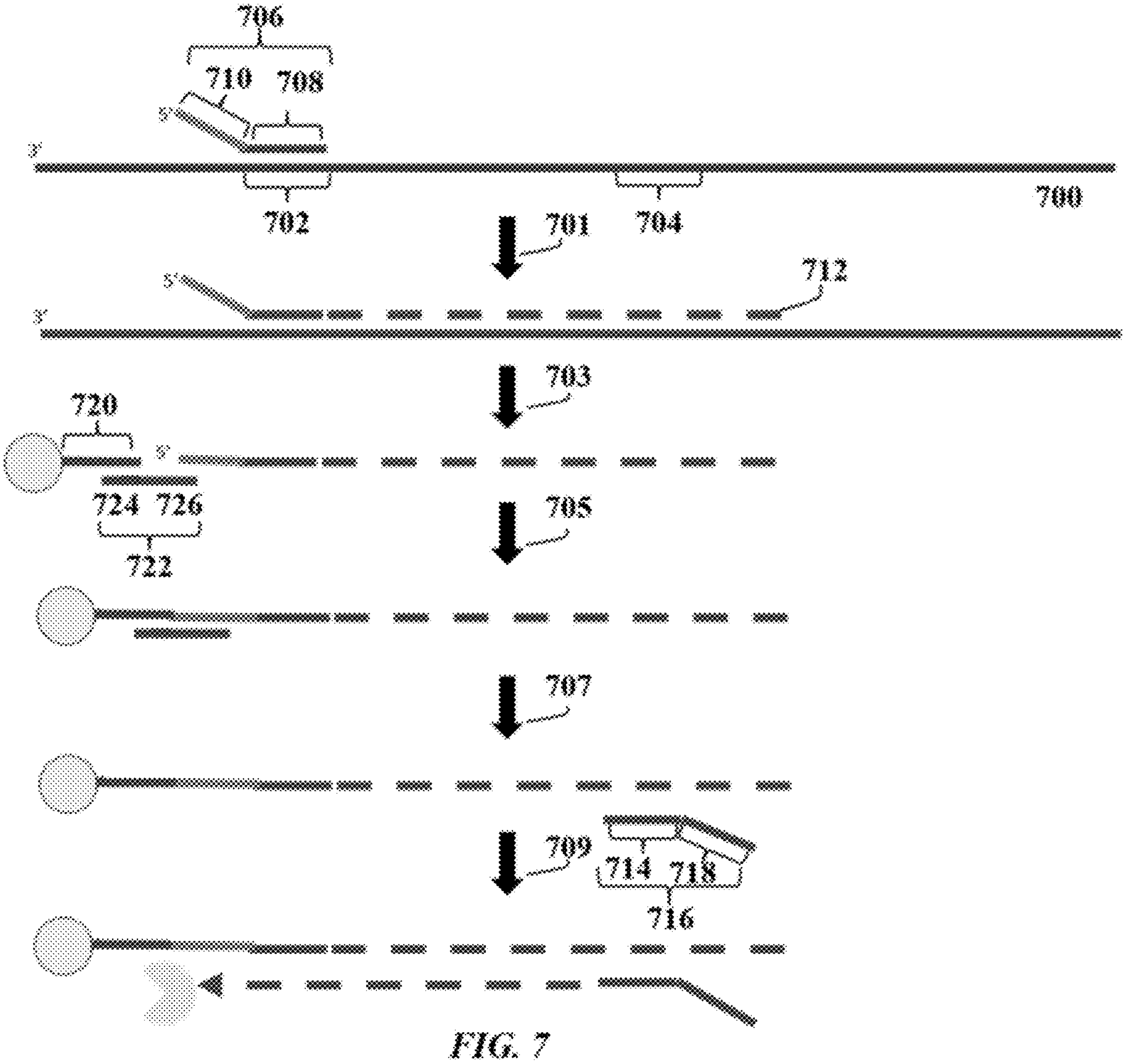
FIG. 7 schematically illustrates another example workflow for processing nucleic acid molecules.

FIG. 7 schematically shows a method for generating a barcoded nucleic acid molecule, as described herein. A nucleic acid molecule (e.g., RNA molecule) 700 comprising a first target region 702 and a second target region 704 may be provided. The nucleic acid molecule 700 may be contacted with a first probe 706 comprising a first probe sequence 708 and, optionally, a functional sequence 710, thereby generating a probe-associated nucleic acid molecule. The first probe sequence 708 may be complementary to the first target region 702. The functional sequence 710 may comprise, for instance, a probe capture sequence used for downstream barcoding, or it may comprise a different functional sequence, such as a primer sequence, a partial primer sequence, a barcode sequence, a sequencing primer sequence, etc.

In operation 701, the probe-associated nucleic acid molecule may be subjected to conditions sufficient to extend the first probe 706, thereby generating an extended probe molecule 712 comprising a sequence complementary to the second target region 704. In some instances, the extended probe molecule 712 may be released from the nucleic acid molecule 700, e.g., via denaturing and/or degrading the nucleic acid molecule 700 (e.g., using an RNAse, increased temperature or heat cycling, pH, etc.). In operation 703, a nucleic acid barcode molecule may be provided. In some instances, the nucleic acid barcode molecule may be partially double-stranded and may comprise a first strand 720 comprising a barcode sequence, and a second strand 722 comprising a sequence 724 at least partially complementary to the barcode sequence and a probe binding sequence 726, which may be at least partially complementary to the functional sequence (e.g., probe capture sequence) 710 of the first probe 706. In some instances, the nucleic acid barcode molecule is single-stranded and comprises only first strand 720 comprising the barcode sequence and a barcode capture sequence. A probe binding molecule (e.g., a splint oligonucleotide) 722 may be provided, comprising barcode-binding sequence 724, which is at least partially complementary to the barcode capture sequence, and the probe binding sequence 726. In some instances, the probe binding molecule and the nucleic acid barcode molecule may be provided as a pre-annealed complex. The nucleic acid barcode molecule (or the pre-annealed complex) may be coupled to a bead, such as a gel bead, as described herein, and may comprise additional functional sequences, including, but not limited to, a unique molecular identifier (UMI), a capture sequence, a primer sequence (e.g., a R1/R2 sequence).

In operation 705, the extended probe molecule may be barcoded by hybridizing the probe binding sequence 726 to the functional sequence (e.g., probe capture sequence 710). In some instances, the nucleic acid barcode molecule may be covalently linked to the extended probe molecule (e.g., via the probe capture sequence), e.g., enzymatically (e.g., using a ligase) or chemically (e.g., using click chemistry). In operation 707, a second probe molecule 716 may be provided. In some instances, operation 707 may also include a denaturation of the double-stranded molecule. The second probe molecule 716 may comprise a second probe sequence 714 corresponding to the second target region 704 and optionally a functional sequence 718, which may comprise a probe capture sequence, a barcode sequence, a primer sequence, a sequencing primer sequence, etc. In operation 709, a nucleic acid extension reaction may be performed, e.g., using a polymerase, to extend the second probe 716 along the extended probe molecule, thereby generating a barcoded molecule comprising a sequence corresponding to the first target region 702, the second target region 704, a sequence corresponding to the probe capture sequence 710, and a sequence corresponding to the barcode sequence 720.

In another example, the first probe and the second probe may be linked (e.g., by chemical ligation or enzymatic extension and/or ligation) prior to barcoding. In such an example, the first probe may be hybridized to the nucleic acid molecule (e.g., via hybridization of the first probe sequence to the first target region) to generate a probe-associated nucleic acid molecule. The probe-associated nucleic acid molecule may be extended from an end of the first probe to an end of the nucleic acid molecule to which it is hybridized, to provide an extended nucleic acid molecule. The extended molecule may be subjected to conditions sufficient to hybridize the second probe to the second target region or complement thereof (e.g., via hybridization of the second probe sequence to the second target region or complement thereof). An additional nucleic acid extension reaction may be performed, to generate an extended, and the resultant extension product may be barcoded, generating a barcoded molecule. The barcoded molecule may comprise a sequence corresponding to the first target region, a sequence corresponding to the second target region, a sequence corresponding to the probe capture sequence, and a sequence corresponding to the barcode sequence. In some instances, the nucleic acid barcode molecule (or the probe binding molecule) may be chemically linked to the first probe or the second probe, such as by ligation or click chemistry. For example, the nucleic acid barcode molecule may comprise a first reactive moiety, and the first or the second probe may comprise a second reactive moiety; the first reactive moiety may be configured to react with the second reactive moiety to generate a covalent linkage. Barcoded nucleic acid molecules or derivatives thereof may then be optionally further processed and analyzed by any suitable technique, including nucleic acid sequencing (e.g., Illumina sequencing).

Figure 8:
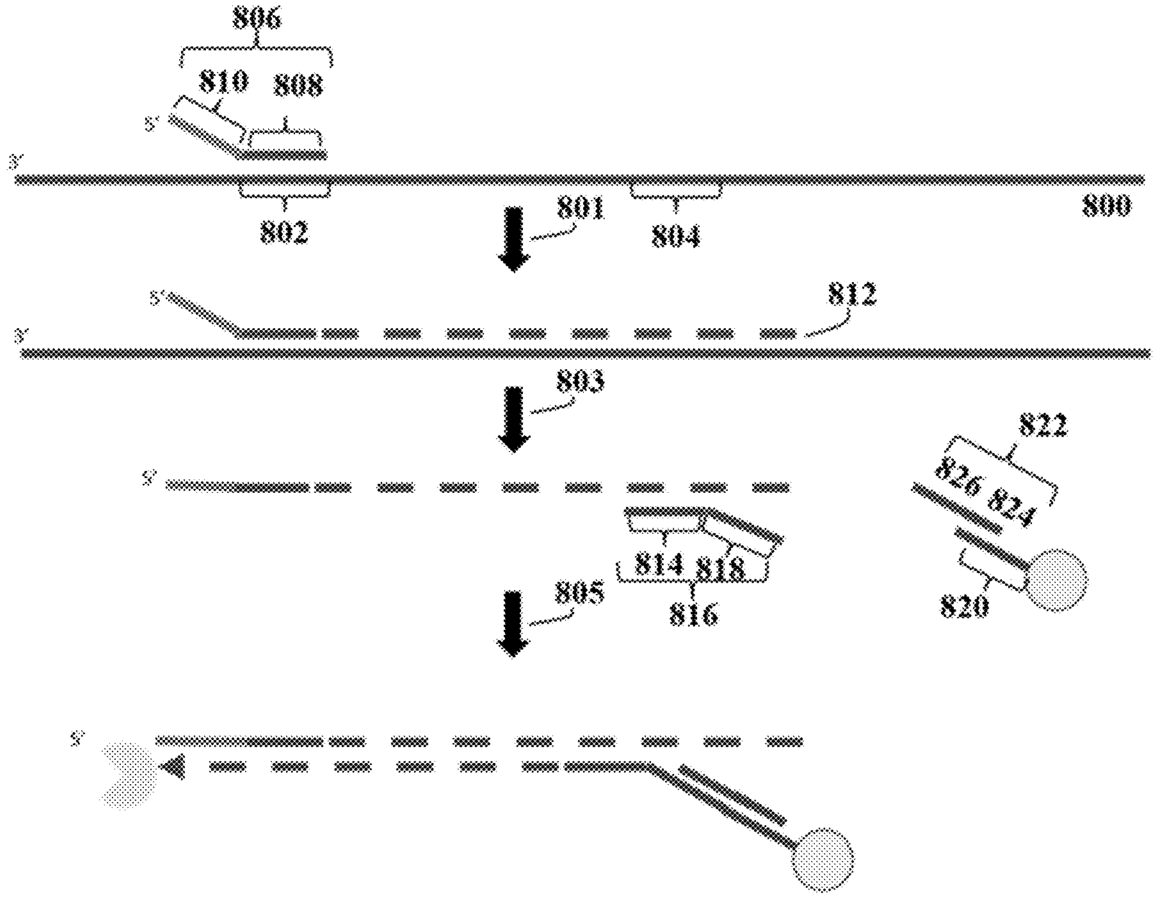
FIG. 8 schematically illustrates another example workflow for processing nucleic acid molecules.

FIG. 8 schematically shows another method for generating a barcoded nucleic acid molecule, as described herein. A nucleic acid molecule (e.g., RNA molecule) 800 comprising a first target region 802 and a second target region 804 may be provided. The nucleic acid molecule 800 may be contacted with a first probe 806 comprising a first probe sequence 808 and, optionally, a functional sequence 810, thereby generating a probe-associated nucleic acid molecule. The first probe sequence 808 may be complementary to the first target region 802. The functional sequence 810 may comprise, for instance, a probe capture sequence used for downstream barcoding, or it may comprise a different functional sequence, such as a primer sequence, a partial primer sequence, a barcode sequence, a sequencing primer sequence, etc.

In operation 801, the probe-associated nucleic acid molecule may be subjected to conditions sufficient to extend the first probe 806, thereby generating an extended probe molecule 812 comprising a sequence complementary to the second target region 804. In some instances, the extended probe molecule 812 may be released from the nucleic acid molecule 800, e.g., via denaturing and/or degrading the nucleic acid molecule 800 (e.g., using an RNAse, increased temperature or heat cycling, pH, etc.). In operation 803, a nucleic acid barcode molecule and a second probe 816 may be provided. The second probe 816 may comprise a second probe sequence 814 corresponding to the second target region 804 and optionally a functional sequence 818, which may comprise a probe capture sequence. In some instances, the nucleic acid barcode molecule may be partially double-stranded and may comprise a first strand 820 comprising a barcode sequence, and a second strand 822 comprising a sequence 824 complementary to the barcode sequence and a probe binding sequence 826, which may be complementary to the functional sequence (e.g., probe capture sequence) 818 of the second probe 816. In some instances, the nucleic acid barcode molecule is single-stranded and comprises only first strand 820 comprising the barcode sequence and a barcode capture sequence. A probe binding molecule (e.g., a splint oligonucleotide) 822 may be provided, comprising barcode-binding sequence 824 that is complementary to the barcode capture sequence, and the probe binding sequence 826. In some instances, the probe binding molecule and the nucleic acid barcode molecule may be provided as a pre-annealed complex. The nucleic acid barcode molecule (or the pre-annealed complex) may be coupled to a bead, such as a gel bead, as described herein, and may comprise additional functional sequences, including, but not limited to, a unique molecular identifier (UMI), a capture sequence, a primer sequence (e.g., a R1/R2 sequence). In operation 803, the second probe 816 may hybridize to the extended probe molecule 812 (e.g., via hybridization of the second probe sequence 814 to the second target region 804 or complement thereof), and the nucleic acid barcode molecule may be attached or coupled to the second probe 816, e.g., via hybridization of the probe binding sequence 826 to the probe capture sequence 818. In some instances, the nucleic acid barcode molecule or the probe binding molecule may be ligated to the second probe 816, e.g., using a ligase or via chemical linkage, such as click chemistry.

In operation 805, a nucleic acid extension reaction may be performed, e.g., using a polymerase (e.g., DNA polymerase, Hot Start polymerase, etc.), to extend the nucleic acid barcode molecule and the second probe 816 along the extended probe molecule, thereby generating a barcoded molecule comprising a sequence corresponding to the first target region 802, the second target region 804, a sequence corresponding to the probe capture sequence 818, and a sequence corresponding to the barcode sequence 820. Barcoded nucleic acid molecules or derivatives thereof may then be optionally further processed and analyzed by any suitable technique, including nucleic acid sequencing (e.g., Illumina sequencing).

Figure 9:
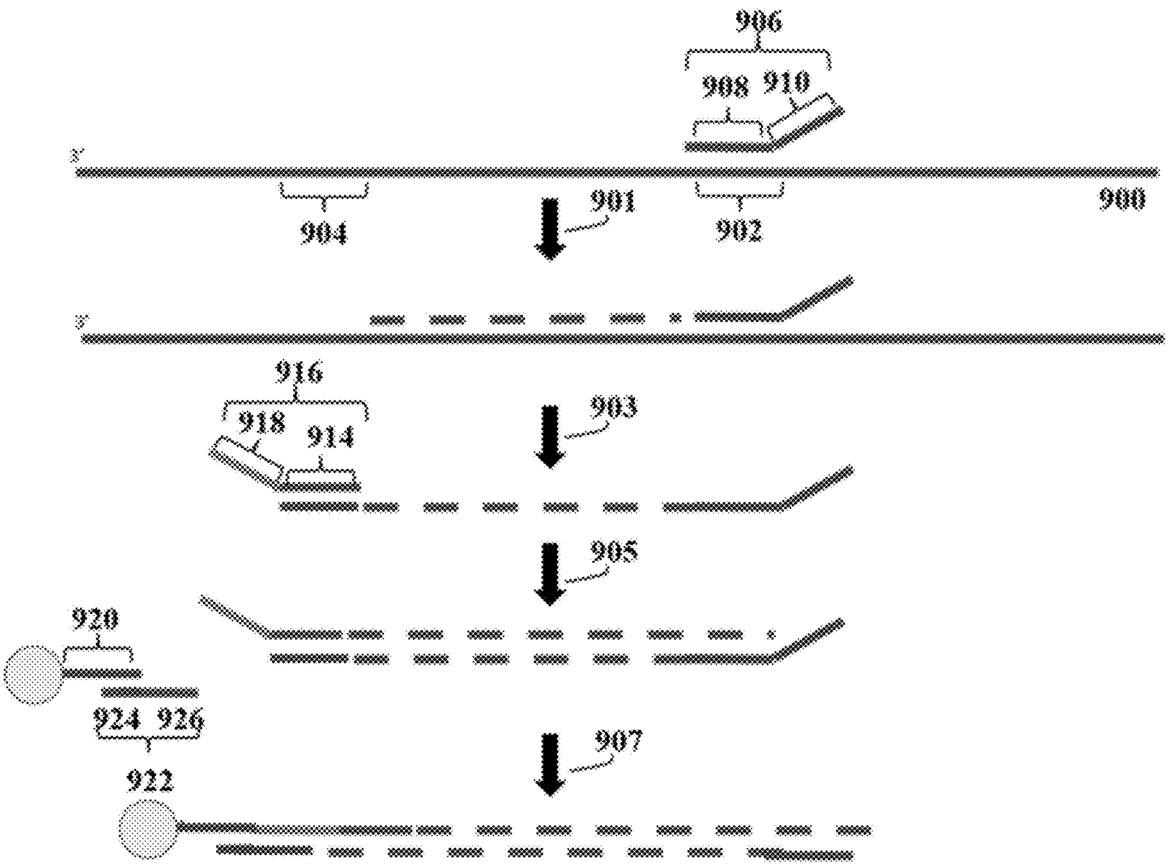
FIG. 9 schematically illustrates another example workflow for processing nucleic acid molecules.

FIG. 9 schematically shows another method for generating a barcoded nucleic acid molecule, similar to that shown in FIG. 8. A nucleic acid molecule (e.g., RNA molecule) 900 comprising a first target region 902 and a second target region 904 may be provided. The nucleic acid molecule 900 may be contacted with a first probe 906 comprising a first probe sequence 908 and, optionally, a functional sequence 910, thereby generating a probe-associated nucleic acid molecule. The first probe sequence 908 may be complementary to the first target region 902. The functional sequence 910 may comprise, for instance, a probe capture sequence, or it may comprise a different functional sequence, such as a primer sequence, a partial primer sequence, a barcode sequence, a sequencing primer sequence, etc.

In operation 901, the probe-associated nucleic acid molecule may be subjected to conditions sufficient to extend the first probe 906, thereby generating an extended probe molecule 912 comprising a sequence complementary to the second target region 906. In some instances, the extended probe molecule 912 may be released from the nucleic acid molecule 900, e.g., via denaturing and/or degrading the nucleic acid molecule 900 (e.g., using an RNAse, increased temperature or heat cycling, pH, etc.). In operation 903, a second probe 916 may be provided. The second probe 916 may comprise a second probe sequence 914 corresponding to the second target region 904 and optionally a functional sequence 918, which may comprise a probe capture sequence. In operation 905, a nucleic acid extension reaction may be performed, e.g., using a polymerase, to extend the nucleic acid barcode molecule and the second probe 916 along the extended probe molecule, thereby generating a probe-linked molecule comprising a sequence corresponding to the first target region 902 and the second target region 904.

In operation 905, a nucleic acid barcode molecule may also be provided with the second probe. In some instances, the nucleic acid barcode molecule may be partially double-stranded and may comprise a first strand 920 comprising a barcode sequence, and a second strand 922 comprising a sequence 924 complementary to the barcode sequence and a probe binding sequence 926, which may be complementary to the functional sequence (e.g., probe capture sequence) 918 of the second probe 916. In some instances, the nucleic acid barcode molecule is single-stranded and comprises only first strand 920 comprising the barcode sequence and a barcode capture sequence. A probe binding molecule (e.g., a splint oligonucleotide) 922 may be provided, comprising barcode-binding sequence 924 that is complementary to the barcode capture sequence, and the probe binding sequence 926. In some instances, the probe binding molecule and the nucleic acid barcode molecule may be provided as a pre-annealed complex. The nucleic acid barcode molecule (or the pre-annealed complex) may be coupled to a bead, such as a gel bead, as described herein, and may comprise additional functional sequences, including, but not limited to, a unique molecular identifier (UMI), a capture sequence, a primer sequence (e.g., a R1/R2 sequence). In operation 907, the nucleic acid barcode molecule may be attached or coupled to the second probe 916, e.g., via hybridization of the probe binding sequence 926 to the probe capture sequence 918. The resultant barcoded product may comprise a sequence corresponding to the first target region 902, the second target region 904, a sequence corresponding to the probe capture sequence 918, and a sequence corresponding to the barcode sequence 920. In some instances, the nucleic acid barcode molecule may be covalently linked to the extended probe molecule (e.g., via the probe capture sequence 918), e.g., enzymatically (e.g., using a ligase) or chemically (e.g., using click chemistry). Barcoded nucleic acid molecules or derivatives thereof may then be optionally further processed and analyzed by any suitable technique, including nucleic acid sequencing (e.g., Illumina sequencing).

In additional examples, the methods of the present disclosure may comprise generating probe-associated nucleic acid molecules, and barcoding the probe-associated nucleic acid molecules, optionally with a linking operation (e.g., prior to or subsequent to barcoding of the probe-associated nucleic acid molecules). For example, a nucleic acid molecule (e.g., RNA molecule) comprising a first target region and a second target region may be provided. The nucleic acid molecule may be contacted with (i) a first probe comprising a first probe sequence complementary to the first target region and (ii) a second probe comprising a second probe sequence complementary to the second target region, thereby generating a probe-associated nucleic acid molecule. In some instances, the probe-associated nucleic acid molecule may be subjected to conditions sufficient to link the first probe to the second probe (e.g., enzymatically, such as with a polymerase, reverse transcriptase, and/or ligase, or chemically), thereby generating a probe-linked nucleic acid molecule. The probe-associated nucleic acid molecule or the probe-linked molecule may subsequently be barcoded (e.g., in a partition) to generate a barcoded nucleic acid molecule.

Figure 25:
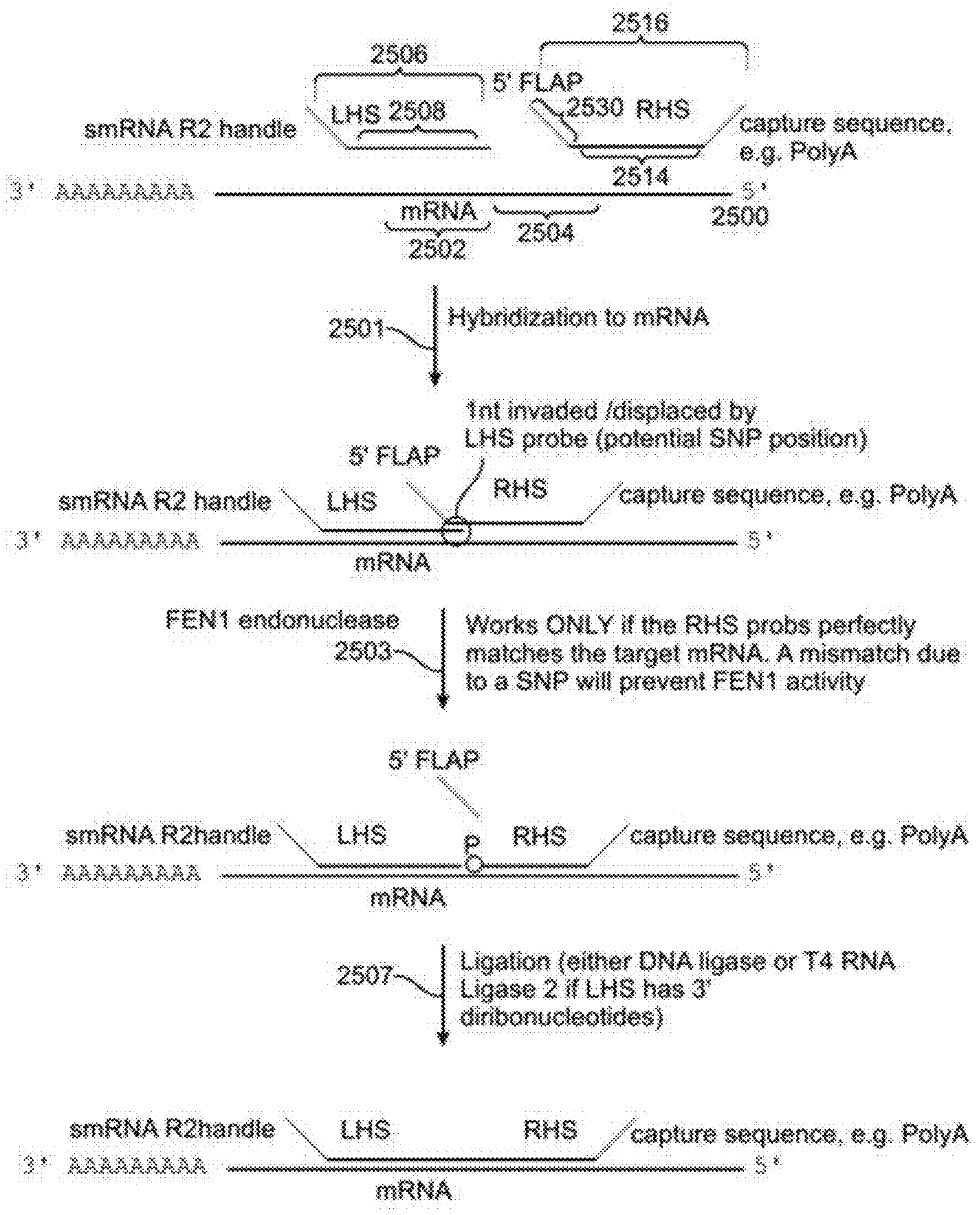
FIG. 25 schematically shows an example method for processing nucleic acid molecules.

For example, FIG. 25 schematically shows an example method for generating a probe-linked nucleic acid molecule, which may subsequently be barcoded, e.g., in a partition, to generate a barcoded nucleic acid molecule. A nucleic acid molecule (e.g., RNA molecule) 2500 comprising a first target region 2502 and a second target region 2504 may be provided. In some instances, the first target region is adjacent to the second target region. The nucleic acid molecule 2500 may be contacted, in operation 2501, with a first probe 2506 comprising a first probe sequence 2508 complementary to the first target region 2502 and a second probe 2516 comprising a second probe sequence 2514 complementary to the second target region 2504, thereby generating a probe-associated nucleic acid molecule. The first probe 2506 and/or the second probe 2516 may comprise a functional sequence, e.g., a probe capture sequence, a primer sequence, a partial primer sequence, a barcode sequence, a sequencing primer sequence, etc.

In some instances, one of the probes (e.g., the second probe 2516) comprises a flap or overhang sequence 2530, which may be recognized by an endonuclease (e.g., FEN1) upon annealing of the second probe sequence 2514 to the second target region 2504. For example, the second probe 2516 may comprise a 5' flap sequence 2530, and subsequent to annealing of the first probe 2506 and the second probe 2516 to the nucleic acid molecule 2500, the flap sequence may be adjacent to an end of the first probe (e.g., a 3' end) as well as an end of the second probe (e.g., a 5' end). In operation 2503, an endonuclease, e.g., FEN1 may be used to remove the flap sequence 2530, leaving a ligatable end (e.g., 5'phosphorylated end) of the second probe 2516. In operation 2507, a ligation reaction may be performed (e.g., using a ligase) to link the first probe to the second probe, thereby generating a probe-linked nucleic acid molecule. The probe-linked nucleic acid molecule may subsequently be barcoded, e.g., in partitions, as is described elsewhere herein. In some instances, the probe-associated nucleic acid molecules may be barcoded and linked (e.g., in partitions).

Figure 26:
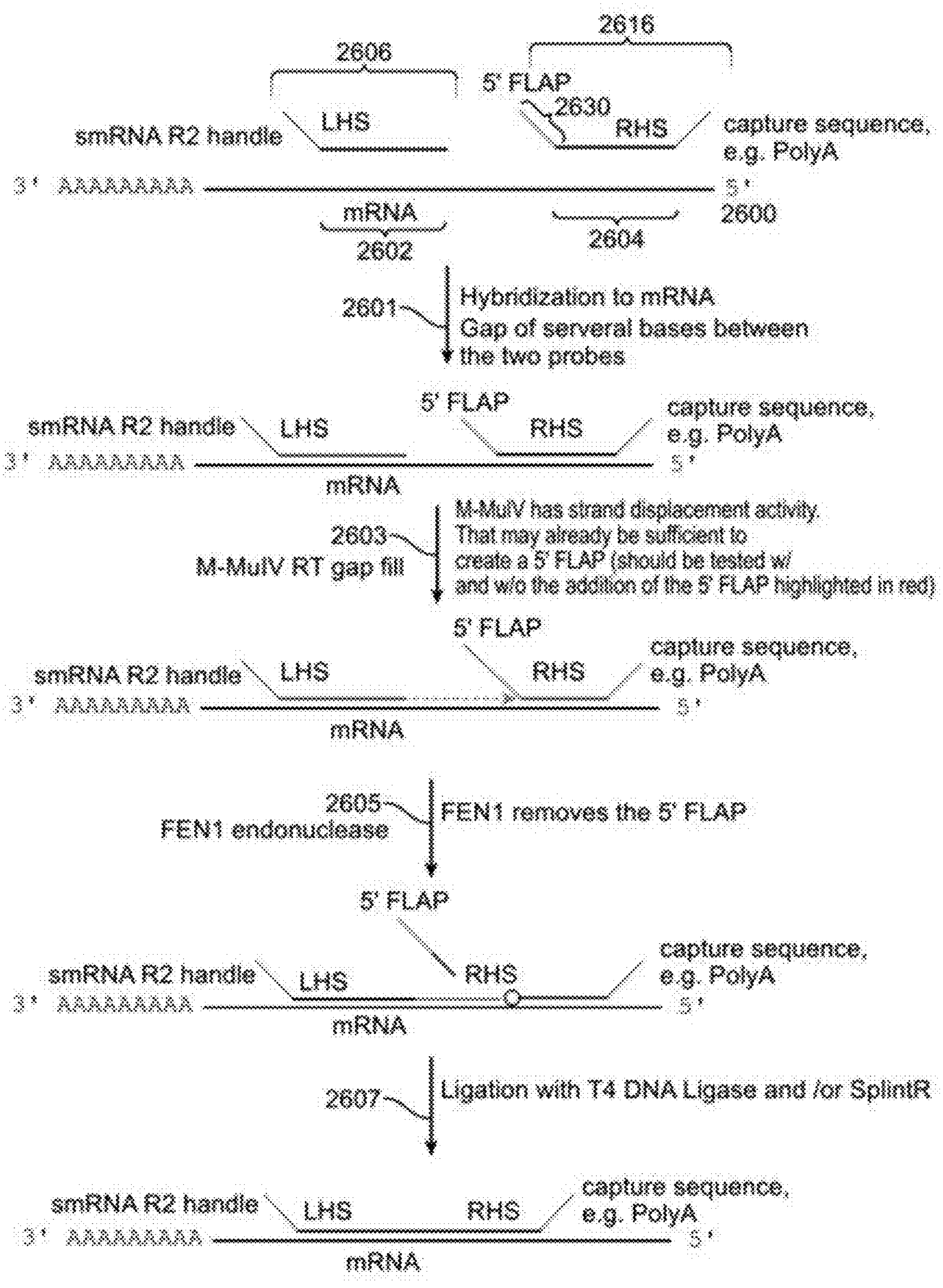
FIG. 26 shows another example method for processing nucleic acid molecules.

FIG. 26 shows another example workflow, similar to that shown in FIG. 25, in which the target regions of the nucleic acid molecule are not adjacent. Such a workflow may comprise an additional gap-fill reaction to generate the probe-associated molecule. In one such example, the first target region 2602 of nucleic acid molecule 2600 may not be adjacent to the second target region 2604. For example, the a gap region may be disposed between the first target region and the second target region. In operation 2601, the first probe 2606 may anneal to the first target region 2602 and the second probe 2616 may anneal to the second target region 2604. In operation 2603, an extension reaction (e.g., using a polymerase, reverse transcriptase, etc.) may be performed to fill in the gap region between the first probe 2606 and the second probe 2616, yielding a gap-filled nucleic acid molecule. In some instances, the second probe 2616 comprises a flap sequence 2630. In such instances, in operation 2605, an endonuclease, e.g., FEN1 may be used to remove the flap sequence 2630, leaving a ligatable end (e.g., 5'phosphorylated end) of the second probe 2616. In operation 2607, a ligation reaction may be performed (e.g., using a ligase) to link the first probe to the second probe, thereby generating a probe-linked nucleic acid molecule. The probe-linked nucleic acid molecule, or alternatively, the un-linked molecule, may be barcoded, e.g., in a partition.

Figure 27:
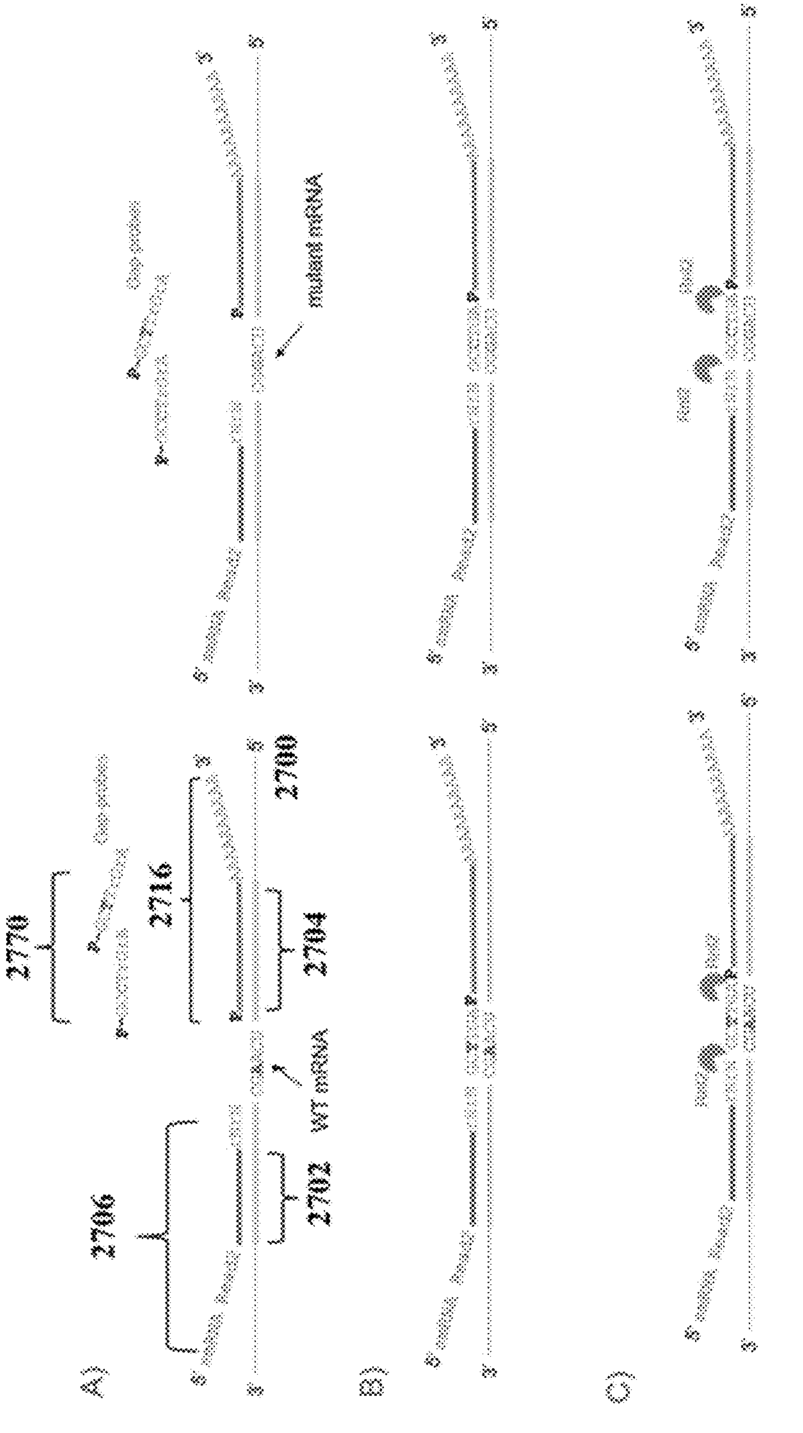
FIG. 27 shows an example workflow for generating probe-linked nucleic acid molecules.

FIG. 27 shows an additional scheme of generating a probe-linked nucleic acid molecule by performing a gap-filling reaction using a third probe. In FIG. 27 Panel A, a first probe 2706 and a second probe 2716 anneal (e.g., via a first probe sequence and a second probe sequence, respectively) to a first target region 2702 and a second target region 2704 of nucleic acid molecule 2700 to generate a probe-associated nucleic acid molecule. A gap sequence may be disposed between the first target region 2702 and the second target region 2704. Third probe molecules 2770 may be provided (illustrated as two different probe molecules, which may be used for SNP detection), which may anneal to the gap sequence (FIG. 27 Panel B). In FIG. 27 Panel C, the first probe, the third probe, and the second probe may be ligated (e.g., using a ligase) to generate a probe-linked nucleic acid molecule. The probe-linked nucleic acid molecule, or alternatively, the probe-associated nucleic acid molecule, may be barcoded, e.g., in a partition.

Figure 28:
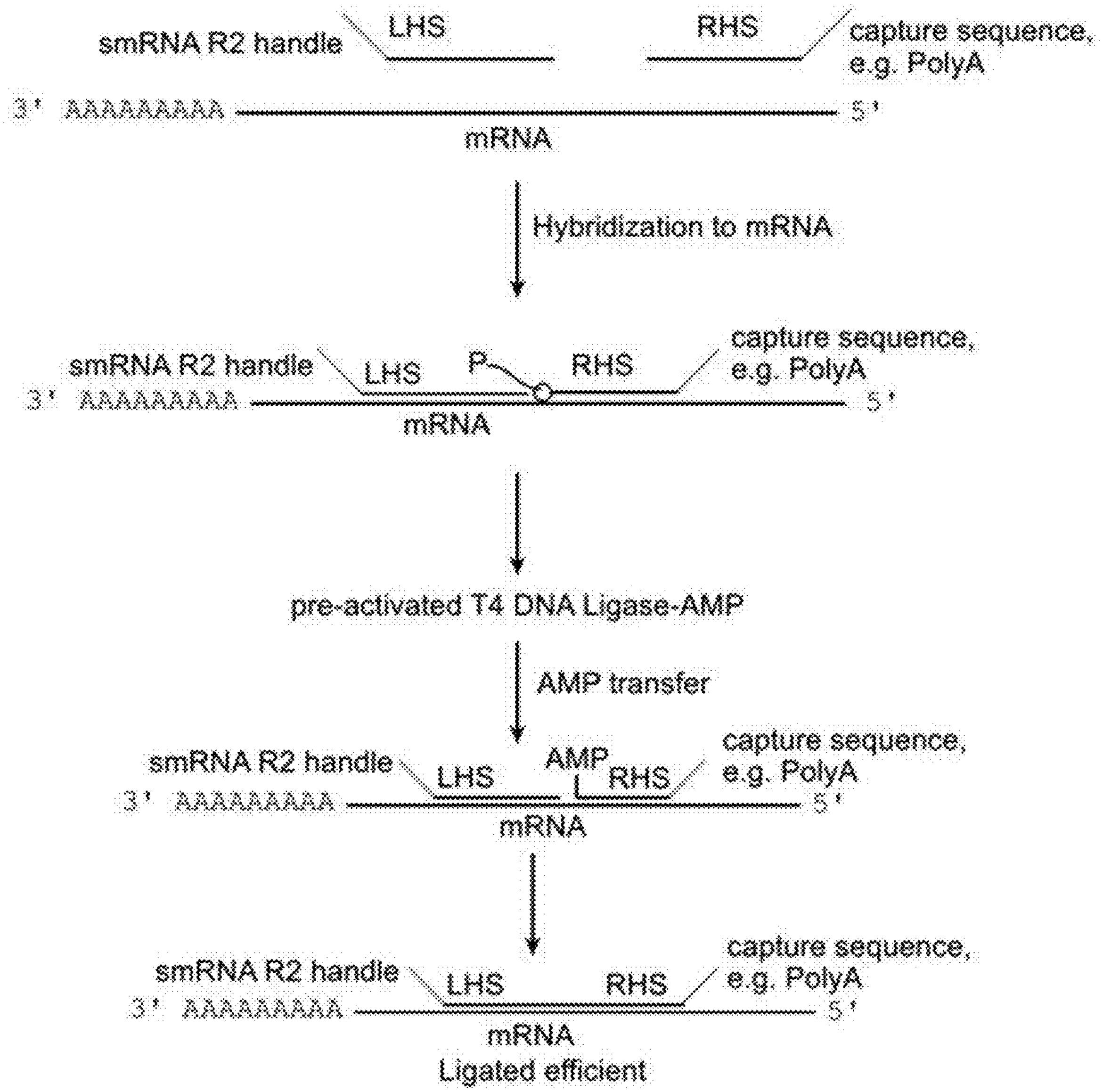
FIG. 28 shows another example workflow for generating probe-linked nucleic acid molecules.

FIG. 28 shows an example of a ligation scheme used to generate probe-linked nucleic acid molecules. In such an example, the probe molecules may hybridize to the nucleic acid molecule. The first probe may be ligated to the second probe, optionally with a gap-fill operation, as described above, using an enzyme. In some instances, the enzyme may be a pre-activated enzyme, e.g., a preactivated T4 DNA ligase, and the ligation may occur under ATP-reduced or ATP-removed conditions, e.g. using Apyrase.

Additional examples of methods and systems for generating probe-associated nucleic acid molecules, and barcoding the probe-associated nucleic acid molecules, can be found in, for example U.S. Pat. Pub. No. 2020/0239874, International Pub. No. WO 2019/165318, International App. No. PCT/US2020/066720, and International Pat. App. No. PCT/US2021/33649, filed May 21, 2021, each of which is incorporated by reference herein in its entirety.

It will be appreciated that, e.g., referring to FIGS. 7-9 and FIGS. 25-28, the nucleic acid barcode molecule may be attached (e.g., via hybridization) to either the first probe and/or the second probe (e.g., via a probe capture sequence comprised in the first probe or the second probe). Similarly, the first probe and the second probe may comprise any useful functional sequences, such as primer sequences, barcode sequences, unique molecular identifier (UMI) sequences, flow cell attachment sequences, primer-binding sequences, capture sequences, etc. The first probe may hybridize to the left-hand side (e.g., a 3' end) of a nucleic acid molecule (e.g., 700, 800, or 900) or to the right-hand side (e.g., a 5' end). Similarly, the second probe may hybridize to the left-hand side or to the right-hand side of the nucleic acid molecule.

As described herein, one or more extension reactions may be performed on the probe-hybridized nucleic acid molecules. For example, the probe may be extended from an end of the probe to an end of the nucleic acid barcode molecule, or a second probe may be extended from an end of the second probe to an end of the first probe of a probe-associated nucleic acid molecule. Extension may comprise the use of an enzyme (e.g., a polymerase, reverse transcriptase) to add one or more nucleotides to the end of the probe. Extension may provide an extended nucleic acid molecule comprising sequences complementary to the target region of the nucleic acid molecule of interest, the barcode sequence, and optionally, one or more additional sequences of the nucleic acid barcode molecule such as one or more binding sequences. In some instances, appropriate conditions and or chemical agents (e.g., as described herein) may be applied to denature the extended nucleic acid molecule from the nucleic acid barcode molecule and the target nucleic acid molecule. In some cases, one or more processes may involve the use of thermosensitive agents. For example, in some cases, probes may be annealed or hybridized under one set of temperature conditions, and extension may occur under a different set of temperature conditions. In some cases, a Warm or Hot Start polymerase may be used. In some cases, hybridization of the nucleic acid barcode molecule to one or more of the probes (e.g., directly hybridizing or via a probe binding molecule such as a splint oligonucleotide) may precede hybridization of the probe to the target region of the nucleic acid molecule. Following barcoding, the barcoded nucleic acid molecule may be duplicated or amplified by, for example, one or more amplification reactions. The amplification reactions may comprise polymerase chain reactions (PCR) and may involve the use of one or more primers or polymerases. The extension, denaturation, and/or amplification processes may take place within a partition, or in bulk. In some cases, the extended nucleic acid molecule or derivatives thereof (e.g., the barcoded molecule) may be duplicated or amplified within a partition to provide an amplified product. The barcoded product, or a complement thereof (e.g., an amplified product), may be detected via sequencing (e.g., as described herein).

The nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or a cell or cell bead comprising the nucleic acid molecule or a derivative thereof may be provided within a partition such as a well or droplet, e.g., as described herein. One or more reagents may be co-partitioned with a nucleic acid molecule or a derivative thereof or a cell comprising the nucleic acid molecule or a derivative thereof. For example, a nucleic acid molecule or a derivative thereof or a cell comprising the nucleic acid molecule or a derivative thereof may be co-partitioned with one or more reagents selected from the group consisting of lysis agents or buffers, permeabilizing agents, enzymes (e.g., enzymes capable of digesting one or more RNA molecules, extending one or more nucleic acid molecules, reverse transcribing an RNA molecule, permeabilizing or lysing a cell, or carrying out other actions), fluorophores, oligonucleotides, primers, probes, barcodes, nucleic acid barcode molecules (e.g., nucleic acid barcode molecules comprising one or more barcode sequences), buffers, deoxynucleotide triphosphates, detergents, reducing agents, chelating agents, oxidizing agents, nanoparticles, beads, and antibodies. In some cases, a nucleic acid molecule or a derivative thereof, or a cell comprising the nucleic acid molecule or a derivative thereof (e.g., a cell bead), may be co-partitioned with one or more reagents selected from the group consisting of temperature-sensitive enzymes, pH-sensitive enzymes, light-sensitive enzymes, reverse transcriptases, proteases, ligase, polymerases, restriction enzymes, nucleases, protease inhibitors, exonucleases, and nuclease inhibitors. For example, a nucleic acid molecule or a derivative thereof or a cell comprising the nucleic acid molecule or a derivative thereof may be co-partitioned with a polymerase and nucleotide molecules. Partitioning a nucleic acid molecule or a derivative thereof or a cell comprising the nucleic acid molecule or a derivative thereof and one or more reagents may comprise flowing a first phase comprising an aqueous fluid, the cell, and the one or more reagents and a second phase comprising a fluid that is immiscible with the aqueous fluid toward a junction. Upon interaction of the first and second phases, a discrete droplet of the first phase comprising the nucleic acid molecule or a derivative thereof or a cell comprising the nucleic acid molecule or a derivative thereof (e.g., a cell bead) and the one or more reagents may be formed. In some cases, the partition may comprise a single cell. The cell may be lysed or permeabilized within the partition (e.g., droplet) to provide access to the nucleic acid molecule of the cell.

One or more processes may be carried out within a partition (e.g., droplet, well, etc.). For instance, the nucleic acid molecule, or a cell or cell bead comprising the nucleic acid molecule, may be co-partitioned with one or more reagents (e.g., as described herein) at any useful stage of the method. For example, the probe-associated nucleic acid molecule (e.g., the nucleic acid molecule with the first probe hybridized thereto) may be generated in bulk (e.g., in a population of cells, which may be alive or fixed and/or permeabilized, in a tissue sample, etc.) and subjected to conditions sufficient for generating for generating an extended probe molecule. The extended probe molecule may be subsequently partitioned in a partition among a plurality of partitions. The partition may comprise the second probe and a nucleic acid barcode molecule and optionally, a probe binding molecule. As described herein, the second probe may hybridize (e.g., via the second probe sequence) to the second target region or complement thereof of the probe-associated molecule. The partition may comprise additional reagents for performing a nucleic acid reaction (e.g., digestion, ligation, extension, amplification). For instance, the probe-associated nucleic acid molecule may comprise or be hybridized to the nucleic acid molecule, and the partition may comprise a degrading enzyme (e.g., RNAse), which may be useful in digesting or removing the template strand (e.g., the nucleic acid molecule, such as an RNA molecule) from the extended probe molecule. The partition may comprise a polymerase, which may be used to extend the second probe hybridized to the extended probe molecule. In some instances, the partition comprises a linking enzyme (e.g., ligase), which may be used to ligate the nucleic acid barcode molecule to the first probe or the second probe (e.g., via a probe capture sequence). The ligase may in some instances be used to ligate the probe binding molecule to the probe capture sequence of the first probe or the second probe. In some instances, the probe binding molecule, the probe capture sequence, and/or the barcode capture sequence comprises one or more reactive moieties, which may be used to chemically or enzymatically link the nucleic acid barcode molecule to the probe capture sequence, or complement thereof. The resultant barcoded product may comprise a sequence corresponding to the first target region, a sequence corresponding to the second target region, a sequence corresponding to the probe capture sequence, and a sequence corresponding to the barcode sequence.

For example, referring again to FIG. 7, operation 701 may be performed in bulk (e.g., outside a partition), while operations 703, 705 may be performed in a partition. Operations 707 and 709 may be performed in bulk or within the partition. Similarly, referring to FIG. 8, operation 801 may be performed in bulk, while operation 803 may be performed in a partition. Operation 805 may be performed in bulk or in a partition. Referring to FIG. 9, operation 901 may be performed in bulk, while operations 903, 905, and 907 may be performed in a partition. It will be appreciated that any of the operations may be performed in bulk or in partitions at any convenient step and that the order of the operations may be changed for a suitable or useful purpose.

Similarly, the nucleic acid molecule or the cell or cell bead comprising the nucleic acid molecule, or derivatives thereof (e.g., the probe-associated molecule, the extended molecule, the barcoded molecule, etc.) may be released from a partition at any useful stage of the method. For example, the extended probe molecule may be hybridized to the second probe and released from the partition subsequent to hybridization of the barcode capture sequence of the nucleic acid barcode molecule to the first probe, the second probe, or the probe binding molecule. Alternatively, the extended probe molecule may be released from the partition subsequent to (i) hybridization of the second probe and nucleic acid barcode molecule and (ii) extension of the second probe to generate the barcoded molecule comprising a sequence corresponding to the first target region, a sequence corresponding to the second target region, a sequence corresponding to the probe capture sequence, and a sequence corresponding to the barcode sequence. Duplication and/or amplification of the extended nucleic acid molecule may be carried out within the partition or in bulk, e.g., within a solution. In some cases, the solution may comprise additional extended nucleic acid molecules generated through the same process carried out in different partitions. Each extended nucleic acid molecule may comprise a different barcode sequence, and the barcode sequence may be useful in identifying the partition or cell from whence the extended nucleic acid molecules originated. In such cases, the solution may comprise a pooled mixture comprising the contents of two or more partitions (e.g., droplets).

Additional processes or operations may be performed within a partition, including, but not limited to: lysis, permeabilization, denaturation, hybridization, extension, duplication, and amplification of one or more components of a sample. In some cases, multiple processes are carried out within a partition.

Hybridization of the probe sequences to the target regions of the nucleic acid molecule may be performed within or outside of a partition. In some cases, hybridization may be preceded by denaturation of a double-stranded nucleic acid molecule to provide a single-stranded nucleic acid molecule or by lysis or permeabilization of a cell. In some cases, the hybridization may occur in a cell bead comprising a cell. The sequence of the probe that is complementary to the target region may be situated at an end of the probe. Alternatively, this sequence may be disposed between other sequences such that when the probe sequence is hybridized to the target region, additional probe sequences extend beyond the hybridized sequence in one or more directions. The probe sequence that hybridizes to the target region of the nucleic acid molecule may be of the same or different length as the target region. For example, the probe sequence may be shorter than the target region and may only hybridize to a portion of the target region. Alternatively, the probe sequence may be longer than the target region and may hybridize to the entirety of the target region and extend beyond the target region in one or more directions. In addition to a probe sequence complementary to a target region of the nucleic acid molecule, the probe may comprise one or more additional probe sequences. For example, the probe may comprise the probe sequence complementary to the target region and a second probe sequence. The second probe sequence may have any useful length and other characteristics.

The probe (e.g., the first probe or the second probe) may comprise one or more additional sequences or moieties, such as one or more barcode sequences or unique molecule identifier (UMI) sequences, adapter sequences, functional sequences (e.g., primer sequences, sequencing primer sequences, etc.). In some cases, one or more probe sequences of the probe may comprise a detectable moiety such as a fluorophore or a fluorescent moiety. In some instances, the first probe or the second probe may comprise a reactive moiety, as described elsewhere herein. For example, the first probe or the second probe may comprise an azide moiety, an alkyne moiety, a phosphorothioate moiety, an iodide moiety, an amine moiety, a phosphate moiety, or a combination thereof. The first probe may comprise a first reactive moiety and the second probe may comprise a second reactive moiety, and reaction of the first reactive moiety and the second reactive moiety may be sufficient to yield a probe-linked molecule comprising the first probe linked to the second probe. In some instances, the first reactive moiety and the second reactive moiety is linked via ligation. Accordingly, the first probe or the second probe may comprise one or more moieties or modified nucleotides to facilitate ligation, e.g., one or more ribonucleotides or dideoxynucleotides (ddNTPs), which may be ligated to a phosphorylated end of the second probe using a ligase (e.g., T4 DNA ligase, SplintR ligase). In some instances, the probe (e.g., the first probe or the second probe) may comprise an overhang or flap sequence which is recognizable or cleavable by an endonuclease (e.g., FEN1 endonuclease). Other suitable enzymes, e.g., ligases, may be used, for example, the enzymes and ligases disclosed in U.S. Provisional App. No. 63/171,031, filed Apr. 5, 2021, which is incorporated herein by reference in its entirety.

As described herein, a probe sequence of the probe may be capable of hybridizing with a sequence of a nucleic acid barcode molecule or a probe binding molecule (e.g., splint oligonucleotide). A nucleic acid barcode molecule may comprise a first binding sequence (e.g., a barcode capture sequence) that is complementary to a probe sequence of the probe (e.g., a probe capture sequence). The nucleic acid barcode molecule may comprise one or more additional functional sequences, e.g., primer sequences, primer annealing sequences, and immobilization sequences. The binding sequences may have any useful length and other characteristics. In some cases, the binding sequence (e.g., barcode capture sequence) that is complementary to a probe sequence of the probe may be the same length as the probe sequence. Alternatively, the binding sequence may be a different length of the probe sequence. For example, the binding sequence may be shorter than the probe sequence and may only hybridize to a portion of the probe sequence. Alternatively, the binding sequence may be longer than the probe sequence and may hybridize to the entirety of the probe sequence and extend beyond the probe sequence in one or more directions. Similarly, in instances when a probe-binding molecule is used, the binding sequence (e.g., barcode capture sequence) of the nucleic acid barcode molecule may be the same length as the barcode binding sequence of the probe-binding molecule, or the binding sequence may be longer or shorter than the barcode binding sequence.

One or more processes described herein may be performed in a cell, nucleus or cell bead. For example, in some embodiments, a plurality of cells, nuclei or cell beads may comprise a plurality of nucleic acid molecules. The cells, nuclei or cell beads may be alive or fixed and/or permeabilized. In some instances, the first probes may be provided to the cells, nuclei or cell beads, such as in a bulk solution. Optionally, the cells, nuclei or cell beads may be washed to remove unbound first probes, and the nucleic acid extension reaction, as described herein, may be performed. Subsequently, the cells, nuclei or cell beads comprising the plurality of nucleic acid molecules (or the extended, probe nucleic acid molecules) may be partitioned into a plurality of separate partitions, where at least a subset of the plurality of separate partitions comprises a single cell, single nucleus, or single cell bead. Access to a target nucleic acid molecule contained within a cell, nucleus or cell bead in a partition may be provided by lysing or permeabilizing the nucleus or cell (e.g., as described herein), which may be performed prior to or during partitioning. Alternatively, access to a target nucleic acid molecule contained within a cell, nucleus, or cell bead may be performed in a bulk solution using the methods described herein. Barcoding of the target nucleic acid may be performed within a cell, within a cell bead, or within a partition comprising the cell or cell bead. In an example, the target nucleic acid molecule may be barcoded in a partition and outside the cell, cell nucleus, or cell bead. Additional probe hybridization (e.g., providing of the second probe) and/or barcoding may be performed within the separate partitions. Barcoding, as described herein, may comprise using a nucleic acid barcode molecule to attach or hybridize to the target nucleic acid molecule or derivative thereof (e.g., the extended probe molecule, or complement thereof). Nucleic acid barcode molecules provided within each partition of the plurality of separate partitions may be provided attached to beads. In some instances, as described elsewhere herein, the nucleic acid barcode molecule may be releasably attached to a bead (e.g., via a labile bond). Each partition (or a subset of partitions) of the plurality of separate partitions may comprise a bead comprising a plurality of nucleic acid barcode molecules attached thereto (e.g., as described herein). The plurality of nucleic acid barcode molecules attached to each bead may comprise a unique barcode sequence, such that each partition of the plurality of separate partitions comprises a different barcode sequence. Upon release of components from the plurality of different partitions of the plurality of separate partitions (e.g., following barcoding), the barcoded molecules arising from a single cell, single nucleus, or single cell bead may have a same barcode sequence (e.g., a common barcode sequence), such that each barcoded nucleic acid molecule can be traced to a given partition and/or, in some instances, a given cell, nucleus or cell bead.

The methods described herein may comprise additional barcoding operations, which may be useful, for example, in indexing nucleic acid molecules to a cell, nucleus, cell bead, a sample, a partition, or a plurality of partitions. Such indexing may be useful in situations when a single partition is occupied by multiple cells, nuclei, or cell beads. In some instances, it may be beneficial to overload partitions such that a partition comprises more than a single cell, single nucleus, or single cell bead; for example, it may be useful in certain situations to overload partitions, e.g., to overcome Poisson loading statistics in partitions and/or to prevent reagent waste (e.g., from unoccupied partitions). Accordingly, such indexing may be useful in attributing cells, nuclei or nucleic acid molecules in multiply-occupied partitions to the originating cell, nucleus, cell bead, partition, sample, etc.

In an example, a barcoded molecule, such as the barcoded molecules generated using the methods described herein (e.g., in FIGS. 7-9, FIGS. 25-28, as well as barcoded, probe-linked nucleic acid molecules described in U.S. Pat. Pub. No. 2020/0239874 and International Pub. No. WO 2019/165318, each of which is incorporated by reference herein) may be provided. The barcoded molecule may comprise, as described herein, a sequence corresponding to the first target region, a sequence corresponding to the second target region, a sequence corresponding to the probe capture sequence (which may be disposed on the first probe or the second probe), and a sequence corresponding to the barcode sequence of the nucleic acid barcode molecule. Such a barcode sequence may be specific to the partition and may differ from other barcode sequences of other partitions and thus may be used to identify a partition from which a nucleic acid molecule (or derivative thereof) originated. In some instances, some of the partitions may comprise a single cell, single nucleus, or single cell bead and thus the nucleic acid barcode molecule or barcode sequence may be used to identify a cell, nucleus, or cell bead from which a nucleic acid molecule (or derivative thereof) originated.

In some instances, the barcoded molecule may be subjected to an additional barcoding operation, e.g., in partitions or in bulk. For example, the barcoded molecule may be re-partitioned in a partition among a plurality of partitions comprising a plurality of additional nucleic acid barcode molecules. The plurality of additional nucleic acid barcode molecules may comprise additional barcode sequences that differ across the partitions. The barcoded molecules may be subjected to conditions sufficient to barcode the barcoded molecules to generate a combinatorially barcoded molecule comprising two barcode sequences. As each barcode sequence pertains to a unique partition, the combination of barcodes may be useful in generating a greater diversity of barcoded molecules, as well as for identifying the originating partitions of the combinatorially barcoded molecule.

In some cases, combinatorial assembly of barcode segments may be performed using, e.g., a split-pool approach. For example, in some embodiments, the probe-linked nucleic acid molecules may be combinatorially barcoded using a split pool approach. In one such example, a plurality of permeabilized cells (or permeabilized nuclei or cell beads) comprising, e.g., probe-linked nucleic acid molecule, which may optionally be barcoded (e.g., the product following operation 709 of FIG. 7, 805 of FIG. 8, or 905 or 907 of FIG. 9) may be partitioned into a plurality of partitions (e.g., a plurality of wells), wherein each partition of the plurality of partitions comprises a different (e.g., unique) barcode sequence segment. Alternatively, the plurality of permeabilized cells (or permeabilized nuclei or cell beads) may be partitioned, and then the different barcode sequence segments delivered to the respective partitions containing the cells, nuclei, and/or cell beads. After addition of the barcode sequence segment, cells (or nuclei or cell beads) can be collected from the plurality of partitions, pooled, and partitioned into an additional plurality of partitions (e.g., a plurality of wells) wherein each partition of the additional plurality of partitions comprises a different (e.g., unique) second barcode sequence segment. Repeating this split-pool process allows the generation of barcodes or barcoded molecules comprising any suitable amount of barcode sequence segments. Combinatorial barcoding as described herein may comprise at least 1, 2, 3, 4, 5, 6, 7, 8 or more operations (e.g., split-pool cycles). Combinatorial barcoding comprising multiple operations may be useful, for example, in generation of greater barcode diversity and to synthesize a unique barcode sequence on nucleic acid molecules derived from each single cell, nucleus, or cell bead of a plurality of cells, nuclei, cell beads. For example, combinatorial barcoding comprising three operations, each comprising attachment of a unique nucleic acid sequence in each of 96 partitions, will yield up to 884,736 unique barcode combinations. Generally, where there are M partitions, and N number of split-pool iterations are performed, up to $M^N$ unique barcode combinations may be generated. Cells or nuclei or cell beads may be partitioned such that at least one cell (or nuclei or cell bead) is present in each partition of a plurality of partitions. Cells, nuclei, or cell beads may be partitioned such that at least 1; 2; 3; 4; 5; 10; 20; 50; 100; 500; 1,000; 5,000; 10,000; 100,000; 1,000,000; or more cells, nuclei, or cell beads are present in a single partition. Cells, nuclei, or cell beads may be partitioned such that at most 1,000,000; 100,000; 10,000; 5,000; 1,000; 500; 100; 50; 20; 10; 5; 4; 3; 2; or 1 cell (or nucleus or cell bead) is present in a single partition. Cells, nuclei, and/or cell beads may be partitioned in a random configuration.

In some instances, the additional barcoding operations may be performed prior to some of the operations described herein. For example, it may be beneficial to combinatorially barcode the first probe in a bulk solution, e.g., prior to or following generation of the extended probe molecule or probe-linked molecule. In such cases, the nucleic acid molecule may be contacted, e.g., in bulk, with a first probe to generate a probe-associated molecule. The probe-associated molecule may optionally be extended, e.g., using the methods described herein, to generate an extended probe molecule. The probe-associated molecule or the extended probe molecule may then be subjected to combinatorial barcoding, e.g., in partitions, as described above, to generate a combinatorially barcoded molecule. The combinatorially barcoded molecule may then be partitioned with a second probe and a nucleic acid barcode molecule, which, as described herein, may attach to either the first probe (or combinatorially barcoded probe), the second probe, or both probes. As each partition of the combinatorial barcoding process comprises a different barcode sequence segment, a plurality of the combinatorially barcoded molecules may be traced back to the individual partitions from which they originated. Moreover, the combinatorial barcoding may be useful in generating greater probe diversity.

Beneficially, the combinatorial barcoding of the first probe may be particularly useful when combined with the second probe and nucleic acid barcode molecule, which may comprise a barcode sequence that is specific to the partition. For example, the presence of the probe-specific barcode(s) and the partition-specific barcode sequence may allow for indexing of individual cells (or nuclei or cell beads) within a partition. For instance, partitions comprising cell/nucleus/cell bead multiplets (e.g., cell doublets, triplets, etc.) can be computationally deconvolved into single cells/nuclei/cell beads. Thus, in some instances, cells, nuclei, or cell beads may be "overloaded" into partitions using conditions such that a higher probability of cell/nucleus/cell bead multiplets (2,3,4,5+ cells, nuclei, or cell beads per partition) are formed, wherein target libraries of these cell multiplets may be computationally deconvolved into single cells, nuclei, or cell beads.

Figure 10:
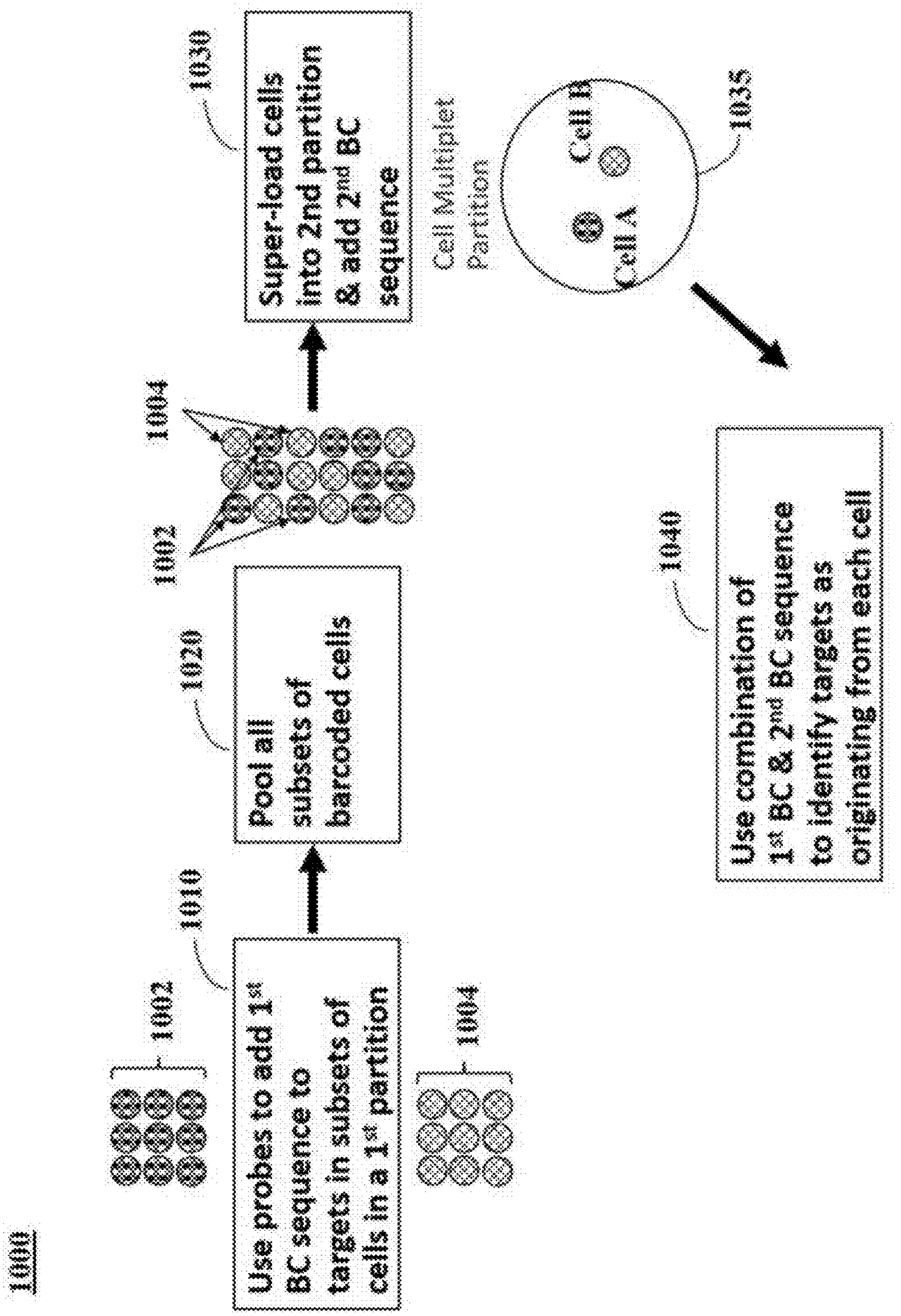
FIG. 10 schematically illustrates an example workflow for analyzing cells, nuclei or cell beads.

FIG. 10 schematically shows an example workflow of barcoding nucleic acid molecules in partitions comprising cell/nucleus/cell bead multiplets. In operation 1010, one or more populations of cells/nuclei/cell beads (or nucleic acid molecules contained therein) may be subjected to barcoding, as described herein (e.g., using processes shown and described in FIGS. 7-9 and FIGS. 15A-16). For example, a first population of cells (or nuclei or cell beads) 1002 (comprising a first plurality of nucleic acid molecules) may be subjected to barcoding in a first subset of a first plurality of partitions, generating a first plurality of barcoded nucleic acid molecules comprising a first barcode sequence. A second population of cells (or nuclei or cell beads) 1004 may be barcoded in a second subset of the first plurality of partitions, generating a second plurality of barcoded nucleic acid molecules comprising a second barcode sequence. The first barcode sequence may be different than the second barcode sequence. In operation 1020, the first population of cells (or nuclei or cell beads) 1002 may be pooled together with the second population of cells (or nuclei or cell beads) 1004 to generate a mixture of cells. In operation 1030, the mixture of cells (or nuclei or cell beads) may be partitioned into a second plurality of partitions. In some instances, the mixture of cells/nuclei/cell beads may be partitioned into the second plurality of partitions such that some partitions of the second plurality of partitions comprises more than one cell (e.g., a cell multiplet partition). For example, a partition 1035 of the second plurality of partitions may comprise a cell, nucleus, or cell bead ("Cell A") from the first population of cells 1002 and a cell, nucleus, or cell bead ("Cell B") from the second population of cells 1004. The partition 1035 may comprise an additional barcode sequence, which may be unique to the partition. The cells/nuclei/cell beads in each partition may be subjected to an additional barcoding operation to append the additional barcode sequence on the barcoded nucleic acid molecules. In operation 1040, the barcoded nucleic acid molecules may be deconvolved, using the different barcode sequences (e.g., the first barcode sequence, the second barcode sequence, and the additional barcode sequences), to identify the originating cell/nucleus/cell bead. For instance, a barcoded nucleic acid molecule comprising the additional barcode sequence from partition 1035 and the first barcode sequence from the first population of cells (or nuclei or cell beads) 1002 may be used to identify that barcoded nucleic acid molecule as originating from Cell A. Similarly, a barcoded nucleic acid molecule comprising the additional barcode sequence from partition 1035 and the second barcode sequence from the second populations of cells (or nuclei or cell beads) 1004 may be used to identify that barcoded nucleic acid molecule as originating from Cell B.

Following partition-based barcoding, the contents of the partitions may be pooled and the barcoded molecules (e.g., barcoded probe-linked nucleic acid molecules) may be duplicated or amplified by, for example, one or more amplification reactions, which may in some instances be isothermal. The amplification reactions may comprise polymerase chain reactions (PCR) and may involve the use of one or more primers or polymerases. The one or more primers may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), etc.) and may facilitate addition of said one or more functional sequences to the extended nucleic acid molecule. The barcoded molecules, or derivatives thereof, may be detected via nucleic acid sequencing (e.g., as described herein).

In some aspects, provided herein are systems useful for barcoding nucleic acid molecules. The systems may comprise any of the components described herein, e.g., a plurality of partitions (e.g., droplets, wells), which may be provided in any useful format, e.g., a microfluidic device, a multi-well array or plate, etc. The systems may include nucleic acid barcode molecules, optionally coupled to supports (e.g., particles, beads, gel beads, etc.). In some instances, the systems may comprise any of the probes described herein, such as a first probe or plurality of first probes, a second probe or plurality of second probes, and any useful reaction components (e.g., for performing a nucleic acid reaction, e.g., extension, ligation, amplification, etc.). Such useful reaction components can include, in non-limiting examples, enzymes (e.g., ligases, polymerases, reverse transcriptases, restriction enzymes, etc.), nucleotides bases, etc.

Also provided herein are compositions useful for systems and methods for barcoding nucleic acid molecules. A composition may comprise any of the probes described herein. For example, a composition may comprise a plurality of first probes, a plurality of second probes, and/or a plurality of first probes and a plurality of second probes. A probe or a set of probes may be designed to target a specific sequence or a set of specific sequences. Such probes may be designed to have the same or different sequences within different partitions. For example, a first composition may comprise a first probe and a second probe designed to target two regions of a first gene, and a second composition may comprise a first probe and a second probe designed to target two regions of a second gene, which second gene is different than the first gene. A composition may comprise nucleic acid barcode molecules, and/or probe binding molecules, which may optionally be provided coupled to a support (e.g., particle, bead). A composition may be a part of or comprise a reaction mixture, which can include reaction components or reagents, e.g., enzymes, nucleotide bases, catalysts, buffers etc.

Multiplexed Analysis of Nucleic Acids and Proteins

In another aspect, the present disclosure provides methods for performing multiplexed assays. Such a multiplexed assay may comprise assaying or analyzing one or more biomolecules (e.g., nucleic acid molecules, proteins, lipids, carbohydrates, etc.). A method may comprise using one or more probes and a nucleic acid barcode molecule to barcode a nucleic acid molecule of a cell/nucleus/cell bead, thereby generating a first barcoded nucleic acid molecule; attaching or coupling a feature-binding group to a feature of the cell/nucleus/cell bead, wherein the feature-binding group comprises a reporter oligonucleotide comprising a reporter sequence that identifies the feature-binding group; using an additional nucleic acid barcode molecule, and optionally, an additional probe, to barcode the reporter sequence to generate a second barcoded nucleic acid molecule; and optionally barcoding the first barcoded nucleic acid molecule and the second barcoded nucleic acid molecule to generate a third barcoded nucleic acid molecule and a fourth barcoded nucleic acid molecule. One or more operations may be performed within a partition (e.g., droplet or well).

The methods described herein may facilitate profiling of one or more biomolecules with single-cell/single nucleus/single cell bead resolution, using, for example, probe hybridization, feature binding groups (e.g., antibodies, antibody fragments, epitope-binding groups, etc.), barcoding, amplification, and sequencing. The methods may be useful in providing genomic, transcriptomic, proteomic, exomic, or other "-omic" information from a single cell/nucleus/cell bead. As described herein, the methods may be used to analyze a pre-determined panel of target genes and a pre-determined panel of target features (e.g., proteins, peptides, or other biomolecules) in a sensitive and accurate manner. Alternatively or in addition to, the methods may be used to analyze whole genomic, whole transcriptomic, whole exomic, etc. characteristics of a cell.

In some aspects, the methods comprise contacting a cell/nucleus/cell bead with a first probe, a second probe, and a third probe under conditions sufficient to generate a first probe-associated molecule and a second probe-associated molecule. The cell/nucleus/cell bead may comprise (i) a nucleic acid molecule (e.g., a target nucleic acid molecule such as RNA or DNA) comprising a first target region and a second target region and (ii) a feature (e.g., protein, peptide, or other biomolecule) coupled to a feature-binding group. The feature binding group may comprise or be coupled to (i) a reporter oligonucleotide comprising a reporter sequence, which may be associated with the feature or may be used to identify the feature, and (ii) a feature probe-binding sequence. The first probe may comprise a first probe sequence complementary to the first target region of the nucleic acid molecule and, optionally, an additional probe sequence, such as a probe capture sequence or other functional sequence. The second probe may comprise a second probe sequence complementary to the second target region and, optionally, a probe capture sequence or functional sequence. The third probe may comprise (i) a third probe sequence complementary to the feature probe-binding sequence and (ii) a probe capture sequence or functional sequence, which may be the same sequence as the probe capture sequence of the first probe and/or second probe.

In some instances, the first probe-associated molecule may comprise the nucleic acid molecule, the first probe, the second probe, or combinations or complements thereof. The second probe-associated molecule may comprise the reporter oligonucleotide (which comprises the reporter sequence) and the third probe, or complements thereof.

In some aspects, the method comprises providing the first probe-associated molecule and the second probe-associated molecule, and barcoding the first probe-associated molecule and the second probe-associated molecules. Such barcoding operations may occur in a first set of partitions (e.g., droplets or wells). Such an example method may comprise contacting the first probe-associated molecule and the second-probe-associated molecule with probe binding molecules (e.g., a splint oligonucleotide) and barcode molecules (e.g., nucleic acid barcode molecules) under conditions sufficient to generate a first barcoded nucleic acid molecule and a second barcoded nucleic acid molecule. The barcode molecules may comprise (i) a barcode capture sequence, e.g., a common sequence that is common to a plurality of barcode molecules and (ii) a first barcode sequence. In instances where partitions are used, the first barcode sequence may be unique to a first partition of a first set of partitions, and the barcode molecules within the first partition may share the same first barcode sequence. The probe-binding molecule may comprise (i) a probe-binding sequence complementary to the probe capture sequence (of the first probe, the second probe, and/or the third probe) and (ii) a barcode binding sequence complementary to the barcode capture sequence (e.g., common sequence) of the plurality of barcode molecules. As such, barcoding of the first probe-associated molecule and the second probe-associated molecule may comprise hybridization of the probe binding molecule to (i) the probe capture sequence (or complement thereof) of the first probe, the second probe, and/or the third probe, and (ii) the barcode capture sequence (or common sequence) of the nucleic acid barcode molecule. In some examples, the first barcoded nucleic acid molecule comprises a sequence corresponding to the first probe sequence, a sequence corresponding to the second probe sequence, and a sequence corresponding to the first barcode sequence. Similarly, the second barcoded nucleic acid molecule may comprise a sequence corresponding to the reporter sequence, a sequence corresponding to the third probe sequence, and a sequence corresponding to the first barcode sequence.

The method may further comprise providing a second set of partitions, and in a second partition of the second set of partitions, (i) contacting the first barcoded nucleic acid molecule, or derivative thereof (e.g., complements, amplicons, extension products thereof), to a first capture molecule of a plurality of capture molecules under conditions sufficient to generate a third barcoded nucleic acid molecule, and (ii) contacting the second barcoded nucleic acid molecule, or derivative thereof, to a second capture molecule of the plurality of capture molecules under conditions sufficient to generate a fourth barcoded nucleic acid molecule. The plurality of capture molecules may each comprise a second barcode sequence, which may be the same or different than the first barcode sequence from the first set of partitions. The second barcode sequence may be unique to the partition (e.g., differ across partitions). The third barcoded nucleic acid molecule and the fourth barcoded molecule may each comprise a sequence corresponding to the first barcode sequence and a sequence corresponding to the second barcode sequence. For example, the third barcoded nucleic acid molecule may comprise a sequence corresponding to the first target region, a sequence corresponding to the second target region, a sequence corresponding to a probe capture sequence, the first barcode sequence and the second barcode sequence. The fourth barcoded nucleic acid molecule may comprise a sequence corresponding to the reporter sequence, a sequence corresponding to the feature probe binding sequence, a sequence corresponding to the third probe, the first barcode sequence and the second barcode sequence.

The feature binding group may comprise a labelling agent, as described elsewhere herein. Accordingly, the feature binding group may comprise, in some examples, an antibody or antibody fragment, an epitope binding moiety, a protein, a peptide, a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof.

The probe capture sequence of the first probe (or the second probe) may be common to a plurality of first probes (or second probes), a plurality of partitions, and/or a plurality of cells/nuclei/cell beads. For instance, the first set of partitions may comprise one or more additional partitions that comprise additional probe-associated nucleic acid molecules. The additional probe-associated nucleic acid molecules may comprise identical sequences (e.g., first probe sequence, second probe sequence) to the probe-associated nucleic acid molecule of the first partition, or the additional probe-associated nucleic acid molecules of the additional partitions may comprise different sequences (e.g., different probe sequences) than the probe-associated nucleic acid molecule of the first partition. In some instances, each of the one or more additional probe-associated nucleic acid molecules comprises a probe capture sequence, which may be identical or different across the first set of partitions.

The probe-associated molecules may be a probe-linked molecule. For example, the probe-associated molecules may be the probe-associated molecules or barcoded molecules described herein (e.g., in FIGS. 7-9), or a probe-linked molecule, such as those described in U.S. Pat. Pub. No. 2020/0239874 and International Pub. No. WO 2019/165318, each of which is incorporated by reference herein in its entirety. In some examples, two sets of probe-associated molecules may be generated, in which: (i) a first probe-associated molecule comprises the nucleic acid molecule, with the first probe and the second probe hybridized thereto (e.g., via hybridization of the first probe sequence to the first target region and the second probe sequence to the second target region) and (ii) a second probe-associated molecule comprises the reporter oligonucleotide (which comprises the reporter sequence), with the third probe hybridized thereto.

The first probe, the second probe, and/or the third probe may comprise a probe capture sequence. The probe capture sequence on the first probe may be the same or different than the probe capture sequence of the second probe or the third probe. Similarly, the probe capture sequence of the second probe may be the same or different than the probe capture sequence of the third probe. Accordingly, the barcoding operations described herein may occur on the first probe, the second probe, the third probe, or any combination thereof. For example, for a probe-associated molecule comprising a nucleic acid molecule and the first probe ("probe 1") and second probe ("probe 2") hybridized thereto, a first barcode molecule comprising the first barcode sequence ("BC1") may hybridize (e.g., directly or via a probe-binding molecule) to the first probe to generate a first barcoded nucleic acid molecule, and subsequently, a capture molecule comprising a second barcode sequence ("BC2") may be annealed to a region of the first barcode molecule, thereby generating a molecule comprising a sequence, or complementary sequences, of BC2-BC1-probe 1-probe 2. Alternatively or in addition to, the first barcode molecule comprising the first barcode sequence ("BC1") may hybridize (e.g., directly or via a probe-binding molecule) to the second probe to generate a first barcoded nucleic acid molecule, and subsequently, a capture molecule comprising the second barcode sequence ("BC2") may be annealed to a region of the first barcode molecule, thereby generating a molecule comprising a sequence of probe 1-probe 2-BC1-BC2. Alternatively or in addition to, the barcode molecules and the capture molecules may be annealed to different probes. For example, the first barcode molecule comprising the first barcode sequence ("BC1") may hybridize (e.g., directly or via a probe-binding molecule) to the first probe to generate a first barcoded nucleic acid molecule, and subsequently, a capture molecule comprising the second barcode sequence ("BC2") may be annealed to the second probe, thereby generating a molecule comprising a sequence of BC1-probe 1-probe 2-BC2. Alternatively or in addition to, the first barcode molecule comprising the first barcode sequence ("BC1") may hybridize (e.g., directly or via a probe-binding molecule) to the second probe to generate a first barcoded nucleic acid molecule, and subsequently, a capture molecule comprising the second barcode sequence ("BC2") may be annealed to the first probe, thereby generating a molecule comprising a sequence of BC2-probe 1-probe 2-BC1. It will be appreciated that while several examples of barcoding schemes are described herein, additional combinations and positioning of barcode sequences are possible; for example, combinatorial barcoding may be used to generate greater barcode diversity, as described herein, and such barcoding may occur on any of the probe molecules (or already barcoded molecules).

In some instances, the barcode molecules may comprise a capture-binding sequence complementary to a capture sequence of the plurality of capture molecules. For example, the first probe may comprise a probe capture sequence which may hybridize to a probe binding molecule, which may mediate hybridization of the barcode molecule (e.g., via hybridization of the barcode binding sequence of the probe binding molecule to the barcode capture sequence (e.g., common sequence) of the barcode molecule). The barcode molecule may additionally comprise the capture-binding sequence, which may allow for hybridization of the capture sequence of the capture molecules to the barcode molecule.

Figure 15A:
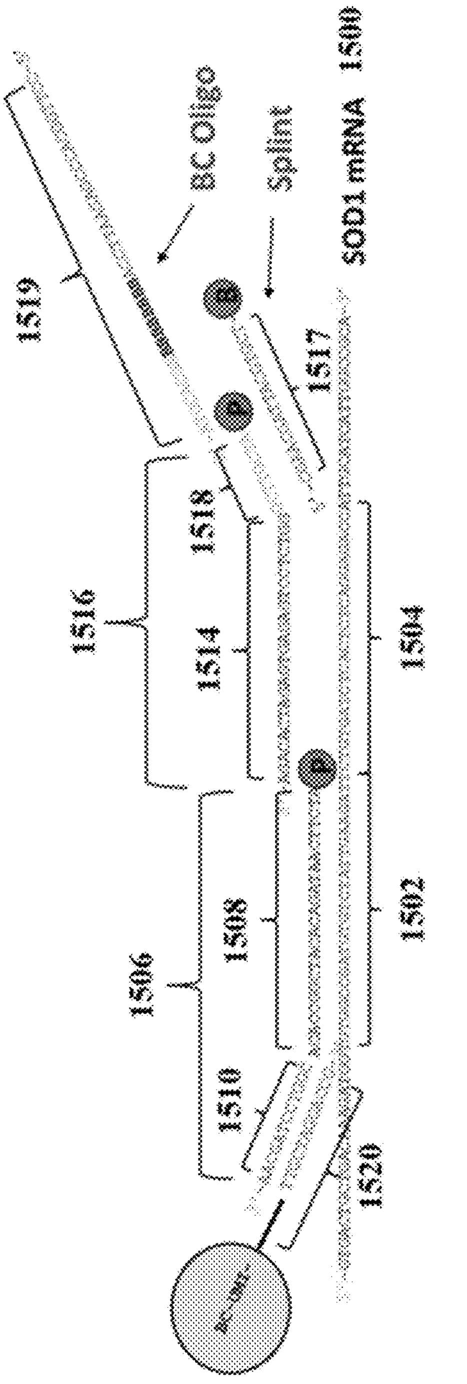
FIGS. 15A-15C shows an example processed nucleic acid molecule described herein.
Figure 15B:
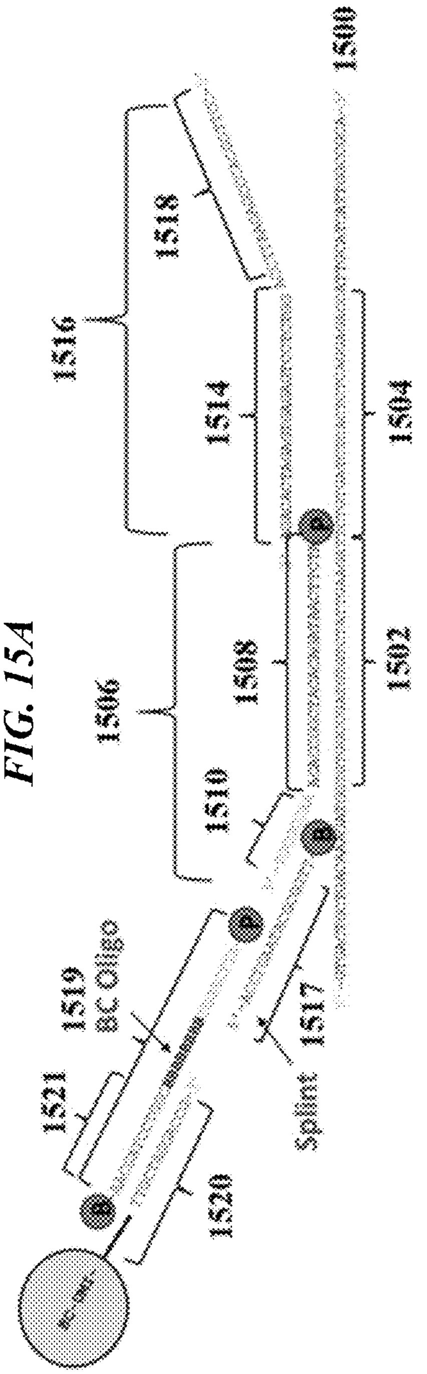
Figure 15C:
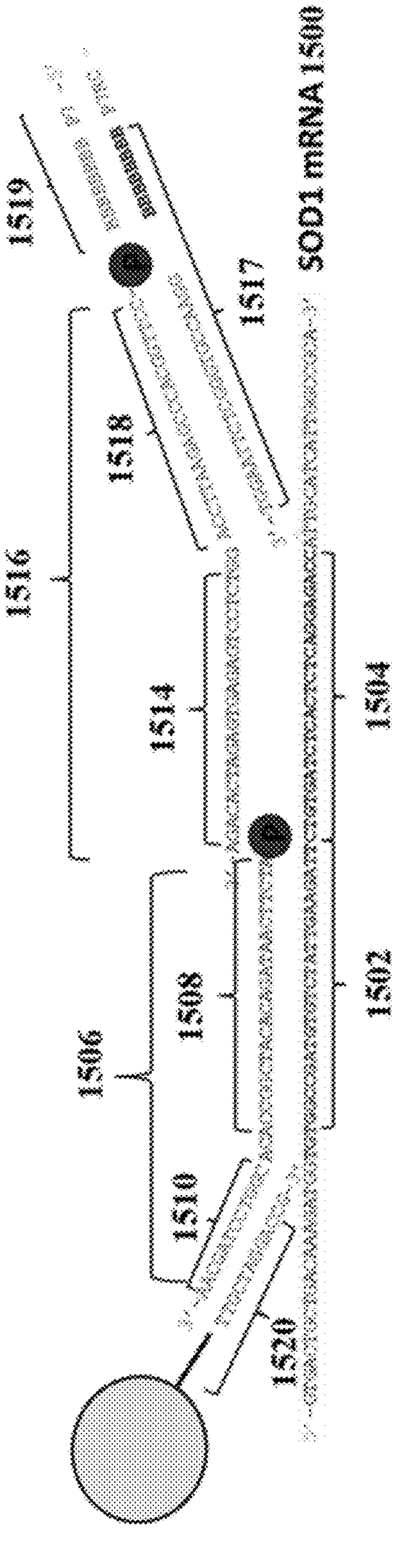

FIGS. 15A-15C schematically illustrates an example barcoded nucleic acid molecule as described herein. Referring to FIG. 15A, a nucleic acid molecule (e.g., RNA molecule) 1500 comprising a first target region 1502 and a second target region 1504 may be provided. The nucleic acid molecule 1500 may be contacted with a first probe 1506 comprising a first probe sequence 1508 and, optionally, a first probe capture sequence 1510. The first probe sequence 1508 may be complementary to the first target region 1502. The first probe capture sequence 1510 may additionally, in some instances, comprise a functional sequence, such as a primer sequence, a partial primer sequence, a barcode sequence, a sequencing primer sequence, etc. The nucleic acid molecule 1500 may also be contacted with a second probe 1516 comprising a second probe sequence 1514 and, optionally, a second probe capture sequence 1518. The second probe sequence 1514 may be complementary to the second target region 1504. The second probe capture sequence 1518 may additionally comprise a functional sequence. Hybridization of the first probe 1506 and the second probe 1516 to the nucleic acid molecule 1500 may generate a probe-associated molecule.

As described herein, the probe-associated molecule may be subjected to one or more barcoding operations. Such a barcoding operation may occur in one or more partitions (e.g., a first set of partitions) and may include hybridizing a probe binding molecule 1517 and a barcode molecule 1519 comprising a barcode capture sequence (e.g., a common sequence), to the probe-associated molecule. In some instances, the probe binding molecule 1517 and the barcode molecule 1519 may be provided as a pre-annealed complex, or they may be provided as separate molecules. The barcode capture sequence (e.g., common sequence) may be a sequence that is common to the plurality of barcode molecules in the first set of partitions, or the common sequence may be unique to the barcode molecules in only a single first partition (e.g., the common sequence differs across partitions of the first set of partitions). The probe binding molecule 1517 may comprise a probe binding sequence complementary to the probe capture sequence 1518 of the second probe 1516, as well as a barcode binding sequence complementary to a sequence of the barcode molecule 1519. The probe-associated molecule may be subjected to conditions sufficient to generate a first barcoded nucleic acid molecule, which can include annealing of the probe-binding molecule 1517 to (i) the probe capture sequence 1518 and (ii) the barcode capture sequence (e.g., common sequence) of the barcode molecule 1519. The barcoding process may comprise additional operations, such as ligation, which may be performed chemically or enzymatically, as described elsewhere herein.

The first barcoded nucleic acid molecule or derivatives thereof (e.g., a complement, an amplicon, an extension product, a combinatorially barcoded nucleic acid molecule, as described elsewhere herein), may be subjected to a second barcoding operation. Such a second barcoding operation may occur in a second set of partitions. For example, the first barcoded nucleic acid molecule may be removed from the first set of partitions, pooled (e.g., with other barcoded nucleic acid molecules from other first partitions of the first set of partitions), and partitioned in a second partition of a second set of partitions. The second partition may comprise a capture molecule 1520. The capture molecule 1520 may comprise a second barcode sequence and a sequence complementary to the probe capture sequence 1510 of the first probe 1506. The second barcode sequence may be a sequence that is common to the plurality of capture molecules in the second set of partitions, or the barcode sequence may be unique to the capture molecules in only the second partition (e.g., differ across partitions). The capture molecule 1520 may hybridize to the probe capture sequence 1510 to generate an additional barcoded molecule (also referred to herein as a "third barcoded nucleic acid molecule"). The additional barcoded molecule may comprise a sequence corresponding to the first barcode sequence (of the barcode molecule 1519), and a sequence corresponding to the second barcode sequence (of the capture molecule 1520).

FIG. 15B schematically illustrates another example barcoded molecule in which the capture molecule 1520 is hybridized to the barcode molecule 1519. Similar to FIG. 15A, in FIG. 15B, the nucleic acid molecule (e.g., RNA molecule) 1500 comprising a first target region 1502 and a second target region 1504 may be provided. The nucleic acid molecule 1500 may be contacted with a first probe 1506 comprising a first probe sequence 1508 and a probe capture sequence 1510. The first probe sequence 1508 may be complementary to the first target region 1502. The probe capture sequence 1510 may additionally comprise a functional sequence, such as a primer sequence, a partial primer sequence, a barcode sequence, a sequencing primer sequence, etc. The nucleic acid molecule 1500 may also be contacted with a second probe 1516 comprising a second probe sequence 1514 and, optionally, an additional sequence 1518. The second probe sequence 1514 may be complementary to the second target region 1504. The additional sequence 1518 may comprise, for instance, a probe capture sequence, or a functional sequence (e.g., primer, primer binding site, sequencing primer sequence, etc.). Hybridization of the first probe 1506 and the second probe 1516 to the nucleic acid molecule 1500 may generate a probe-associated molecule.

The probe-associated molecule may be contacted with one or more barcode molecules. Such barcoding operations, as described herein, may occur in a plurality of partitions (e.g., a first partition of a first set of partitions and/or a second partition of a second set of partitions). The probe-associated molecule may be contacted with a probe binding molecule 1517 and a barcode molecule 1519, which may comprise a first barcode capture sequence (e.g., a common sequence) and a second barcode capture sequence 1521 (also referred to herein as "capture binding sequence"). In some instances, the probe binding molecule 1517 and the barcode molecule 1519 may be provided as a pre-annealed complex or as separate molecules. The first barcode capture sequence (e.g., common sequence) may be a sequence that is common to the plurality of barcode molecules in the first set of partitions, or the common sequence may be unique to the barcode molecules in only the first partition (e.g., differ across partitions). The probe binding molecule 1517 may comprise a probe binding sequence complementary to the probe capture sequence 1510 as well as a barcode binding sequence complementary to the first barcode capture sequence (e.g., common sequence) of the barcode molecule 1519. The probe-associated molecule may be subjected to conditions sufficient to generate a first barcoded nucleic acid molecule, which can include annealing of the probe-binding molecule 1517 to (i) the probe capture sequence 1510 and (ii) the first barcode capture sequence (e.g., common sequence) of the barcode molecule 1519. The barcoding process may comprise additional operations, such as ligation, which may be performed chemically or enzymatically, as described elsewhere herein.

The first barcoded nucleic acid molecule or derivatives thereof, may be subjected to a second barcoding operation. Such a second barcoding operation may occur in a second set of partitions. For example, the first barcoded nucleic acid molecule may be removed from the first partition and partitioned in a second partition of a second set of partitions (e.g., droplets). The second partition may comprise a capture molecule 1520. The capture molecule 1520 may comprise a second barcode sequence and a sequence complementary to the second barcode capture sequence 1521 of the barcode molecule 1519. The second barcode sequence may be a sequence that is common to the plurality of capture molecules in the second set of partitions, or the barcode sequence may be unique to the capture molecules in only the second partition (e.g., differ across partitions). The capture molecule may hybridize to the second barcode capture sequence 1521 to generate an additional barcoded molecule (also referred to herein as a "third barcoded nucleic acid molecule"). The additional barcoded molecule may comprise a sequence corresponding to the first barcode sequence (of the barcode molecule 1519), and a sequence corresponding to the second barcode sequence (of the capture molecule 1520).

FIG. 15C illustrates another example barcoded nucleic acid molecule. A nucleic acid molecule (e.g., RNA molecule) 1500 comprising a first target region 1502 and a second target region 1504 may be provided. The nucleic acid molecule 1500 may be contacted with a first probe 1506 comprising a first probe sequence 1508 and, optionally, a first probe capture sequence 1510. The first probe sequence 1508 may be complementary to the first target region 1502. The first probe or first probe capture sequence 1510 may additionally, in some instances, comprise a functional sequence, such as a primer sequence, a partial primer sequence, a barcode sequence, a sequencing primer sequence, etc. The nucleic acid molecule 1500 may also be contacted with a second probe 1516 comprising a second probe sequence 1514 and, optionally, a second probe capture sequence 1518. The second probe sequence 1514 may be complementary to the second target region 1504. The second probe capture sequence 1518 may additionally comprise a functional sequence. Hybridization of the first probe 1506 and the second probe 1516 to the nucleic acid molecule 1500 may generate a probe-associated molecule or complex.

As described herein, the probe-associated molecule may be subjected to one or more barcoding operations. Such a barcoding operation may occur in one or more partitions (e.g., a first set of partitions) and may include hybridizing a probe binding molecule 1517 and a barcode molecule 1519 comprising a barcode capture sequence (e.g., a common sequence), to the probe-associated molecule or complex. In some instances, the probe binding molecule 1517 and the barcode molecule 1519 are provided as a pre-annealed complex (e.g., a partially double-stranded molecule comprising the probe binding molecule 1517 and the barcode molecule 1519), or they may be provided as separate molecules, which may separately anneal to the probe-associated molecule or complex (e.g., the probe binding molecule 1517 may hybridize to the probe-associated molecule or complex, e.g., via the second probe capture sequence 1518, and the barcode molecule 1519 may hybridize to the probe binding molecule 1517). The barcode capture sequence (e.g., common sequence) may be a sequence that is common to the plurality of barcode molecules in the first set of partitions, or the common sequence may be unique to the barcode molecules in only a single first partition (e.g., the common sequence differs across partitions of the first set of partitions). The probe binding molecule 1517 may comprise a probe binding sequence complementary to the probe capture sequence 1518 of the second probe 1516, as well as a barcode binding sequence complementary to a sequence of the barcode molecule 1519. In some instances, the probe binding molecule 1517 and/or the barcode molecule 1519 comprise an additional sequence, e.g., an adapter sequence, a primer sequence (e.g., sequencing primer sequence or partial sequencing primer sequence), a UMI, a sample index sequence, etc. In some instances, the probe binding molecule 1517 comprises the entire sequence of the barcode molecule 1519, such that no overhang remains. In some instances, the probe binding molecule 1517 and barcode molecule 1519 comprise a sample index sequence, which may be useful in identifying the partition, cell, nucleus, or cell bead from which the target nucleic acid molecule 1500 originates. The probe-associated molecule may be subjected to conditions sufficient to generate a first barcoded nucleic acid molecule, which can include annealing of the probe-binding molecule 1517 to (i) the probe capture sequence 1518 and (ii) the barcode capture sequence (e.g., common sequence) of the barcode molecule 1519. The barcoding process may comprise additional operations, such as ligation (e.g., ligation of the barcode molecule 1519 to the probe capture sequence 1518), which may be performed chemically or enzymatically, as described elsewhere herein.

The first barcoded nucleic acid molecule or derivatives thereof (e.g., a complement, an amplicon, an extension product, a combinatorially barcoded nucleic acid molecule, as described elsewhere herein), may be subjected to a second barcoding operation. Such a second barcoding operation may occur in a second set of partitions. For example, the first barcoded nucleic acid molecule may be removed from the first set of partitions, pooled (e.g., with other barcoded nucleic acid molecules from other first partitions of the first set of partitions), and partitioned in a second partition of a second set of partitions. The second partition may comprise a capture molecule 1520. The capture molecule 1520 may comprise a second barcode sequence and a sequence complementary to the probe capture sequence 1510 of the first probe 1506 (and/or the second probe 1516). The second barcode sequence may be a sequence that is common to the plurality of capture molecules in the second set of partitions, or the barcode sequence may be unique to the capture molecules in only the second partition (e.g., differ across partitions). The capture molecule 1520 may hybridize to the probe capture sequence 1510 to generate an additional barcoded molecule (also referred to herein as a "third barcoded nucleic acid molecule"). The additional barcoded molecule may comprise a sequence corresponding to the first barcode sequence (of the barcode molecule 1519), and a sequence corresponding to the second barcode sequence (of the capture molecule 1520).

In addition to barcoding of nucleic acid molecules, the present disclosure provides for methods of multiplexed analysis, e.g., processing of additional biomolecule types, such as proteins and peptides. The method may comprise providing a feature-binding group (e.g., antibody, protein, binding moiety, etc.), which may couple to or bind to a feature (e.g., protein, peptide) of a cell, nucleus or cell bead. Such a method may comprise providing a cell, nucleus or cell bead having a feature of interest (e.g., protein) and contacting the cell, nucleus or cell bead with the feature-binding group. The feature-binding group may couple to the feature of interest. The feature-binding group may comprise a reporter oligonucleotide comprising a reporter sequence coupled thereto, which may be specific for a particular feature and thus be used to identify the feature. For example, the feature-binding group may be an antibody and the reporter oligonucleotide may comprise a reporter sequence that identifies the antigen or binding moiety (e.g., epitope, epitope fragment) to which the antibody couples or binds. Alternatively or in addition to, the feature binding group may comprise a feature probe binding sequence, which may be used for downstream probe-binding and/or barcoding. Following the contacting of the cell (nucleus or cell bead) with the feature binding group, the cell/nucleus/cell bead may comprise the feature coupled to the feature binding group.

In some instances, the methods described herein may additionally comprise: providing a cell, nucleus or cell bead comprising (i) the nucleic acid molecule comprising the first target region and the second target region and (ii) the feature coupled to the feature binding group and contacting the cell, nucleus or cell bead with a plurality of probes. The cell/nucleus/cell bead may be contacted (e.g., in a first partition) with a first probe, a second probe, and a third probe. As described herein, the first probe and the second probe may associate with the first target region and the second target region of the nucleic acid molecule, thereby generating a first probe-associated molecule. Similarly, the third probe may associate with (e.g., via hybridization) with the feature binding group, thereby generating a second probe-associated molecule. In some instances, the third probe may comprise a third probe sequence that is complementary to the feature probe binding sequence, and in some instances, the third probe may additionally comprise a probe capture sequence. The first probe and/or the second comprise may also comprise a probe capture sequence, which may be the same or different than the probe capture sequence of the third probe.

In the first set of partitions, the first probe-associated molecule (e.g., the nucleic acid molecule with the first probe and the second probe associated therewith) and the second-probe-associated molecule (e.g., the feature binding group with the third probe associated therewith) may be barcoded. Such a barcoding operation may comprise, for example, providing barcode molecules comprising a first barcode sequence and a barcode-capture sequence such as a common sequence, which may hybridize directly with the first probe-associated molecule and the second probe-associated molecule, e.g., via the probe capture sequences. Alternatively or in addition to, the barcode molecules may be provided with probe-binding molecules which comprise (i) a probe binding sequence complementary to the probe capture sequence of the first probe, the second probe, and/or the third probe and (ii) a barcode binding sequence, which may be complementary to the common sequence of the barcode molecules. In some instances, the probe binding molecules and the barcode molecules may be provided as a pre-annealed complex. Barcoding of the first probe-associated molecule and the second probe-associated molecule may include hybridization of the barcode molecules (e.g., the barcode capture sequence such as a common sequence) to a portion (e.g., the probe capture sequence) of the first probe-associated molecule and the second probe-associated molecule, or the barcoding may include hybridization of the barcode molecules to the probe binding molecule and hybridization of the probe binding molecule to the first probe-associated molecule or the second probe-associated molecule. Additional operations such as ligation (e.g., enzymatic or chemical ligation) may be performed to generate the first barcoded molecule and the second barcoded molecule.

The first barcoded molecule and the second barcoded molecule may be subjected to additional barcoding operations, e.g., in a second set of partitions. Such additional barcoding operations may include: contacting the first barcoded nucleic acid molecule or derivative thereof to a first capture molecule of a plurality of capture molecules to generate a third barcoded nucleic acid molecule and contacting the second barcoded nucleic acid molecule or derivative thereof to a second capture molecule of the plurality of capture molecules to generate a fourth barcoded nucleic acid molecule. The capture molecules within a partition may each comprise a second barcode sequence, which may be unique to the partition (e.g., differ across partitions). Accordingly, both the third barcoded nucleic acid molecule and the fourth barcoded nucleic acid molecule may comprise a first barcode sequence (or complement thereof) and a second barcode sequence (or complement thereof).

Figure 16A:
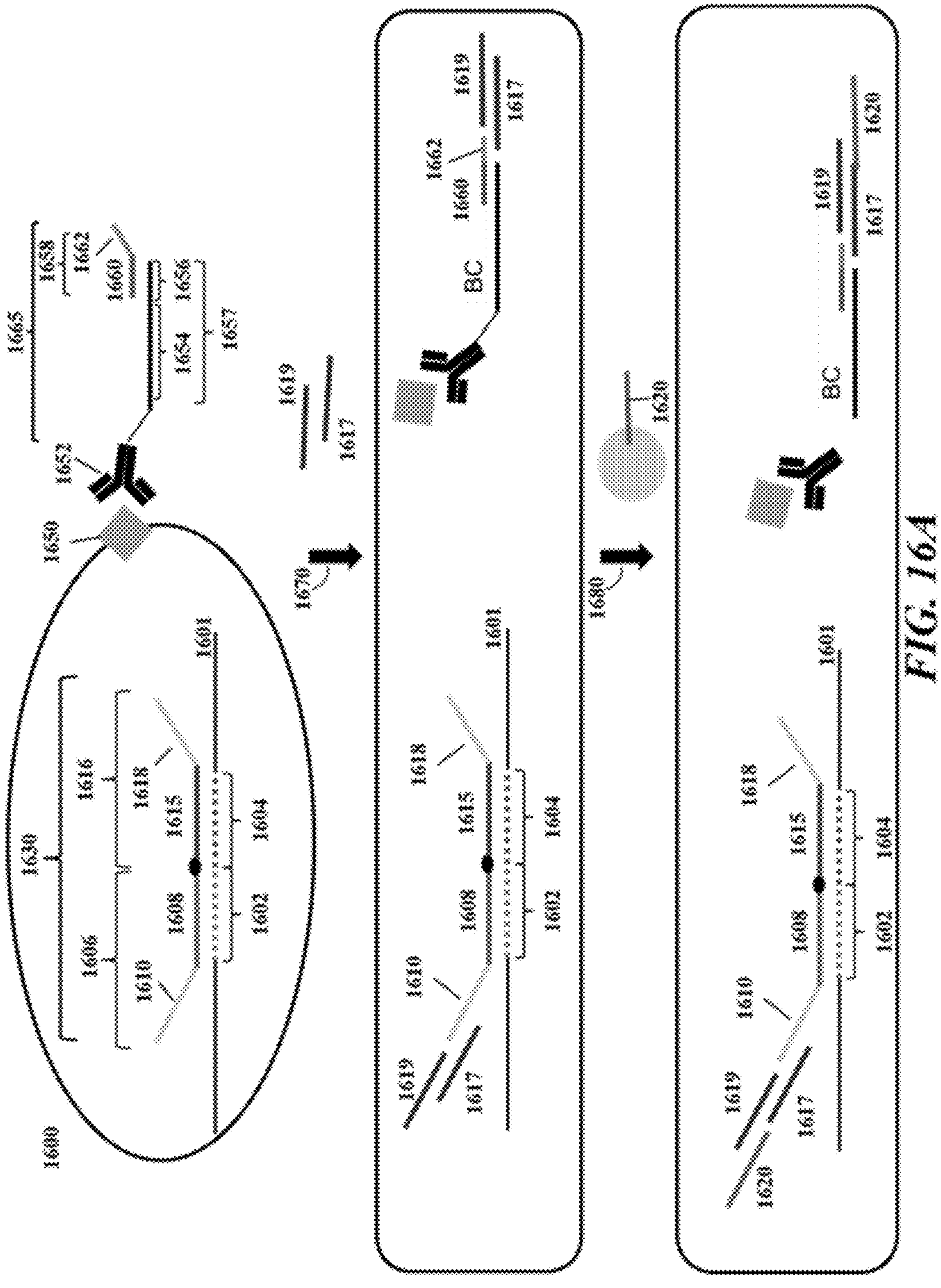
FIG. 16A shows an example workflow for processing multiple analytes in a partition.

FIG. 16A schematically illustrates an example workflow for barcoding multiple analytes of a cell, nucleus or cell bead. The cell, nucleus or cell bead 1600 may comprise a nucleic acid molecule (e.g., RNA molecule or other target nucleic acid molecule) 1601 comprising a first target region 1602 and a second target region 1604. The cell, nucleus or cell bead may additionally comprise a feature (e.g., a protein, such as a cell surface receptor (or nuclear membrane protein) or an intracellular/intranuclear protein) 1650. In some instances, the cell, nucleus or cell bead 1600 may be processed, e.g., fixed, permeabilized, treated with a treatment, etc. In some instances, such processing may include providing one or more feature binding groups (e.g., antibodies, antibody fragments, etc.) 1652, which may couple to the feature 1650. The feature binding group 1652 may comprise or be coupled to a reporter oligonucleotide 1657, which may comprise a reporter sequence 1654. The reporter sequence 1654 may be indicative of the feature binding group 1652 or feature 1650. For instance, the reporter sequence 1654 may be pre-indexed or assigned to a particular antibody or other feature binding group, such that presence of the reporter sequence 1654 indicates presence of the particular feature 1650 in a sample. The feature binding group 1652 or the reporter oligonucleotide 1657 may also comprise or be coupled to feature probe binding sequence 1656. In some instances, the cell, nucleus or cell bead 1600 may be contacted with the feature binding group 1652 and fixed, e.g., either in addition to or alternatively to a fixation and permeabilization operation before the contacting.

In some cases, the analysis of both intracellular and/or intranuclear proteins and membrane proteins of a cell (or nucleus) can be performed. In one embodiment, a permeabilized (and optionally fixed) cell (or nucleus) may be contacted with (i) one or more feature binding groups (or labeling agents) that are configured to couple to intracellular proteins (or intranuclear proteins) and/or (ii) one or more feature binding groups (or labeling agents) that are configured to couple to cell membrane proteins (or nuclear membrane proteins). As further described herein, permeabilization may involve partially or completely dissolving or disrupting a cell membrane (or nuclear membrane) or a portion thereof. Permeabilization may be achieved by, for example, contacting a cell membrane (or a nuclear membrane) with an organic solvent (e.g., methanol) or a detergent such as Triton® X-100 (t-Octylphenoxypolyethoxyethanol) or NP-40 (octylphenoxypolyethoxyethanol). The cell, nucleus, or cell bead may be fixed, as described elsewhere herein.

Referring again to FIG. 16A, a second feature binding group (or labeling agent) similar to 1652 (not shown) can be used to couple to an intracellular feature, such as an intracellular protein, and comprise or be coupled to a second reporter oligonucleotide, which may comprise a second reporter sequence. The second reporter sequence may be indicative of the second feature binding group or the intracellular feature. For instance, the second reporter sequence may be pre-indexed or assigned to a particular antibody or other feature binding group, such that presence of the second reporter sequence indicates presence of the particular intracellular feature in a sample. The second feature binding group or the second reporter oligonucleotide may also comprise or be coupled to a second feature probe binding sequence, similar to that of 1656.

The cell, nucleus or cell bead 1600 may be contacted with a first probe 1606, a second probe 1616, and a third probe 1658, under conditions sufficient to generate a first probe-associated molecule (or probe-associated complex) 1630 and a second probe-associated molecule (or probe-associated complex) 1665. The first probe-associated molecule 1630 may be or comprise a probe-linked molecule, as described elsewhere herein. For example, the first probe-associated molecule 1630 (or probe-linked molecule) may be any of the probe-associated molecules or probe-linked molecules described herein (e.g., generated from an extended probe, a barcoded extended probe, etc.). The first probe 1606 may comprise a first probe sequence 1608 and, optionally, a probe capture sequence 1610. The first probe sequence 1608 may be complementary to the first target region 1602. The second probe 1616 may comprise a second probe sequence 1615 and, optionally, a probe capture sequence 1618. The second probe sequence 1615 may be complementary to the second target region 1604. The third probe 1658 may comprise a third probe sequence 1660 and a probe capture sequence 1662. The third probe sequence 1660 may be complementary to the feature probe binding sequence 1656. In some instances, the probe capture sequence 1662 is the same probe capture sequence as the probe capture sequences 1610, 1618 of the first probe and/or the second probe, respectively.

In one embodiment, the cell, cell bead or nucleus 1600 may be further contacted with additional probes under conditions to generate additional probe-associated molecules or probe-associated complexes. The additional probe-associated molecule(s) may be or comprise a probe-linked molecule, as described elsewhere herein. For example, the additional probe-associated molecule(s) or probe-linked molecule(s) may be any of the probe-associated molecules or probe-linked molecules described herein (e.g., generated from an extended probe, a barcoded extended probe, etc.). In one embodiment, the cell (or cell bead or nucleus) 1600 may be further contacted with a fourth probe (not shown) similar to 1658 which comprises (i) a fourth probe sequence similar to 1660 and (ii) a fourth probe capture sequence similar to 1662. The fourth probe sequence may be complementary to the second feature probe binding sequence, as further described herein. In some instances, the fourth probe capture sequence is the same probe capture sequence as the probe capture sequences 1610, 1618 of the first probe and/or the second probe, respectively.

In one embodiment, the cell, nucleus or cell bead 1600 may be partitioned into a first partition of a first set of partitions prior to any processing operations described above including, without limitation, fixing, permeabilizing, contacting with probes, and generating probe-associated or probe-linked molecules. In another embodiment, the cell, nucleus or cell bead 1600 may be fixed and optionally permeabilized prior to partitioning in the first partition and then subsequently processed in the first partition, e.g., contacting with probes and generating molecules.

In operation 1670, the cell, nucleus or cell bead 1600 comprising the first probe-associated molecule 1630 and the second probe-associated molecule 1665 may be partitioned into a first partition of a first set of partitions or further processed in the first partition. In another embodiment, the cell, cell bead or nucleus 1600 may further comprise additional probe-associated molecules or complexes. For instance, referring to FIG. 16A, 1600 may comprise a third probe-associated complex (not shown) that is similar to 1665 but comprises (i) a fourth probe comprising a fourth probe sequence complementary to the second feature probe binding sequence and (ii) a reporter oligonucleotide (similar to 1657) as further described herein. The reporter oligonucleotide may be provided as part of or coupled to the second feature binding group, e.g., a feature binding group configured to couple to an intracellular protein. In some instances, the cell, nucleus or cell bead 1600 may be subjected to processing within the partition, such as lysis, to release the cellular/nuclear components (e.g., the first probe-associated molecule and the second probe-associated molecule) within the partition. Alternatively, the cell, nucleus or cell bead 1600 may remain intact. In one embodiment, the cell bead is processed to release cellular components while keeping the cell bead intact. Within the first partition, a probe binding molecule 1617 and a barcode molecule 1619 may be provided. The first probe-associated molecule 1630 and the second probe-associated molecule 1665 may be contacted with one or more probe binding molecules 1617 and barcode molecules 1619. In some examples, the first partition further comprises one or more additional probe-associated molecules or complexes similar to 1665 (not shown). The additional probe-associated complex may comprise the third probe-associated complex described above, which comprises a fourth probe and a reporter oligonucleotide for a second feature binding group, e.g., a feature binding group configured to couple to an intracellular protein. Additional probe-associated complexes, such as the third probe-associated complex, may be contacted with one or more probe binding molecules 1617 and barcode molecules 1619. In one embodiment, the contacting of a cell, nucleus or cell bead 1600 in the first partition with one or more probe binding molecules may be simultaneously as the contacting with the probes (e.g., 1606, 1616, 1658 and optionally the fourth probe) as described above. The barcode molecules 1619 may comprise a barcode capture sequence or a common sequence common to a plurality of barcode molecules and a first barcode sequence common to the first partition of the first set of partitions. The nucleic acid barcode molecule may, in some instances, be coupled to a bead, such as a gel bead, or other support, as described herein, and can comprise additional functional sequences, including, but not limited to, a unique molecular identifier (UMI), a capture sequence, a primer sequence (e.g., a R1/R2 sequence), additional barcode sequence segments, etc., The probe binding molecules 1617 may comprise a probe binding sequence complementary to any or a combination of the probe capture sequences 1610, 1618, 1662, a fourth probe capture sequence, and a barcode binding sequence complementary to the common sequence of the barcode molecule 1619. In some instances, the probe binding molecules 1617 and the barcode molecules 1619 may be provided as a pre-annealed complex. The probe binding molecules 1617 and the barcode molecules 1619 may hybridize to the first probe-associated molecule 1630 and the second probe-associated molecule 1665 and/or an additional probe-associated complex, such as the third probe-associated complex (e.g., via hybridization of the probe binding molecules 1617 to the probe capture sequences 1610, 1618, 1662, and the fourth probe capture sequence), thereby generating a first barcoded nucleic acid molecule and a second barcoded nucleic acid molecule, and optionally additional barcoded nucleic acid molecules. Additional processing may occur within the first partition, e.g., ligation of the barcode molecules 1619 to the probes (1606, 1616, 1658 or the fourth probe). In one additional embodiment, the additional barcoded nucleic acid molecule is generating using an additional probe-associated complex, e.g., the third probe-associated complex (not shown), probe binding molecules 1617 and barcode molecules 1619.

Figure 16B:
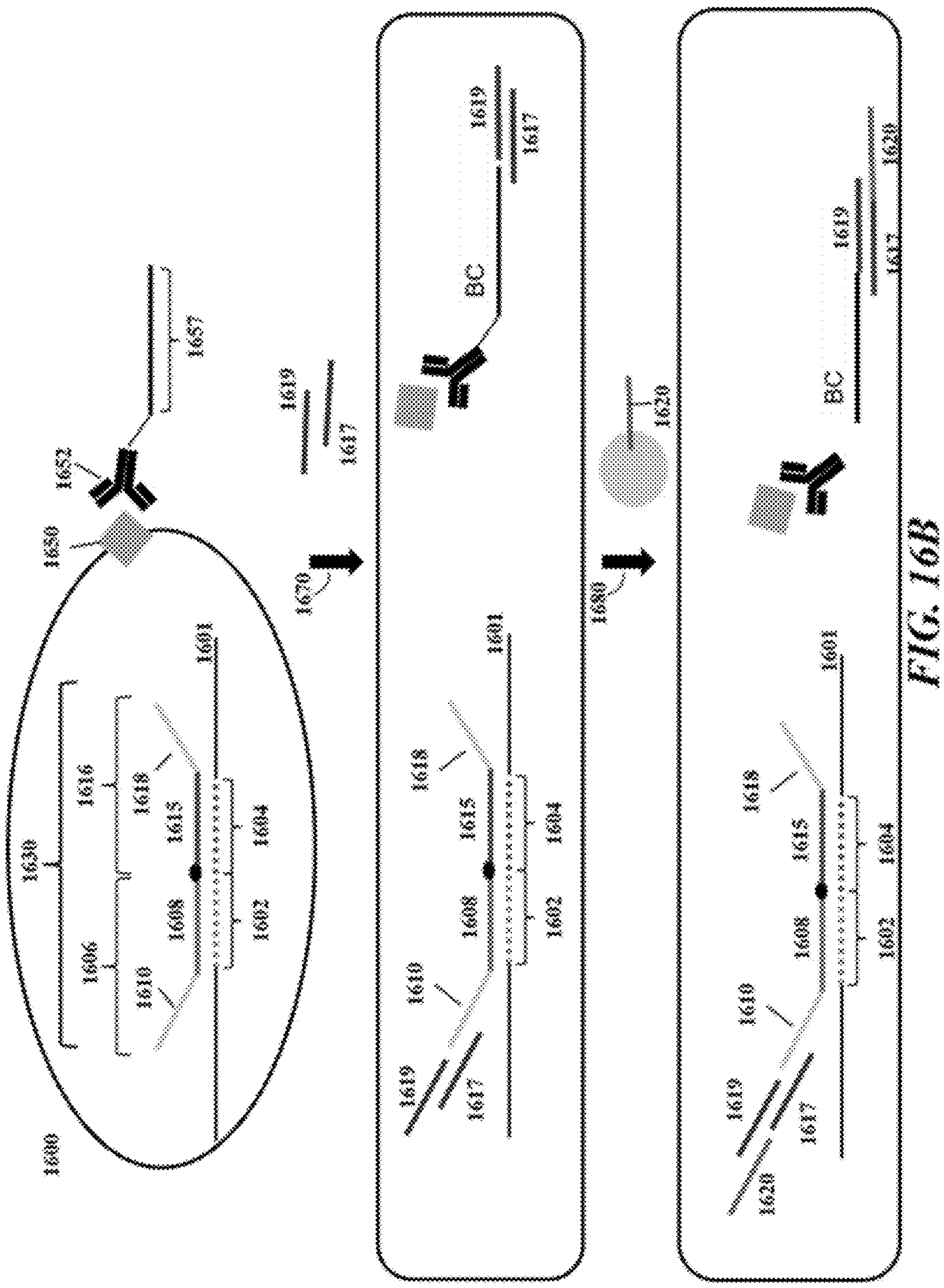
FIG. 16B shows another example workflow for processing multiple analytes in a partition.

In operation 1680, the contents of each partition or a subset of the first set of partitions may be collected from the first set of partitions, e.g., from operation 1670, and re-partitioned into a second set of partitions. The contents of the first set of partitions may comprise the cell, nucleus or cell bead 1600 and/or the processed cellular or nuclear components, e.g., the first barcoded nucleic acid molecule, the second barcoded nucleic acid molecule, and optionally the additional barcoded nucleic acid molecule(s). The contents of the partitions of the first set of partitions may be pooled together and re-distributed to a second set of partitions. Accordingly, a second partition of the second set of partitions may comprise the cell, nucleus or cell bead 1600 and/or the processed cellular/nuclear components. In some instances, the cell, nucleus or cell bead 1600 may be subjected to processing within the second partition, such as lysis, to release the cellular/nuclear components (e.g., the first barcoded nucleic acid molecule, the second barcoded nucleic acid molecule, and optionally the additional barcoded nucleic acid molecule(s)) within the second partition. Alternatively, the cell, nucleus or cell bead 1600 may remain intact. Within the second partition, a plurality of capture molecules 1620 may be provided. In some instances, the plurality of capture molecules 1620 may be coupled to a support (e.g., a particle, bead, gel bead, etc.). In some instances, the plurality of capture molecules 1620 may be releasably coupled to the support and the plurality of capture molecules 1620 may be released in the second partition. The capture molecules 1620 may each comprise a second barcode sequence, which may be the same sequence or a different sequence as the first barcode sequence (of the barcode molecule 1619). The second barcode sequence may be unique to the second partition and differ from the second barcode sequences of other partitions of the second set of partitions. The first barcoded nucleic acid molecule and the second barcoded nucleic acid molecule may each be contacted with a capture molecule 1620. The capture molecules 1620 may comprise a second barcode capture sequence, which may be complementary to a sequence of the barcode molecule 1619. Hybridization of the capture molecules 1620 to the first barcoded molecule and the second barcoded nucleic acid molecule may be sufficient to generate a third barcoded nucleic acid molecule and a fourth barcoded nucleic acid molecule. In addition, hybridization of capture molecules 1620 to the additional barcoded nucleic acid molecule(s), e.g., from additional reporter oligonucleotides 1657 on additional feature binding groups 1652, may be sufficient to generate a fifth barcoded nucleic acid molecule. Alternatively, hybridization of the capture molecules 1620 to the first barcoded molecule and the second barcoded nucleic acid molecule may be sufficient to couple the capture molecule (comprising the second barcode sequence) to both the first barcoded molecule and the second barcoded nucleic acid molecule. In addition, hybridization of a capture molecule 1620 to the additional barcoded nucleic acid molecule may be sufficient to couple the capture molecule (comprising the second barcode sequence) to the additional barcoded nucleic acid molecule. Optionally, further processing may be performed, e.g., ligation of the capture molecules 1620 to the first barcoded nucleic acid molecule and the second barcode nucleic acid molecule (and optionally the additional barcoded nucleic acid molecule). Following ligation, the first and second barcoded nucleic acid molecule may comprise the capture molecule 1620. The third barcoded nucleic acid molecule, the fourth barcoded nucleic acid molecule, and the fifth barcoded nucleic acid molecule may each comprise a sequence corresponding to the first barcode sequence and a sequence corresponding to the second barcode sequence. In some instances, an extension reaction is performed (e.g., from the capture molecule 1620 toward the reporter oligonucleotide sequence 1657) to generate the fourth barcoded molecule and/or the fifth barcoded nucleic acid molecule. FIG. 16B schematically illustrates another example workflow for barcoding multiple analytes of a cell, nucleus or cell bead. In such an example, the workflow for processing a nucleic acid molecule (e.g., RNA molecule) may be substantially similar to that depicted in FIG. 16A, but the workflow for processing a feature (e.g., protein) may differ. For instance, the feature binding group 1652 or the reporter oligonucleotide 1657 may comprise a binding sequence that is capable of hybridizing to a probe binding molecule 1617 and/or barcode molecule 1619.

As described herein, a permeabilized (and optionally fixed) cell or nucleus may be contacted with one or more feature binding groups 1652, which may (a) comprise the reporter oligonucleotide 1657 and (b) be configured to couple to (i) an intracellular protein (or an intranuclear protein) or (ii) a cell membrane protein (or nuclear membrane protein). In some embodiments, the one or more feature binding groups 1652 includes (i) a first feature binding group that comprises the reporter oligonucleotide 1657 and is configured to couple to an intracellular (or an intranuclear protein) and (ii) a second feature binding group that comprises the reporter oligonucleotide 1657 and is configured to couple to a cell membrane protein (or a nuclear membrane protein).

In operation 1670, the cell, nucleus or cell bead 1600 comprising the first probe-associated molecule 1630 and the one or more feature binding group 1652 may be partitioned into a first partition of a first set of partitions or further processed in the first partition. Within the first partition, a probe binding molecule 1617 and a barcode molecule 1619 may be provided. The feature binding group 1652 (e.g., one or more feature binding groups configured to couple to an intracellular protein or an intranuclear protein) coupled to the reporter oligonucleotide 1657 may be contacted with one or more probe binding molecules 1617 and barcode molecules 1619. A barcode molecule 1619 may comprise a barcode capture sequence or a common sequence common to a plurality of barcode molecules and a first barcode sequence common to the first partition of the first set of partitions. The nucleic acid barcode molecule may, in some instances, be coupled to a bead, such as a gel bead, or other support, as described herein, and can comprise additional functional sequences, including, but not limited to, a unique molecular identifier (UMI), a capture sequence, a primer sequence (e.g., a R1/R2 sequence), additional barcode sequence segments, etc., The probe binding molecules 1617 may comprise a probe binding sequence complementary to a sequence of the reporter oligonucleotide 1657. In some instances, the probe binding molecules 1617 and the barcode molecules 1619 may be provided as a pre-annealed complex. The probe binding molecules 1617 and the barcode molecules 1619 may hybridize to the first probe-associated molecule 1630 (as described above) and the reporter oligonucleotide 1657 (e.g., via hybridization of the probe binding molecules 1617 to a sequence of the reporter oligonucleotide 1657), thereby generating a first barcoded nucleic acid molecule and a second barcoded nucleic acid molecule. Additional barcoded nucleic acid molecules may be generated using additional reporter oligonucleotides 1657 from additional feature binding groups 1652 (e.g., configured to couple to cell or nuclear membrane proteins and/or intracellular or intranuclear proteins). Additional processing may occur within the first partition, e.g., ligation of the barcode molecules 1619 to the probes (1606, 1616) or to the reporter oligonucleotide 1657.

In operation 1680, the contents of each partition or a subset of the first set of partitions may be collected from the first set of partitions, e.g., from operation 1670, and re-partitioned into a second set of partitions. The contents of the first set of partitions may comprise the cell, nucleus or cell bead 1600 and/or the processed cellular/nuclear components, e.g., the first barcoded nucleic acid molecule, the second barcoded nucleic acid molecule, and optionally the additional barcoded nucleic acid molecule(s). The contents of the partitions of the first set of partitions may be pooled together and re-distributed to a second set of partitions. Accordingly, a second partition of the second set of partitions may comprise the cell, nucleus or cell bead 1600 and/or the processed cellular/nuclear components (e.g., barcoded products). In some instances, the cell, nucleus or cell bead 1600 may be subjected to processing within the second partition, such as lysis, to release the cellular/nuclear components (e.g., the first barcoded nucleic acid molecule, the second barcoded nucleic acid molecule, and optionally the additional barcoded nucleic acid molecule(s)) within the second partition. Alternatively, the cell, nucleus or cell bead 1600 may remain intact. Within the second partition, a plurality of capture molecules 1620 may be provided. In some instances, the plurality of capture molecules 1620 may be coupled to a support (e.g., a particle, bead, gel bead, etc.). In some instances, the plurality of capture molecules 1620 may be releasably coupled to the support and the plurality of capture molecules 1620 may be released in the second partition. The capture molecules 1620 may each comprise a second barcode sequence, which may be the same sequence or a different sequence as the first barcode sequence (of the barcode molecule 1619). The second barcode sequence may be unique to the second partition and differ from the second barcode sequences of other partitions of the second set of partitions. The first barcoded nucleic acid molecule and the second barcoded nucleic acid molecule may each be contacted with a capture molecule 1620. The capture molecules 1620 may comprise a second barcode capture sequence, which may be complementary to a sequence of the barcode molecule 1619. Alternatively, the capture molecules 1620 may comprise a sequence complementary to an additional probe-binding molecule (e.g., splint oligonucleotide, not shown), and the probe-binding molecule may comprise a sequence complementary to a sequence of the barcode molecule 1619. Hybridization of the capture molecules 1620 to the first barcoded molecule and the second barcoded nucleic acid molecule (or to the additional probe-binding molecule, which may hybridize to the first barcoded molecule and the second barcoded molecule) may be sufficient to generate a third barcoded nucleic acid molecule and a fourth barcoded nucleic acid molecule. In addition, hybridization of 1620 to the additional barcoded nucleic acid molecule(s), e.g., from additional reporter oligonucleotides 1657 on additional feature binding groups 1652, may be sufficient to generate a fifth barcoded nucleic acid molecule. Alternatively, hybridization of the capture molecules 1620 to the first barcoded molecule and the second barcoded nucleic acid molecule may be sufficient to couple the capture molecule (comprising the second barcode sequence) to both the first barcoded molecule and the second barcoded nucleic acid molecule. In addition, hybridization of 1620 to the additional barcoded nucleic acid molecule may be sufficient to couple the capture molecule (comprising the second barcode sequence) to the additional barcoded nucleic acid molecule e.g., generated from additional reporter oligonucleotides 1657 on additional feature binding groups 1652. Optionally, further processing may be performed, e.g., performing an extension reaction, ligation of the capture molecules 1620 to the first barcoded nucleic acid molecule, the second barcode nucleic acid molecule, and optionally the additional barcoded nucleic acid molecule. Following ligation, the first and second barcoded nucleic acid molecule may comprise the capture molecule 1620. The third barcoded nucleic acid molecule, the fourth barcoded nucleic acid molecule, and the fifth barcoded nucleic acid molecule may each comprise a sequence corresponding to the first barcode sequence and a sequence corresponding to the second barcode sequence. In some instances, an extension reaction is performed (e.g., from the capture molecule 1620 toward the reporter oligonucleotide sequence 1657) to generate the fourth barcoded molecule and/or the fifth barcoded nucleic acid molecule.

Figure 17:
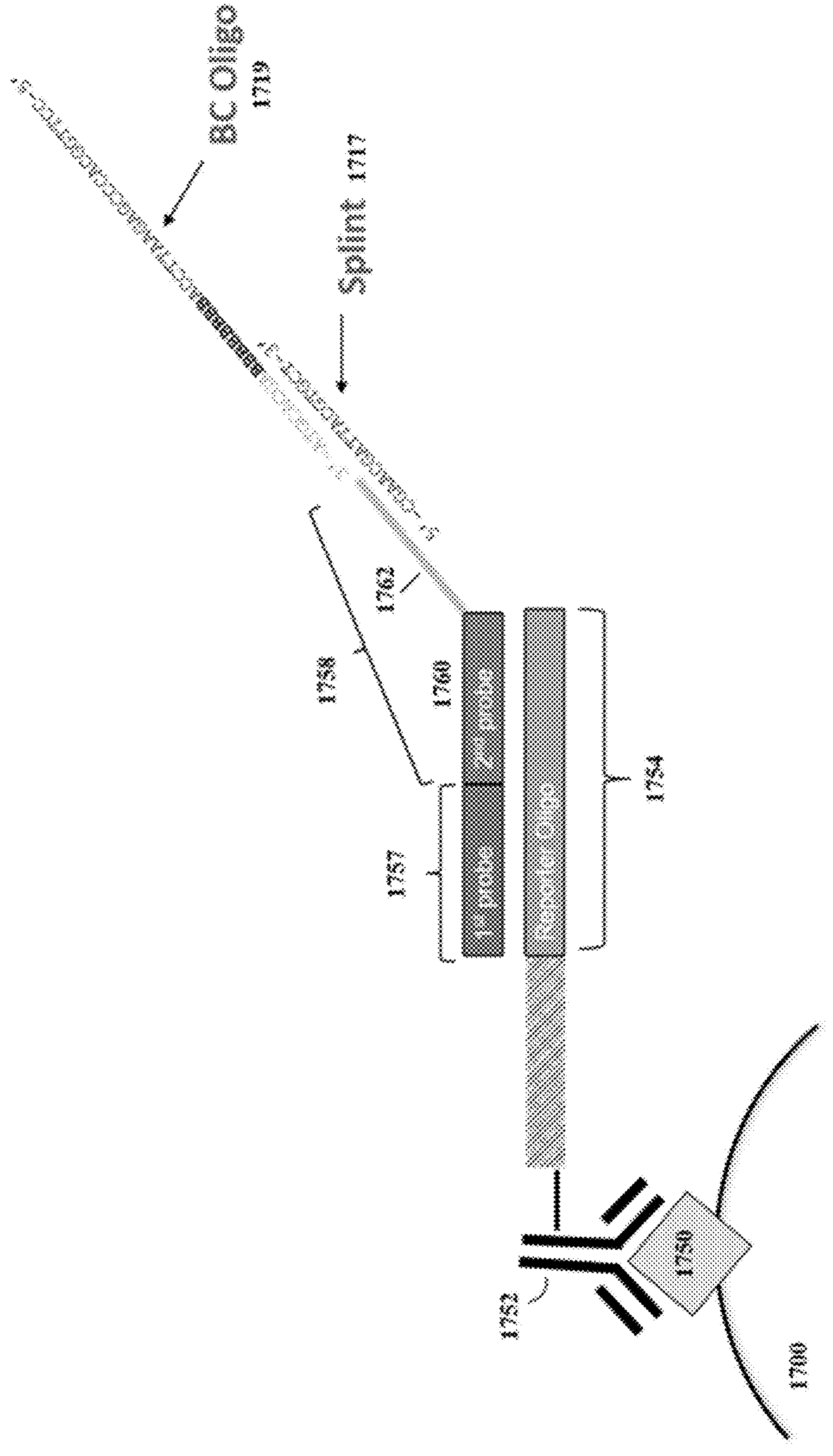
FIG. 17 schematically shows a feature-binding group described herein.

In some instances, the reporter oligonucleotide (comprising the reporter sequence) of the feature binding group may be contacted with a plurality of probes. For example, it may be beneficial for the feature binding group to be contacted with a pair of probes. In some instances, the reporter oligonucleotide comprises one or more feature probe binding sequences, which may comprise sequences complementary to the pair of probes. For example, referring to FIG. 17, a cell, nucleus or cell bead 1700 may comprise a feature (e.g., a protein such as a cell/nuclear membrane protein or an intracellular/intranuclear protein) 1750. A feature binding group 1752 may be coupled to the feature 1750. The feature binding group 1752 may comprise or be coupled to an oligonucleotide comprising a reporter oligonucleotide (comprising a reporter sequence) 1754 and, in some instances, additional functional sequences, such as primer sequences, sequencing primer sequences, UMIs, etc., as described elsewhere herein. The reporter oligonucleotide 1754 may comprise any number of target regions. For example, the reporter oligonucleotide 1754 may comprise two target regions to which a first probe 1757 and a second probe 1758 may hybridize. The two target regions may be adjacent or non-adjacent, and they may be disposed on the same strand of the reporter oligonucleotide 1754. As described herein, the probes may comprise sequences that are complementary to the target regions of the reporter oligonucleotide 1754, and each probe may comprise other useful sequences. For example, a probe (e.g., the first probe 1757 or the second probe 1758) may comprise (i) a probe sequence (e.g., 1760) complementary to a target region of the reporter oligonucleotide 1754, and (ii) a probe capture sequence 1762, which may be complementary to a sequence of a probe binding molecule 1717 (also referred to as a splint or splint oligonucleotide). The probe binding molecule 1717 may also comprise a sequence complementary to a sequence (e.g., capture sequence) of a barcode molecule 1719. Such barcoding (e.g. hybridization of the probe binding molecule 1717 and barcode molecule 1719 to the probe capture sequence 1762) may occur in bulk or in a partition. In some embodiments, barcoding may be performed without a probe binding molecule. For example, the barcode molecule 1719 may comprise a sequence complementary to the probe capture sequence 1762 and directly anneal to the probe.

In some instances, after contacting the feature binding group with the probe molecules 1757 and 1758 (e.g., in bulk or in a partition), the feature binding group 1752 is subjected to conditions sufficient for hybridization of the probe molecules to the reporter oligonucleotide 1754, thereby generating a probe-associated reporter oligonucleotide complex. The coupling of the probes to the reporter oligonucleotide 1754 may occur in bulk or in a partition. In some instances, following coupling or hybridization of the probes to the reporter oligonucleotide 1754, the probes may be linked together (e.g., enzymatically or chemically), thereby generating a probe-linked nucleic acid molecule (or complex). For example, the first probe 1757 may comprise a first reactive moiety and the second probe 1758 may comprise a second reactive moiety. The reactive moieties may be positioned such that, following hybridization of the first probe 1757 and the second probe 1758 to the reporter oligonucleotide 1754, the reactive moieties are adjacent. The reactive moieties may then be subjected to conditions sufficient to cause them to react to yield a probe-linked nucleic acid molecule (or complex) comprising the first probe 1757 linked to the second probe 1758. In some instances, the probes comprise "click chemistry" moieties. Alternatively or in addition to, the first probe may be enzymatically linked (e.g., via ligation) to the second probe. In other instances, a gap region (not shown) may be disposed between the first probe 1757 and the second probe 1758, following hybridization of the probes to the reporter oligonucleotide 1754. In such cases, the first probe 1757 may be linked to the second probe 1758 using a gap-fill approach, such as those described above.

The probe-linked nucleic acid molecule (or complex) may then be subjected to barcoding (e.g., contacting with the probe binding molecule 1717 and the barcode molecule 1719), which may occur in a partition. Alternatively, the barcoding may occur prior to the linking of the probes. For example, the reporter oligonucleotide 1754 may be hybridized to the probes, partitioned, barcoded, and then the probes may be linked. Alternatively, the reporter oligonucleotide 1754 may be hybridized to the probes, linked, partitioned, then barcoded. In yet another example, the reporter oligonucleotide 1754 may be hybridized to the probes, partitioned, linked, then barcoded. As will be appreciated, the operations described herein (e.g., hybridization, probe-linking, barcoding) may occur at any useful process, or in any useful order. In some instances, multiple partitioning operations maybe performed, e.g., for combinatorial barcoding.

The reporter oligonucleotide may comprise the same target sequences (e.g., 702, 704, 802, 804, 902, 904, 1502, 1504, 1602, 1604, etc.) as the nucleic acid molecule (e.g., RNA molecule). For example, referring to FIG. 17, the first probe may have a first sequence that is complementary to both the first target sequence of a nucleic acid molecule (e.g., 702, 802, 902, 1502, 1602) and a first sequence of the reporter oligonucleotide 1754, and the second probe may have a second sequence that is complementary to both the second target sequence of a nucleic acid molecule (e.g., 704, 804, 904, 1504, and 1604) and a second sequence of the reporter oligonucleotide 1754. In such instances, the provision of just two probe types (e.g., a first probe and a second probe) to a cell, nucleus or cell bead may be sufficient to generate the first barcoded molecule (e.g., generated from the nucleic acid molecule, e.g., RNA molecule), the second barcoded molecule (e.g., generated from the reporter oligonucleotide of the feature binding group, such as a group configured to couple to a cell/nuclear membrane protein), and additional barcoded molecules (e.g., generated from the reporter oligonucleotide of an additional feature binding group, such as a group configured to couple to an intracellular/intranuclear protein). As described herein, each of the probes (e.g., the first probe and the second probe) may be capable of or configured to hybridize to a barcode molecule (e.g., in the first partition) and/or a capture molecule. As is also described elsewhere herein, each of the probes may be multiplexed or combinatorially barcoded, such that multiplet partitions (e.g., partitions comprising more than one cell, one nucleus or cell bead) may be deconvolved, for example to determine the originating partition or sample of each cell, nucleus or cell bead within a partition (see, e.g., FIG. 10). Similarly, the barcoded molecules may be used to determine the origin of different analyte types (e.g., proteins, nucleic acid molecule, etc.); for example, two analyte types may be attributed to the same originating cell, nucleus, cell bead, sample, or partition(s).

In some instances, the reporter oligonucleotide comprises two or more target sequences which are different than the target sequences of the nucleic acid molecule (e.g., RNA molecule). Accordingly, four probe types may be provided for performing multiplexed assays; a first probe and a second probe may hybridize to a first target region and a second target region of a nucleic acid molecule, and a third probe and a fourth probe may hybridize to target regions of a reporter oligonucleotide (e.g., a reporter oligonucleotide from a feature binding group, such as a feature binding group configured to couple to a cell/nuclear membrane protein). Additional probe types may be provided, such as a fifth probe and a sixth probe, that hybridize to target regions of an additional reporter oligonucleotide (e.g., a reporter oligonucleotide from a feature binding group, such as a feature binding group configured to couple to an intracellular/intranuclear protein). Each of the probes or a combination of the probes may comprise probe capture sequences, which may be used for subsequent barcoding. For example, each of the probes (e.g., the first probe, the second probe, the third probe, the fourth probe, fifth probe, sixth probe, or a combination thereof) may be capable of or configured to hybridize to a barcode molecule (e.g., in the first partition) and/or a capture molecule (e.g., in a second partition). As is described elsewhere herein, each of the probes may be multiplexed or combinatorially barcoded, such that multiplet partitions (e.g., partitions comprising more than one cell, nucleus or cell bead) may be deconvolved, for example to determine the originating partition or sample of each cell, nucleus or cell bead within a partition (see, e.g., FIG. 10). Similarly the barcoded molecules may be used to determine the origin of different analyte types (e.g., proteins, nucleic acid molecules, etc.); for example, two analyte types may be attributed to the same originating cell, nucleus, cell bead, sample, or partition(s).

As described elsewhere herein, the nucleic acid molecules (e.g., from a cell, a nucleus or cell bead, or a reporter oligonucleotide) may comprise one or more target regions. The one or more target regions may correspond to a gene or a portion thereof, or another known sequence. The target regions may have the same or different sequences, and may be located within the same strand or on different strands. The target regions may be located adjacent to one another or may be spatially separated along a strand of the nucleic acid molecule. The target regions may be located on the same strand or different strands. Analyzing two or more target regions may involve providing two or more probes, where a first probe has a sequence that is complementary to the first target region, a second probe has a sequence that is complementary to the second target region, etc. As described elsewhere herein, the nucleic acid molecule may be a target nucleic acid molecule and may comprise any number of nucleic acid features or nucleotides.

As is also described elsewhere herein, any of the probes (e.g., the first probe, the second probe, the third probe, etc.), reporter oligonucleotides, or the barcode or capture molecules, may comprise any number of additional adaptor or functional sequences, such as an additional probe sequence, a unique molecule identifier, a barcode sequence, a primer sequence, a capture sequence, a sequencing primer sequence, etc.

As described herein, one or more operations may be performed within a partition, such as a droplet or well. For instance, the nucleic acid molecule (e.g., RNA molecule) and the feature (e.g., protein), or a cell, nucleus or cell bead comprising the nucleic acid molecule and feature, may be co-partitioned with one or more reagents (e.g., as described herein) at any useful stage of the method. For example, the probe-linked or probe-associated nucleic acid molecule, optionally comprised within or on a cell, nucleus or cell bead, may be generated in a bulk solution or in a partition. Similarly, the cell, nucleus or cell bead may be contacted with a feature binding group in a bulk solution or in a partition. Provision of the probes (e.g., the first probe, the second probe, and the third probe) may occur in the bulk solution or in individual partitions. In the instances where partitions are used, a partition (e.g., a first partition of a first set of partitions) may comprise the first probe, the second probe, the third probe, or a combination thereof. Different partitions within the first set of partitions may comprise the same or different probes (e.g., for different target sequences or different reporter sequences). Alternatively or in addition to, the probe binding molecules and the nucleic acid barcode molecules may be provided in a partition. For example, the cell, nucleus or cell bead comprising the feature and the nucleic acid molecule may be contacted with the probes in bulk, and partitioned into a first set of partitions. The first set of partitions may comprise the probe binding molecule and the nucleic acid barcode molecules comprising a common sequence. Different partitions among the first set of partitions may comprise barcode molecules with different barcode sequences; for instance, an additional partition of the first set of partitions may comprise numerous barcode molecules that each have a barcode sequence that is unique to the partition (e.g. differs across partitions). The partition may comprise additional reagents for performing a nucleic acid reaction (e.g., digestion, ligation, extension, amplification). For example, the partition may comprise a linking enzyme (e.g., ligase), which may be used to ligate the nucleic acid barcode molecule to the first probe, the second probe, or the third probe (e.g., via the probe capture sequence of each probe). In some instances, the probe binding molecule, the probe capture sequence, and/or the barcode capture sequence (e.g., common sequence) comprises one or more reactive moieties, which may be used to chemically link the nucleic acid barcode molecule to the probe capture sequence. The resultant barcoded products may comprise: a first barcoded product comprising a sequence corresponding to the first target region, a sequence corresponding to the second target region, a sequence corresponding to the probe capture sequence of the first probe or the second probe, and a sequence corresponding to the barcode sequence; and a second barcoded product comprising a sequence corresponding to the reporter sequence, the probe capture sequence of the third probe (which may be the same or different than that of the first probe or second probe), and the barcode sequence.

As described herein, one or more processes described herein may be performed in a cell (e.g., a cell in solution, or a cell comprised within a tissue sample), nucleus or cell bead. For example, a plurality of cells, nuclei or cell beads may comprise a plurality of nucleic acid molecules and features. The cells, nuclei or cell beads may be alive or fixed and/or permeabilized. In some instances, the cells, nuclei or cell beads may be contacted with a feature binding group comprising a reporter sequence. The first probe, the second probe, and the third probe may also be provided to the cells, nuclei or cell beads, in bulk solution or in a partition to generate the first probe-associated molecule and the second probe-associated molecule. Optionally, the cells, nuclei or cell beads may be washed to remove unbound probes.

Subsequently, the cells, nuclei or cell beads comprising the probe-associated molecules may be partitioned into a plurality of separate partitions, where at least a subset of the plurality of separate partitions comprises a single cell, single nucleus, or single cell bead. Barcoding may be performed within the separate partitions. Barcoding, as described herein, may comprise attaching or hybridizing a nucleic acid barcode molecule to the first probe-associated molecule and the second probe-associated molecule. The nucleic acid barcode molecules provided within each partition of the plurality of separate partitions may be provided attached to beads. In some instances, as described elsewhere herein, the nucleic acid barcode molecule may be releasably attached to a bead (e.g., via a labile bond). Each partition (or a subset of partitions) of the plurality of separate partitions may comprise a bead comprising a plurality of nucleic acid barcode molecules attached thereto (e.g., as described herein). The plurality of nucleic acid barcode molecules attached to each bead may comprise a unique barcode sequence, such that each partition of the plurality of separate partitions comprises a different barcode sequence. Upon release of components from the plurality of different partitions of the plurality of separate partitions (e.g., following barcoding), the barcoded molecules arising from a single cell, single nucleus, or single cell bead may have a same barcode sequence (e.g., a common barcode sequence), such that each barcoded nucleic acid molecule can be traced to a given partition and/or, in some instances, a single cell, a single nucleus, or a single cell bead. The released components may then be partitioned, as described herein, in a second set of partitions comprising capture molecules with a second barcode sequence, such that different partitions of the second set of partitions have a unique second barcode sequence.

The cells, nuclei, or cell beads described herein may be processed either prior to, during, or following barcoding. For example, the cells, nuclei, or cell beads may be fixed or permeabilized at any useful point in time. In some instances, the cells, nuclei, or cell beads may be fixed and permeabilized prior to or following hybridization of the probes, or prior to or following contact with the feature binding groups. In some instances, the cells, nuclei, or cell beads may be fixed and permeabilized prior to contact with the feature binding groups, and then contacted with the probes. The fixation or permeabilization process may be repeated. For example, a cell, nucleus, or cell bead may be fixed and permeabilized, contacted with the probes and the feature binding groups (either simultaneously or in a step-wise fashion), and then fixed again.

Following fixation and/or permeabilization, the cells, nuclei, or cell beads may be stored for a duration of time prior to further processing, e.g., contacting the cells, nuclei, or cell beads with the probes and/or feature binding groups. For example, the cells, nuclei, or cell beads may be fixed and/or permeabilized and then contacted with the probes and/or feature binding groups after about 1 minute, 10 minutes, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more. The cells, nuclei, or cell beads may be fixed and/or permeabilized and then contacted with the probes and/or feature binding groups after about 1 day, 2 days, 3 days, 4 days, 5 days, 6 days, 7 days or more. The cells, nuclei, or cell beads may be fixed and/or permeabilized and then contacted with the probes and/or feature binding groups after about 1 week, 2 weeks, 3 weeks, 4 weeks, 5 weeks, 6 weeks, 7 weeks, 8 weeks, 9 weeks, 10 weeks, 20 weeks, 30 weeks, 40 weeks, 50 weeks or more. The cells, nuclei, or cell beads may be fixed and/or permeabilized and then contacted with the probes and/or feature binding groups after about 1 month, 2 months, 3 months, 4 months, 5 months, 6 months, 7 months, 8 months, 9 months, 10 months, 11 months, 12 months, or more. The cells, nuclei, or cell beads may be fixed and/or permeabilized and then contacted with the probes and/or feature binding groups at any useful time, which may fall within a range of times, e.g., after about 2-5 weeks, after about 3-6 months, after about 1-2 years, etc.

In some instances, the cells, nuclei, or cell beads may be frozen, e.g., subsequent to fixation and/or permeabilization. Such freezing of the cells, nuclei, or cell beads may be useful in storage of samples for longer durations, e.g., if a sample is to be stored for greater than 1-2 weeks prior to contacting the sample with the probes and/or feature binding groups. For example, the cells, nuclei, or cell beads may be fixed, optionally permeabilized, and then frozen for any useful duration of time, followed by contacting of the cells, nuclei, or cell beads with the probes and/or feature binding groups. Alternatively, the cells, nuclei, or cell beads may be fixed, frozen, and permeabilized, either prior to or following contacting of the cells, nuclei or cell beads with the probes and/or feature binding groups. As will be appreciated, the freezing operation may be performed at any useful or convenient time, e.g., prior to, concurrently with, or following fixation, permeabilization, contacting with probes, contacting with feature binding groups, etc.

The cells, nuclei, or cell beads may be contacted with the probes and feature binding groups at any useful time, in partitions or in bulk. For example, the cells, nuclei, or cell beads may be contacted with the probes prior to, during, or following contact with the feature binding groups. Contact with the probes and/or feature binding groups may occur in bulk or in partitions (e.g., droplets, wells). In some instances, the cells, nuclei, or cell beads may be contacted with the probes and feature binding groups (either simultaneously, or in a step-wise fashion), and then barcoded in partitions. In other instances, the cells, nuclei, or cell beads may be contacted with the probes and feature binding groups in partitions.

Figure 29:
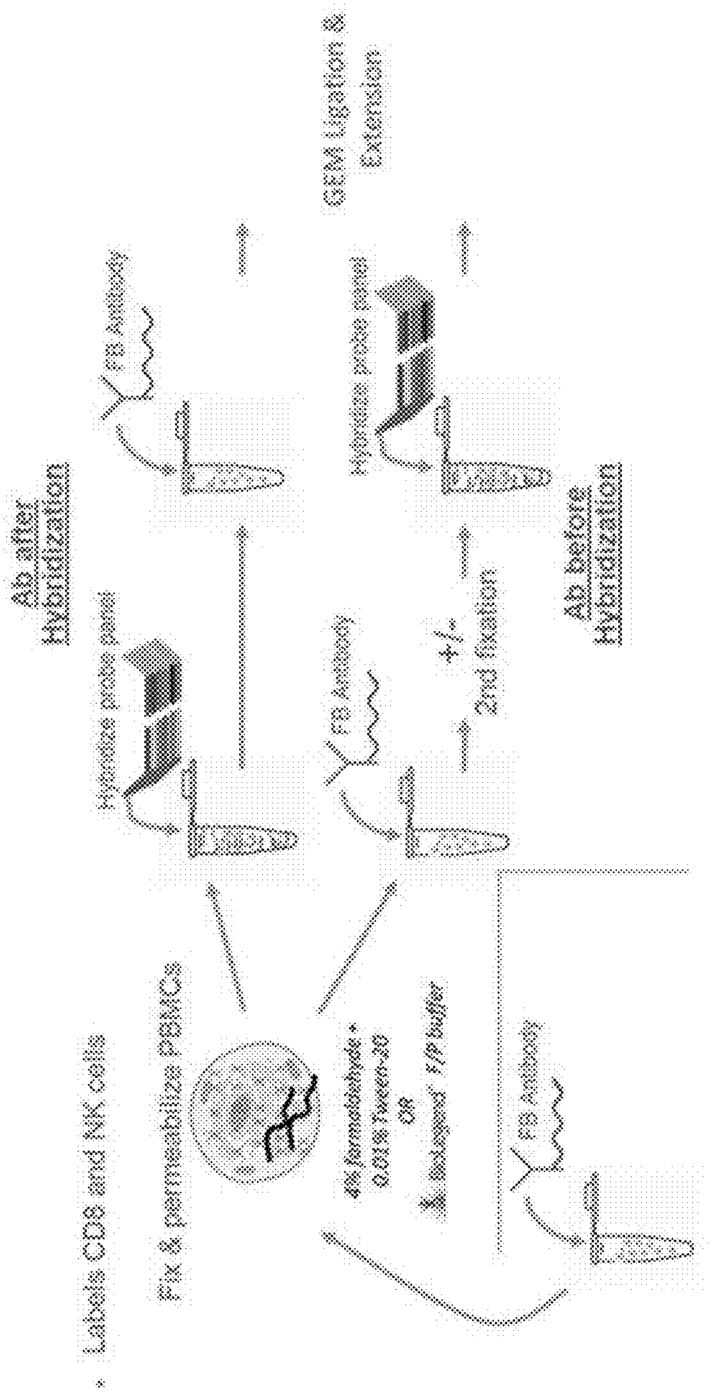
FIG. 29 shows an example workflow for processing cells according to the methods described herein.

FIG. 29 shows an example workflow of processing cells, according to the methods described herein. A cell may be fixed and permeabilized, e.g., in 4% formaldehyde and 0.01% Tween® 20 (polysorbate 20) or a commercially available fixation and permeabilization buffer (e.g., commercially available BioLegend® fixation and permeabilization buffer). In one example, the fixed and permeabilized cell may be incubated with a first probe and a second probe to generate a first probe-associated molecule (e.g., a probe-associated RNA molecule). The cell may then be contacted with a feature binding group (e.g., antibody) comprising a reporter oligonucleotide to generate a cell comprising a feature coupled to a feature-binding group. Subsequent barcoding may be performed, e.g., in partitions.

In some examples, the fixed and permeabilized cell may be incubated with a feature binding group, optionally fixed again, and then contacted with a first probe and a second probe to generate a probe-associated molecule (e.g., a probe-associated RNA molecule). Alternatively, the fixed and permeabilized cell may be incubated with the first probe and the second probe to generate a probe-associated molecule, and then contacted with the feature binding groups. Subsequent barcoding may be performed, e.g., in partitions.

In some instances, it may be useful (e.g., as a negative control) to permeabilize the cell prior to contacting the cell with a probe or feature-binding group. Accordingly, a cell may be fixed, contacted with the probe and/or feature binding group, then subsequently permeabilized. It will be appreciated that any order of operations of fixation, permeabilization, probe hybridization, contacting with the feature binding groups, etc., may be performed at any convenient or useful step and in any order, and that any of the processes may be repeated. For example, a cell, nucleus, or cell bead may be contacted with the feature binding groups, fixed and/or permeabilized, contacted with additional feature binding groups, which may be beneficial for assaying extracellular and intracellular peptides, polypeptides, or proteins, and optionally, fixed again. Alternatively, the cell, nucleus, or cell bead may be fixed and/or permeabilized, then contacted with feature binding groups (e.g. for intracellular and/or extracellular analytes) and optionally, fixed again. Prior to or following such processes, the cell, nucleus, or cell bead may be contacted with the sets of probes (e.g., first probe, second probe, and/or third probe). See also, Examples 8 and 9.

The methods, compositions, kits, and systems of the present disclosure may comprise providing methods for processing fixed biological particles (e.g., a cell, nucleus, or cell bead). In one embodiment, the method comprises a) fixing and permeabilizing a biological particle or providing a fixed and permeabilized biological particle.

The method may further comprise b) contacting the fixed and permeabilized biological particle with a first reagent configured to couple to an analyte of the biological particle. In one embodiment, the analyte is an intracellular analyte, such as a nucleic acid or a polypeptide, and the biological particle is a cell. In another embodiment, the analyte is an intranuclear analyte, such as a nucleic acid or a polypeptide, and the biological particle is a nucleus. The first reagent configured to couple to an analyte may be (i) a first reagent configured to couple to a nucleic acid (such as one or more nucleic acid probes as described herein) or (ii) a first reagent configured to couple to a peptide, polypeptide, or protein (such as one or more feature binding groups as described herein). In one other embodiment, b) provides a fixed and permeabilized biological particle, e.g., cell or nucleus, comprising the first reagent coupled to the analyte, e.g., nucleic acid or polypeptide, of the biological particle.

The method may further comprise c) performing an additional fixation of the biological particle from b). In one embodiment, c) comprises additional fixation of the biological particle from b), wherein the biological particle from b) comprises the first reagent configured to couple to an analyte of the biological particle. The first reagent may be coupled to the analyte (nucleic acid or polypeptide) of the biological particle (e.g., cell or nucleus). The first reagent may be a reagent configured to couple to a nucleic acid analyte or a reagent configured to couple to a polypeptide. In one embodiment, c) comprises additional fixation of the biological particle, such as a cell, wherein the cell comprises a first reagent coupled to a polypeptide. In another embodiment, the polypeptide is an intracellular polypeptide.

The method may further comprise d) comprising contacting the biological particle (e.g., cell or nucleus) from c) (which has been initially fixed and permeabilized, contacted with the first reagent or comprises the first reagent, and additionally fixed) with a second reagent configured to couple to an analyte (e.g., a nucleic acid or polypeptide), wherein the second reagent is different from the first reagent and/or the second reagent is configured to couple to an analyte that is different than the analyte that the first reagent is configured to couple to. In one embodiment, the first reagent is configured to couple to a polypeptide (such as one or more feature binding groups as described herein) and the second reagent is configured to couple to a nucleic acid (such as one or more nucleic acid probes as described herein). The biological particle of d) may comprise the first reagent coupled to a polypeptide and the second reagent coupled to a nucleic acid.

Any number of barcoding operations may be performed for a given nucleic acid molecule and/or feature binding group, e.g., using a combinatorial barcoding (e.g., split-pool) approaches. As described herein, additional barcoding operations may be useful, for example, in indexing nucleic acid molecules and features (e.g., proteins) to a cell, a nucleus, a cell bead, a sample, a partition, or a plurality of partitions. Such indexing may be useful in situations when a single partition is occupied by multiple cells, nuclei, or cell beads. In some instances, it may be beneficial to overload partitions such that a partition comprises more than one cell, nucleus or cell bead; for example, it may be useful in certain situations to overload partitions, e.g., to overcome Poisson loading statistics in partitions and/or to prevent reagent waste (e.g., from unoccupied partitions). Accordingly, such indexing may be useful in attributing (i) nucleic acid molecules and (ii) features (e.g., proteins) in multiply-occupied partitions to the originating cell, nucleus, cell bead, partition, sample, etc., as is described elsewhere herein.

For example, the workflow provided in FIG. 10 may be performed for nucleic acid molecules and features (e.g., proteins) within a population of cells, nuclei or cell beads. In such an example, prior to operation 1010, a first population of cells, nuclei or cell beads 1002 may be contacted with the first probe, the second probe, and optionally, the third probe (e.g., as shown in FIG. 16A and FIG. 16B). The first probe and the second probe may hybridize to the nucleic acid molecule, generating a first probe-associated molecule (or complex), and optionally, the third probe may hybridize to a reporter oligonucleotide (comprising a reporter sequence) or feature probe-binding sequence of a feature binding group (e.g., a group configured to couple to a cell/nuclear membrane protein) to generate a second probe-associated molecule (or complex). Additional probe(s) may be provided to hybridize to additional reporter oligonucleotide(s) or feature probe-binding sequence(s) of an additional feature binding group (e.g., a group configured to couple to an intracellular/intranuclear protein) of the first population of cells, nuclei or cell beads to generate additional probe-associated molecule(s). A second population of cells, nuclei or cell beads 1004 may be also be treated in the same way, e.g., with a fourth probe, a fifth probe, and optionally a sixth probe. The fourth probe and the fifth probe may hybridize to the nucleic acid molecule of the second population of cells, nuclei or cell beads to generate a third-probe-associated molecule, and optionally, the sixth probe may hybridize to a reporter oligonucleotide or feature probe-binding sequence of a feature binding group of the second population of cells, nuclei or cell beads to generate a fourth probe-associated molecule. Additional probe(s) may be provided to hybridize to additional reporter oligonucleotide(s) or feature probe-binding sequence(s) of an additional feature binding group (e.g., a group configured to couple to an intracellular/intranuclear protein) of the second population of cells, nuclei or cell beads to generate additional probe-associated molecule(s). The first population of cells 1002 (or nuclei or cell beads) and the second population of cells 1004 (or nuclei or cell beads) may be barcoded with a first barcode sequence, as described herein, such that the first population of cells (or components therein, such as the first probe-associated molecule and the second-probe-associated molecule) 1002 has a different first barcode sequence than the second population of cells (or nuclei or cell beads or components within the cell, nuclei or cell beads, such as the third probe-associated molecule and the fourth probe-associated molecule) 1004. In operation 1020, the first population of cells 1002 (or nuclei or cell beads) may be pooled together with the second population of cells 1004 (or nuclei or cell beads) to generate a mixture of cells (or nuclei or cell beads). In operation 1030, the mixture of cells (or nuclei or cell beads) may be partitioned into a second plurality of partitions. In some instances, the mixture of cells (or nuclei or cell beads) may be partitioned into the second plurality of partitions such that some partitions of the second plurality of partitions comprises more than one cell (e.g., a cell, nucleus or cell bead multiplet partition). For example, a partition 1035 of the second plurality of partitions may comprise a cell, nucleus, or cell bead ("Cell A") from the first population of cells 1002 (or nuclei or cell beads) and a cell, nucleus, or cell bead ("Cell B") from the second population of cells 1004 (or nuclei or cell beads). The partition 1035 may comprise an additional barcode sequence, which may be unique to the partition. The cells (or nuclei or cell beads) in each partition may be subjected to an additional barcoding operation to append the additional barcode sequence on the barcoded nucleic acid molecules. In operation 1040, the barcoded nucleic acid molecules may be deconvolved, using the different barcode sequences (e.g., the first barcode sequence, the second barcode sequence, and the additional barcode sequences), to identify the originating cell, nucleus, or cell bead. For instance, a barcoded nucleic acid molecule comprising the additional barcode sequence from partition 1035 and the first barcode sequence from the first population of cells 1002 may be used to identify that barcoded nucleic acid molecule as originating from Cell A. Similarly, a barcoded nucleic acid molecule comprising the additional barcode sequence from partition 1035 and the second barcode sequence from the second populations of cells 1004 may be used to identify that barcoded nucleic acid molecule from originating from Cell B.

In some instances, the feature binding group(s) (e.g., a feature binding group configured to couple to an intracellular/intranuclear protein and/or a feature binding group configured to couple to an intracellular/intranuclear protein) may be pre-indexed to a partition. For example, rather than the feature binding group having a feature probe-binding sequence that can be hybridized to a probe (e.g., a third probe) and subsequently barcoded (e.g., as described in FIG. 16A-B) with barcode sequences that identify the cell, nucleus, cell bead, or partition, the feature binding group may be provided in the partitions in a pre-indexed manner, e.g., using a barcode sequence unique to the partition. For instance, the feature binding group may be provided at a later operation of the method, subsequent to barcoding of the nucleic acid molecules within the cell. For example, during the second barcoding operating (e.g., operation 1680 of FIG. 16A-B), the feature binding group may be provided and contacted with the feature 1650 of the cell, nucleus or cell bead (or released from the cell, nucleus or cell bead in the second partition). The feature binding group may comprise or be hybridized to a barcode sequence that is specific to the second partition and that differs across the second partitions. Accordingly, the barcode sequence can be used to index the feature binding group to the particular partition and back to the originating cell or cell bead, instead of using the first barcode sequence and the second barcode sequence from the first partition and second partition, respectively, to identify the partition, cell, nucleus, or cell bead.

In other examples, the feature binding group(s) may be indexed to a partition by attaching or coupling a partition-specific barcode sequence directly to the feature binding group, thus obviating the usage of a third probe. In such instances, the feature binding group may comprise or be coupled to a reporter oligonucleotide comprising the reporter sequence and an attachment sequence, which may be used to attach a barcode molecule directly to the feature binding group. For example, the feature binding group may comprise a probe capture sequence (e.g., 1662), thereby obviating the need for a third probe comprising the probe capture sequence. The probe capture sequence may subsequently be barcoded, e.g., with the first barcode sequence of the barcode molecule within the first partition and with the second barcode sequence of the capture molecule within the second partition. In some instances, the attachment sequence may be used to hybridize a probe-binding molecule (e.g., splint molecule or splint oligonucleotide), which may be partially complementary to the barcode molecule (as described herein). For example, the attachment sequence of the reporter oligonucleotide may be used to hybridize the probe-binding molecule, which may hybridize (or be pre-annealed) to the barcode molecule, e.g., in a first partition. A second barcode sequence from the capture molecule may be provided in the first partition or in a different (e.g., second) partition, which may anneal to a portion of the first barcode molecule. In some instances, additional operations are performed, e.g., extension, ligation, etc. to generate a barcoded molecule comprising sequences corresponding to the first barcode sequence, the second barcode sequence, and the reporter sequence.

Following partition-based barcoding, the contents of the partitions may be pooled and the barcoded molecules may be duplicated or amplified by, for example, one or more amplification reactions, which may in some instances be isothermal. The amplification reactions may comprise polymerase chain reactions (PCR) and may involve the use of one or more primers or polymerases. The one or more primers may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), etc.) and may facilitate addition of said one or more functional sequences to the extended nucleic acid molecule. The barcoded molecules, or derivatives thereof, may be detected via nucleic acid sequencing (e.g., as described herein).

In some aspects, provided herein are systems useful for barcoding nucleic acid molecules. The systems may comprise any of the components described herein, e.g., a plurality of partitions (e.g., droplets, wells), which may be provided in any useful format, e.g., a microfluidic device, a multi-well array or plate, etc. In some instances, the system may comprise a first set of partitions and a second set of partitions. The first set of partitions may be the same or different types of partitions as the second set of partitions. For example, the first set of partitions may comprise microwells and the second set of partitions may comprise droplets. As another example, both the first set of partitions and the second set of partitions may comprise droplets. The systems may include nucleic acid barcode molecules, optionally coupled to supports (e.g., particles, beads, gel beads, etc.). In some instances, the systems may comprise any of the probes described herein, such as a first probe or plurality of first probes, a second probe or plurality of second probes, a third probe or plurality of third probes, and any useful reaction components (e.g., for performing a nucleic acid reaction, e.g., extension, ligation, amplification, etc.). The systems may comprise one or more feature-binding groups. The feature binding groups may be the same or different across partitions; for example, the feature binding groups may comprise a variety of antibodies that bind to different epitopes within a single partition, or the partitions may comprise different feature binding groups that bind to different epitopes or moieties. The systems may include reaction components that are useful, such as, in non-limiting examples, enzymes (e.g., ligases, polymerases, reverse transcriptases, restriction enzymes, etc.), nucleotides bases, etc.

Also provided herein are compositions useful for systems and methods for barcoding multiple analytes, e.g., nucleic acid molecules and proteins (e.g., via a nucleic acid molecule, such as a reporter oligonucleotide, comprised in or coupled to a feature binding group). A composition may comprise any of the probes described herein. For example, a composition may comprise a plurality of first probes, a plurality of second probes, a plurality of third probes, and/or a plurality of first probes, a plurality of second probes, and a plurality of third probes. A probe or a set of probes may be designed to target a specific sequence or a set of specific sequences. Such probes may be designed to have the same or different sequences within different partitions. For example, a first composition may comprise a first probe and a second probe designed to target two regions of a first gene, and a second composition may comprise a first probe and a second probe designed to target two regions of a second gene, which second gene is different than the first gene. Similarly, the third probe (or pair of probes) may be designed to target a region of the reporter oligonucleotide (comprising the reporter sequence) or feature probe-binding sequence, which may be the same or different across partitions. A composition may comprise nucleic acid barcode molecules, and/or probe binding molecules, which may optionally be provided coupled to a support (e.g., particle, bead). A composition may comprise capture molecules, optionally coupled to a support. A composition may be a part of or comprise a reaction mixture, which can include reaction components or reagents, e.g., enzymes, nucleotide bases, catalysts, etc.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion or a well. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more beads. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a support (e.g., bead), as described elsewhere herein.

The methods and systems of the present disclosure may comprise methods and systems for generating one or more partitions such as droplets. The droplets may comprise a plurality of droplets in an emulsion. In some examples, the droplets may comprise droplets in a colloid. In some cases, the emulsion may comprise a microemulsion or a nanoemulsion. In some examples, the droplets may be generated with aid of a microfluidic device and/or by subjecting a mixture of immiscible phases to agitation (e.g., in a container). In some cases, a combination of the mentioned methods may be used for droplet and/or emulsion formation.

Droplets can be formed by creating an emulsion by mixing and/or agitating immiscible phases. Mixing or agitation may comprise various agitation techniques, such as vortexing, pipetting, tube flicking, or other agitation techniques. In some cases, mixing or agitation may be performed without using a microfluidic device. In some examples, the droplets may be formed by exposing a mixture to ultrasound or sonication. Systems and methods for droplet and/or emulsion generation by agitation are described in International Application No. PCT/US20/17785, which is entirely incorporated herein by reference for all purposes.

Microfluidic devices or platforms comprising microfluidic channel networks (e.g., on a chip) can be utilized to generate partitions such as droplets and/or emulsions as described herein. Methods and systems for generating partitions such as droplets, methods of encapsulating biological particle methods of increasing the throughput of droplet generation, and various geometries, architectures, and configurations of microfluidic devices and channels are described in U.S. Patent Publication Nos. 2019/0367997 and 2019/0064173, each of which is entirely incorporated herein by reference for all purposes.

In some examples, individual particles can be partitioned to discrete partitions by introducing a flowing stream of particles in an aqueous fluid into a flowing stream or reservoir of a non-aqueous fluid, such that droplets may be generated at the junction of the two streams/reservoir, such as at the junction of a microfluidic device provided elsewhere herein.

The methods of the present disclosure may comprise generating partitions and/or encapsulating particles, such as biological particles, in some cases, individual biological particles such as single cells, nuclei or cell beads. In some examples, reagents may be encapsulated and/or partitioned (e.g., co-partitioned with biological particles) in the partitions. Various mechanisms may be employed in the partitioning of individual particles. An example may comprise porous membranes through which aqueous mixtures of cells may be extruded into fluids (e.g., non-aqueous fluids).

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
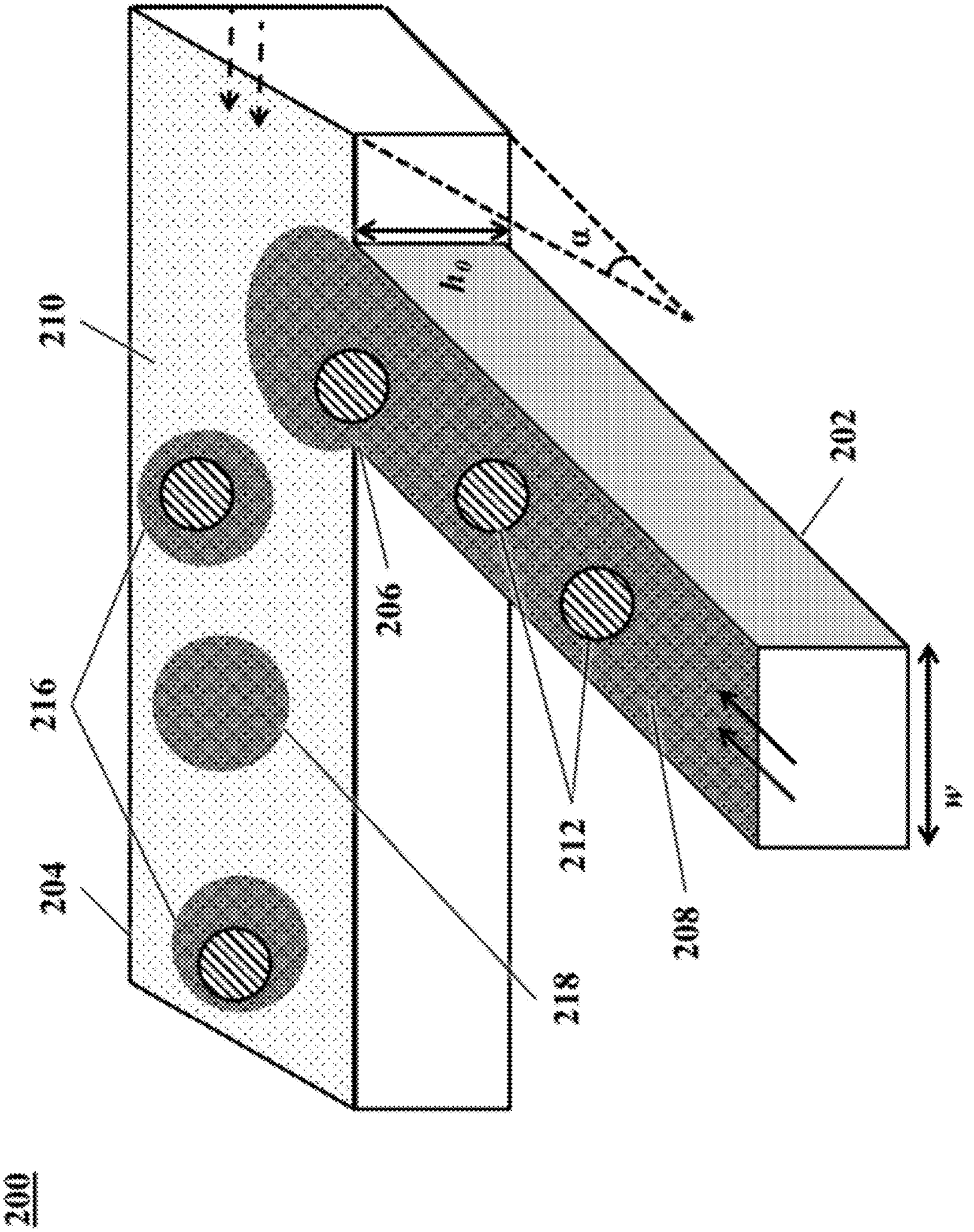
FIG. 2 shows an example of a microfluidic channel structure for the controlled partitioning of beads into discrete droplets.

As will be appreciated, the above-described occupancy rates are also applicable to partitions that include both biological particles and additional reagents, including, but not limited to, supports such as beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a support (e.g., bead) comprising barcoded nucleic acid molecules and a biological particle.

In another aspect, in addition to or as an alternative to droplet based partitioning, biological particles may be encapsulated within a support that comprises an outer shell, layer or porous matrix in which is entrained one or more individual biological particles or small groups of biological particles. The support may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through crosslinking, polymerization initiation of the precursor (e.g., through added initiators)), mechanical stimuli, or a combination thereof.

Preparation of supports comprising biological particles (e.g., cells) may be performed by a variety of methods. For example, air knife droplet or aerosol generators may be used to dispense droplets of precursor fluids into gelling solutions in order to form beads (e.g., gel beads) that include individual biological particles or small groups of biological particles. Likewise, membrane-based encapsulation systems may be used to generate beads comprising encapsulated biological particles as described herein. Microfluidic systems of the present disclosure, such as that shown in FIG. 1, may be readily used in encapsulating biological particles (e.g., cells) as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the porous matrix that includes the entrained biological particles. Examples of polymer precursor/initiator pairs include those described in U.S. Patent Application Publication No. 2014/0378345, which is entirely incorporated herein by reference for all purposes.

In some cases, encapsulated biological particles can be selectively releasable from the support, such as through passage of time or upon application of a particular stimulus, that degrades the microcapsule sufficiently to allow the biological particles (e.g., cell), or its other contents to be released from the support, such as into a partition (e.g., droplet). See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead."

A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles. Cell beads may be or include a cell, cell derivative, cellular material and/or material derived from the cell in, within, or encased in a matrix, such as a polymeric matrix. In some cases, a cell bead may comprise a live cell. In some instances, the live cell may be capable of being cultured when enclosed in a gel or polymer matrix, or of being cultured when comprising a gel or polymer matrix. In some instances, the polymer or gel may be diffusively permeable to certain components and diffusively impermeable to other components (e.g., macromolecular constituents).

Wells

As described herein, one or more processes may be performed in a partition, which may be a well. The well may be a well of a plurality of wells of a substrate, such as a microwell of a microwell array or plate, or the well may be a microwell or microchamber of a device (e.g., microfluidic device) comprising a substrate. The well may be a well of a well array or plate, or the well may be a well or chamber of a device (e.g., fluidic device). Accordingly, the wells or microwells may assume an "open" configuration, in which the wells or microwells are exposed to the environment (e.g., contain an open surface) and are accessible on one planar face of the substrate, or the wells or microwells may assume a "closed" or "sealed" configuration, in which the microwells are not accessible on a planar face of the substrate. In some instances, the wells or microwells may be configured to toggle between "open" and "closed" configurations. For instance, an "open" microwell or set of microwells may be "closed" or "sealed" using a membrane (e.g., semi-permeable membrane), an oil (e.g., fluorinated oil to cover an aqueous solution), or a lid, as described elsewhere herein.

The well may have a volume of less than 1 milliliter (mL). For instance, the well may be configured to hold a volume of at most 1000 microliters (μL), at most 100 μL, at most 10 μL, at most 1 μL, at most 100 nanoliters (nL), at most 10 nL, at most 1 nL, at most 100 picoliters (pL), at most 10 (pL), or less. The well may be configured to hold a volume of about 1000 μL, about 100 μL, about 10 μL, about 1 μL, about 100 nL, about 10 nL, about 1 nL, about 100 μL, about 10 μL, etc. The well may be configured to hold a volume of at least 10 μL, at least 100 μL, at least 1 nL, at least 10 nL, at least 100 nL, at least 1 μL, at least 10 μL, at least 100 μL, at least 1000 μL, or more. The well may be configured to hold a volume in a range of volumes listed herein, for example, from about 5 nL to about 20 nL, from about 1 nL to about 100 nL, from about 500 μL to about 100 μL, etc. The well may be of a plurality of wells that have varying volumes and may be configured to hold a volume appropriate to accommodate any of the partition volumes described herein.

In some instances, a microwell array or plate comprises a single variety of microwells. In some instances, a microwell array or plate comprises a variety of microwells. For instance, the microwell array or plate may comprise one or more types of microwells within a single microwell array or plate. The types of microwells may have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate may comprise any number of different types of microwells. For example, the microwell array or plate may comprise 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well may have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate comprises different types of microwells that are located adjacent to one another within the array or plate. For instance, a microwell with one set of dimensions may be located adjacent to and in contact with another microwell with a different set of dimensions. Similarly, microwells of different geometries may be placed adjacent to or in contact with one another. The adjacent microwells may be configured to hold different articles; for example, one microwell may be used to contain a cell, cell bead, or other sample (e.g., cellular components, nucleic acid molecules, etc.) while the adjacent microwell may be used to contain a support (e.g., a bead such as a gel bead), droplet, or other reagent. In some cases, the adjacent microwells may be configured to merge the contents held within, e.g., upon application of a stimulus, or spontaneously, upon contact of the articles in each microwell.

As is described elsewhere herein, a plurality of partitions may be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000,000 wells, at least about 500,000,000 wells, at least about 1,000,000,000 wells, or more wells can be generated or otherwise provided. Moreover, the plurality of wells may comprise both unoccupied wells (e.g., empty wells) and occupied wells.

A well may comprise any of the reagents described herein, or combinations thereof. These reagents may include, for example, barcode molecules, enzymes, adapters, and combinations thereof. The reagents may be physically separated from a sample (e.g., a cell, cell bead, or cellular components, e.g., proteins, nucleic acid molecules, etc.) that is placed in the well. This physical separation may be accomplished by containing the reagents within, or coupling to, a support (e.g., a bead such as a gel bead) that is placed within a well. The physical separation may also be accomplished by dispensing the reagents in the well and overlaying the reagents with a layer that is, for example, dissolvable, meltable, or permeable prior to introducing the polynucleotide sample into the well. This layer may be, for example, an oil, wax, membrane (e.g., semi-permeable membrane), or the like. The well may be sealed at any point, for example, after addition of the support (e.g., bead), after addition of the reagents, or after addition of either of these components. The sealing of the well may be useful for a variety of purposes, including preventing escape of beads or loaded reagents from the well, permitting select delivery of certain reagents (e.g., via the use of a semi-permeable membrane), for storage of the well prior to or following further processing, etc.

A well may comprise free reagents and/or reagents encapsulated in, or otherwise coupled to or associated with, supports (e.g., beads) or droplets. Any of the reagents described in this disclosure may be encapsulated in, or otherwise coupled to, a support (e.g., bead) or droplet, with any chemicals, particles, and elements suitable for sample processing reactions involving biomolecules, such as, but not limited to, nucleic acid molecules and proteins. For example, a bead or droplet used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, oligonucleotides, nucleotides, deoxyribonucleotide triphosphates (dNTPs), dideoxyribonucleotide triphosphates (ddNTPs), DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, IRNA, tRNA, nRNA, siRNA, snRNA, snoRNA, scaRNA, microRNA, dsRNA, ribozyme, riboswitch and viral RNA, polymerase, ligase, restriction enzymes, proteases, nucleases, protease inhibitors, nuclease inhibitors, chelating agents, reducing agents, oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds. As described herein, one or more reagents in the well may be used to perform one or more reactions, including but not limited to: cell lysis, cell fixation, permeabilization, nucleic acid reactions, e.g., nucleic acid extension reactions, amplification, reverse transcription, transposase reactions (e.g., tagmentation), etc.

The wells may be provided as a part of a kit. For example, a kit may comprise instructions for use, a microwell array or device, and reagents (e.g., beads). The kit may comprise any useful reagents for performing the processes described herein, e.g., nucleic acid reactions, barcoding of nucleic acid molecules, sample processing (e.g., for cell lysis, fixation, and/or permeabilization).

In some cases, a well comprises a support (e.g., a bead), or droplet that comprises a set of reagents that has a similar attribute (e.g., a set of enzymes, a set of minerals, a set of oligonucleotides, a mixture of different barcode molecules, a mixture of identical barcode molecules). In other cases, a support or droplet comprises a heterogeneous mixture of reagents. In some cases, the heterogeneous mixture of reagents can comprise all components necessary to perform a reaction. In some cases, such mixture can comprise all components necessary to perform a reaction, except for 1, 2, 3, 4, 5, or more components necessary to perform a reaction. In some cases, such additional components are contained within, or otherwise coupled to, a different support or droplet, or within a solution within a partition (e.g., microwell) of the system.

Figure 5:
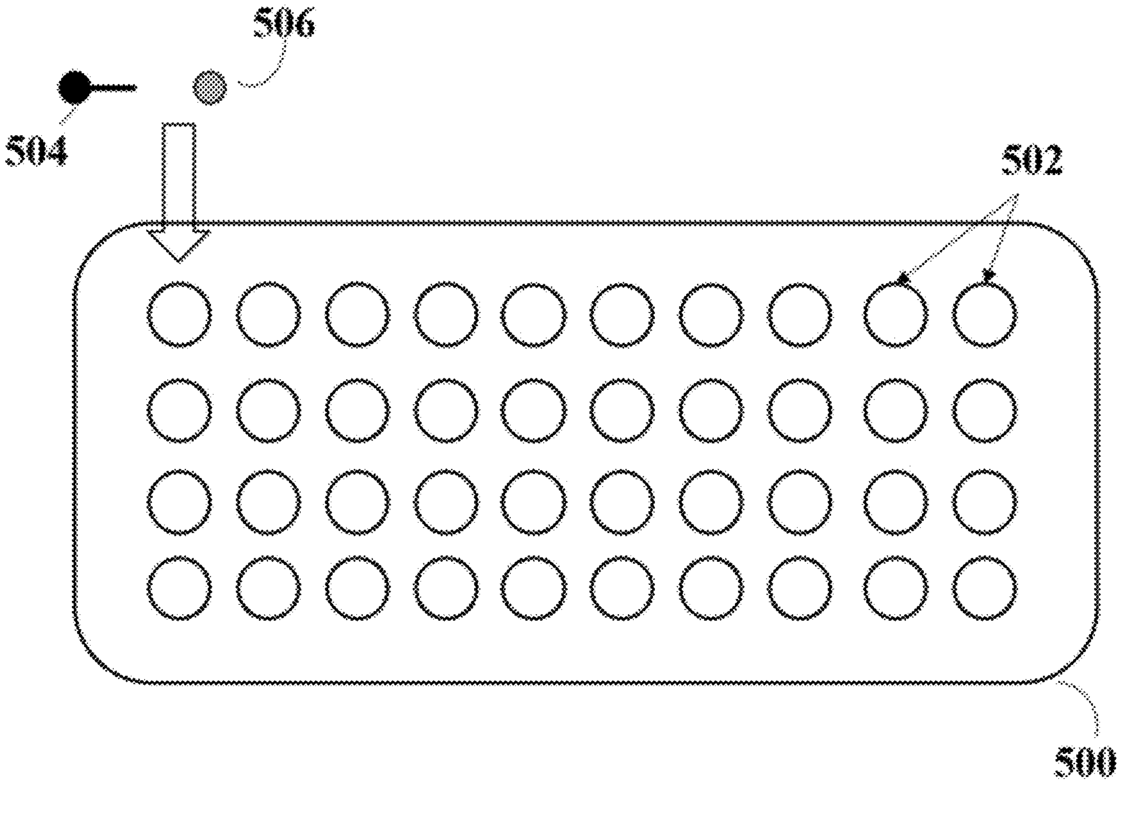
FIG. 5 schematically illustrates an example microwell array.

FIG. 5 schematically illustrates an example of a microwell array. The array can be contained within a substrate 500. The substrate 500 comprises a plurality of wells 502. The wells 502 may be of any size or shape, and the spacing between the wells, the number of wells per substrate, as well as the density of the wells on the substrate 500 can be modified, depending on the particular application. In one such example application, a sample molecule 506, which may comprise a cell or cellular components (e.g., nucleic acid molecules) is co-partitioned with a bead 504, which may comprise a nucleic acid barcode molecule coupled thereto. The wells 502 may be loaded using gravity or other loading technique (e.g., centrifugation, liquid handler, acoustic loading, optoelectronic, etc.). In some instances, at least one of the wells 502 contains a single sample molecule 506 (e.g., cell) and a single bead 504.

Reagents may be loaded into a well either sequentially or concurrently. In some cases, reagents are introduced to the device either before or after a particular operation. In some cases, reagents (which may be provided, in certain instances, in supports or droplets) are introduced sequentially such that different reactions or operations occur at different steps. The reagents (or supports or droplets) may also be loaded at operations interspersed with a reaction or operation step. For example, supports (or droplets) comprising reagents for fragmenting polynucleotides (e.g., restriction enzymes) and/or other enzymes (e.g., transposases, ligases, polymerases, etc.) may be loaded into the well or plurality of wells, followed by loading of supports or droplets comprising reagents for attaching nucleic acid barcode molecules to a sample nucleic acid molecule. Reagents may be provided concurrently or sequentially with a sample, e.g., a cell or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a support (e.g., a bead), or droplet. These supports, or droplets may be loaded into a partition (e.g., a microwell) before, after, or concurrently with the loading of a cell, such that each cell is contacted with a different support or droplet. This technique may be used to attach a unique nucleic acid barcode molecule to nucleic acid molecules obtained from each cell. Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells, nuclei, cell beads, or partitions.

The samples or reagents may be loaded in the wells or microwells using a variety of approaches. The samples (e.g., a cell, cell bead, or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell) and a single bead (such as those described herein, which may, in some instances, also be encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where intact or live cells are loaded in the microwells, one of the droplets may comprise lysis reagents for lysing the cell upon droplet merging.

A droplet or support (e.g., a bead) may be partitioned into a well. The droplets may be selected or subjected to pre-processing prior to loading into a well. For instance, the droplets may comprise cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. For instance, the nucleic acid barcode molecules may comprise a chemical cross-linker which may be cleaved upon application of a stimulus (e.g., photo-, magnetic, chemical, biological, stimulus). The released nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell, cell bead, or cellular components) or derivatives thereof. Characterization techniques such as microscopy or imaging may be useful in measuring sample profiles in fixed spatial locations. For instance, when cells (or nuclei or cell beads) are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, etc. In some instances, imaging may be used to characterize live cells in the wells, including, but not limited to: dynamic live-cell tracking, cell-cell interactions (when two or more cells are co-partitioned), cell proliferation, etc. Alternatively or in addition to, imaging may be used to characterize a quantity of amplification products in the well.

In operation, a well may be loaded with a sample and reagents, simultaneously or sequentially. When cells, nuclei, or cell beads are loaded, the well may be subjected to washing, e.g., to remove excess cells (or nuclei or cell beads) from the well, microwell array, or plate. Similarly, washing may be performed to remove excess beads or other reagents from the well, microwell array, or plate. In the instances where live cells are used, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Once sealed, the well may be subjected to conditions for further processing of a biological particle (e.g., a cell, a cell bead or a nucleus) in the well. For instance, reagents in the well may allow further processing of the biological particle, e.g., lysis of the cell or nucleus, as further described herein. Alternatively, the well (or wells such as those of a well-based array) comprising the biological particle (e.g., cell, cell bead, or nucleus) may be subjected to freeze-thaw cycling to process the biological particle(s), e.g., lysis of a cell or nucleus. The well containing the biological particle (e.g., cell, cell bead, or nucleus) may be subjected to freezing temperatures (e.g., 0° C., below 0° C., −5° C., −10° C., −15° C., −20° C., −25° C., −30° C., −35° C., −40° C., −45° C., −50° C., −55° C., −60° C., −65° C., −70° C., −80° C., or −85° C.). Freezing may be performed in a suitable manner, e.g., sub-zero freezer or a dry ice/ethanol bath. Following an initial freezing, the well (or wells) comprising the biological particle(s) (e.g., cell(s), cell bead(s), nucleus or nuclei) may be subjected to freeze thaw cycles to lyse biological particle(s). In one embodiment, the initially frozen well (or wells) are thawed to a temperature above freezing (e.g., room temperature or 25° C.). In another embodiment, the freezing is performed for less than 10 minutes (e.g., 5 minutes or 7 minutes) followed by thawing at room temperature for less than 10 minutes (e.g., 5 minutes or 7 minutes). This freeze-thaw cycle may be repeated a number of times, e.g., 2, 3, or 4 times, to obtain lysis of the biological particle(s) (e.g., cell(s), cell bead(s), nucleus, or nuclei) in the well (or wells). In one embodiment, the freezing, thawing and/or freeze/thaw cycling is performed in the absence of a lysis buffer.

Figure 6:
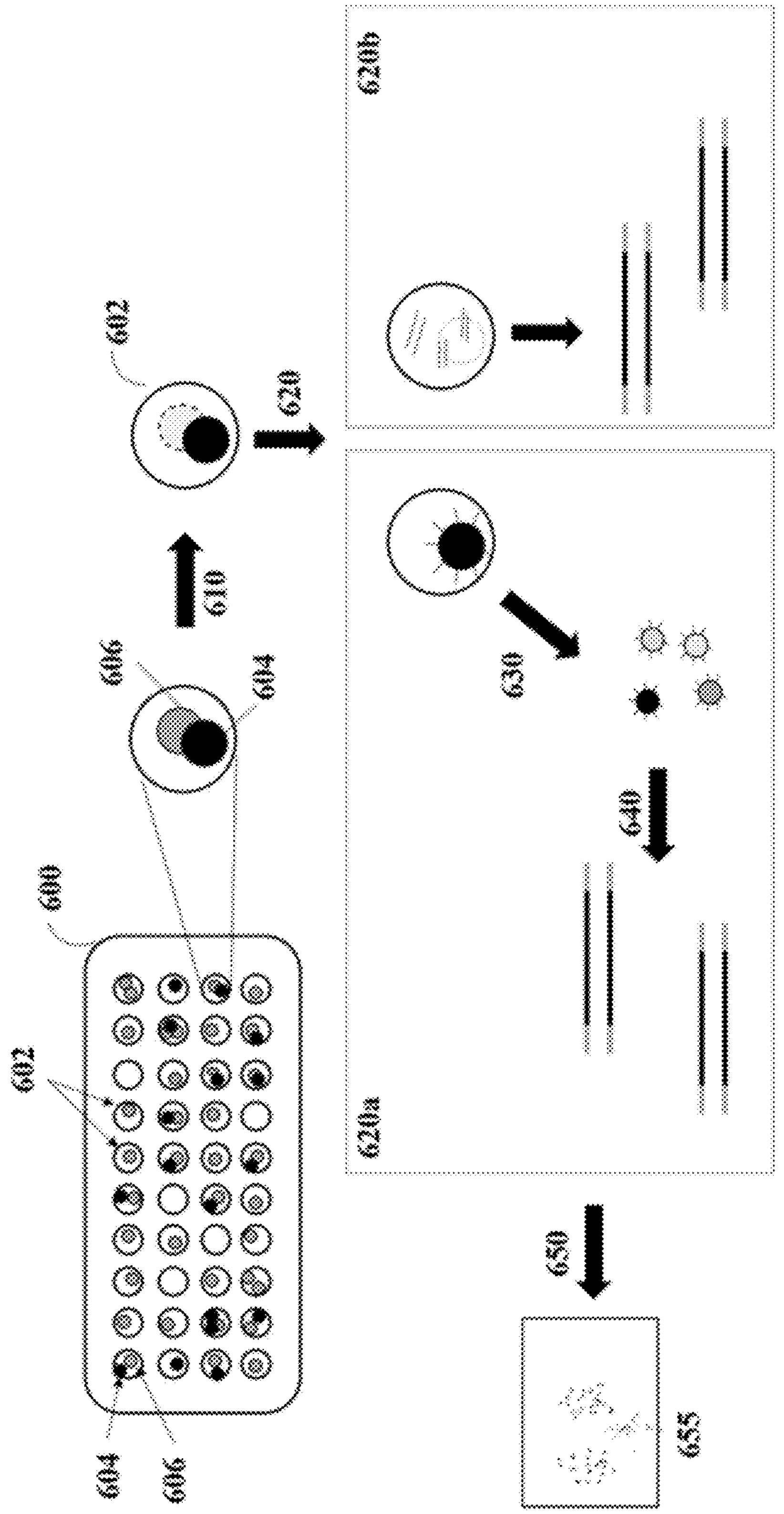
FIG. 6 schematically illustrates an example workflow for processing nucleic acid molecules.

FIG. 6 schematically shows an example workflow for processing nucleic acid molecules within a sample. A substrate 600 comprising a plurality of microwells 602 may be provided. A sample 606 which may comprise a cell, cell bead, cellular components or analytes (e.g., proteins and/or nucleic acid molecules) can be co-partitioned, in a plurality of microwells 602, with a plurality of beads 604 comprising nucleic acid barcode molecules. During process 610, the sample 606 may be processed within the partition. For instance, in the case of live cells, the cell may be subjected to conditions sufficient to lyse the cells or nuclei and release the analytes contained therein. In process 620, the bead 604 may be further processed. By way of example, processes 620*a* and 620*b* schematically illustrate different workflows, depending on the properties of the bead 604.

In 620*a*, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 630, the beads 604 from multiple wells 602 may be collected and pooled. Further processing may be performed in process 640. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

In 620*b*, the bead comprises nucleic acid barcode molecules that are releasably attached thereto, as described below. The bead may degrade or otherwise release the nucleic acid barcode molecules into the well 602; the nucleic acid barcode molecules may then be used to barcode nucleic acid molecules within the well 602. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 655.

Beads

Nucleic acid barcode molecules may be delivered to a partition (e.g., a droplet or well) via a solid support or carrier (e.g., a bead). In some cases, nucleic acid barcode molecules are initially associated with the solid support and then released from the solid support upon application of a stimulus, which allows the nucleic acid barcode molecules to dissociate or to be released from the solid support. In specific examples, nucleic acid barcode molecules are initially associated with the solid support (e.g., bead) and then released from the solid support upon application of a biological stimulus, a chemical stimulus, a thermal stimulus, an electrical stimulus, a magnetic stimulus, and/or a photo stimulus.

A nucleic acid barcode molecule may contain a barcode sequence and a functional sequence, such as a nucleic acid primer sequence or a template switch oligonucleotide (TSO) sequence.

The solid support may be a bead. A solid support, e.g., a bead, may be porous, non-porous, hollow (e.g., a microcapsule), solid, semi-solid, and/or a combination thereof. Beads may be solid, semi-solid, semi-fluidic, fluidic, and/or a combination thereof. In some instances, a solid support, e.g., a bead, may be at least partially dissolvable, disruptable, and/or degradable. In some cases, a solid support, e.g., a bead, may not be degradable. In some cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In some cases, the solid support, e.g., the bead, may be a silica bead. In some cases, the solid support, e.g., a bead, can be rigid. In other cases, the solid support, e.g., a bead, may be flexible and/or compressible.

A partition may comprise one or more unique identifiers, such as barcodes. Barcodes may be previously, subsequently or concurrently delivered to the partitions that hold the compartmentalized or partitioned biological particle. For example, barcodes may be injected into droplets or deposited in microwells previous to, subsequent to, or concurrently with droplet generation or providing of reagents in the microwells, respectively. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a support (e.g., a bead). A support, in some instances, can comprise a bead. Beads are described in further detail below.

In some cases, barcoded nucleic acid molecules can be initially associated with the support (e.g., bead) and then released from the support. Release of the barcoded nucleic acid molecules can be passive (e.g., by diffusion from or out of the support). In addition or alternatively, release from the support can be upon application of a stimulus which allows the barcoded nucleic acid nucleic acid molecules to dissociate or to be released from the support (e.g., bead). Such stimulus may disrupt the support, an interaction that couples the barcoded nucleic acid molecules to or within the support, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof. Methods and systems for partitioning barcode carrying beads into droplets are provided in US. Patent Publication Nos. 2019/0367997 and 2019/0064173, and International Application No. PCT/US20/17785, each of which is herein entirely incorporated by reference for all purposes.

In some examples, beads, biological particles, and droplets may flow along channels (e.g., the channels of a microfluidic device), in some cases at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide) that comprises one or more functional sequences, such as a TSO sequence or a primer sequence (e.g., a poly T sequence, or a nucleic acid primer sequence complementary to a target nucleic acid sequence and/or for amplifying a target nucleic acid sequence, a random primer, or a primer sequence for messenger RNA) that is useful for incorporation into the bead, etc.) and/or one or more barcode sequences. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence (or a portion thereof) for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence (or a portion thereof) for attachment to a sequencing flow cell for Illumina sequencing. In some cases, the nucleic acid molecule can comprise a barcode sequence. In some cases, the nucleic acid molecule can further comprise a unique molecular identifier (UMI). In some cases, the nucleic acid molecule can comprise an R1 primer sequence for Illumina sequencing. In some cases, the nucleic acid molecule can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

In some cases, the nucleic acid molecule can comprise one or more functional sequences. For example, a functional sequence can comprise a sequence for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the functional sequence can comprise a barcode sequence or multiple barcode sequences. In some cases, the functional sequence can comprise a unique molecular identifier (UMI). In some cases, the functional sequence can comprise a primer sequence (e.g., an R1 primer sequence for Illumina sequencing, an R2 primer sequence for Illumina sequencing, etc.). In some cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In some cases, a downstream procedure may extend the partial sequence, or derivative thereof, to achieve a full sequence of the partial sequence, or derivative thereof.

Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 3:
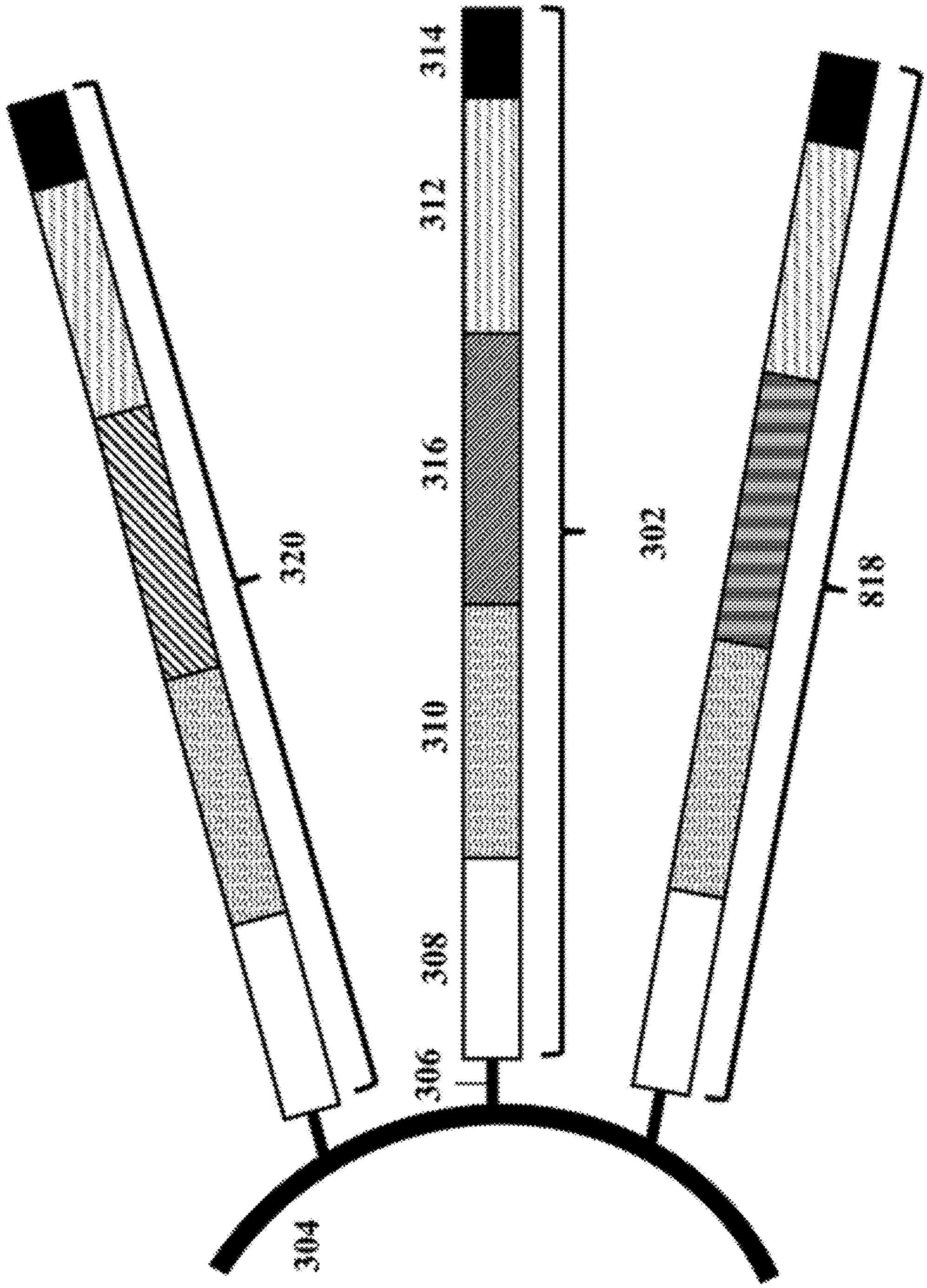
FIG. 3 illustrates an example of a barcode carrying bead.

FIG. 3 illustrates an example of a barcode carrying bead. A nucleic acid molecule 302, such as an oligonucleotide, can be coupled to a bead 304 by a releasable linkage 306, such as, for example, a disulfide linker. The same bead 304 may be coupled (e.g., via releasable linkage) to one or more other nucleic acid molecules 318, 320. The nucleic acid molecule 302 may be or comprise a barcode. As noted elsewhere herein, the structure of the barcode may comprise a number of sequence elements. The nucleic acid molecule 302 may comprise a functional sequence 308 that may be used in subsequent processing. For example, the functional sequence 308 may include one or more of a sequencer specific flow cell attachment sequence (e.g., a P5 sequence for Illumina® sequencing systems) and a sequencing primer sequence (e.g., a R1 primer for Illumina® sequencing systems), or partial sequence(s) thereof. The nucleic acid molecule 302 may comprise a barcode sequence 310 for use in barcoding the sample (e.g., DNA, RNA, protein, etc.). In some cases, the barcode sequence 310 can be bead-specific such that the barcode sequence 310 is common to all nucleic acid molecules (e.g., including nucleic acid molecule 302) coupled to the same bead 304. Alternatively or in addition, the barcode sequence 310 can be partition-specific such that the barcode sequence 310 is common to all nucleic acid molecules coupled to one or more beads that are partitioned into the same partition. The nucleic acid molecule 302 may comprise a specific priming sequence 312, such as an mRNA specific priming sequence (e.g., poly-T sequence), a targeted priming sequence, and/or a random priming sequence. The nucleic acid molecule 302 may comprise an anchoring sequence 314 to ensure that the specific priming sequence 312 hybridizes at the sequence end (e.g., of the mRNA). For example, the anchoring sequence 314 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 302 may comprise a unique molecular identifying sequence 316 (e.g., unique molecular identifier (UMI)). In some cases, the unique molecular identifying sequence 316 may comprise from about 5 to about 8 nucleotides. Alternatively, the unique molecular identifying sequence 316 may compress less than about 5 or more than about 8 nucleotides. The unique molecular identifying sequence 316 may be a unique sequence that varies across individual nucleic acid molecules (e.g., 302, 318, 320, etc.) coupled to a single bead (e.g., bead 304). In some cases, the unique molecular identifying sequence 316 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 3 shows three nucleic acid molecules 302, 318, 320 coupled to the surface of the bead 304, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 308, 310, 312, etc.) and variable or unique sequence segments (e.g., 316) between different individual nucleic acid molecules coupled to the same bead.

In operation, a biological particle (e.g., cell, DNA, RNA, etc.) can be co-partitioned along with a barcode bearing bead 304. The nucleic acid barcode molecules 302, 318, 320 can be released from the bead 304 in the partition. By way of example, in the context of analyzing sample RNA, the poly-T segment (e.g., 312) of one of the released nucleic acid molecules (e.g., 302) can hybridize to the poly-A tail of a mRNA molecule. Reverse transcription may result in a cDNA transcript of the mRNA, but which transcript includes each of the sequence segments 308, 310, 316 of the nucleic acid molecule 302. Because the nucleic acid molecule 302 comprises an anchoring sequence 314, it will more likely hybridize to and prime reverse transcription at the sequence end of the poly-A tail of the mRNA. Within any given partition, all of the cDNA transcripts of the individual mRNA molecules may include a common barcode sequence segment 310. However, the transcripts made from the different mRNA molecules within a given partition may vary at the unique molecular identifying sequence 312 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing).

The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where the nucleic acid molecules from the sample remain attached to the bead, the beads from various partitions may be collected, pooled, and subjected to further processing (e.g., reverse transcription, adapter attachment, amplification, clean up, sequencing). In other instances, the processing may occur in the partition. For example, conditions sufficient for barcoding, adapter attachment, reverse transcription, or other nucleic acid processing operations may be provided in the partition and performed prior to clean up and sequencing.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc. A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte. In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, a biological particle (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead. In some instances, a capture sequence coupled to a bead (or other support) may be configured to attach to a linker molecule, such as a splint molecule, wherein the linker molecule is configured to couple the bead (or other support) to other molecules through the linker molecule, such as to one or more analytes or one or more other linker molecules.

Figure 4:
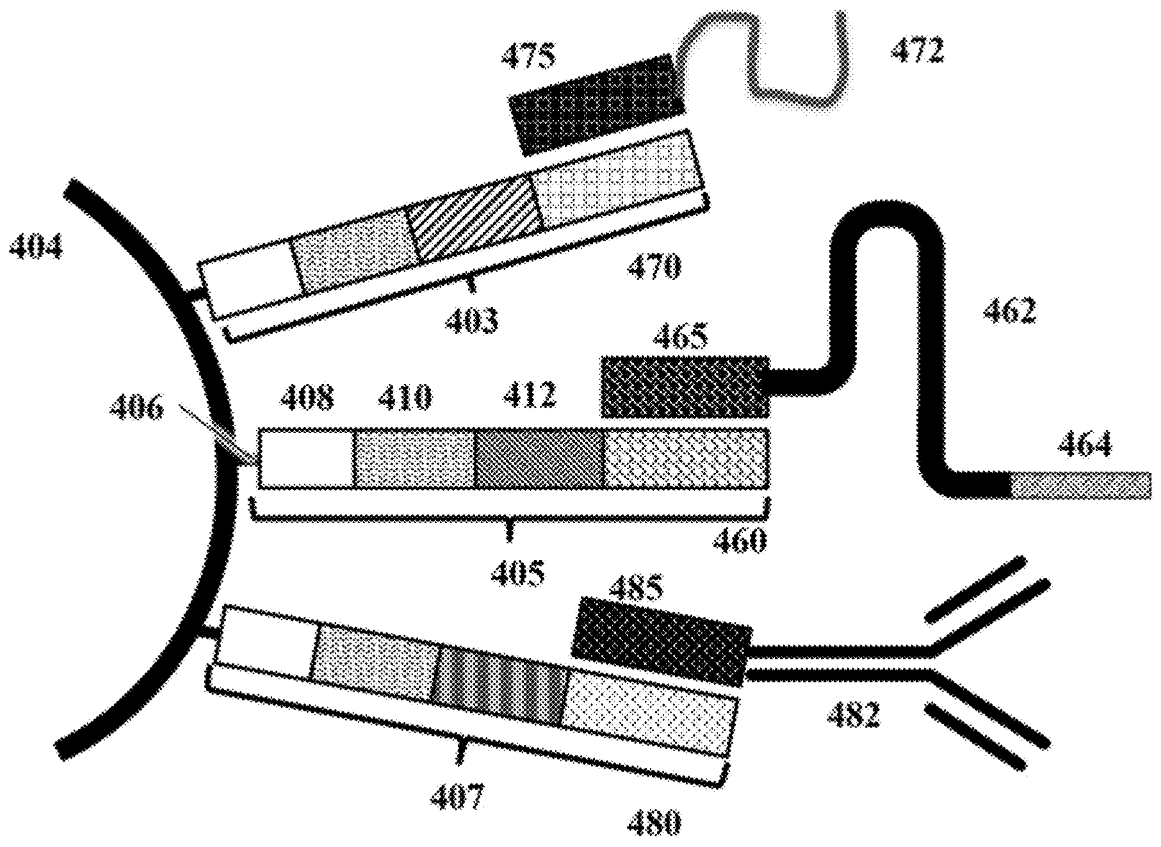
FIG. 4 illustrates another example of a barcode carrying bead.

FIG. 4 illustrates another example of a barcode carrying bead. A nucleic acid molecule 405, such as an oligonucleotide, can be coupled to a bead 404 by a releasable linkage 406, such as, for example, a disulfide linker. The nucleic acid molecule 405 may comprise a first capture sequence 460. The same bead 404 may be coupled (e.g., via releasable linkage) to one or more other nucleic acid molecules 403, 407 comprising other capture sequences. The nucleic acid molecule 405 may be or comprise a barcode. As noted elsewhere herein, the structure of the barcode may comprise a number of sequence elements, such as a functional sequence 408 (e.g., flow cell attachment sequence, sequencing primer sequence, etc.), a barcode sequence 410 (e.g., bead-specific sequence common to bead, partition-specific sequence common to partition, etc.), and a unique molecular identifier 412 (e.g., unique sequence within different molecules attached to the bead), or partial sequences thereof. The capture sequence 460 may be configured to attach to a corresponding capture sequence 465. In some instances, the corresponding capture sequence 465 may be coupled to another molecule that may be an analyte or an intermediary carrier. For example, as illustrated in FIG. 4, the corresponding capture sequence 465 is coupled to a guide RNA molecule 462 comprising a target sequence 464, wherein the target sequence 464 is configured to attach to the analyte. Another oligonucleotide molecule 407 attached to the bead 404 comprises a second capture sequence 480 which is configured to attach to a second corresponding capture sequence 485. As illustrated in FIG. 4, the second corresponding capture sequence 485 is coupled to an antibody 482. In some cases, the antibody 482 may have binding specificity to an analyte (e.g., surface protein). Alternatively, the antibody 482 may not have binding specificity. Another oligonucleotide molecule 403 attached to the bead 404 comprises a third capture sequence 470 which is configured to attach to a second corresponding capture sequence 475. As illustrated in FIG. 4, the third corresponding capture sequence 475 is coupled to a molecule 472. The molecule 472 may or may not be configured to target an analyte. The other oligonucleotide molecules 403, 407 may comprise the other sequences (e.g., functional sequence, barcode sequence, UMI, etc.) described with respect to oligonucleotide molecule 405. While a single oligonucleotide molecule comprising each capture sequence is illustrated in FIG. 4, it will be appreciated that, for each capture sequence, the bead may comprise a set of one or more oligonucleotide molecules each comprising the capture sequence. For example, the bead may comprise any number of sets of one or more different capture sequences. Alternatively or in addition, the bead 404 may comprise other capture sequences. Alternatively or in addition, the bead 404 may comprise fewer types of capture sequences (e.g., two capture sequences). Alternatively or in addition, the bead 404 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl) cystamine can be co-polymerized together to generate a gel bead comprising free COOH groups. The COOH groups of the gel bead can be activated (e.g., via 1-Ethyl-3-(3-dimethylaminopropyl) carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmaleimide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent: gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the support (e.g., a bead such as a gel bead).

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In some cases, a species (e.g., oligonucleotide molecules comprising barcodes) that are attached to a solid support (e.g., a bead) may comprise a U-excising element that allows the species to release from the bead. In some cases, the U-excising element may comprise a single-stranded DNA (ssDNA) sequence that contains at least one uracil. The species may be attached to a solid support via the ssDNA sequence containing the at least one uracil. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms “reducing agent free” or “DTT free” preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may comprise pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl)phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

In some examples, a partition of the plurality of partitions may comprise a single biological particle (e.g., a single cell or a single nucleus of a cell). In some examples, a partition of the plurality of partitions may comprise multiple biological particles. Such partitions may be referred to as multiply occupied partitions, and may comprise, for example, two, three, four or more cells and/or supports (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional supports (e.g., beads) can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction. In such cases, the flow and frequency of the different beads into the channel or junction may be controlled to provide for a certain ratio of supports from each source, while ensuring a given pairing or combination of such beads into a partition with a given number of biological particles (e.g., one biological particle and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with supports, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Multiplexing

The present disclosures provides methods and systems for multiplexing, and otherwise increasing throughput in, analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cell features may be used to characterize biological particles and/or cell features. In some instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of example labelling agents, reporter oligonucleotides, and methods of use, see, e.g., U.S. Pat. No. 10,550,429; U.S. Pat. Pub. 20190177800; and U.S. Pat. Pub. 20190367969, each of which is herein entirely incorporated by reference for all purposes.

In a particular example, a library of potential cell feature labelling agents or binding groups may be provided, where the respective cell feature labelling agents are associated with nucleic acid reporter molecules (or reporter oligonucleotides), such that a different reporter oligonucleotide sequence is associated with each labelling agent capable of binding to a specific cell feature. In some aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

Labelling agents capable of binding to or otherwise coupling to one or more biological particles may be used to characterize a biological particle as belonging to a particular set of biological particles. For example, labeling agents may be used to label a sample of cells, nuclei, or cell beads, or a group of cells, nuclei, or cell beads. In this way, a group of cells may be labeled as different from another group of cells (or nuclei or cell beads). In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling a biological particle may comprise subjecting the antibody-linked barcode molecule or the epitope binding fragment-linked barcode molecule to conditions suitable for binding the antibody to a molecule present on a surface of the biological particle. The binding affinity between the antibody or the epitope binding fragment thereof and the molecule present on the surface may be within a useful range to ensure that the antibody or the epitope binding fragment thereof remains bound to the molecule. For example, the binding affinity may be within a useful range to ensure that the antibody or the epitope binding fragment thereof remains bound to the molecule during various sample processing steps, such as partitioning and/or nucleic acid amplification or extension. A dissociation constant (Kd) between the antibody or an epitope binding fragment thereof and the molecule to which it binds may be less than about 100 μM, 90 μM, 80 μM, 70 μM, 60 μM, 50 μM, 40 μM, 30 μM, 20 μM, 10 μM, 9 μM, 8 μM, 7 μM, 6 μM, 5 μM, 4 μM, 3 μM, 2 μM, 1 μM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 pM, 800 pM, 700 pM, 600 pM. 500 pM, 400 pM, 300 pM. 200 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, or 1 pM. For example, the dissociation constant may be less than about 10 pM.

In another example, a reporter oligonucleotide may be coupled to a cell-penetrating peptide (CPP), and labeling cells may comprise delivering the CPP coupled reporter oligonucleotide into a biological particle. Labeling biological particles may comprise delivering the CPP conjugated oligonucleotide into a cell and/or cell bead by the cell-penetrating peptide. A cell-penetrating peptide that can be used in the methods provided herein can comprise at least one non-functional cysteine residue, which may be either free or derivatized to form a disulfide link with an oligonucleotide that has been modified for such linkage. Non-limiting examples of cell-penetrating peptides that can be used in embodiments herein include penetratin, transportan, plsl, TAT(48-60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The cell-penetrating peptide may be an arginine-rich peptide transporter. The cell-penetrating peptide may be Penetratin or the Tat peptide.

In another example, a reporter oligonucleotide may be coupled to a fluorophore or dye, and labeling cells (or nuclei or cell beads) may comprise subjecting the fluorophore-linked barcode molecule to conditions suitable for binding the fluorophore to the surface of the biological particle. In some instances, fluorophores can interact strongly with lipid bilayers and labeling biological particles may comprise subjecting the fluorophore-linked barcode molecule to conditions such that the fluorophore binds to or is inserted into a membrane of the biological particle. In some cases, the fluorophore is a water-soluble, organic fluorophore. In some instances, the fluorophore is Alexa 532 maleimide, tetramethylrhodamine-S-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B, Alexa 594 maleimide, Texas Red maleimide, Alexa 633 maleimide, Abberior STAR 635P azide, Atto 647N maleimide, Atto 647 SE, or Sulfo-Cy5 maleimide. See, e.g., Hughes L D, et al. *PLoS One*. 2014 Feb. 4; 9(2):e87649, which is hereby incorporated by reference in its entirety for all purposes, for a description of organic fluorophores.

A reporter oligonucleotide may be coupled to a lipophilic molecule, and labeling biological particles may comprise delivering the nucleic acid barcode molecule to a membrane of the biological particle or a nuclear membrane by the lipophilic molecule. Lipophilic molecules can associate with and/or insert into lipid membranes such as cell membranes and nuclear membranes. In some cases, the insertion can be reversible. In some cases, the association between the lipophilic molecule and biological particle may be such that the biological particle retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to, during, or following partitioning, the cells (or nuclei or cell beads) may be incubated with the library of labelling agents, that may be labelling agents to a broad panel of different cell features, e.g., receptors, proteins, etc., and which include their associated reporter oligonucleotides. Unbound labelling agents may be washed from the cells, and the cells (or nuclei or cell beads) may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, which is hereby entirely incorporated by reference for all purposes.

As described elsewhere herein, libraries of labelling agents may be associated with a particular cell feature as well as be used to identify analytes as originating from a particular biological particle, population, or sample. The biological particles may be incubated with a plurality of libraries and a given biological particle may comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In some instances, these reporter oligonucleotides may comprise nucleic acid barcode sequences that permit identification of the labelling agent which the reporter oligonucleotide is coupled to. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 11:
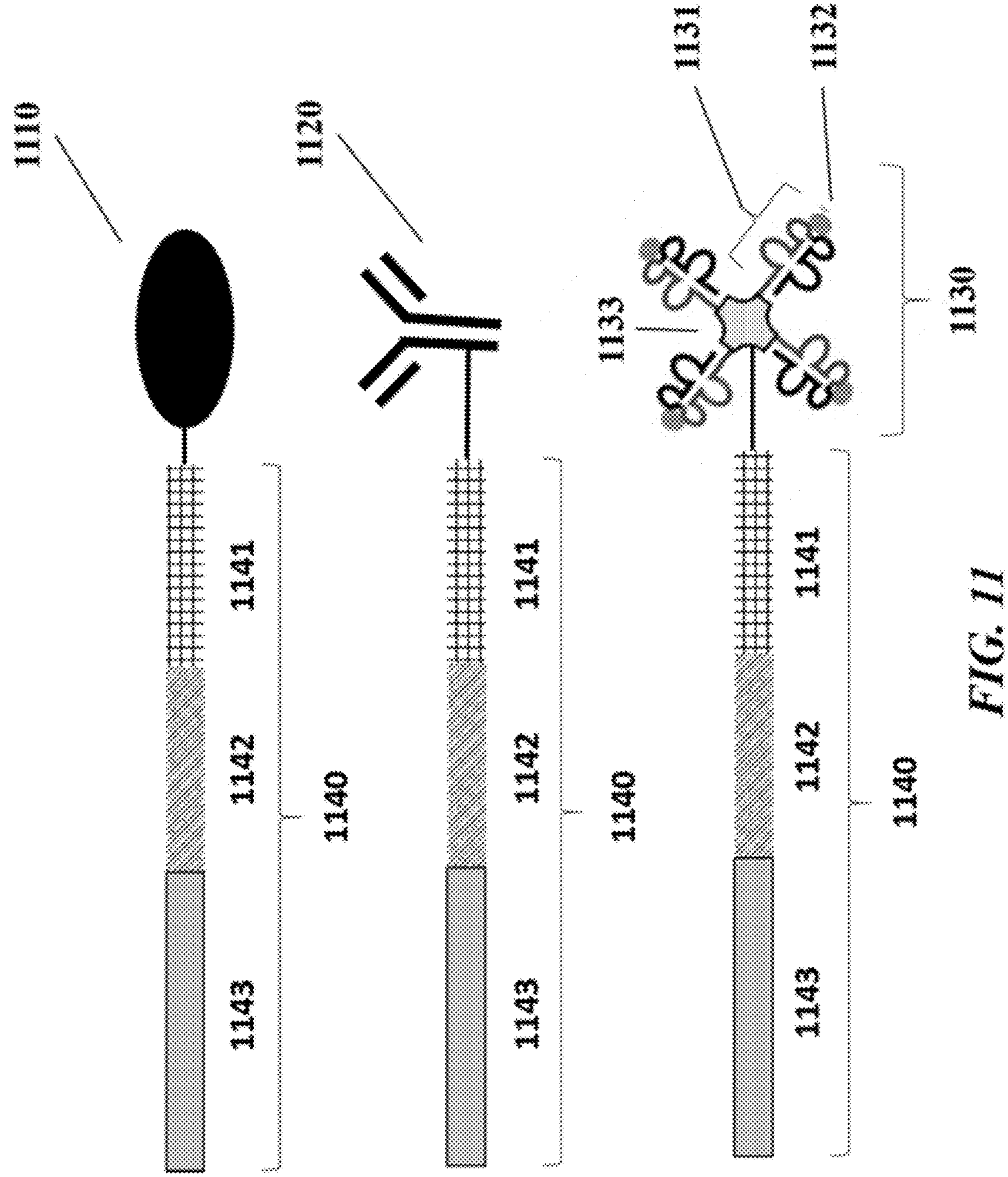
FIG. 11 schematically illustrates example labelling agents with nucleic acid molecules attached thereto.

FIG. 11 describes example labelling agents (1110, 1120, 1130) comprising reporter oligonucleotides (1140) attached thereto. Labelling agent 1110 (e.g., any of the labelling agents described herein) is attached (either directly, e.g., covalently attached, or indirectly) to reporter oligonucleotide 1140. Reporter oligonucleotide 1140 may comprise barcode sequence 1142 that identifies labelling agent 1110. Reporter oligonucleotide 1140 may also comprise one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer biding sequence (such as an R1, R2, or partial R1 or R2 sequence).

Referring to FIG. 11, in some instances, reporter oligonucleotide 1140 conjugated to a labelling agent (e.g., 1110, 1120, 1130) comprises a primer sequence 1141, a barcode sequence that identifies the labelling agent (e.g., 1110, 1120, 1130), and functional sequence 1143. Functional sequence 1143 may be configured to hybridize to a complementary sequence, such as a complementary sequence present on a nucleic acid barcode molecule 1190 (not shown), such as those described elsewhere herein. In some instances, nucleic acid barcode molecule 1190 is attached to a support (e.g., a bead, such as a gel bead), such as those described elsewhere herein. For example, nucleic acid barcode molecule 1190 may be attached to the support via a releasable linkage (e.g., comprising a labile bond), such as those described elsewhere herein. In some instances, reporter oligonucleotide 1140 comprises one or more additional functional sequences, such as those described above.

In some instances, the labelling agent 1110 is a protein or polypeptide (e.g., an antigen or prospective antigen) comprising reporter oligonucleotide 1140. Reporter oligonucleotide 1140 comprises barcode sequence 1142 that identifies polypeptide 1110 and can be used to infer the presence of an analyte, e.g., a binding partner of polypeptide 1110 (e.g., a molecule or compound to which polypeptide 1110 can bind). In some instances, the labelling agent 1110 is a lipophilic moiety (e.g., cholesterol) comprising reporter oligonucleotide 1140, where the lipophilic moiety is selected such that labelling agent 1110 integrates into a membrane of a cell or nucleus. Reporter oligonucleotide 1140 comprises barcode sequence 1142 that identifies lipophilic moiety 1110 which in some instances is used to tag cells (e.g., groups of cells, cell samples, etc.) and may be used for multiplex analyses as described elsewhere herein. In some instances, the labelling agent is an antibody 1120 (or an epitope binding fragment thereof) comprising reporter oligonucleotide 1140. Reporter oligonucleotide 1140 comprises barcode sequence 1142 that identifies antibody 1120 and can be used to infer the presence of, e.g., a target of antibody 1120 (e.g., a molecule or compound to which antibody 1120 binds). In other embodiments, labelling agent 1130 comprises an MHC molecule 1131 comprising peptide 1132 and reporter oligonucleotide 1140 that identifies peptide 1132. In some instances, the MHC molecule is coupled to a support 1133. In some instances, support 1133 may be a polypeptide, such as streptavidin, or a polysaccharide, such as dextran. In some instances, reporter oligonucleotide 1140 may be directly or indirectly coupled to MHC labelling agent 1130 in any suitable manner. For example, reporter oligonucleotide 1140 may be coupled to MHC molecule 1131, support 1133, or peptide 1132. In some embodiments, labelling agent 1130 comprises a plurality of MHC molecules, (e.g. is an MHC multimer, which may be coupled to a support (e.g., 1133)). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of example labelling agents, including antibody and MHC-based labelling agents, reporter oligonucleotides, and methods of use, see, e.g., U.S. Pat. No. 10,550,429 and U.S. Pat. Pub. 20190367969, each of which is herein entirely incorporated by reference for all purposes.

Figure 12A:
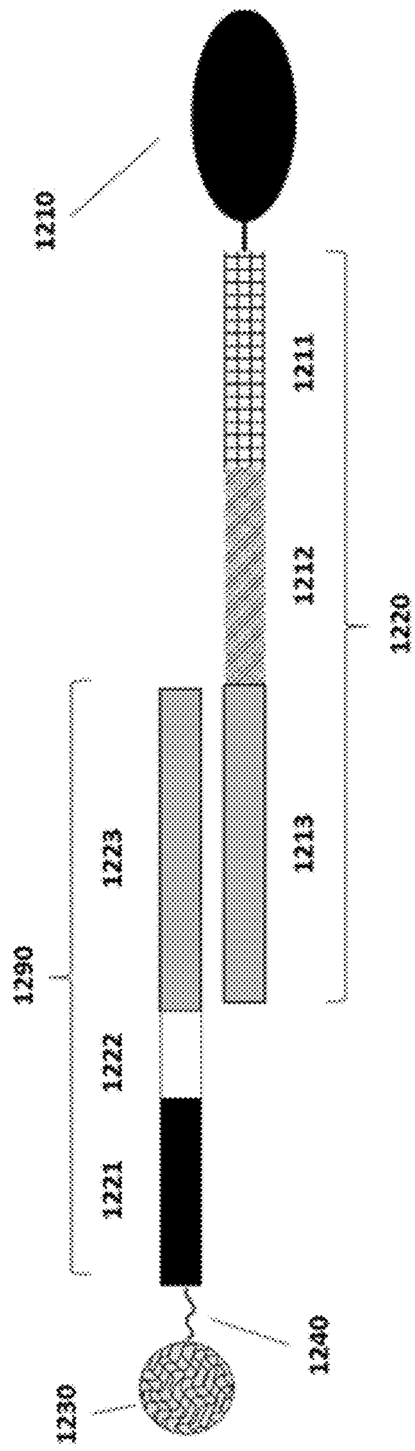
FIG. 12A schematically shows an example of labelling agents.
Figure 12B:
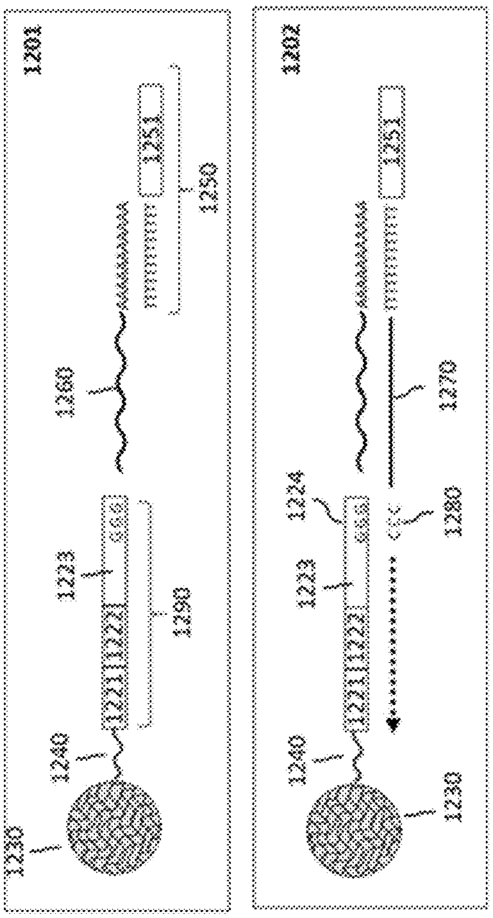
FIG. 12B schematically shows another example workflow for processing nucleic acid molecules.
Figure 12C:
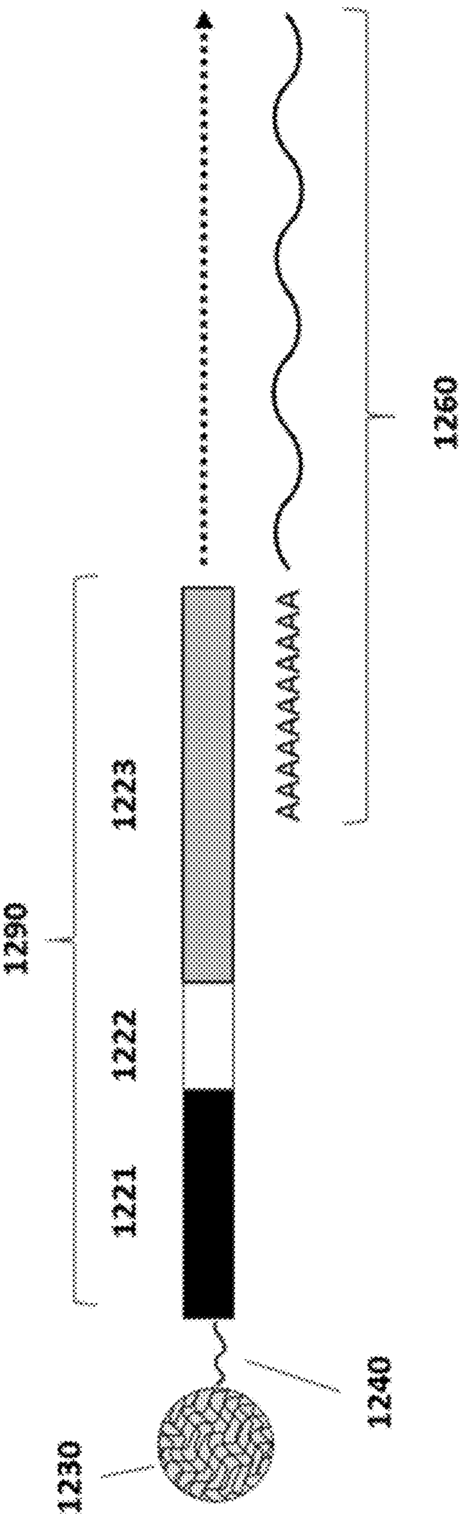
FIG. 12C schematically shows another example workflow for processing nucleic acid molecules.
Figure 13:
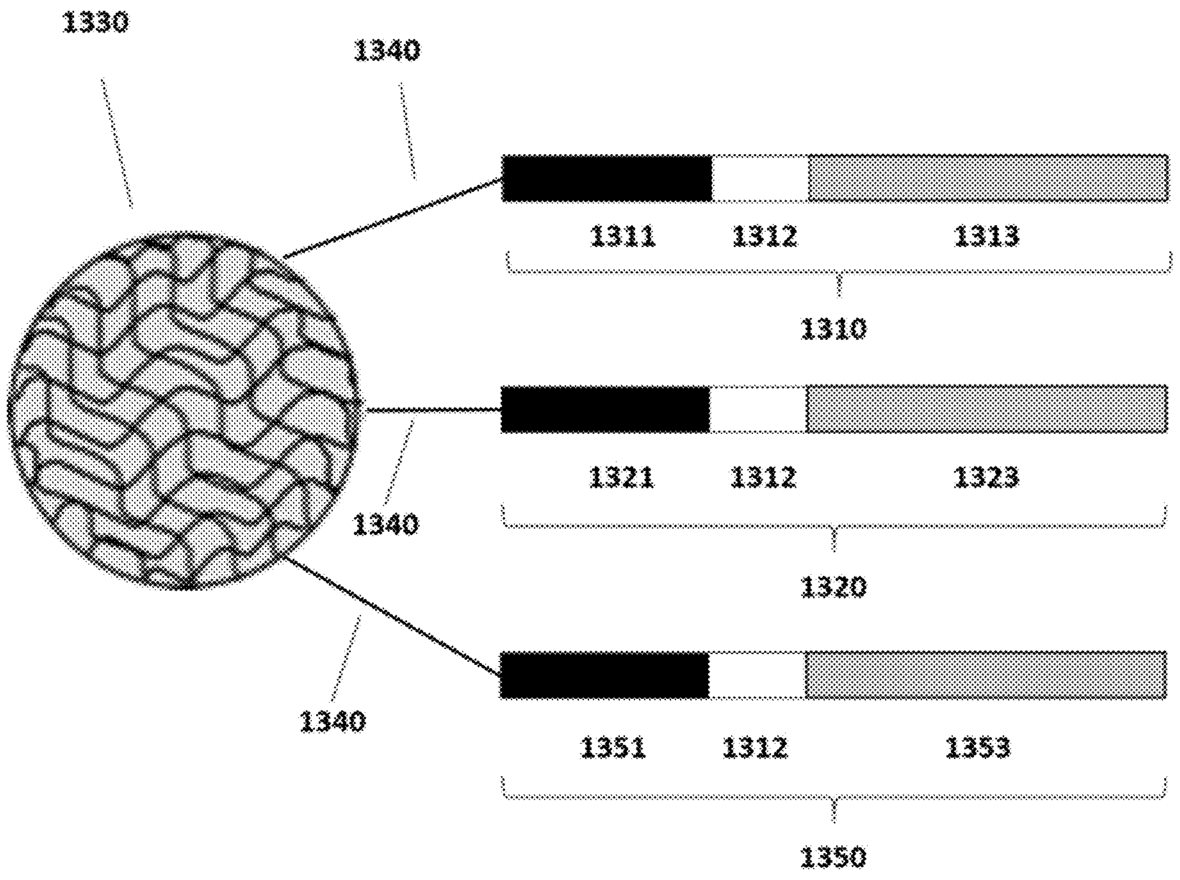
FIG. 13 schematically shows another example of a barcode-carrying bead.

FIG. 13 illustrates another example of a barcode carrying bead. In some embodiments, analysis of multiple analytes (e.g., RNA and one or more analytes using labelling agents described herein) may comprise nucleic acid barcode molecules as generally depicted in FIG. 13. In some embodiments, nucleic acid barcode molecules 1310 and 1320 are attached to support 1330 via a releasable linkage 1340 (e.g., comprising a labile bond) as described elsewhere herein. Nucleic acid barcode molecule 1310 may comprise adapter sequence 1311, barcode sequence 1312 and adapter sequence 1313. Nucleic acid barcode molecule 1320 may comprise adapter sequence 1321, barcode sequence 1312, and adapter sequence 1323, wherein adapter sequence 1323 comprises a different sequence than adapter sequence 1313. In some instances, adapter 1311 and adapter 1321 comprise the same sequence. In some instances, adapter 1311 and adapter 1321 comprise different sequences. Although support 1330 is shown comprising nucleic acid barcode molecules 1310 and 1320, any suitable number of barcode molecules comprising common barcode sequence 1312 are contemplated herein. For example, in some embodiments, support 1330 further comprises nucleic acid barcode molecule 1350. Nucleic acid barcode molecule 1350 may comprise adapter sequence 1351, barcode sequence 1312 and adapter sequence 1353, wherein adapter sequence 1353 comprises a different sequence than adapter sequence 1313 and 1323. In some instances, nucleic acid barcode molecules (e.g., 1310, 1320, 1350) comprise one or more additional functional sequences, such as a UMI or other sequences described herein. The nucleic acid barcode molecules 1310, 1320 or 1350 may interact with analytes as described elsewhere herein, for example, as depicted in FIGS. 12A-C.

Referring to FIG. 12A, in an instance where cells are labelled with labeling agents, sequence 1223 may be complementary to an adapter sequence of a reporter oligonucleotide. Cells (or nuclei or cell beads) may be contacted with one or more reporter oligonucleotide 1220 conjugated labelling agents 1210 (e.g., polypeptide, antibody, or others described elsewhere herein). In some cases, the cells (or nuclei or cell beads) may be further processed prior to barcoding. For example, such processing may include one or more washing and/or cell sorting operations. In some instances, a cell that is bound to labelling agent 1210 which is conjugated to oligonucleotide 1220 and support 1230 (e.g., a bead, such as a gel bead) comprising nucleic acid barcode molecule 1290 is partitioned into a partition amongst a plurality of partitions (e.g., a droplet of a droplet emulsion or a well of a microwell array). In some instances, the partition comprises at most a single cell bound to labelling agent 1210. In some instances, reporter oligonucleotide 1220 conjugated to labelling agent 1210 (e.g., polypeptide, an antibody, pMHC molecule such as an MHC multimer, etc.) comprises a first adapter sequence 1211 (e.g., a primer sequence), a barcode sequence 1212 that identifies the labelling agent 1210 (e.g., the polypeptide, antibody, or peptide of a pMHC molecule or complex), and an adapter sequence 1213. Adapter sequence 1213 may be configured to hybridize to a complementary sequence, such as sequence 1223 present on a nucleic acid barcode molecule 1290. In some instances, oligonucleotide 1220 comprises one or more additional functional sequences, such as those described elsewhere herein.

Barcoded nucleic may be generated (e.g., via a nucleic acid reaction, such as nucleic acid extension or ligation)

from the constructs described in FIGS. 12A-C. For example, sequence 1213 may then be hybridized to complementary sequence 1223 to generate (e.g., via a nucleic acid reaction, such as nucleic acid extension or ligation) a barcoded nucleic acid molecule comprising cell (e.g., partition specific) barcode sequence 1222 (or a reverse complement thereof) and reporter barcode sequence 1212 (or a reverse complement thereof). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, which is hereby entirely incorporated by reference for all purposes. Barcoded nucleic acid molecules, or derivatives generated therefrom, can then be sequenced on a suitable sequencing platform.

In some instances, analysis of multiple analytes (e.g., nucleic acids and one or more analytes using labelling agents described herein) may be performed. For example, the workflow may comprise a workflow as generally depicted in any of FIGS. 12A-C, or a combination of workflows for an individual analyte, as described elsewhere herein. For example, by using a combination of the workflows as generally depicted in FIGS. 12A-C, multiple analytes can be analyzed.

In some instances, analysis of an analyte (e.g. a nucleic acid, a polypeptides, a carbohydrate, a lipid, etc.) comprises a workflow as generally depicted in FIG. 12A. A nucleic acid barcode molecule 1290 may be co-partitioned with the one or more analytes. In some instances, nucleic acid barcode molecule 1290 is attached to a support 1230 (e.g., a bead, such as a gel bead), such as those described elsewhere herein. For example, nucleic acid barcode molecule 1290 may be attached to support 1230 via a releasable linkage 1240 (e.g., comprising a labile bond), such as those described elsewhere herein. Nucleic acid barcode molecule 1290 may comprise a barcode sequence 1221 and optionally comprise other additional sequences, for example, a UMI sequence 1222 (or other functional sequences described elsewhere herein). The nucleic acid barcode molecule 1290 may comprise a sequence 1223 that may be complementary to another nucleic acid sequence, such that it may hybridize to a particular sequence.

For example, sequence 1223 may comprise a poly-T sequence and may be used to hybridize to mRNA. Referring to FIG. 12C, in some embodiments, nucleic acid barcode molecule 1290 comprises sequence 1223 complementary to a sequence of RNA molecule 1260 from a cell. In some instances, sequence 1223 comprises a sequence specific for an RNA molecule. Sequence 1223 may comprise a known or targeted sequence or a random sequence. In some instances, a nucleic acid extension reaction may be performed, thereby generating a barcoded nucleic acid product comprising sequence 1223, the barcode sequence 1221, UMI sequence 1222, any other functional sequence, and a sequence corresponding to the RNA molecule 1260.

In another example, sequence 1223 may be complementary to an overhang sequence or an adapter sequence that has been appended to an analyte. For example, referring to FIG. 12B, panel 1201, in some embodiments, primer 1250 comprises a sequence complementary to a sequence of nucleic acid molecule 1260 (such as an RNA encoding for a BCR sequence) from a biological particle. In some instances, primer 1250 comprises one or more sequences 1251 that are not complementary to RNA molecule 1260. Sequence 1251 may be a functional sequence as described elsewhere herein, for example, an adapter sequence, a sequencing primer sequence, or a sequence the facilitates coupling to a flow cell of a sequencer. In some instances, primer 1250 comprises a poly-T sequence. In some instances, primer 1250 comprises a sequence complementary to a target sequence in an RNA molecule. In some instances, primer 1250 comprises a sequence complementary to a region of an immune molecule, such as the constant region of a TCR or BCR sequence. Primer 1250 is hybridized to nucleic acid molecule 1260 and complementary molecule 1270 is generated (see Panel 1202). For example, complementary molecule 1270 may be cDNA generated in a reverse transcription reaction. In some instances, an additional sequence may be appended to complementary molecule 1270. For example, the reverse transcriptase enzyme may be selected such that several non-templated bases 1280 (e.g., a poly-C sequence) are appended to the cDNA. In another example, a terminal transferase may also be used to append the additional sequence. Nucleic acid barcode molecule 1290 comprises a sequence 1224 complementary to the non-templated bases, and the reverse transcriptase performs a template switching reaction onto nucleic acid barcode molecule 1290 to generate a barcoded nucleic acid molecule comprising cell (e.g., partition specific) barcode sequence 1222 (or a reverse complement thereof) and a sequence of complementary molecule 1270 (or a portion thereof). In some instances, sequence 1223 comprises a sequence complementary to a region of an immune molecule, such as the constant region of a TCR or BCR sequence. Sequence 1223 is hybridized to nucleic acid molecule 1260 and a complementary molecule 1270 is generated. For example complementary molecule 1270 may be generated in a reverse transcription reaction generating a barcoded nucleic acid molecule comprising cell (e.g., partition specific) barcode sequence 1222 (or a reverse complement thereof) and a sequence of complementary molecule 1270 (or a portion thereof). Additional methods and compositions suitable for barcoding cDNA generated from mRNA transcripts including those encoding V (D) J regions of an immune cell receptor and/or barcoding methods and composition including a template switch oligonucleotide are described in International Patent Application WO2018/075693, U.S. Patent Publication No. 2018/0105808, U.S. Patent Publication No. 2015/0376609, filed Jun. 26, 2015, and U.S. Patent Publication No. 2019/0367969, each of which applications is herein entirely incorporated by reference for all purposes.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

The methods and systems of the present disclosure may comprise microfluidic devices and methods of use thereof, which may be used for co-partitioning biological particles or biological particles with reagents. Such systems and methods are described in U.S. Patent Publication No. US/20190367997, which is herein incorporated by reference in its entirety for all purposes.

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments of the microfluidic devices described elsewhere herein may be coupled to any of a variety of different fluid sources or receiving components, including reservoirs, tubing, manifolds, or fluidic components of other systems. As will be appreciated, the microfluidic channel structures may have various geometries and/or configurations. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, Triton® X-100 (t-Octylphenoxypolyethoxyethanol) and Tween® 20 (polysorbate 20). In some cases, lysis solutions may include ionic surfactants such as, for example, Sarcosyl® (sodium lauroyl sarcosinate) and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., a cell or a nucleus in a polymer matrix), the biological particles may be exposed to an appropriate stimulus to release the biological particles or their contents from a co-partitioned support (e.g., bead). For example, in some cases, a chemical stimulus may be co-partitioned along with an encapsulated biological particle to allow for the degradation of the support and release of the cell or its contents into the larger partition. In some cases, this stimulus may be the same as the stimulus described elsewhere herein for release of nucleic acid molecules (e.g., oligonucleotides) from their respective support (e.g., bead). In alternative examples, this may be a different and non-overlapping stimulus, in order to allow an encapsulated biological particle to be released into a partition at a different time from the release of nucleic acid molecules into the same partition. For a description of methods, compositions, and systems for encapsulating cells (also referred to as a "cell bead"), see, e.g., U.S. Pat. No. 10,428,326 and U.S. Pat. Pub. 20190100632, which are each incorporated by reference in their entirety.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxy Inosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells (or nuclei or cell beads) are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, e.g., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying nucleic acids (e.g., mRNA, the genomic DNA) from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides (e.g., attached to a bead) into partitions, e.g., droplets within microfluidic systems.

In an example, supports, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000, 000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

FIG. 2 shows an example of a microfluidic channel structure for the controlled partitioning of beads into discrete droplets. A channel structure 200 can include a channel segment 202 communicating at a channel junction 206 (or intersection) with a reservoir 204. The reservoir 204 can be a chamber. Any reference to "reservoir," as used herein, can also refer to a "chamber." In operation, an aqueous fluid 208 that includes suspended beads 212 may be transported along the channel segment 202 into the junction 206 to meet a second fluid 210 that is immiscible with the aqueous fluid 208 in the reservoir 204 to create droplets 216, 218 of the aqueous fluid 208 flowing into the reservoir 204. At the junction 206 where the aqueous fluid 208 and the second fluid 210 meet, droplets can form based on factors such as the hydrodynamic forces at the junction 206, flow rates of the two fluids 208, 210, fluid properties, and certain geometric parameters (e.g., w, $h_0$, $\alpha$, etc.) of the channel structure 200. A plurality of droplets can be collected in the reservoir 204 by continuously injecting the aqueous fluid 208 from the channel segment 202 through the junction 206.

A discrete droplet generated may include a bead (e.g., as in occupied droplets 216). Alternatively, a discrete droplet generated may include more than one bead. Alternatively, a discrete droplet generated may not include any beads (e.g., as in unoccupied droplet 218). In some instances, a discrete droplet generated may contain one or more biological particles, as described elsewhere herein. In some instances, a discrete droplet generated may comprise one or more reagents, as described elsewhere herein.

In some instances, the aqueous fluid 208 can have a substantially uniform concentration or frequency of beads 212. The beads 212 can be introduced into the channel segment 202 from a separate channel (not shown in FIG. 2). The frequency of beads 212 in the channel segment 202 may be controlled by controlling the frequency in which the beads 212 are introduced into the channel segment 202 and/or the relative flow rates of the fluids in the channel segment 202 and the separate channel. In some instances, the beads can be introduced into the channel segment 202 from a plurality of different channels, and the frequency controlled accordingly.

In some instances, the aqueous fluid 208 in the channel segment 202 can comprise biological particles. In some instances, the aqueous fluid 208 can have a substantially uniform concentration or frequency of biological particles. As with the beads, the biological particles can be introduced into the channel segment 202 from a separate channel. The frequency or concentration of the biological particles in the aqueous fluid 208 in the channel segment 202 may be controlled by controlling the frequency in which the biological particles are introduced into the channel segment 202 and/or the relative flow rates of the fluids in the channel segment 202 and the separate channel. In some instances, the biological particles can be introduced into the channel segment 202 from a plurality of different channels, and the frequency controlled accordingly. In some instances, a first separate channel can introduce beads and a second separate channel can introduce biological particles into the channel segment 202. The first separate channel introducing the beads may be upstream or downstream of the second separate channel introducing the biological particles.

The second fluid 210 can comprise an oil, such as a fluorinated oil, that includes a fluorosurfactant for stabilizing the resulting droplets, for example, inhibiting subsequent coalescence of the resulting droplets.

In some instances, the second fluid 210 may not be subjected to and/or directed to any flow in or out of the reservoir 204. For example, the second fluid 210 may be substantially stationary in the reservoir 204. In some instances, the second fluid 210 may be subjected to flow within the reservoir 204, but not in or out of the reservoir 204, such as via application of pressure to the reservoir 204 and/or as affected by the incoming flow of the aqueous fluid 208 at the junction 206. Alternatively, the second fluid 210 may be subjected and/or directed to flow in or out of the reservoir 204. For example, the reservoir 204 can be a channel directing the second fluid 210 from upstream to downstream, transporting the generated droplets.

The channel structure 200 at or near the junction 206 may have certain geometric features that at least partly determine the sizes of the droplets formed by the channel structure 200. The channel segment 202 can have a height, $h_0$ and width, w, at or near the junction 206. By way of example, the channel segment 202 can comprise a rectangular cross-section that leads to a reservoir 204 having a wider cross-section (such as in width or diameter). Alternatively, the cross-section of the channel segment 202 can be other shapes, such as a circular shape, trapezoidal shape, polygonal shape, or any other shapes. The top and bottom walls of the reservoir 204 at or near the junction 206 can be inclined at an expansion angle, a. The expansion angle, a, allows the tongue (portion of the aqueous fluid 208 leaving channel segment 202 at junction 206 and entering the reservoir 204 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and α:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and α=3°, the predicted droplet size is 121 μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, α, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15° 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 208 entering the junction 206 can be between about 0.04 microliters (μL)/minute (min) and about 40 μL/min. In some instances, the flow rate of the aqueous fluid 208 entering the junction 206 can be between about 0.01 microliters (μL)/minute (min) and about 100 μL/min. Alternatively, the flow rate of the aqueous fluid 208 entering the junction 206 can be less than about 0.01 μL/min. Alternatively, the flow rate of the aqueous fluid 208 entering the junction 206 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 208 entering the junction 206.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 206) between aqueous fluid 208 channel segments (e.g., channel segment 202) and the reservoir 204. Alternatively or in addition, the throughput of droplet generation can be increased by increasing the flow rate of the aqueous fluid 208 in the channel segment 202.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Figure 40:
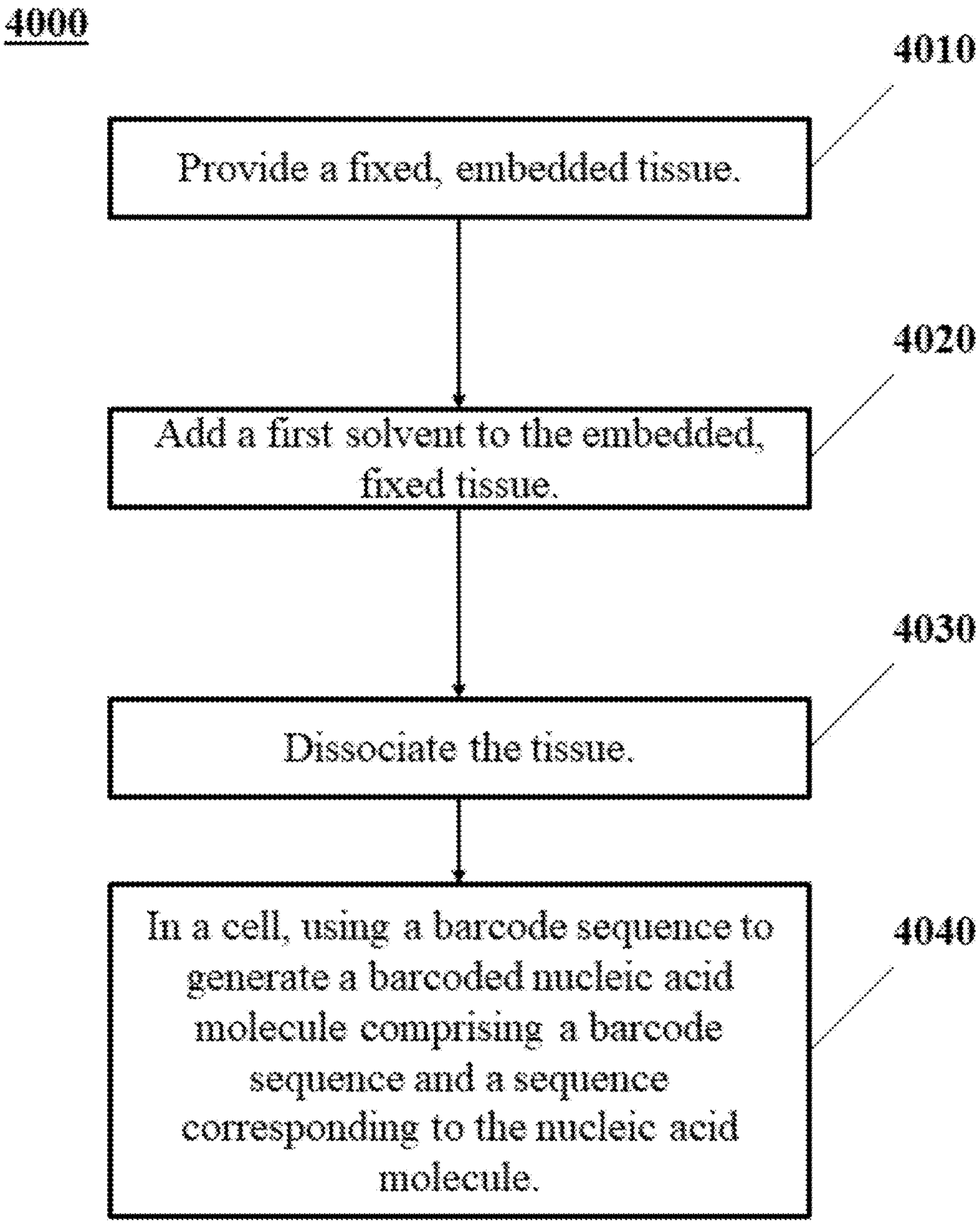
FIG. 40 shows a flowchart of a method for analyzing a nucleic acid molecule of an embedded, fixed tissue, according to some embodiments.

FIG. 40 shows a flowchart of a method 4000 for analyzing a nucleic acid molecule of an embedded, fixed tissue, according to some embodiments. In an operation 4010, the method 4000 may comprise providing the embedded, fixed tissue. The embedded, fixed tissue may comprise a plurality of cells. A cell of the plurality of cells may comprise the nucleic acid molecule. The embedded, fixed tissue may be embedded in a solid medium. The nucleic acid molecule may be as described elsewhere herein. For example, the nucleic acid molecule may comprise a ribonucleic acid (RNA) molecule. In another example, the nucleic acid molecule may comprise a messenger RNA molecule.

The fixed tissue may be fixed at least about 1 day (d), 2 d, 3 d, 4 d, 5 d, 6 d, 1 week (w), 2 w, 3 w, 1 month (m), 2 m, 3 m, 4 m, 5 m, 6 m, 7 m, 8 m, 9 m, 10 m, 11 m, 1 year (y), 2 y, 3 y, 4 y, 5 y, 10 y, 15 y, 20 y, or more prior to operation 4010. The fixed tissue may be fixed at most about 20 y, 15 y, 10 y, 5 y, 4 y, 3 y, 2y, 1 y, 11 m, 10 m, 9 m, 8 m, 7 m, 6 m, 5 m, 4 m, 3 m, 2 m, 1 m, 3 w, 2 w, 1 w, 6 d, 5 d, 4 d, 3 d, 2 d, 1 d, or less prior to operation 4010. The fixed tissue may be fixed at a time as defined by a range of any two of the proceeding values.

The fixed tissue may comprise one or more of, for example, connective tissue, epithelial tissue, organ tissue, muscle tissue, ligaments, tendons, a skin tissue, breast tissue, bladder, kidney tissue, liver tissue, colon tissue, thyroid tissue, cervical tissue, prostate tissue, lung tissue, cardiac tissue, heart tissue, muscle tissue, pancreas tissue, anal tissue, bile duct tissue, a bone tissue, bone marrow, uterine tissue, ovarian tissue, endometrial tissue, vaginal tissue, vulvar tissue, stomach tissue, ocular tissue, nasal tissue, sinus tissue, penile tissue, salivary gland tissue, gut tissue, gallbladder tissue, gastrointestinal tissue, bladder tissue, brain tissue, spinal tissue, neurons, cells representative of a blood-brain barrier, blood, hair, nails, keratin, collagen, or any combination thereof. For example, the fixed tissue may comprise fixed human tissue. For example, the fixed tissue may comprise fixed cancer tissue (e.g., fixed breast cancer tissue).

In some cases, the solid medium comprises paraffin. The solid medium may comprise, for example, other long chain hydrophobic compounds (e.g., waxes, etc.), glycerin, gels, epoxy, resin, or the like, or any combination thereof. The fixed tissue may be fixed using, for example, formaldehyde (e.g., formalin), ethanolic fixatives, polyethylene glycol, glycerol, acetic acid, zinc-based fixatives, khandsari, honey, or the like, or any combination thereof.

In another operation 4020, the method 4000 may comprise removing at least a portion of the solid medium from the embedded, fixed tissue, thereby obtaining a fixed tissue comprising the plurality of cells.

In some cases, operation 4020 may comprise adding a first solvent to the embedded, fixed tissue, thereby dissolving the solid medium, thereby obtaining a fixed tissue. In some cases, the first solvent comprises a non-polar solvent. Examples of non-polar solvents include, but are not limited to, alkanes (e.g., butane, pentane, hexanes, etc.), aromatic compounds (e.g., benzene, toluene, xylenes, etc.), xylene alternative compounds (e.g., neo-Clear® xylene alternative, etc.), or the like, or any combination thereof. The non-polar solvent may have no or substantially no dipole moment over the solvent molecule. The non-polar solvent may be configured to dissolve at least a portion of the solid medium. For example, the solid medium may comprise a non-polar portion dissolvable by the first solvent.

The operation 4020 may comprise removing the first solvent from the fixed tissue. The removing may comprise removing without damaging the fixed tissue. For example, the first solvent can be removed without physical damage to the fixed tissue. In this example, the fixed tissue can remain as a tissue scroll subsequent to the removal of the solid medium and the first solvent. The removing may comprise use of a pipette. For example, the first solvent can be removed via pipetting away the first solvent without disrupting the fixed tissue. The removing may comprise decanting the first solvent away from the fixed tissue.

The operation 4020 may further comprise adding a second solvent into the fixed tissue. The second solvent may comprise a polar solvent. Examples of polar solvents include, but are not limited to, alcohols (e.g., methanol, ethanol, propanol, iso-propanol, etc.), carbonyl containing compounds (e.g., acetone, ethyl acetate, etc.), haloforms (e.g., chloroform, etc.), dimethyl sulphoxide (DMSO), N-methyl formamide (NMF), or the like, or any combination thereof. In an example, the polar solvent is ethanol. The operation 4020 may comprise removing the second solvent from the fixed tissue. The removing may be as described elsewhere herein. For example, the removing may comprise not disrupting the fixed tissue.

The operation 4020 may comprise adding a rehydration agent to the fixed tissue. The rehydration agent may comprise water. In an example, the rehydration agent can be water. In another example, the rehydration agent can comprise a buffer solution. The rehydration agent may comprise one or more of buffers, salts, ions, ore the like, or any combination thereof. The operation 4020 may comprise removing the rehydration agent from the tissue as described elsewhere herein. The operation 4020 may comprise adding a buffer to the fixed tissue. Examples of buffers include, but are not limited to, tris buffers, phosphate buffers, glycine buffers, boric acid buffers, carboxylic acid buffers (e.g., malic acid, formic acid, lactic acid, etc.), or the like, or any combination thereof. In some cases, the buffer may be removed from the fixed tissue. The removing may be as described elsewhere herein.

In another operation 4030, the method 4000 may comprise dissociating the fixed tissue into cells of the plurality of cells. The cells may comprise the cell comprising the nucleic acid molecule.

Operation 4030 may comprise dissociating the tissue. The dissociating the tissue may comprise us of one or more of a manual dissociator (e.g., a manual pulverizer, a mortar and pestle, a manual chopper, etc.), an automated dissociator (e.g., a gentleMACS™ Octo Dissociator, a Kerafast® PCT shredder, a Covaris® cryoPREP automated dry pulverizer, etc.), or the like, or any combination thereof.

Operation 4030 may comprise resuspending the tissue. The resuspending may comprise adding a resuspension solution to the tissue. The resuspension solution may comprise, for example, water, surfactants, buffers, salts, or the like, or any combination thereof. The resuspension solution may be configured to solubilize at least a portion of the tissue and/or components of the tissue (e.g., biological molecules, nucleic acids, etc.). The resuspending may make the contents of the tissue available for the methods and systems described elsewhere herein. The resuspending may provide the tissue for additional process operations.

Operation 4030 may comprise washing the tissue. The washing may remove non-predetermined molecules (e.g., waste molecules, non-target molecules, etc.). The washing may comprise use of one or more solvents (e.g., water, non-polar solvents, polar solvents, etc.) as described elsewhere herein. The tissue may be washed at least about 1, 2, 3, 4, 5, 6, 7, 8, 9, 10, or more times. The tissue may be washed at most about 10, 9, 8, 7, 6, 5, 4, 3, 2, 1, or fewer times. Subsequent to the washing the tissue, the tissue may be resuspended. For example, the tissue can be resuspended as described elsewhere herein.

The method 4000 may provide a yield of cells from two 25 micrometer sections of fixed tissue of at least about $1\times10^3$ (1E3), 5E3, 1E4, 5E4, 1E4, 5E5, 1E5, 5E6, 1E6, 5E7, 1E7, 5E8, 1E8, 5E9, 1E9, 5E10, or more cells. The method 4000 may provide a yield of cells from two 25 micrometer sections of fixed tissue of at most about 5E10, 1E10, 5E10, 1E9, 5E9, 1E8, 5E8, 1E7, 5E7, 1E6, 5E6, 1E5, 5E5, 1E4, 5E4, 1E4, 5E3, 1E3, or fewer cells. Non-limiting examples of experimentally realized cell yields per two 50 micrometer sections include human breast tissue (0.6E6 cells), human lymph node (2.33E6 cells), human lung cancer (5.05E6 cells), human brain (9.36E6 cells), human pancreas (5.45E6 cells), human heart (1.11E6 cells), human testis (1.99E6 cells), and human tonsil (5.6E6 cells). Non-limiting examples of experimentally realized cell yields per two 25 micrometer sections includes normal human pancreas (0.6E6 cells), human brain glioblastoma multiforme (0.14E6 cells), human tonsil chronic tonsillitis with lymphoid hyperplasia (5.6E6 cells), human lung cancer (0.38E6 cells), human liver-hepatocellular carcinoma (0.52E6 cells), normal human thymus (2.56E6 cells), human kidney normal adjacent 2.49E6 cells), human ovarian cancer (0.33E6 cells), normal human spleen (1.89E6 cells), human heart myxoma (0.34E6 cells), human skin melanoma (0.51E6 cells), human prostate diseased (0.3E6 cells), human lymph node adenocarcinoma (0.46E6 cells), and human colon colorectal cancer (1.34E6 cells).

The nucleic acid molecule can be partitioned into a partition. The partitioning can occur prior to operation 4040. The partition may be a well of a plurality of wells. For example, the partitioning can comprise placing the nucleic acid molecule into a well of a 96 well plate. The partition may be a droplet of a plurality of droplets, as described elsewhere herein. For example, the droplet can be an oil emulsion droplet of a plurality of oil emulsion droplets. The droplet can be a phase that is immiscible with a surrounding phase. The droplet can be a droplet surrounded by gas (e.g., air). In some cases, the partition may comprise a support. The support may be as described elsewhere herein. For example, the support may comprise a solid support. In another example, the support can comprise a bead. The barcode sequence may be attached to the support.

In another operation 4040, the method 4000 may comprise, in the cell, using a barcode sequence to generate a barcoded nucleic acid molecule comprising a barcode sequence and a sequence corresponding to the nucleic acid molecule.

In some cases, the operation 4040 may comprise hybridizing the barcode sequence to the nucleic acid molecule. The hybridizing may be as described elsewhere herein. The barcode can be extended to form the barcoding nucleic acid molecule as described elsewhere herein. For example, the extending can comprise the use of an enzyme. The extending can comprise use of ligation. For example, the extending can comprise ligating the barcode sequence to a probe as described elsewhere herein. The probe can comprise a portion at least partially complementary to the nucleic acid molecule.

Figure 41:
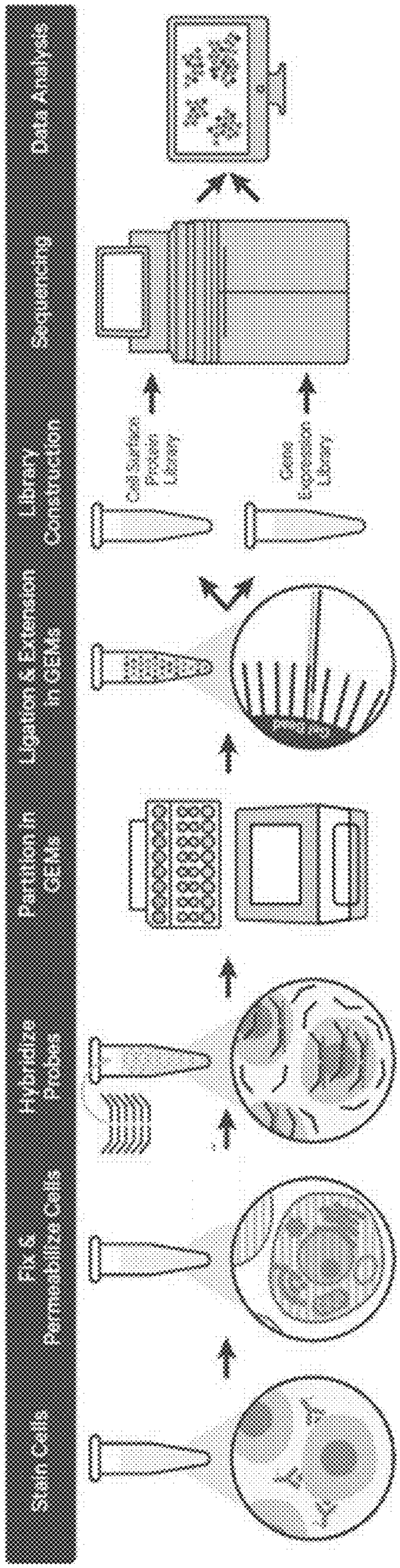
FIG. 41 shows an example of a nucleic acid profiling workflow, according to some embodiments.

FIG. 41 shows an example of a nucleic acid profiling workflow, according to some embodiments. The nucleic acid profiling workflow can be combined with the other portions of the present disclosure such as, for example, fixed tissue preparation methods. The nucleic acid profiling workflow of FIG. 41 may be a singleplex workflow. The nucleic acid profiling workflow can be performed on one or more samples (e.g., cells, nucleic acid In some cases, the nucleic acid profiling workflow can comprise a staining operation. The staining operation may be as described elsewhere herein.

Subsequent to the staining operation, the workflow can comprise fixing and/or permeabilizing the cells. The fixing may comprise fixation as described elsewhere herein. The fixing may comprise embedding. For example, the fixed cells can be fixed and subsequently embedded in a matrix. The permeabilizing the cells may comprise use of one or more permeabilization reagents (e.g., methanol, ethanol, acetone, detergents, etc.). The permeabilizing may comprise an at least partial degradation of the cell wall of a cell of the sample. The permeabilizing may be configured to make accessible the contents of the cell (e.g., nucleic acids). Subsequent to the fixation and/or permeabilization of the sample, the sample may be stored. The storage may be for at least about 1 day (d), 2 d, 3 d, 4 d, 5 d, 6 d, 1 week (w), 2 w, 3 w, 1 month (m), 2 m, 3 m, 4 m, 5 m, 6 m, 7 m, 8 m, 9 m, 10 m, 11 m, 1 year (y), 2 y, 3 y, 4 y, 5 y, 10 y, 15 y, 20 y, or more. The storage may be for at most about 20 y, 15 y, 10 y, 5 y, 4 y, 3 y, 2y, 1 y, 11 m, 10 m, 9 m, 8 m, 7 m, 6 m, 5 m, 4 m, 3 m, 2 m, 1 m, 3 w, 2 w, 1 w, 6 d, 5 d, 4 d, 3 d, 2 d, 1 d, or less.

Subsequent to the fixation and/or permeabilization (and optional storage if performed), the workflow can comprise hybridizing one or more probes to the sample as described elsewhere herein. The hybridizing may comprise use of a probe molecule such as the probe molecule of FIG. 43. In the workflow of FIG. 41, the hybridizing may not comprise multiplexing. For example, each sample can be run through the workflow individually. Each sample run through the workflow can comprise a probe barcode. In some cases, the singleplex format can be compatible with a cell labeling scheme (e.g., cell surface protein labeling).

Figure 43:
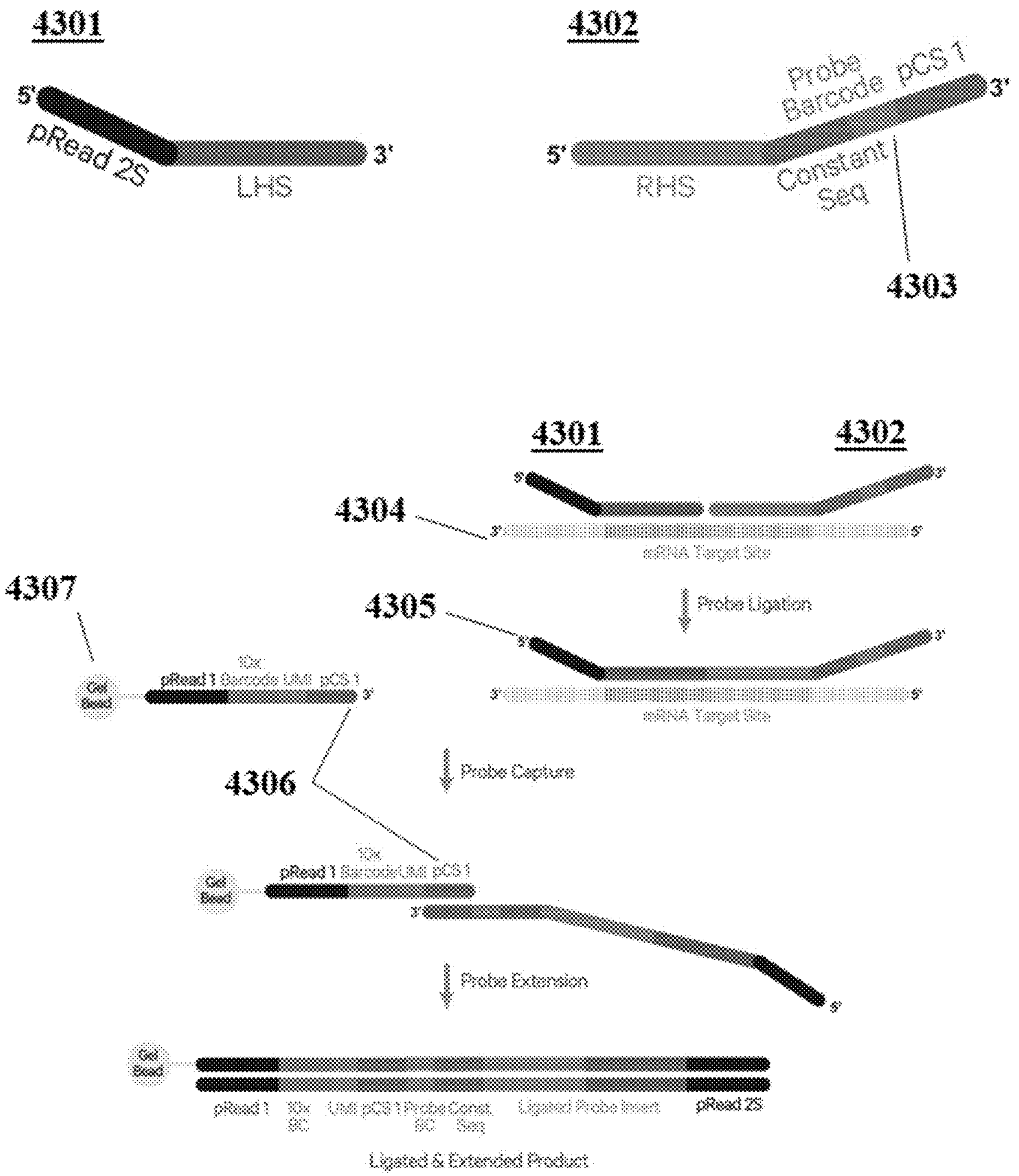
FIG. 43 show an example of a plurality of probe molecules, according to some embodiments.

Subsequent to the hybridizing, the barcoded nucleic acids can be portioned as described elsewhere herein. For example, the barcoded nucleic acids can be partitioned into a plurality of droplets. In another example, the barcoded nucleic acids can be partitioned into a plurality of wells. Subsequent to the partitioning, ligation and extension can be performed as described elsewhere herein. Library construction may comprise one or more of construction of a cell surface protein library and a gene expression library as described elsewhere herein. The partitioning may be as described in FIG. 43. FIG. 43 shows an example of droplet partition generation, according to some embodiments. A plurality of barcoded beads 4301 (e.g., barcoded gel beads) can be provided. The washed fixed sample can be provided to the barcoded beads as shown and partitioned into a plurality of droplets suspended in oil. In this way, the sample can be partitioned such that, on average, less than one sample is present in each partition as shown.

Subsequent to the library construction, the nucleic acid molecule from the sample can be sequenced as described elsewhere herein. For example, the sequencing can be sequencing by synthesis. Subsequent to the sequencing, the data generated by the sequencing can be analyzed as described elsewhere herein.

Figure 42:
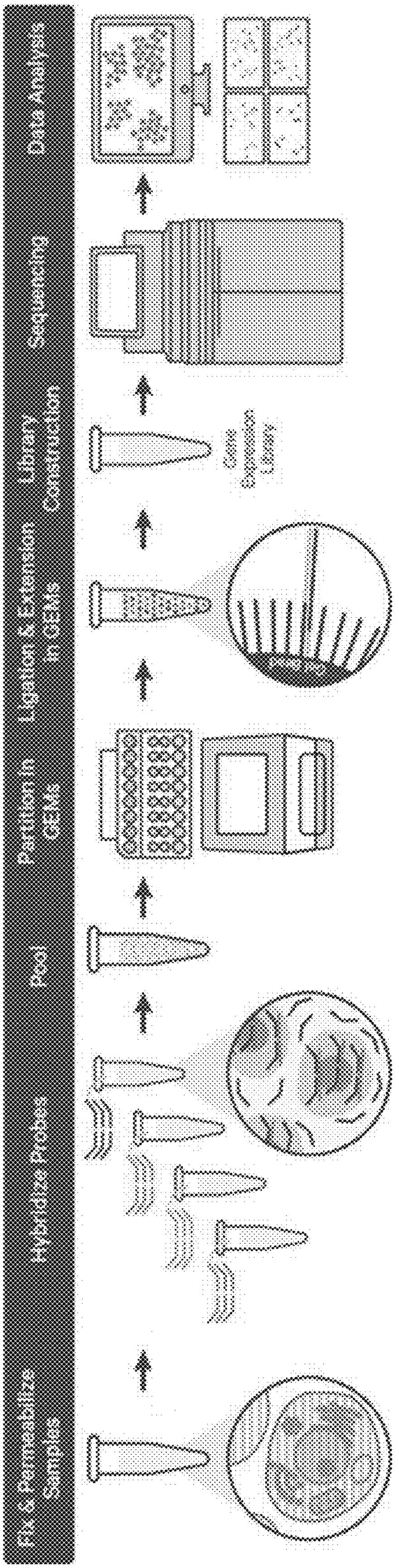
FIG. 42 shows an example of a nucleic acid profiling workflow, according to some embodiments.

FIG. 42 shows an example of a nucleic acid profiling workflow, according to some embodiments. The nucleic acid profiling workflow of FIG. 42 may be a multiplex workflow (e.g., multiple samples can be processed at a same time). In some cases, the multiplexed workflow may not be compatible with cellular labeling. The operations of the nucleic acid profiling workflow can be as described elsewhere herein. For example, cells may be fixed in formaldehyde and nucleic acid molecules from the cells may be hybridized with probe sets. Each probe set may comprise a unique probe barcode to permit sample multiplexing and read level demux. Samples may be hybridized overnight, pooled, washed, and partitioned. The probes may be ligated along with additional barcodes. Library construction, sequencing, and data analysis may be performed after ligation. The nucleic acid profiling workflow can comprise use of a sample as described elsewhere herein. For example, the sample can comprise a nucleic acid. For example, the fixation and/or permeabilization operations may be as described elsewhere herein. As described elsewhere herein, the sample may be stored subsequent to the fixation and/or permeabilization. Subsequent to the fixation, probes can be hybridized to nucleic acid molecules of the sample. For example, different probes can be hybridized to different nucleic acid molecules in the sample. In some cases, each sample used in the workflow can be correlated to a different barcode probe. The multiplexing may comprise simultaneous hybridizing of at least about 2, 3, 4, 5, 6, 7, 8, 9, 10, 11, 12, 13, 14, 15, 16, 17, 18, 19, 20, or more samples. The multiplexing may comprise simultaneous hybridizing of at most about 20, 19, 18, 17, 16, 15, 14, 13, 12, 11, 10, 9, 8, 7, 6, 5, 4, 3, or fewer samples. As described elsewhere herein, the nucleic acid molecules can be stored subsequent to the hybridization of the probes.

Subsequent to the hybridization, the nucleic acid molecules can be pooled and partitioned as described elsewhere herein (e.g., FIG. 43). The barcode molecules can be ligated and/or extended as described elsewhere herein. A library (e.g., a gene expression library) can be constructed, the barcode molecule can be sequenced, and the sequencing data can be analyzed.

In some cases, the pooling operations described elsewhere herein can comprise one or more washing operations. The washing may comprise removal of a supernatant from a centrifuged solution. In some cases, the removal of the supernatant can be a complete removal (e.g., all of the supernatant can be removed). In some cases, the removal of the supernatant can be a partial removal (e.g., a portion of the supernatant can be left behind). For example, at most about 100, 90, 80, 70, 60, 50, 40, 30, 20, 10, or fewer microliters of supernatant can be left during a wash operation. Leaving supernatant can provide benefits for processing samples with low cell numbers (e.g., less than about 500,000 cells in the sample). Incomplete removal of the supernatant can enhance cell recovery without significantly impacting the performance of the assays of the present disclosure.

FIG. 43 show an example of a plurality of probe molecules 4301 and 4302, according to some embodiments. In some cases, the probe can be as described elsewhere herein. The probe can be configured to analyze a gene. In some cases, the probe can be configured with a barcode portion 4303. The barcode portion can be a barcode as described elsewhere herein. The barcode can be attached to the probe prior to a user using the probe for analysis of a nucleic acid molecule. For example, the barcode can be pre-affixed to the probe. In this example, the probe can be supplied to a user with the barcode already a part of the probe. Within a partition (e.g., a droplet suspended in oil), the probe molecule can bind to an analyte nucleic acid 4304. Subsequent to the binding, the probes can be ligated together. The ligation may comprise sealing a nick (e.g., ligating adjacent probes without gap filling). The ligation may comprise a gap filling ligation reaction (e.g., filling a gap of one or more nucleotides between the probes during the ligation). Subsequent to the ligation, the single, unified probe 4305 can be dissociated from the analyte nucleic acid and captured by a capture region 4306 of a nucleic acid associated with a bead 4307. The probe can then be extended to incorporate one or more barcode molecules, primers, or the like as described elsewhere herein. The probe may then be amplified as described elsewhere herein.

In some cases, the methods and systems of the present disclosure can provide improvements on the efficacy of analysis of fixed samples. Fixation can improve the mechanical resilience of a cellular sample, as well as lock in transient cellular states. In this way, the analysis of the cells of a sample can provide information about the state of the cell when fixed, which can provide additional insight about short lived cellular states. The improvements of the present disclosure can also enable larger longitudinal studies. For example, high quality data generated from fixed samples permits study of the samples over longer periods of time. Additionally, modern techniques to be used with historical samples, unlocking new information previously unavailable. The methods and systems of the present disclosure can also reduce transportation and/or storage constraints on samples. For example, fixed and embedded samples can be more resilient to poor storage conditions than unfixed samples. This can enable new paradigms of sample analysis where samples are transported greater distances for analysis (e.g., globally). This can enable all samples of a study to be transported to a single lab for analysis, which can thereby reduce the error associated with different labs processing samples. Additionally, the variability between samples can be reduced by matching samples and samples can be multiplexed with unique sample barcodes. The fixation of samples can also reduce or eliminate infectious agents present within the samples, which can improve safety in the analysis of such a sample.

Computer Systems

Figure 14:
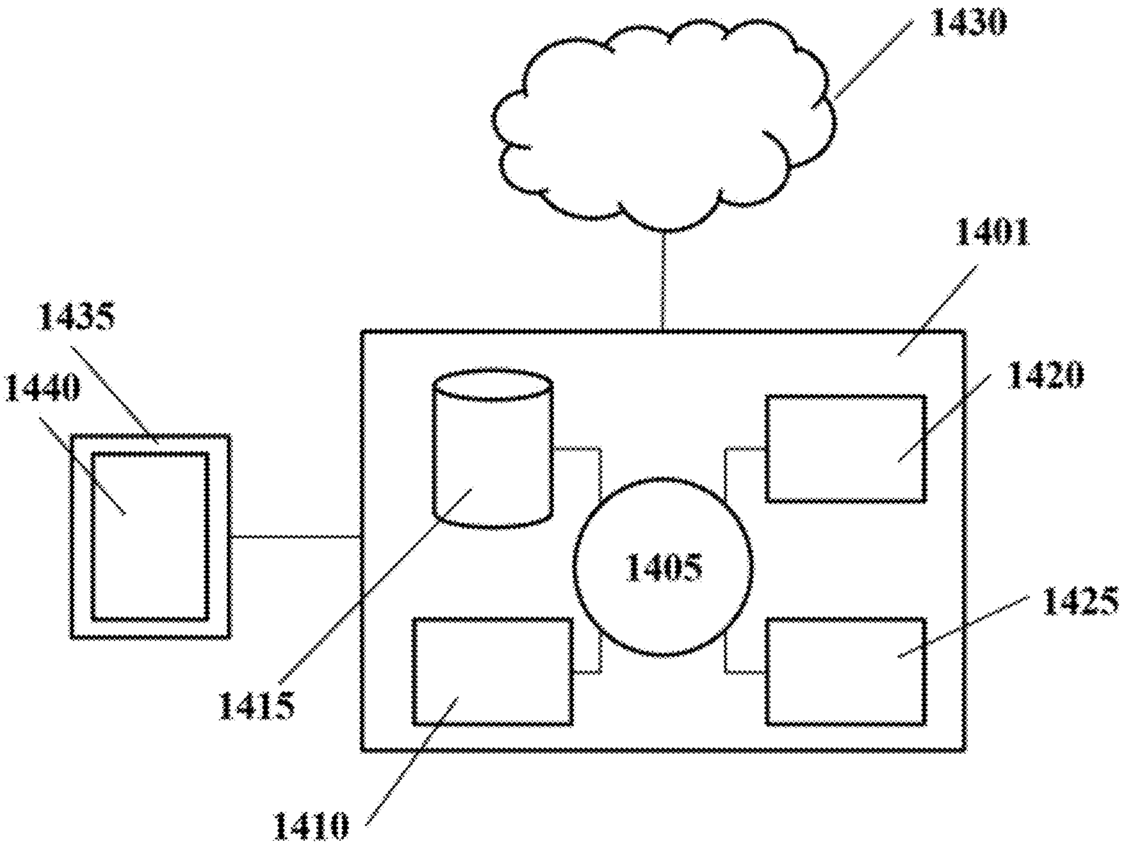
FIG. 14 shows a computer system that is programmed or otherwise configured to implement methods provided herein.

The present disclosure provides computer systems that are programmed to implement methods of the disclosure. FIG. 14 shows a computer system 1401 that is programmed or otherwise configured to process or analyze sequencing reads. The computer system 1401 can regulate various aspects of the present disclosure, such as, for example, aligning sequencing reads, indexing sequencing reads to a cell, partition, etc. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, perform sequencing.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

EXAMPLES

Prophetic Example 1—RNA Templated Ligation and Barcoding

Generation of one or more barcoded molecules, e.g., within or on a cell or cell bead, may be performed sequentially, within one or more sets of partitions. For example, the cell or cell bead may comprise a target RNA molecule for barcoding and/or a feature, which may have a feature binding group comprising a reporter oligonucleotide (comprising a reporter sequence) coupled thereto. The target RNA molecule may be hybridized to a first probe and a second probe; for example, the target RNA molecule may have a first target region and a second target region complementary to a first probe sequence of the first probe and a second probe sequence of the second probe. In some instances, a probe-linked molecule may be generated, e.g., via ligation of the probes when hybridized to the RNA molecule, or using one or more nucleic acid reactions, e.g., via an extension reaction, and/or enzymatic or chemical ligation. The probe-linked molecule may be barcoded in one or more sets of partitions.

In one example, cells (or nuclei or cell beads) may be partitioned in a first set of partitions (e.g., microwells or other vessels) and contacted with a hybridization buffer comprising the first probe, the second probe, a probe binding molecule (e.g., a splint oligonucleotide) and a barcode molecule. The hybridization buffer may comprise reagents (e.g., formamide, ethylene carbonate, salts, etc.) to facilitate hybridization of the first probe and the second probe to a target nucleic acid molecule. Cells (or nuclei or cell beads) from multiple partitions may then be pooled and washed, e.g., to remove unhybridized probes. The cells (or nuclei or cell beads) may then be counted and re-partitioned in a second set of partitions, e.g., droplets. Within the droplets or within the cells or cell beads within the droplets, a ligation and extension reaction may be performed to generate barcoded nucleic acid molecules. In some instances, the droplets may additionally comprise a capture molecule comprising an additional barcode sequence. Accordingly, the barcoded nucleic acid molecules within the droplets may comprise two barcode sequences.

In another example, the cells (or nuclei or cell beads) may be partitioned in a first set of partitions (e.g., microwells) and contacted with a hybridization buffer comprising the first probe, the second probe, a probe binding molecule (e.g., a splint oligonucleotide) and a barcode molecule. Cells (or nuclei or cell beads) within the partitions may then be washed, e.g., to remove unhybridized probes, then pooled together. The cells (or nuclei or cell beads) may then be counted and re-partitioned in a second set of partitions, e.g., droplets. Within the droplets, a ligation and extension reaction may be performed to generate barcoded nucleic acid molecules. In some instances, the droplets may additionally comprise a capture molecule comprising an additional barcode sequence. Accordingly, the barcoded nucleic acid molecules within the droplets may comprise two barcode sequences.

In yet another example, cells (or nuclei or cell beads) may be partitioned in a first set of partitions (e.g., microwells) and contacted with a hybridization buffer comprising the first probe, the second probe, a probe binding molecule (e.g., a splint oligonucleotide) and a barcode molecule. Cells (or nuclei or cell beads) from multiple partitions may then be pooled and washed, e.g., to remove unhybridized probes. The cells (or nuclei or cell beads) may then be counted and subjected to conditions sufficient to ligate the barcode molecules to the probe-hybridized nucleic acid molecules. The ligated molecules may then be partitioned, e.g., into droplets. Within the droplets, an extension reaction may be performed to generate barcoded nucleic acid molecules. In some instances, the droplets may additionally comprise a capture molecule comprising an additional barcode sequence. Accordingly, the barcoded nucleic acid molecules within the droplets may comprise two barcode sequences.

In another example, the cells (or nuclei or cell beads) may be partitioned in a first set of partitions (e.g., microwells) and contacted with a hybridization buffer comprising the first probe, the second probe, a probe binding molecule (e.g., a splint oligonucleotide) and a barcode molecule. Cells (or nuclei or cell beads) within the partitions may then be washed, e.g., to remove unhybridized probes, then pooled together. The cells (or nuclei or cell beads) may then be counted and subjected to conditions sufficient to ligate the barcode molecules to the probe-hybridized nucleic acid molecules. The ligated molecules may then be partitioned, e.g., into droplets. Within the droplets, an extension reaction may be performed to generate barcoded nucleic acid molecules. In some instances, the droplets may additionally comprise a capture molecule comprising an additional barcode sequence. Accordingly, the barcoded nucleic acid molecules within the droplets may comprise two barcode sequences.

After each example, the barcoded nucleic acid molecules may be subjected to additional barcoding operations in additional partitions, e.g., in droplets. Alternatively or in addition to, the contents of the droplets may be pooled and processed downstream for analysis, e.g., via sequencing.

In some instances, several operations may be performed in a different order. For instance, cells, nuclei, or cell beads, which may optionally be fixed and permeabilized, may be first hybridized to a set of probes and then barcoded (e.g., in partitions).

In one example, the cells (or nuclei or cell beads) may be contacted, e.g., in a bulk solution, with a hybridization buffer comprising the first probe and the second probe. The cells (or nuclei or cell beads) may then be washed, e.g., to remove unhybridized probes, then partitioned into a first set of partitions (e.g., microwells). The first set of partitions may each comprise a probe binding molecule and a barcode molecule. The cells (or nuclei or cell beads) in the first set of partitions may be subjected to conditions sufficient to hybridize the probe binding molecule and the barcode molecule to the target nucleic acid molecule, the probe molecules, or derivatives thereof (e.g., extended probe-associated molecules, etc.).

In some examples, the contents of the partitions may then be pooled together and optionally, washed. The cells (or nuclei or cell beads) may then be counted and partitioned into a second set of partitions and subjected to conditions sufficient to extend and/or ligate the barcode molecules to the probe-hybridized nucleic acid molecules, thereby generating barcoded nucleic acid molecules. In some instances, the droplets may additionally comprise a capture molecule comprising an additional barcode sequence. Accordingly, the barcoded nucleic acid molecules within the droplets may comprise two barcode sequences.

In other examples, the partitions may be washed and then pooled together. The cells (or nuclei or cell beads) may then be counted and partitioned into a second set of partitions and subjected to conditions sufficient to extend and/or ligate the barcode molecules to the probe-hybridized nucleic acid molecules, thereby generating barcoded nucleic acid molecules. In some instances, the droplets may additionally comprise a capture molecule comprising an additional barcode sequence. Accordingly, the barcoded nucleic acid molecules within the droplets may comprise two barcode sequences.

In other examples, the contents of the partitions may then be pooled together and optionally, washed. The cells (or nuclei or cell beads) may then be subjected to conditions sufficient to ligate the barcode molecules to the probe-hybridized nucleic acid molecules. The ligated molecules may be partitioned in a second set of partitions, e.g., droplets, and subjected to conditions sufficient to extend the ligated molecules to generate barcoded nucleic acid molecules. In some instances, the droplets may additionally comprise a capture molecule comprising an additional barcode sequence. Accordingly, the barcoded nucleic acid molecules within the droplets may comprise two barcode sequences.

In other examples, the partitions may be first washed, then the contents of the partitions may be pooled together. The cells (or nuclei or cell beads) may then be subjected to conditions sufficient to ligate the barcode molecules to the probe-hybridized nucleic acid molecules. The ligated molecules may be partitioned in a second set of partitions, e.g., droplets, and subjected to conditions sufficient to extend the ligated molecules to generate barcoded nucleic acid molecules. In some instances, the droplets may additionally comprise a capture molecule comprising an additional barcode sequence. Accordingly, the barcoded nucleic acid molecules within the droplets may comprise two barcode sequences.

In some instances, the cells, nuclei, or cell beads may be first hybridized to a set of probes, washed, counted, subjected to conditions sufficient to ligate the probes or generate a probe-linked nucleic acid molecule, washed again, and then partitioned. In one example, the cells (or nuclei or cell beads) may be partitioned in a first set of partitions (e.g., microwells) with a probe binding molecule and a barcode molecule. Within the first set of partitions, the probe binding molecule and the barcode molecule may hybridize to the probe-associated molecule (or probe-linked molecules), pooled, washed (or alternatively, washed in partitions, then pooled), counted and then loaded into a second set of partitions (e.g., droplets). The cells (or nuclei or cell beads) may then be subjected to conditions sufficient to extend and/or ligate the barcode molecules to the probe-associated or probe-linked nucleic acid molecules, thereby generating barcoded nucleic acid molecules. Alternatively, the cells (or nuclei or cell beads) may be ligated in bulk and extended within the second set of partitions. In some instances, the droplets may additionally comprise a capture molecule comprising an additional barcode sequence. Accordingly, the barcoded nucleic acid molecules within the droplets may comprise two barcode sequences.

Prophetic Example 2—Multiplexed Assay: Barcoding of RNA Templated Ligation Product and Probe-Associated Reporter Oligonucleotide As described herein, it may be beneficial to assay multiple analytes in a population of cells, nuclei, or cell beads. The cell or cell beads may be contacted with a feature binding group comprising or coupled to a reporter oligonucleotide (comprising a reporter sequence), as described herein. The feature binding group may couple to one or more features (e.g., proteins) of the cell. The cell may also comprise target nucleic acid molecules (e.g., RNA molecules) for assaying.

Example Protocol 1: In one example protocol, the cells, nuclei, or cell beads having the feature binding groups coupled thereto may be partitioned in a first set of partitions. Each partition of the first set of partitions may comprise, for example, ~50,000 cells in a 50 microliter volume. The partitions may each comprise a set of probes (e.g., a first probe, a second probe, and a third probe), which may be provided at a 2 micromolar concentration. Each partition may additionally comprise 5 micromolar of splint oligonucleotides (probe-binding molecules), and 7.5 micromolar barcode molecules. The barcode molecules may differ across the partitions. Within the first set of partitions, the probe molecules may be hybridized to (i) the target nucleic acid (e.g., RNA) molecule (e.g., via the first and second probes) and (ii) the feature binding group (e.g., via the third probe). The contents of the first set of partitions may then be pooled, washed, and analyzed, e.g., using optical approaches such as absorbance, fluorescence, etc., gel electrophoresis, or via sequencing.

Example Protocol 2: In another example protocol, the cells, nuclei, or cell beads having the feature binding groups coupled thereto may hybridized, in bulk, to the first set of probes (e.g., a first probe, a second probe, and a third probe), which may be provided at a 2 micromolar concentration. The cells, nuclei, or cell beads may be subjected to conditions sufficient to hybridize the probe molecules to the target nucleic acid and/or the feature binding group. The cells, nuclei, or cell beads may then be washed and then partitioned in a first set of partitions. Each partition of the first set of partitions may comprise, for example, ~50,000 cells in a 50 microliter volume. The partitions may each comprise 1 micromolar of splint oligonucleotides (probe-binding molecules), and 2 micromolar barcode molecules. The barcode molecules may differ across the first set of partitions. Within the first set of partitions, the barcode molecules may hybridize to the probe-associated molecules. The contents of the first set of partitions may then be pooled, washed, and analyzed, e.g., using optical approaches such as absorbance, fluorescence, etc., gel electrophoresis, or via sequencing.

Figure 18:
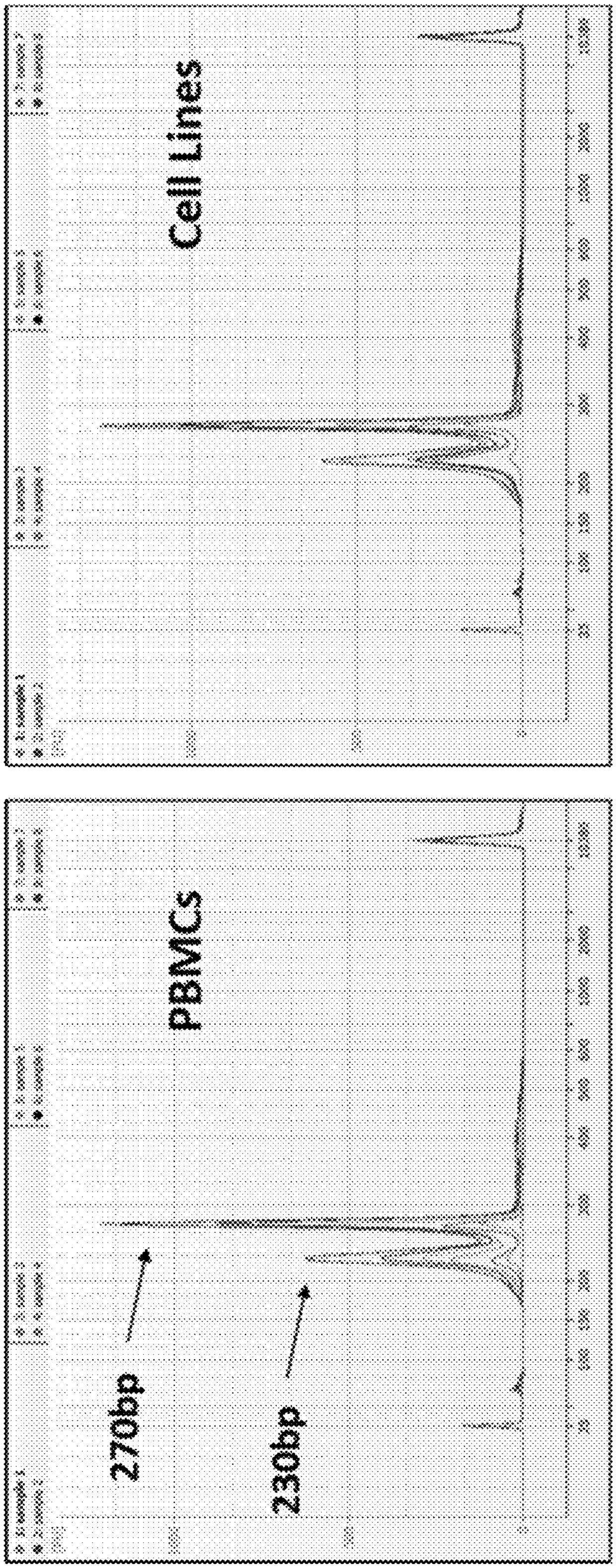
FIG. 18 shows example data from a workflow described herein.

FIG. 18 shows example data of a barcoding scheme described herein (Example Protocol 1). FIG. 18 shows two plots of fluorescence intensity as a function of sequence length (in base pairs). Each line represents a sample of barcoded cells, where each sample has a different barcode sequence attached thereto (n=8 samples). The left plot shows barcoding performed in peripheral blood mononuclear cells (PBMCs) and the right plot shows barcoding performed in various cell lines. Two peaks can be identified: a 230 bp sequence and 270 base pair sequence. The 270 base pair sequence corresponds to the first target region and the second target region of the target RNA molecule of the first and second probe.

Figure 19:
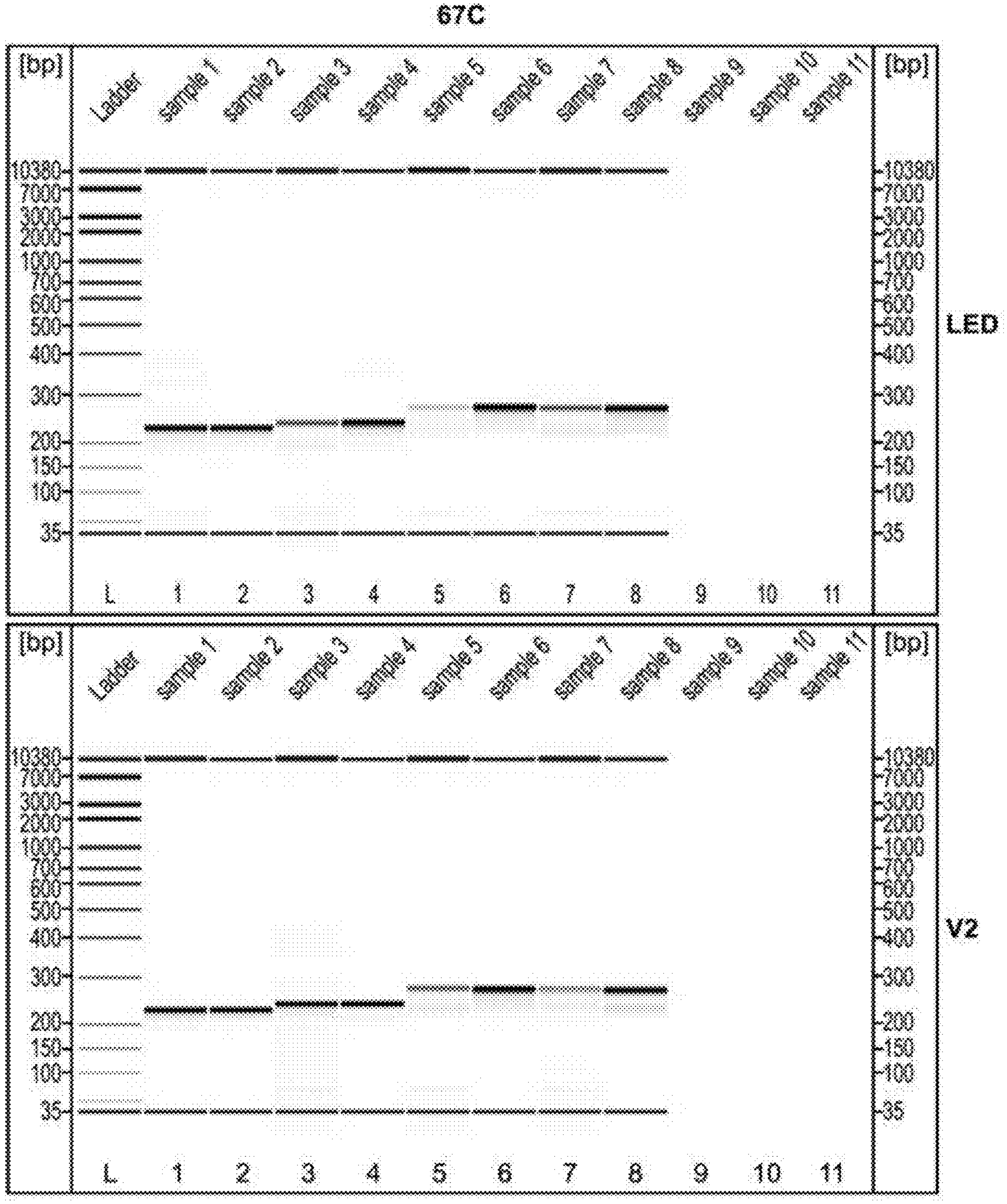
FIG. 19 shows additional example data from a workflow described herein.
Figure 19:
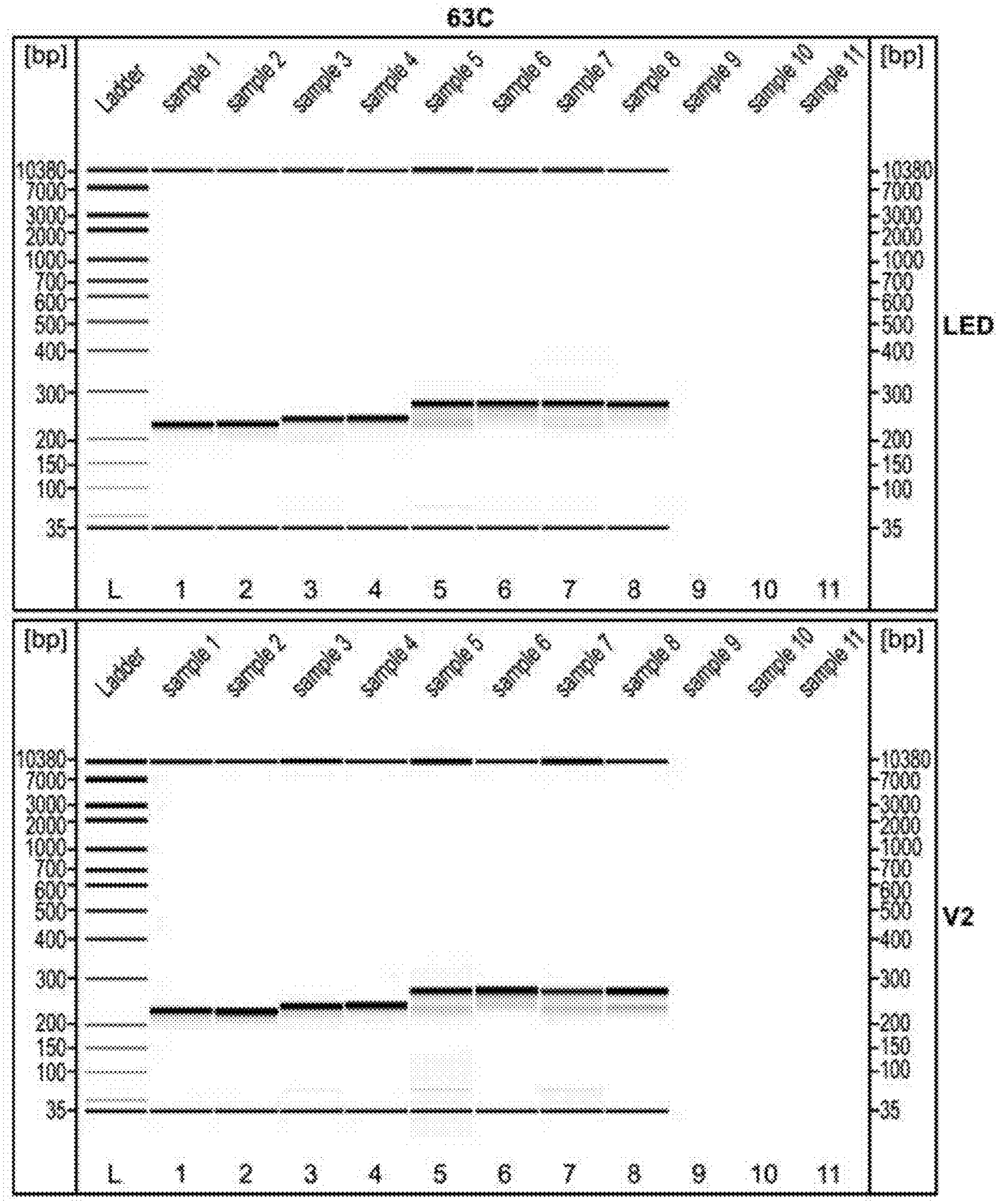

FIG. 19 shows example data of DNA gel electrophoresis of the barcoded molecules described herein. The left plots indicate an annealing temperature of 67 degrees Celsius, whereas the right plots indicate an annealing temperature of 63 degrees Celsius. The top plots indicate one method of verifying the barcode products using LED. The bottom plots indicate another method of verifying the barcode products using V2.

The first lane ("Lane 0") in each gel electrophoresis plot is a nucleic acid standard ladder. Lane 1 is a PBMC without barcode (negative control), Lane 2 is a cell line sample without barcode (negative control), Lane 3 is a PBMC with a synthetic barcode (positive control), Lane 4 is a cell line with a synthetic barcode (positive control), Lane 5 is a PBMC with a splint molecule, performed according to Example Protocol 1, Lane 6 is a cell line with a splint molecule, performed according to Example Protocol 1, Lane 7 is a PBMC with a splint molecule, performed according to Example Protocol 2, and Lane 8 is a cell line with a splint, performed according to Example Protocol 2. As can be seen, the 63 degree annealing temperature results in higher yield (darker bands).

Figure 20:
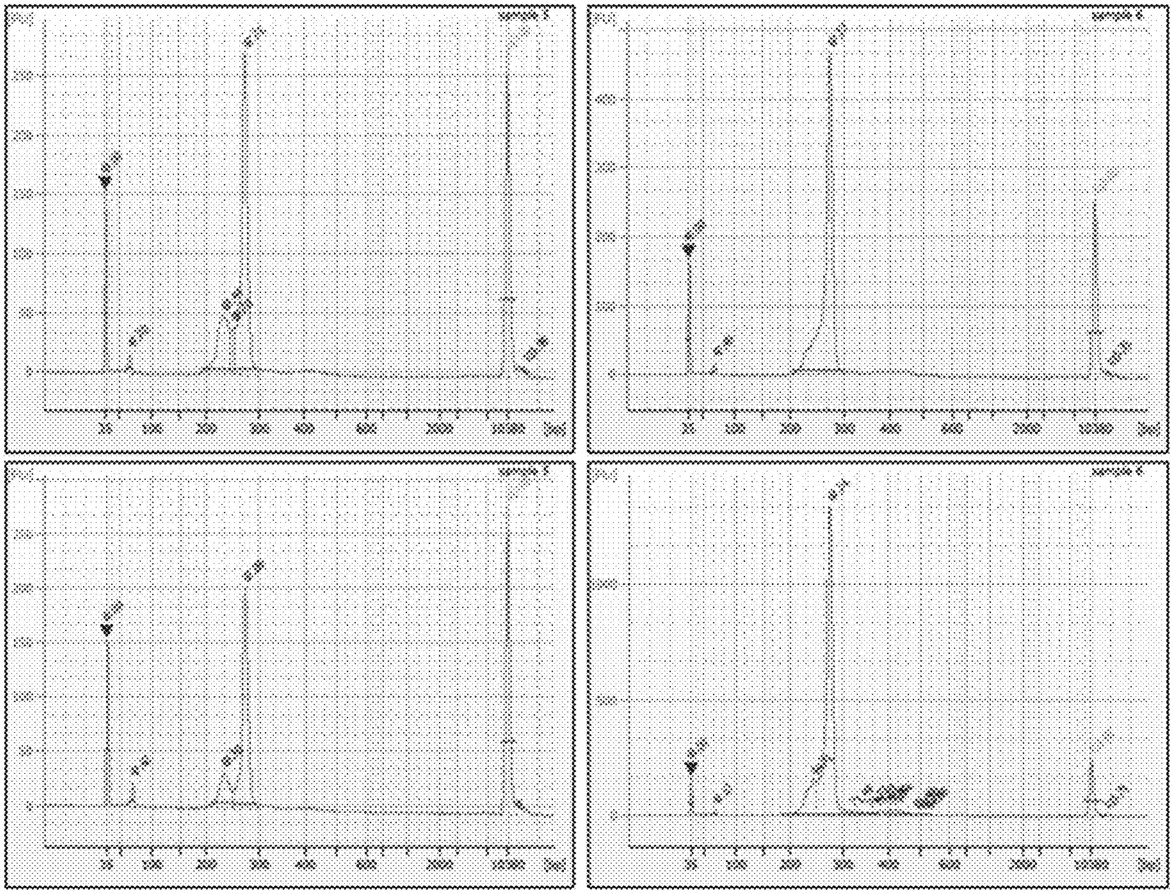
FIG. 20 shows additional example data from a workflow described herein.

FIG. 20 shows additional example data of a barcoding scheme described herein. The left plots show fluorescence intensity as a function of sequence length of the PBMC cells barcoded using Example Protocol 1. The right plots show the fluorescence intensity as a function of sequence length of the cell lines barcoded using Example Protocol 1. Altogether, the results indicate that barcoding using dual probes using Example Protocol 1 and Example Protocol 2 result in relatively clean barcoding.

Example 3—Fixed RNA Profiling on a PBMC Sample

Figure 21A:
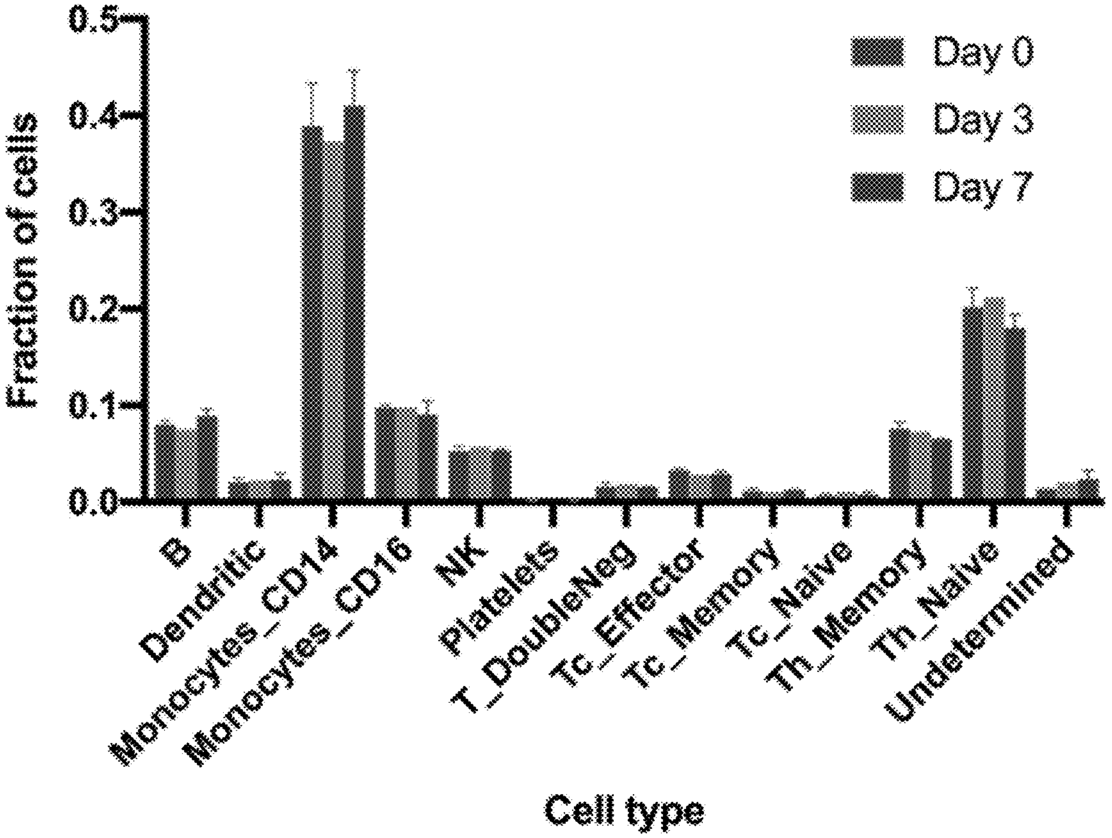
FIG. 21A shows example data comparing fixed cells and unfixed cells.
Figure 21B:
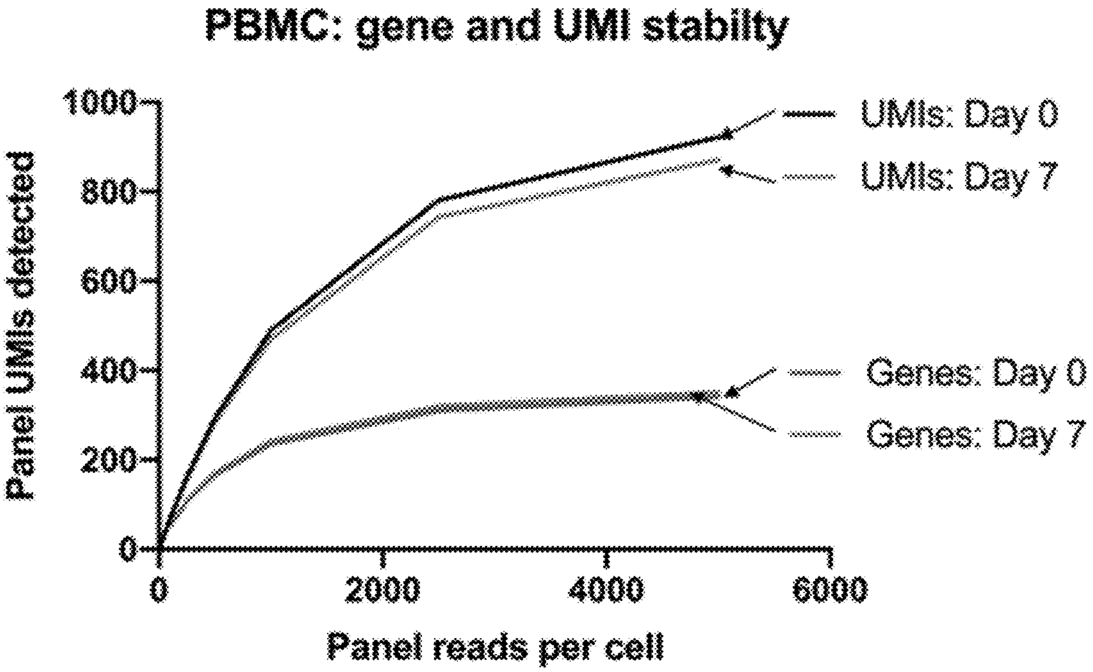
FIG. 21B shows additional example data comparing fixed cells and unfixed cells.
Figure 21C:
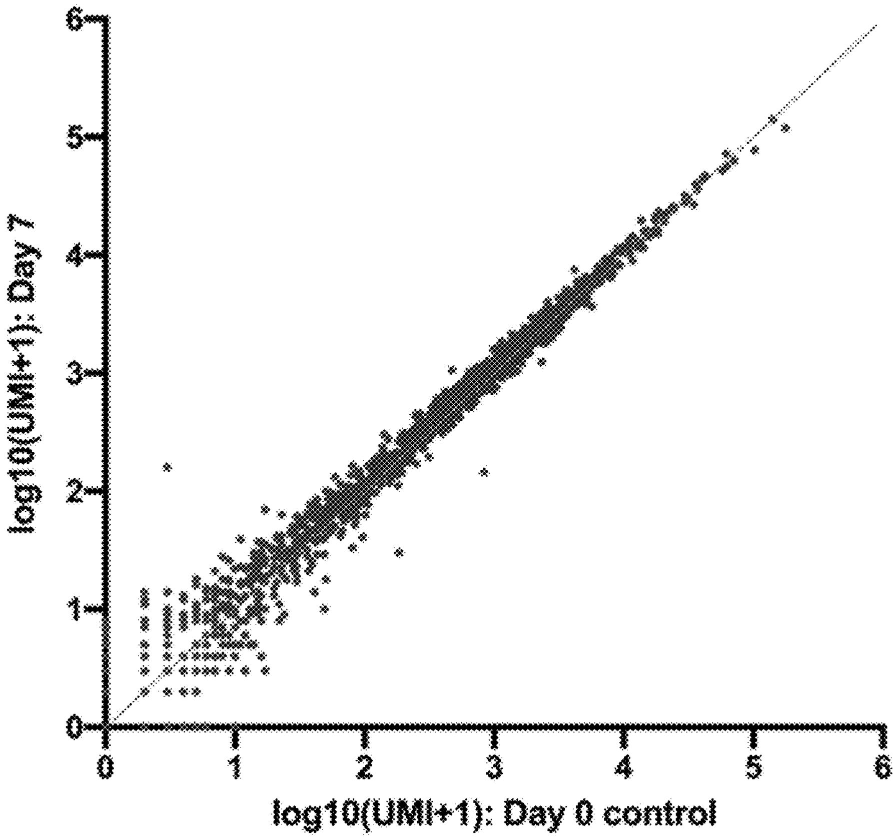
FIG. 21C shows additional example data comparing fixed cells and unfixed cells.

A PBMC sample may be paraformaldehyde-fixed and then stored for 7 days at 4° C. Fixed cells (or nuclei or cell beads) may be processed according to the protocols described herein. Sequencing libraries may be prepared, enriched using a 2000-gene immuno-oncology panel and analyzed. FIG. 21A-C shows example data comparing fixed cells and un-fixed control samples. FIG. 21A shows a bar plot and illustrate that fixed cells, when compared to a Day 0 un-fixed control sample, demonstrate stable cell type annotation over seven days of storage. FIG. 21B shows a line plot of the panel reads per cell as a function of the UMIs detected. The data illustrate a comparable median number of genes and UMI counts per cell. FIG. 21C shows a log plot of the per-gene UMI counts between the Day 0 and Day 7 sample. An excellent correlation between the per-gene UMI counts between Day 0 control and the Day 7 can be visualized. The results demonstrate that the fixed sample is effectively stabilized for 7 days, which allows for further various manipulations following fixation, e.g., sample collection, storage, shipment, batching with other samples, etc.

In addition, fixed PBMCs may be processed according to the protocols described herein and the resulting libraries compared to fresh PBMCs processed with the 3' Single Cell Gene Expression solution (10× Genomics). UMI detection over the 2000-gene panel illustrate comparable sensitivity between the fresh and fixed workflows. In addition, cell type annotation is similar between the two samples as well. Major PBMC cell types can be detected in each of the two samples.

Example 4—Multiplexed Assay: Barcoding of RNA Templated Ligation Product and Probe-Associated Reporter Oligonucleotide As described herein, it may be beneficial to assay multiple analytes in a population of cells, nuclei, or cell beads. The cells, nuclei, or cell beads may be contacted with a feature binding group comprising or coupled to a reporter oligonucleotide (comprising a reporter sequence), as described herein. The feature binding group may couple to one or more features (e.g., proteins) of the cell. The cell may also comprise target nucleic acid molecules (e.g., RNA molecules) for assaying.

Figure 22:
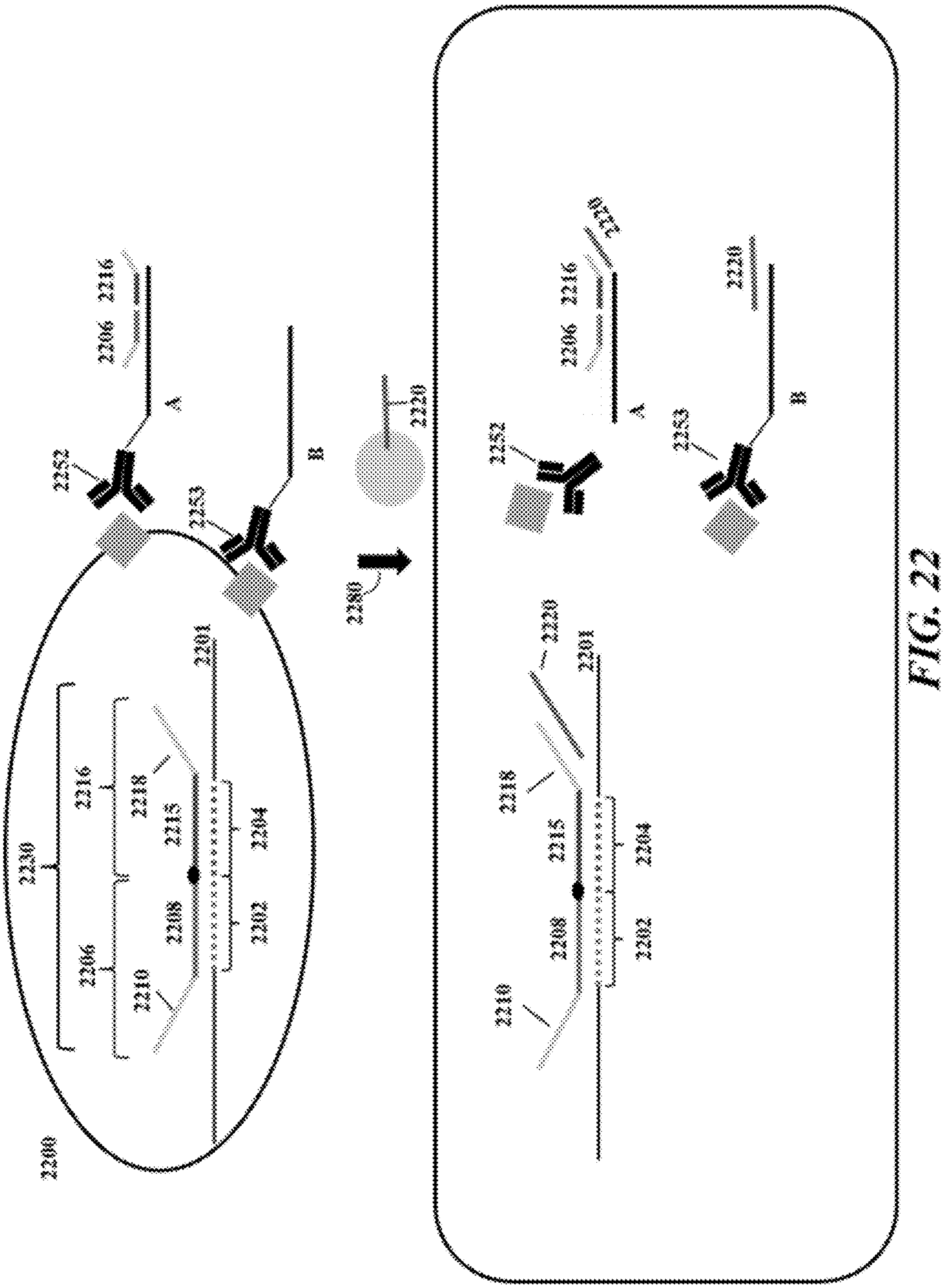
FIG. 22 schematically shows an example workflow for assaying two different analyte types.

In one example, cells are contacted with two sets of antibodies, as depicted schematically in FIG. 22. The first set of antibodies ("Antibody A") 2252 comprises a reporter oligonucleotide comprising two target sequences. The second set of antibodies ("Antibody B") 2253 comprises a reporter oligonucleotide comprising a capture sequence. The cells (e.g., 2200) are then contacted with a pair of probes. The pair of probes ("probe 1" 2206 and "probe 2" 2216) are configured to hybridize to a first target region 2202 and a second target region 2204 of a nucleic acid molecule 2201 in the cell (e.g., mRNA), thereby generating a probe-associated molecule 2230. At least one of the probes of the pair of probes may comprise a capture sequence (e.g., 2210 and/or 2218). Additionally, in some instances, the pair of probes 2206, 2216 are configured to hybridize to the two target sequences of Antibody A. In other instances, an additional pair of probes ("probe 3" and "probe 4", not shown) that are different from probe 1 and probe 2 may be provided; the additional pair of probes may comprise complementary sequences to the target sequences of Antibody A and may hybridize to the reporter oligonucleotide of Antibody A.

Subsequent barcoding (e.g., operation 2280) may be performed, either in bulk or in partitions (e.g., wells or droplets). A barcode molecule 2220 comprising a first barcode sequence may hybridize, either directly or via a splint molecule, to the (i) probe associated molecule 2230 or derivative thereof (e.g., a complement or amplification product thereof), (ii) Antibody A-probe pair complex comprising the pair of probes (e.g., probe 1 2206 and probe 2 2216, or probe 3 and probe 4 (not shown)) hybridized to the reporter oligonucleotide of Antibody A 2252, and/or (iii) Antibody B 2253 (e.g., via the capture sequence of the reporter oligonucleotide). The barcode molecule 2220 may optionally be coupled to a bead. In FIG. 22, the barcode molecule is shown as hybridizing directly to the probes or capture sequence, but barcode molecule hybridization may be mediated via a splint molecule (e.g., as shown in FIG. 16A). Additional barcoding operations may also be performed (not shown). The barcoded molecules or derivatives thereof are then sequenced.

Figure 23:
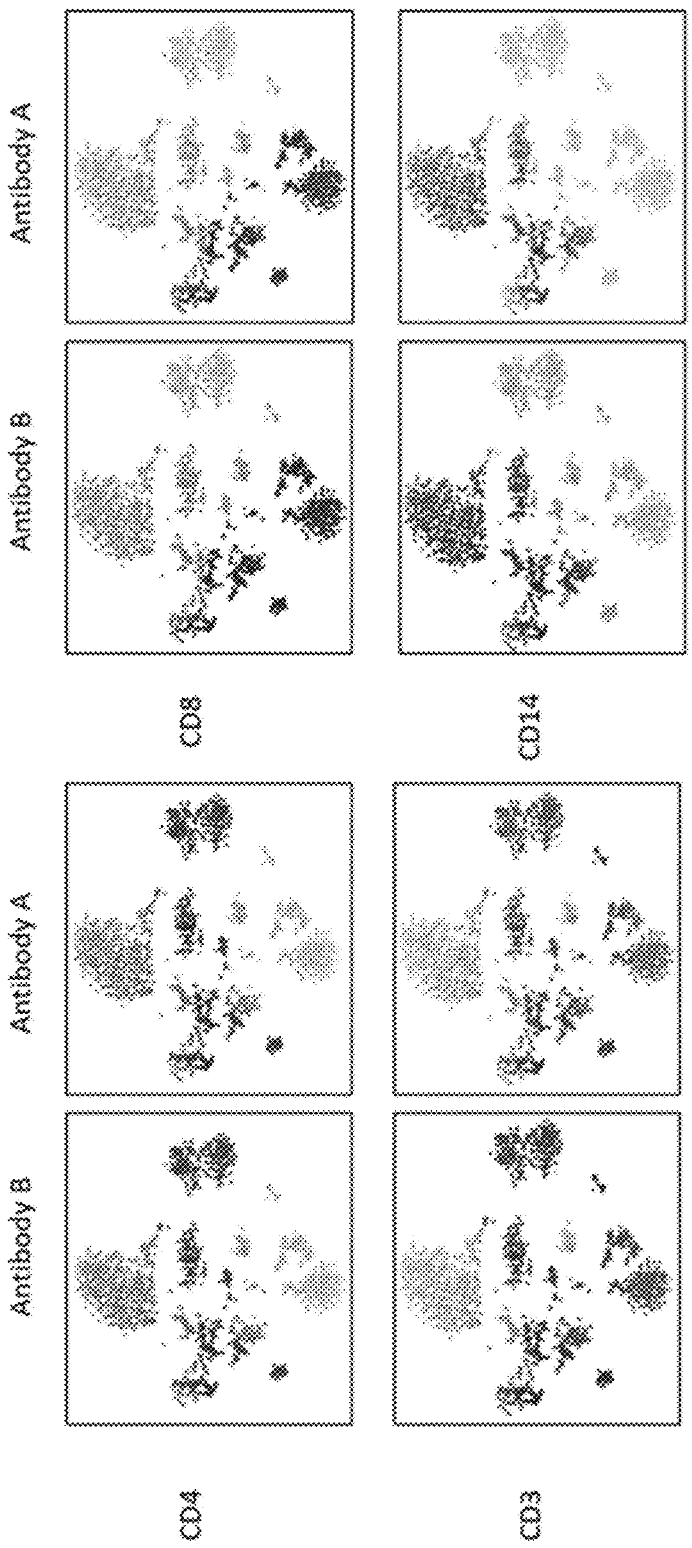
FIG. 23 shows example data of a barcoding approach described herein.

FIG. 23 shows example data resulting from such a barcoding operation as described in FIG. 22. FIG. 23 shows gene expression plots of four biomarkers (CD4, CD8, CD3 and CD14) which are obtained from sequencing of the barcoded RNA products (e.g., the barcoded probe-associated molecule 2230). The intensity of the spots indicate the overlap between the gene expression detected from using the dual probes and the protein expression using either the first set of antibodies ("Antibody A") or the second set of antibodies ("Antibody B"). Overall, the plots indicate that usage of either set of antibodies (Antibody A or Antibody B) have similar coverage in detecting the analyte of interest. Accordingly, either or both sets of antibodies may be used to detect the protein analytes (e.g., CD4, CD8, CD3, CD14). In some instances, it may be advantageous to use the first set of Antibodies ("Antibody A"), as the dual probes used for barcoding the reporter oligonucleotide allow for additional multiplexing or combinatorial barcoding, which allows for improved indexing and determination of cell, sample, or partition origin. Alternatively or in addition to, the use of one or more probes for barcoding the reporter oligonucleotides may be useful for appending additional functional sequences (e.g., primers, capture sequences, UMI, barcode sequences, etc.) to the reporter oligonucleotide, or derivative thereof.

In some instances, the data shown in FIG. 23 may be generated without barcoding of any RNA molecules. For example, it may be useful to compare the efficacy of barcoding of feature binding groups using two different approaches. In an example, referring again to FIG. 22, the cell may be contacted with (i) the first set of antibodies ("Antibody A") 2252 comprising a reporter oligonucleotide comprising two target sequences and (ii) the second set of antibodies ("Antibody B") 2253 comprising a capture sequence. The cells (e.g., 2200) may then be contacted with a pair of probes. The pair of probes ("probe 1" 2206 and "probe 2" 2216) are configured to hybridize to the target regions of the reporter oligonucleotide of Antibody A. At least one of the probes of the pair of probes may comprise a capture sequence (e.g., 2210 and/or 2218). Barcoding as described above may be performed, resulting in two barcoded products: (i) Antibody A-probe pair comprising the pair of probes (e.g., probe 1 2206 and probe 2 2216) hybridized to the reporter oligonucleotide of Antibody A 2252, and (ii) Antibody B 2253 (e.g., via the capture sequence). The barcoded products or derivatives thereof may then be sequenced and the sequence reads may be overlapped to generate the plots of FIG. 23. By comparing the barcoded products of Antibody A and Antibody B, it may be inferred that the barcoding efficiency using either approach (Antibody A versus Antibody B) is similar, and that both or either approach is viable in detecting analytes (e.g., proteins). As described above, in some instances, it may be advantageous to use the first set of Antibodies ("Antibody A"), as the dual probes used for barcoding the reporter oligonucleotide allow for additional multiplexing or combinatorial barcoding, which allows for improved indexing and determination of cell, sample, or partition origin. Alternatively or in addition to, the use of one or more probes for barcoding the reporter oligonucleotides may be useful for appending additional functional sequences (e.g., primers, capture sequences, UMI, barcode sequences, etc.) to the reporter oligonucleotide, or derivative thereof.

Example 5—Multiplexed Assay: Barcoding of RNA Templated Ligation Product and Reporter Oligonucleotide of a Feature-Binding Group As described herein, it may be beneficial to assay multiple analytes in a population of cells, nuclei, or cell beads. The cells, nuclei, or cell beads may be contacted with a feature binding group comprising or coupled to a reporter oligonucleotide (comprising a reporter sequence), as described herein. The feature binding group may couple to one or more features (e.g., proteins) of the cell. The cell may also comprise target nucleic acid molecules (e.g., RNA molecules) for assaying.

In an example, and referring to FIG. 22, cells may be contacted with a set of antibodies ("Antibody B") 2253, in which the antibodies of the set comprise a capture sequence. In some instances, the cells may be processed, e.g., subjected to fixation and/or permeabilization, which may occur prior to, subsequent to, or both prior to and subsequent to contacting the cells with the antibodies. The cells (or fixed and/or permeabilized cells) (e.g., 2200) are then contacted with a pair of probes. The pair of probes ("probe 1" 2206 and "probe 2" 2216) are configured to hybridize to a first target region 2202 and a second target region 2204 of a nucleic acid molecule 2201 in the cell (e.g., mRNA), thereby generating a probe-associated molecule 2230. The probes may optionally be linked to one another (e.g., using an extension reaction, ligation, and/or chemical linkage). At least one of the probes of the pair of probes may comprise a capture sequence (e.g., 2210 and/or 2218).

Subsequent barcoding (e.g., operation 2280) may be performed, either in bulk or in partitions (e.g., wells or droplets). A barcode molecule 2220 comprising a first barcode sequence may hybridize, either directly or via a splint molecule, to the (i) probe associated molecule 2230 or derivative thereof (e.g., a complement or amplification product thereof), and/or (ii) Antibody B 2253 (e.g., via the capture sequence). The barcode molecule 2220 may optionally be coupled to a bead. The barcoded molecules or derivatives thereof are then sequenced.

Figure 24:
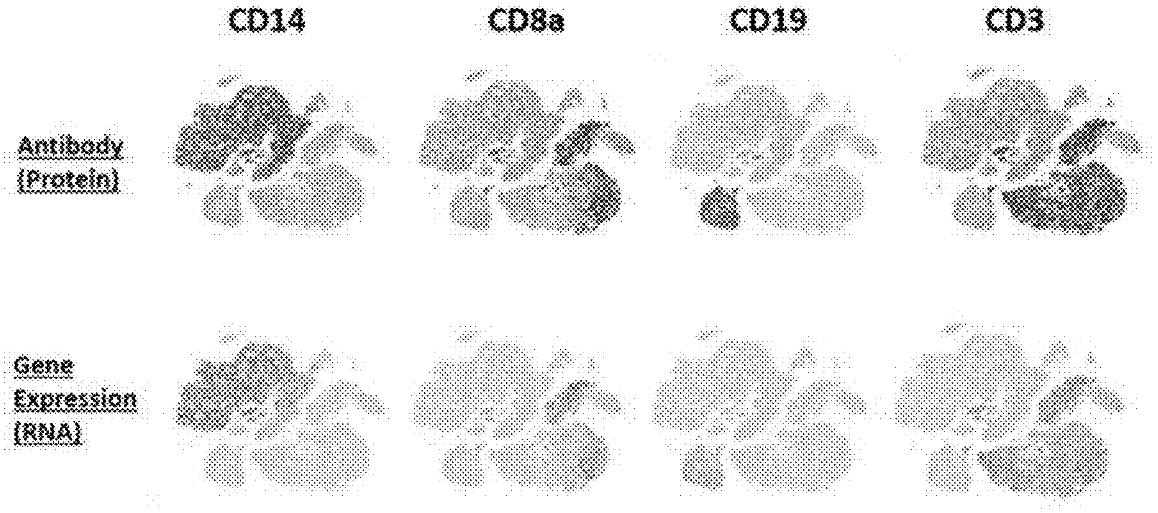
FIG. 24 shows example data of different analyte types using the barcoding approaches described herein.

FIG. 24 shows example data of gene expression and protein analysis data resulting from the barcoding scheme described above. Each plot shows a plot of a biomarker (CD14, CD8a, CD19 and CD3) which are obtained from sequencing of the (i) barcoded RNA products (e.g., the barcoded probe-associated molecule 2230) and (ii) barcoded Antibody B (e.g., barcoded reporter oligonucleotide). The intensity of the spots indicate the relative expression levels (e.g., gene expression or protein expression) detected from the barcoded products. Overall, the plots indicate that the antibody barcoded products (e.g., barcoded reporter oligonucleotides) have similar coverage in detecting a particular analyte or biomarker as the barcoded RNA products (e.g., barcoded probe-associated molecules). Accordingly, a biomarker profile may be determined by assaying the biomarker protein (e.g., barcoding a reporter oligonucleotide of a feature binding group which binds to the biomarker protein), or the biomarker profile may be determined by assaying the biomarker gene expression (e.g., barcoding RNA using dual probes for gene expression profiling). In some instances, both the gene expression profile and the protein profile may be useful in characterizing a cell, e.g., to determine a correlation between gene expression and protein expression.

Example 6—Overloading Cells in Partitions

Cells (or nuclei or cell beads) may be contacted with feature binding groups comprising reporter oligonucleotides that identify the feature or feature-binding group and one or more probes (e.g., for hybridizing to target regions of a target nucleic acid molecule, e.g., mRNA).

As described elsewhere herein, the reporter oligonucleotides and/or the one or more probes (or the probe-associated molecules) may be barcoded in a plurality of partitions. Partitions may be overloaded such that fewer partitions of a plurality of partitions are unoccupied. In one non-limiting example, a population of ~100,000 cells may be loaded into ~80,000 partitions.

If partitions are overloaded, there may still be many partitions that comprise a single cell. The single-cell partitions and may be identified or filtered. For example, the plurality of partitions may be filtered (e.g., using 10×

Genomics CellPlex), such that only singly-occupied partitions are analyzed. The protein information and RNA information may be obtained from the singly-occupied partitions.

For the multiplet partitions (comprising more than one cell), the protein information (from the reporter oligonucleotides) may be inferred, e.g., using the gene expression and the protein profile of cells with similar profiles (e.g., obtained from the single-cell analysis). Such an example of cell overloading may be useful in decreasing reagent waste while providing useful, multiplexed data on gene expression and protein profiles in individual cells.

Example 7—Fixation of Cells, Nuclei, and/or Cell Beads

Cells, nuclei, and/or cell beads may be fixed. In some instances, fixation may be performed prior to hybridization of the probe molecules described herein. An example protocol and list of reagents for fixing a sample comprising cells, nuclei, or cell beads is listed below.

Preparation Buffers

| Buffer | Composition | Final Conc. |
|---|---|---|
| Cell Resuspension Buffer (maintain at 4 C.) | PBS | 1x |
| | BSA | 0.040% |

| Buffer | Composition | Final Conc. |
|---|---|---|
| Fixation Buffer (maintain at RT) | PBS | 0.89x |
| | Formaldehyde | 4% |
| | Tween ® 20 (polysorbate 20) | 0.01% |

| Buffer | Composition | Final Conc. |
|---|---|---|
| Quenching Buffer (maintain at 4 C.) | PBS | 1x |
| | Tris pH 8.0 | 50 mM |
| | BSA (RNase-free) | 0.020% |
| | RNase Inhibitor | 0.1 U/uL |
| | Nuclease-free water | 1x |

Reagents & Consumables

| Vendor | Item | Part Number |
|---|---|---|
| Millipore-Sigma | Albumin, Bovine Serum, 10% Aqueous Solution | 126615 |
| Corning-Cellgro | Phosphate-Buffered Saline 1X without Calcium & Magnesium | 21-040-CV |
| ThermoFisher Scientific | Formaldehyde (37% by Weight/Molecular Biology) | BP531-25 |
| Millipore-Sigma | Trizma ® Hydrochloride (TRIS HCl) Solution, pH 8.0 Sodium Chloride Solution, 1M | T2663 |
| Bio-Rad | 10% Tween ® 20 (polysorbate 20) | 1662404 |

-continued

| Vendor | Item | Part Number |
|---|---|---|
| Millipore-Sigma | Protector RNase Inhibitor | 3335399001 |
| Thermo Fisher Scientific | Nuclease-free Water | AM9937 |
| NEB | Ribonucleoside Vanadyl Complex (RVC) | S1402S |
| 10x Genomics | Surrogate Fluid | 220021 |
| Bel-Art | Flowmi ™ Cell Strainer, (cell strainer for filtering), 40 μm | H13680- 0040 |

Example Protocol a. Thaw up to 10 million cells with warm media.
b. Centrifuge at 300 g for 5 minutes at 4 C.
c. Remove supernatant without disturbing the cell pellet, and resuspend cell pellet with 1 mL of cold Cell Resuspension Buffer.
d. Transfer to a 1.5-mL tube and measure concentration and viability. If cell suspension has visible debris chunks, Flowmi and count again.
e. Centrifuge at 300 g for 5 minutes at 4 C.
f. Remove supernatant without disturbing the cell pellet.
g. Using a regular-bore pipette tip, add 1 mL Fixation Buffer to the cell pellet and gently pipette mix 15×.
h. Incubate at room temperature for 1 hour.
i. Near the end of fixation, prepare a 1 mL aliquot of Quenching buffer. Chill on wet ice.
j. Centrifuge at 850 g for 5 minutes at room temperature.
k. Remove the supernatant without touching the bottom of the tube to avoid dislodging the pellet.
l. Resuspend the cell pellet in 1 mL of ice cold Quenching Buffer. Store on ice.
m. Store the fixed cells.

Example 8—Multiplexed Analysis of RNA and Proteins in Single Cells with Double Fixation The methods disclosed herein may be useful in assaying multiple analytes in single cells. In some instances, a plurality of cells may be assayed for two analytes: (i) RNA, using a pair of probes (e.g., comprising sequences complementary to a target region of RNA), and (ii) peptides, polypeptides, or proteins, using feature binding groups (e.g., antibodies) comprising reporter oligonucleotides. The RNA and protein data may be correlated to better understand transcriptomic and proteomic profiles within single cells, e.g., by assaying gene and protein expression within a cell.

In an example, a plurality of cells may be fixed and permeabilized and contacted with (i) a plurality of probes, including a first probe and a second probe and (ii) an antibody comprising a reporter oligonucleotide. The first probe and the second probe may hybridize to a first target region and a second target region of an RNA molecule within the cells to generate a probe-associated molecule, and the antibody may bind to a target protein on or within the cells. Subsequently, barcoding may be performed, e.g., in partitions, to barcode the probe-associated molecule and the reporter oligonucleotide. Barcoded molecules (e.g., barcoded probe-associated molecules or derivatives thereof and barcoded reporter oligonucleotides or derivatives thereof) may be sequenced and attributed to single cells based on the barcode sequences.

A variety of parameters for preparing the RNA and protein molecules for barcoding within a cell may be tested. In some instances, it may be advantageous to provide additional fixation operations, e.g., after contacting the antibody with the target protein (also referred to herein as "antibody staining"), which may aid in securing the antibody to the target protein during downstream processing, e.g., barcoding. In some instances, the antibody staining may be performed prior to or following hybridization of the first probe and the second probe (also collectively referred to as "the probes"). In some instances, the fixation or permeabilization of the cells may be performed using different fixative and permeabilization methods. In some instances, it may be advantageous to quench an antibody, e.g., in a blocking buffer. Such example parameters may be tested experimentally.

For example, a plurality of cell fixation schemes may be performed (e.g., as shown in FIG. 29). Multiple experimental groups may be used: 1. Negative control group: cells are contacted with reporter-oligonucleotide conjugated antibodies, fixed and permeabilized, quenched, then contacted with the first and second probes. 2. Group A: cells are fixed and permeabilized and optionally quenched (e.g., in a blocking buffer comprising bovine serum albumin (0.5%) and Tween (0.01%), then contacted with the antibodies, then the probes; 3. Group B: cells are fixed and permeabilized and optionally quenched (e.g., in a blocking buffer comprising bovine serum albumin (0.5%) and Tween (0.01%), then contacted with the antibodies, fixed again, quenched again, then contacted with the probes; 4. Group C: cells are fixed and permeabilized and optionally quenched (e.g., in a blocking buffer comprising bovine serum albumin (0.5%) and Tween (0.01%), then contacted with the antibodies, fixed and permeabilized again, quenched, then contacted with the probes; 5. Group D: cells are fixed and permeabilized and optionally quenched (e.g., in a blocking buffer comprising bovine serum albumin (0.5%) and Tween (0.01%), then contacted with the probes, rinsed, and then contacted with the antibodies; 6. Group E: cells are fixed and permeabilized and optionally quenched (e.g., in a blocking buffer comprising bovine serum albumin (0.5%) and Tween (0.01%), then contacted with the probes, rinsed, and contacted with antibodies in a blocking solution (e.g., 0.5% BSA); 7. Group F: cells are fixed and permeabilized using commercially available BioLegend® reagents, washed using BioLegend® Permwash, contacted with the antibodies, then contacted with the probes, 8. Group G: cells are fixed and permeabilized using BioLegend® reagents, washed using BioLegend® Permwash, contacted with the antibodies, quenched, fixed and permeabilized again, quenched, then contacted with the probes. All groups may then be subjected to barcoding (e.g. of the probes or probe-associated molecules, or derivatives thereof, and reporter oligonucleotides of the antibodies, or derivatives thereof), sequencing, and association of the RNA and reporter oligonucleotides (indicative of a target protein being present in a cell) to single cells.

In one experimental setup, PBMC cells are used. The cells are contacted with reporter oligonucleotide-conjugated antibodies to Perforin (dG9) (ab270703) and Granzyme B (QA18A28) antibodies.

Figure 30A:
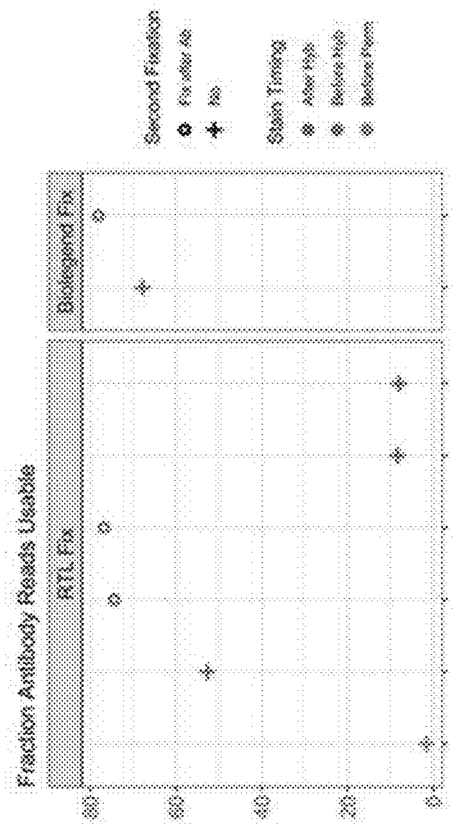
FIG. 30A shows example protein expression data resulting from barcoding of multiple analytes using different sample preparation parameters.

FIG. 30A shows example data resulting from the experimental groups listed above. From left to right, the samples indicate the fraction of antibody reads that are "usable" (e.g., can be attributed back to a single cell from a barcode sequence) for the following groups: Negative control, Group A, Group B, Group C, Group D, Group E, Group F, Group G. As can be seen in FIG. 30A, performing antibody staining prior to hybridization of the probes (e.g., Groups A, B and C) results in a higher percentage of usable antibody reads, and that performing an additional fixation operation following antibody staining (Groups B, C, and G) further improves the fraction of antibody reads (as compared to no second fixation, Groups A, D, E, F). The negative control group (fixation and permeabilization after antibody staining), as expected, result in low fraction of usable antibody reads. Interestingly, the samples that are antibody stained after hybridization of the probes, and not fixed again (Groups D and E) produce low fractions of usable antibodies, suggesting that in some instances, it may be useful to perform the antibody staining prior to hybridization of the probes to achieve a higher usable read count.

Figure 30B:
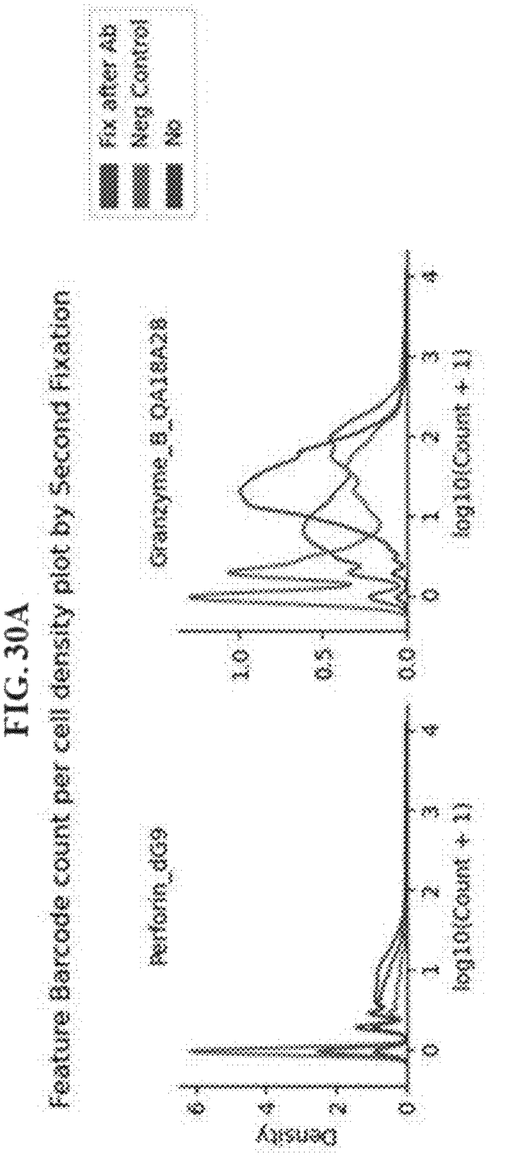
FIG. 30B shows additional protein expression data resulting from barcoding of multiple analytes using different sample preparation parameters.

FIG. 30B shows example data from the same experiment indicating the results of a second fixation operation after antibody staining. The plots indicate a density of antibodies detected, using sequencing and barcode identification, per cell density for two proteins: Perforin (left) and Granzyme (right). Three conditions are categorized: fixation after antibody staining (e.g., Groups B, C, and G), negative control, and no second fixation.

For the Perforin, an initial peak is shown in all three conditions, which may be attributable to background signal. A non-substantial difference among the groups is observed. For Granzyme, the negative control (labeled Neg control, 2) has two first peaks, possibly attributable to background signal, and a third peak, possibly due to non-specific binding of the antibodies. For the no-second fixation condition (labeled No, 3), a single peak is observed. For the fixation-after-antibody-staining condition (labeled Fix after Ab, 1), two peaks are observed, which may indicate two populations of cells, which may be one negative population (e.g., monocytes having background signal or nonspecific staining) and one positive population (e.g., cells having higher signal for the second fixation, e.g., specific staining of Natural Killer and/or cytotoxic T cells) or possibly two positive populations. Further studies may seek to elucidate the specific populations, e.g., by running isotype controls.

Figure 31:
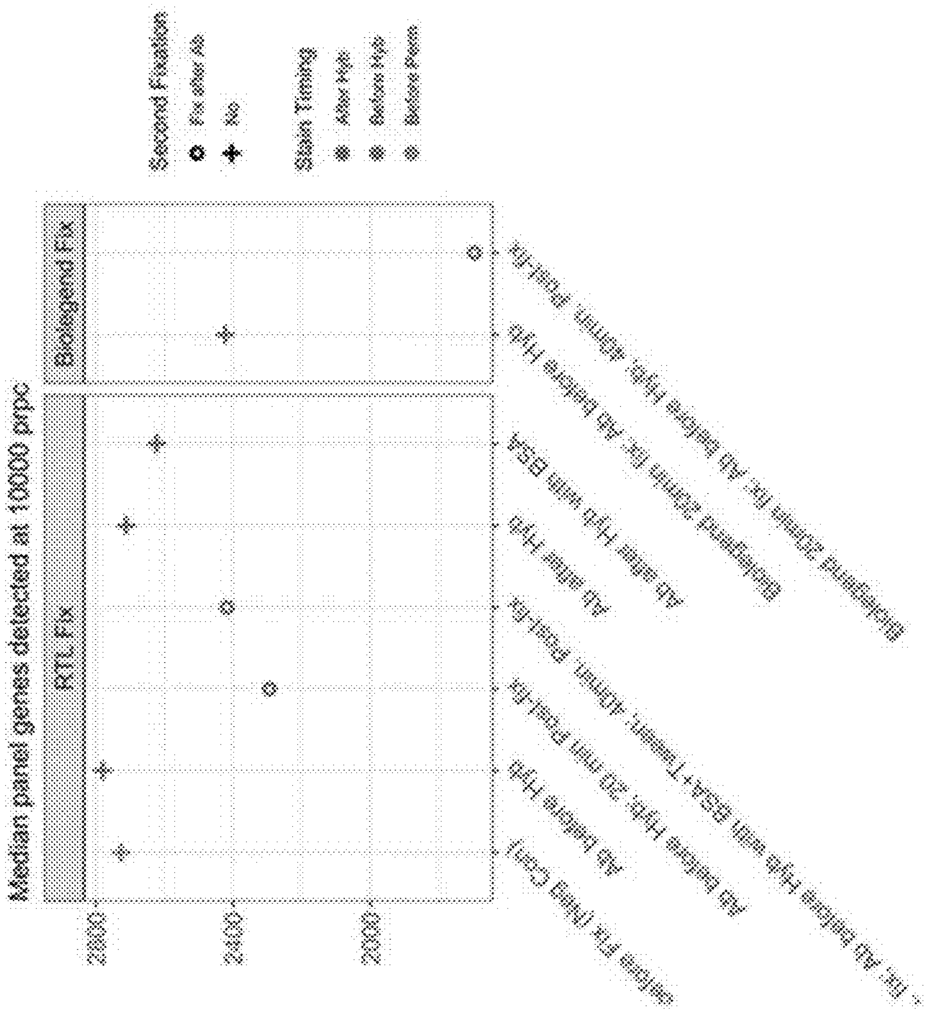
FIG. 31 shows example gene expression data resulting from barcoding of multiple analytes using different sample preparation parameters.
Figure 32B:
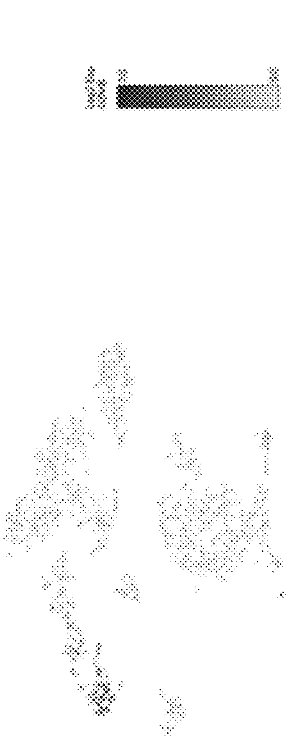
FIGS. 32A-C shows example data of multiple analyte probing for a negative control group.
Figure 32C:
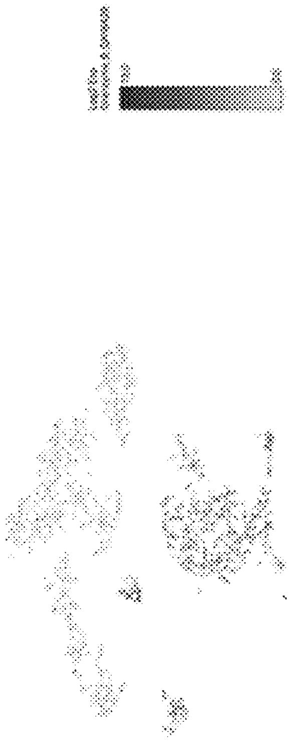
Figure 32A:
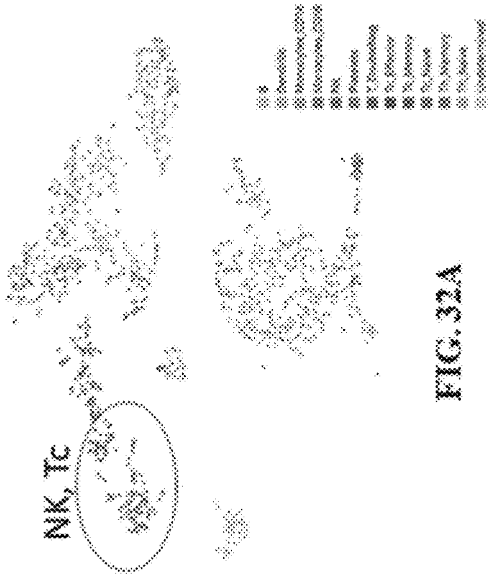

FIG. 31 shows example gene expression data resulting from the experimental groups listed above. From left to right, the samples indicate the median number of genes detected (e.g., from sequencing the probe-associated molecules or derivatives thereof) for the following groups: Negative control, Group A, Group B, Group C, Group D, Group E, Group F, Group G. As can be seen in FIG. 31, performing an additional fixation operation following antibody staining (Groups B, C, and G) may reduce the number of genes detected (e.g., the sensitivity) of the assay. As such, a tradeoff between antibody sensitivity and gene expression sensitivity when using a second fixation operation may be observed. The negative control group (fixation and permeabilization after antibody staining), results in a relatively high number of genes detected.

FIGS. 32-37 show example data of gene expression and antibody staining results of some of the experimental groups described above. FIGS. 32A-C show t-SNE plots of the negative control group (cells that are stained with antibodies prior to fixing and permeabilization). FIG. 32A shows a plot of different immune cell clusters, with the oval indicating natural killer and cytotoxic T cell types; FIG. 32B shows the gene expression profile of GZMB in the immune cells (e.g., resulting from barcoding of the probes targeting GZMB, or probe-associated molecules) and FIG. 32C shows the antibody staining profile in the immune cells. The GZMB gene expression profile indicates GZMB expression in natural killer and cytotoxic T cells. The antibody staining shows some non-specific staining on monocytes and B cells and limited staining on natural killer cells.

Figure 33A:
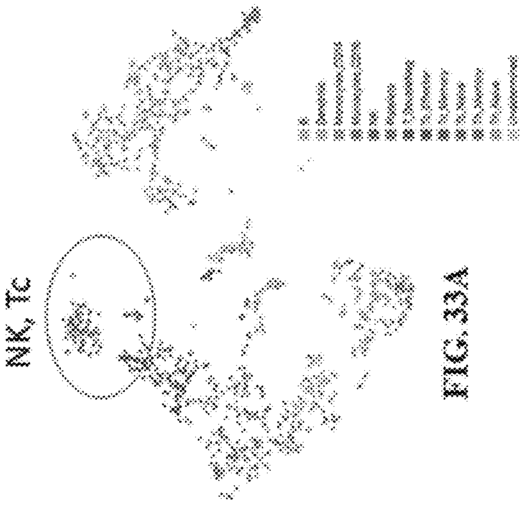
FIGS. 33A-C shows example data of multiple analyte probing for an experimental group.
Figure 33B:
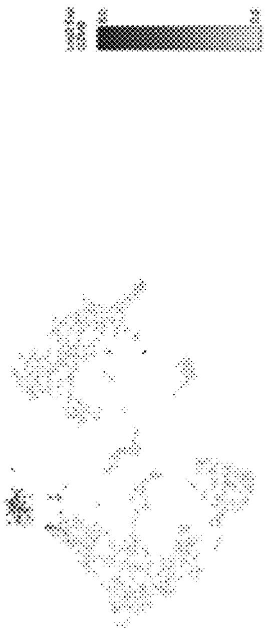
Figure 33C:
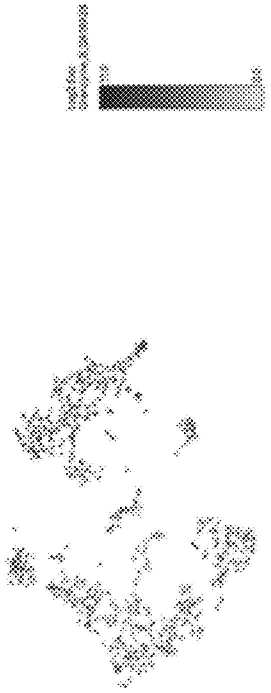

FIGS. 33A-C show t-SNE plots for Group D (cells that are fixed and permeabilized, contacted with the probes, then stained with antibodies). FIG. 33A shows a plot of different immune cell clusters, with the oval indicating natural killer and cytotoxic T cell types; FIG. 33B shows the gene expression profile of GZMB in the immune cells (e.g., resulting from barcoding of the probes targeting GZMB, or probe-associated molecules) and FIG. 33C shows the antibody staining profile in the immune cells. For the Group D cells, the GZMB gene expression profile indicates GZMB expression in natural killer and cytotoxic T cells. The antibody staining shows some non-specific staining on monocytes and B cells, and some specific staining on natural killer cells.

Figure 34B:
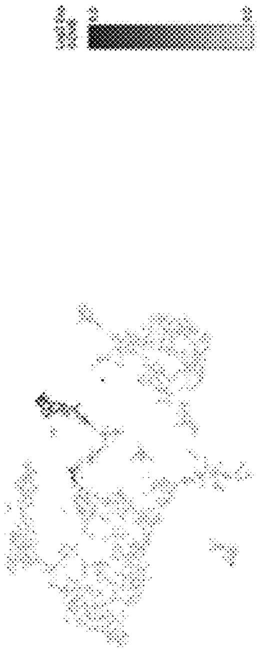
FIGS. 34A-C shows example data of multiple analyte probing for an experimental group.
Figure 34C:
Figure 34A:
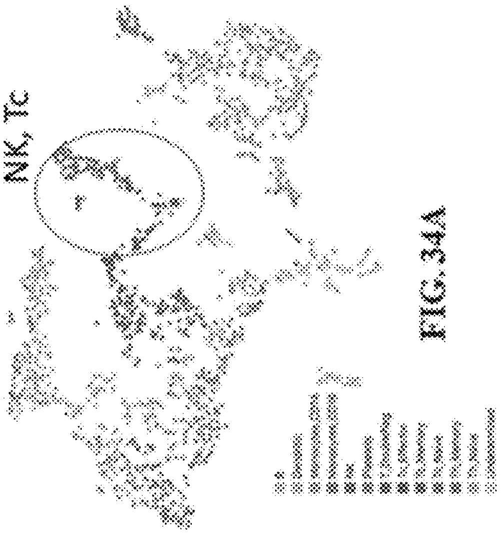

FIGS. 34A-C show t-SNE plots for Group B (cells that are fixed and permeabilized, contacted with the antibodies, fixed again, then contacted with the probes). FIG. 34A shows a plot of different immune cell clusters, with the oval indicating natural killer and cytotoxic T cell types; FIG. 34B shows the gene expression profile of GZMB in the immune cells (e.g., resulting from barcoding of the probes targeting GZMB, or probe-associated molecules) and FIG. 34C shows the antibody staining profile in the immune cells. For the Group B cells, the GZMB gene expression profile indicates GZMB expression in natural killer and cytotoxic T cells. The antibody staining shows some non-specific staining on monocytes, and stronger specific staining on natural killer cells compared to the Group D cells.

Figure 35B:
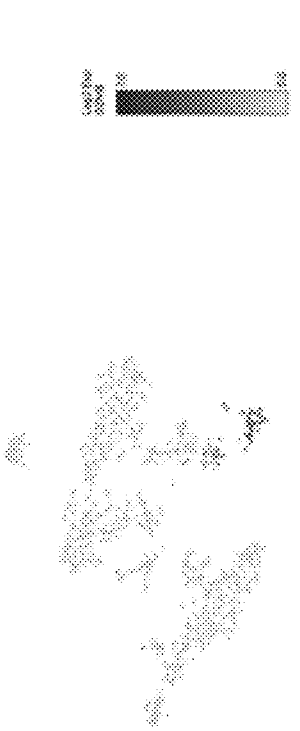
FIGS. 35A-C shows example data of multiple analyte probing for an experimental group.
Figure 35C:
Figure 35A:

FIGS. 35A-C show t-SNE plots for Group E (cells that are fixed and permeabilized, contacted with the probes, then stained with antibodies in a blocking solution). FIG. 35A shows a plot of different immune cell clusters, with the oval indicating natural killer and cytotoxic T cell types; FIG. 35B shows the gene expression profile of GZMB in the immune cells (e.g., resulting from barcoding of the probes targeting GZMB, or probe-associated molecules) and FIG. 35C shows the antibody staining profile in the immune cells. For the Group E cells, the GZMB gene expression profile indicates GZMB expression in natural killer and cytotoxic T cells. The antibody staining shows some non-specific staining.

Figure 36A:
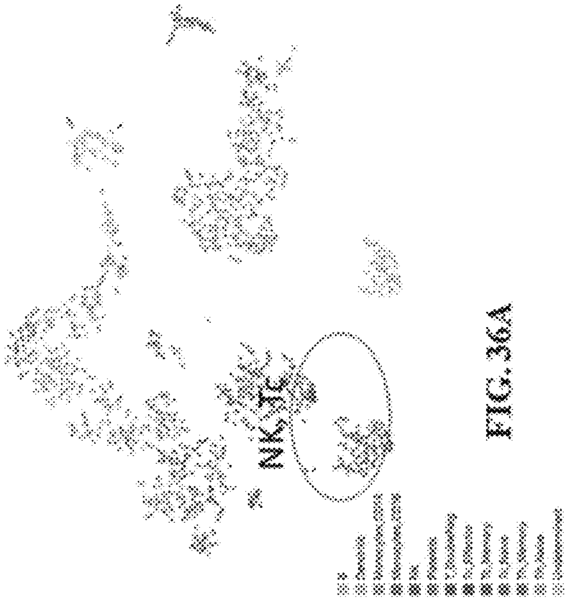
FIGS. 36A-C shows example data of multiple analyte probing for an experimental group.
Figure 36B:
Figure 36C:
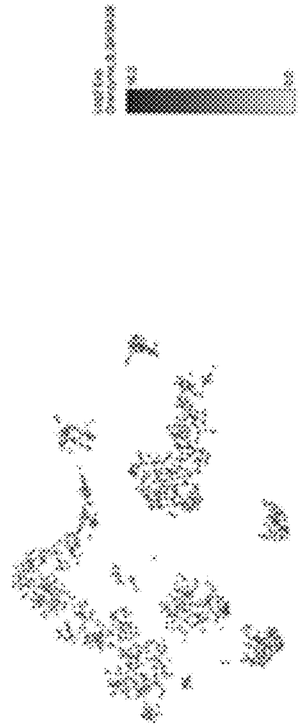

FIGS. 36A-C show t-SNE plots for Group F (cells that are fixed and permeabilized using a commercially available BioLegend® kit, stained with antibodies, then contacted with the probes). FIG. 36A shows a plot of different immune cell clusters, with the oval indicating natural killer and cytotoxic T cell types; FIG. 36B shows the gene expression profile of GZMB in the immune cells (e.g., resulting from barcoding of the probes targeting GZMB, or probe-associated molecules) and FIG. 36C shows the antibody staining profile in the immune cells. For the Group F cells, the GZMB gene expression profile indicates GZMB expression in natural killer and cytotoxic T cells. The antibody staining shows some non-specific staining.

Figure 37B:
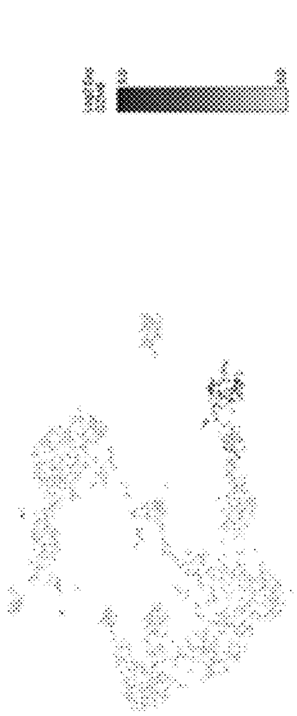
FIGS. 37A-C shows example data of multiple analyte probing for an experimental group.
Figure 37C:
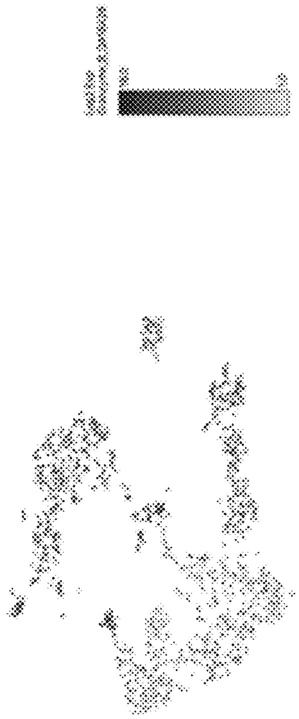
Figure 37A:
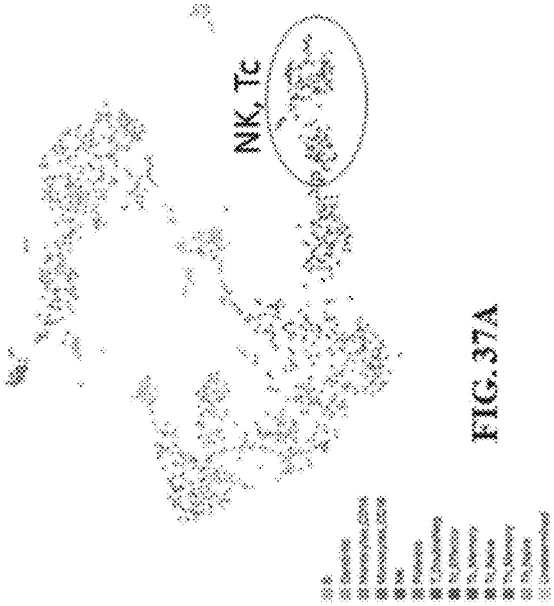

FIGS. 37A-C show t-SNE plots for Group G (cells that are fixed and permeabilized using a commercially available BioLegend® kit, stained with antibodies, fixed again, then contacted with the probes). FIG. 37A shows a plot of different immune cell clusters, with the oval indicating natural killer and cytotoxic T cell types; FIG. 37B shows the gene expression profile of GZMB in the immune cells (e.g., resulting from barcoding of the probes targeting GZMB, or probe-associated molecules) and FIG. 37C shows the antibody staining profile in the immune cells. For the Group F cells, the GZMB gene expression profile indicates GZMB expression in natural killer and cytotoxic T cells. The antibody staining shows some non-specific staining among monocytes and other cells, but preferential staining on the natural killer cells. More specific staining is observed with the second fixation, compared to without the second fixation.

Altogether, these results suggest that some specific staining occurs on the natural killer and cytotoxic T cells in certain conditions. The greatest specificity is observed in the samples where the cells are fixed and permeabilized, stained (contacted with the antibodies), fixed again, then contacted with the probes. As some nonspecific staining of monocytes is observed, specificity of antibody staining can be evaluated or observed by excluding monocytes from consideration. Overall, these results suggest the a second fixation process may help improve protein expression signal when probing for multiple analytes (e.g., protein and RNA).

Example 9—Multiplexed Assay: Barcoding of RNA Templated Ligation Product and Reporter Oligonucleotide of a Feature-Binding Group The methods described herein may be useful in assaying multiple analytes in a population of cells, nuclei, or cell beads. The cells, nuclei, or cell beads may be contacted with a feature binding group comprising or coupled to a reporter oligonucleotide (comprising a reporter sequence), as described herein. The feature binding group may couple to one or more features (e.g., proteins) of the cell. The cell may also comprise target nucleic acid molecules (e.g., RNA molecules) for assaying.

Figure 38:
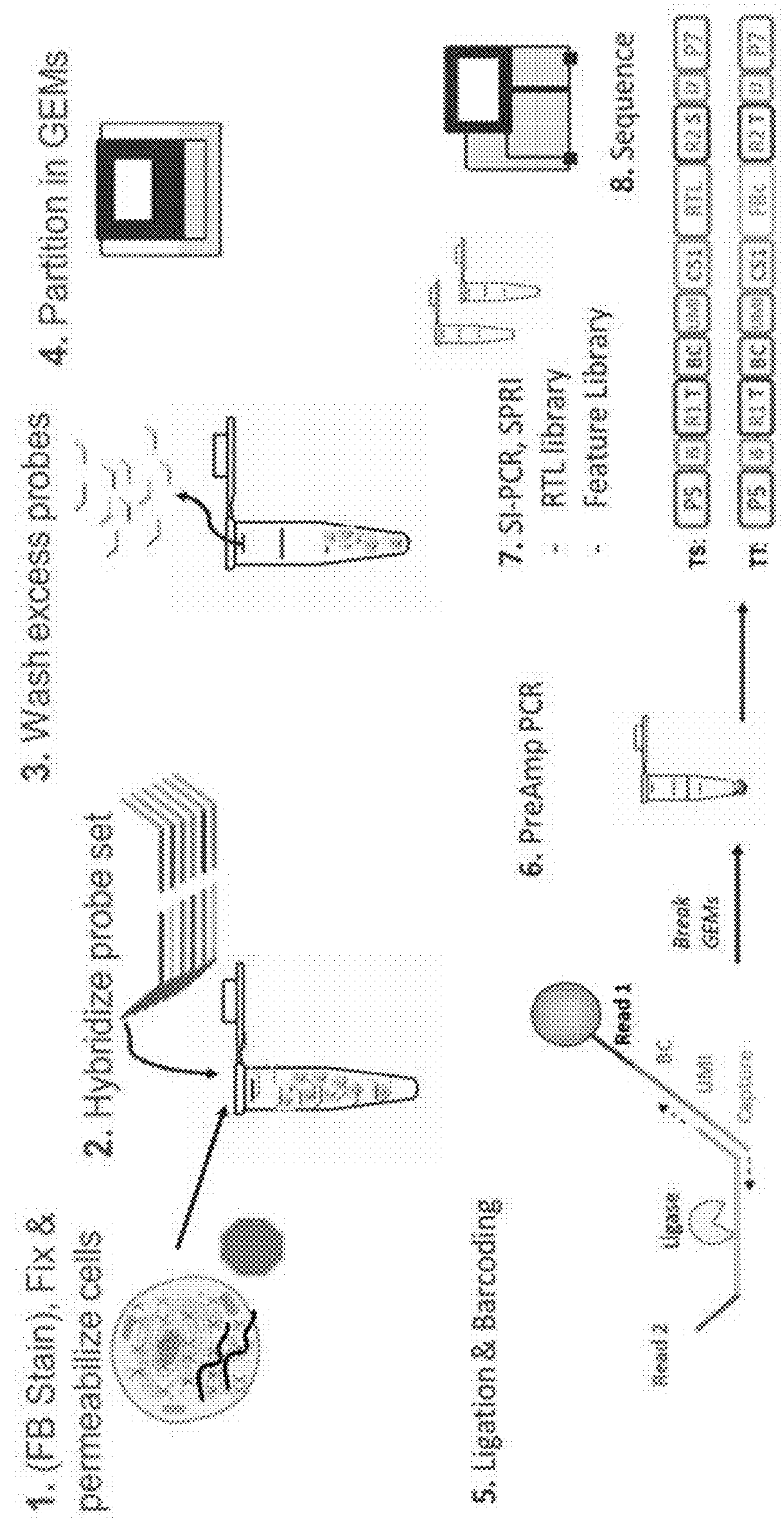
FIG. 38 shows another example workflow for assaying two different analyte types.

FIG. 38 shows another example multiplexed workflow for assaying cell features (e.g., proteins) and target nucleic acid molecules (e.g., RNA molecules). A cell, nucleus, or cell bead may be fixed and permeabilized, e.g., in 4% formaldehyde and 0.01% Tween® 20 (polysorbate 20) or a commercially available fixation and permeabilization buffer (e.g., commercially available BioLegend® fixation and permeabilization buffer). In some instances, prior to or subsequent to fixation and permeabilization, the cell, nucleus, or cell bead may be contacted with one or more feature binding groups comprising reporter oligonucleotides. The one or more feature binding groups may specifically bind to cell features (e.g., specific proteins) if present on or within the cell, nucleus, or cell bead. In some instances, the reporter oligonucleotides may be used to identify the feature binding group and thus the presence or absence of a target cell feature (e.g., specific protein). For example, a plurality of cells may be contacted with a plurality of feature binding groups, which may be the same or different, and may comprise the same or different reporter oligonucleotides. In one non-limiting example, a cell of the plurality of cells may be contacted with different feature binding groups that can bind to different cell features (e.g., different surface or intracellular proteins). As each feature binding group comprises a reporter oligonucleotide comprising a barcode sequence that identifies the feature binding group, the presence of such different cell features (e.g., different surface or intracellular proteins) may be assessed (e.g., via sequencing) by the presence of the barcode sequences.

Alternatively or in addition to contacting a cell, nucleus, or cell bead with the one or more feature binding groups, the cell, nucleus, or cell bead may be contacted with a first probe and a second probe to generate a probe-associated molecule (e.g., a probe-associated RNA molecule), as described herein. For example, the cell, nucleus, or cell bead, which may optionally be fixed and permeabilized, may comprise a target nucleic acid molecule (e.g., RNA molecule) comprising a first target region and a second target region. The first probe may comprise a first probe sequence that is at least partially complementary to the first target region, and the second probe may comprise a second probe sequence that is at least partially complementary to the second target region. Hybridization of the first probe sequence to the first target region and the second probe sequence to the second target region may be sufficient to generate the probe-associated molecule.

In some instances, the cell, nucleus, or cell bead may be contacted with a plurality of different probes. The plurality of different probes may specifically hybridize to target regions of target nucleic acid molecules, if present. In some instances, the probe sequences may comprise probe barcode sequences that may be used to identify the probe. For example, a plurality of cells may be contacted with a plurality of probes, which may be the same or different, and may comprise the same or different sequences (e.g., barcode sequences, probe sequences, adapter sequences). In one non-limiting example, a cell of the plurality of cells may be contacted with different probes that can hybridize to different target regions of a target nucleic acid molecule (e.g., RNA molecule). Each probe may comprise a probe barcode sequence that identifies the probe, and the presence of such different target sequences may be assessed (e.g., via sequencing) by the presence of the probe barcode sequences or the probe sequences. In some instances, the probe barcode sequences may be used to identify the originating sample or to deconvolve a sequence and identify the sequence as originating from a cell, nucleus, or cell bead (e.g., as shown in FIG. 10).

Subsequent to contacting of the cell, nucleus, or cell bead with the probes (e.g., a first probe and a second probe), the cell, nucleus, or cell bead may be washed to remove any unbound or non-hybridized probes. The cell, nucleus, or cell bead may then be partitioned (e.g., in a droplet or well) for barcoding, as described herein. In one non-limiting example, the cell, nucleus, or cell bead may be partitioned with a nucleic acid barcode molecule (shown in FIG. 38 as coupled to a bead). The nucleic acid barcode molecule may comprise a barcode sequence and a capture sequence complementary to a sequence of one of the probes (e.g., the first probe or the second probe). The nucleic acid barcode molecule may comprise additional sequences, e.g., a UMI, a primer sequence, a sequencing primer sequence (e.g., P5, P7, R1, R2 sequences). The capture sequence of the nucleic acid barcode molecule may anneal to the complementary sequence of one of the probes (e.g., the first probe or the second probe), and optionally, an extension reaction may be performed to generate a barcoded nucleic acid molecule comprising the barcode sequence or complement thereof and a sequence of at least one of the probes, or complements thereof.

In some instances, if the cell, nucleus, or cell bead comprises a feature binding group coupled thereto, the nucleic acid barcode molecule capture sequence may also anneal to a sequence of the reporter oligonucleotide (not shown in FIG. 38). In some instances, an extension reaction may be performed to generate an additional barcoded nucleic acid molecule comprising a sequence of the reporter oligonucleotide or complement thereof and the barcode sequence or complement thereof.

Following barcoding, the barcoded nucleic acid molecule and the additional barcoded nucleic acid molecule may be removed from the partitions and subjected to conditions sufficient for sequencing, e.g., amplification, cleanup, sample-index PCR, etc. Such an example workflow may be useful in obtaining multiplexed information regarding cell features (e.g., proteins) and correlating the features with nucleic acid information, e.g., the presence or genotype of target nucleic acid molecules (e.g., RNA).

It will be appreciated that the processes described herein may be performed in any useful or convenient order. For example, for the cells, nuclei, or cell beads, the fixation, permeabilization, contacting with the feature binding groups, and contacting with the first probe and the second probe may occur in any useful order and may be repeated any number of times. Any of these processes, e.g., fixation, permeabilization, contacting with the feature binding groups, and contacting with the first probe and the second probe, may occur in bulk or in partitions.

Example 10—RNA Templated Ligation for Whole Transcriptome Analysis in Tissue Samples The methods described herein may be useful in assaying nucleic acid molecules (e.g., mRNA) in tissue samples, e.g., fresh tissue samples, frozen (e.g., flash-frozen) tissue samples, etc. In some instances, whole transcriptome analysis may be performed in tissue samples. In one such example, a tissue sample may comprise mRNA molecules that can be contacted with a plurality of first probes and second probes. The plurality of first probes and second probes may comprise a set of whole transcriptome analysis probes, such that hundreds, thousands, or millions of RNA targets may be analyzed. For example, the plurality of first probes and second probes may comprise thousands of different first probes and second probes that may hybridize to different target sequences (e.g., coding or non-coding) of mRNA. Altogether, the plurality of first probes and second probes may have sufficient sequence diversity and coverage to analyze the entire transcriptome of a sample. The plurality of first probes and second probes may comprise gene-specific sequences, which may be species specific (e.g., able to distinguish from different animal cell types, e.g., human and mouse).

In some instances, the use of a dual-probe (e.g., using a first probe and a second probe that hybridize to first and second target regions, respectively of an mRNA molecule) approach to conduct mRNA analysis may be advantageous in providing higher analyte sensitivity, improved efficiency of barcoding, and/or discernment of a greater number of barcodes, UMIs, or both, as compared to the use of a single probe (e.g., the 3' Single Cell Gene Expression solution (10× Genomics)). Table 1 shows example data of a comparison of the number of UMIs detected in flash-frozen human and mouse tissue samples for whole-transcriptome analysis using either (i) a single probe approach, e.g., as shown and described in FIG. 12B, labeled in Table 1 as single-cell 3' ("SC3P") or (ii) a dual-probe approach, e.g., as shown in the nucleic acid analysis in FIGS. 16A-16B, labeled in Table 1 as RNA-templated ligation ("RTL"). Five different human samples, from the liver, colon, jejunum, ileum, testis, and one mouse sample from the brain are tested. All samples are flash frozen. Each column of the numeric columns of Table 1 illustrate the number of UMIs detected at either 5,000 panel reads per cell ("PRPC") or 10,000 PRPC in both the RTL (dual-probe whole transcriptome analysis) and SC3P (single-probe whole transcriptome analysis) approaches. As can be seen in Table 1, the RTL workflow results in a higher number of UMIs detected in all the different flash frozen tissue samples.

TABLE 1

Comparison of number of UMIs detected using a single-probe or dual-probe approach for whole transcriptome analysis in flash frozen tissue samples.

| Tissue Type | Format | RTL Median Panel UMIs at 5k prpc | RTL Median Panel UMIs at 10k prpc | RTL Median Panel Genes at 5k prpc | RTL Median Panel Genes at 10k prpc | SC3P Median UMIs at 5k prpc | SC3P Median UMIs at 10k prpc | SC3P Median Genes at 5k prpc | SC3P Median Genes at 10k prpc | Which is higher? |
|---|---|---|---|---|---|---|---|---|---|---|
| Human Liver | Flash Frozen | 2843 | 4231 | 1194 | 1549 | 878 | — | 503 | — | RTL |
| Human Colon | Flash Frozen | 1122 | 1310 | 829 | 943 | 92 | 242 | 130 | 155 | RTL |
| Human Jejunum | Flash Frozen | 1594 | 1965 | 1061 | 1232 | 174 | — | 160 | — | RTL |
| Human Ileum | Flash Frozen | 1312 | 1534 | 956 | 1053 | 357 | — | 321 | — | RTL |
| Human Testis | Flash Frozen | 1982 | 3102 | 1354 | 1859 | 1011 | — | 821 | — | RTL |
| Mouse E18 Brain | Flash Frozen | 3345 | 5993 | 2211 | 3258 | 2579 | 4683 | 1592 | 1915 | RTL |

Similarly, Table 2 shows example data of a comparison of the number of UMIs detected in fresh mouse tissue samples for whole-transcriptome analysis using either (i) a single probe approach ("SC3P") or (ii) a dual-probe approach ("RTL"). Five different mouse samples, from the brain, colon, kidney, lung, and liver are tested. All samples are fresh. Each column of the numeric columns of Table 2 illustrate the number of UMIs detected at either 5,000 panel reads per cell ("PRPC") or 10,000 PRPC in both the RTL (dual-probe whole transcriptome analysis) and SC3P (single-probe whole transcriptome analysis) approaches. As can also be seen in Table 2, the RTL workflow results in a higher number of UMIs detected in all the fresh tissue samples.

TABLE 2

Comparison of number of UMIs detected using a single-probe or dual-probe approach for whole transcriptome analysis in fresh tissue samples.

| Tissue Type | Format | RTL Median Panel UMIs at 5k prpc | RTL Median Panel UMIs at 10k prpc | RTL Median Panel Genes at 5k prpc | RTL Median Panel Genes at 10k prpc | SC3P Median UMIs at 5k prpc | SC3P Median UMIs at 10k prpc | SC3P Median Genes at 5k prpc | SC3P Median Genes at 10k prpc | Which is higher? |
|---|---|---|---|---|---|---|---|---|---|---|
| Mouse E18 Brain | Fresh | 3412 | 6258 | 2249 | 3412 | 2579 | 4683 | 1592 | 1915 | RTL |
| Mouse Colon | Fresh | 2351 | — | 1358 | — | 987 | — | 369 | — | RTL |
| Mouse Kidney | Fresh | 2281 | 4231 | 1324 | 2009 | 486 | 804 | 131 | 194 | RTL |
| Mouse Lung | Fresh | 2212 | 3740 | 1373 | 1989 | 1871 | 3120 | 819 | 1159 | RTL |
| Mouse Liver | Fresh | 2057 | — | 1036 | — | 2007 | — | 507 | — | RTL |

Altogether, these data suggest that using a dual probe approach for analysis of mRNA provides a sensitive approach to assaying whole transcriptomes in tissue samples.

Example 11—Preparation of Samples from Fixed Tissues

The methods described herein may be used to prepare a fixed tissue sample for analysis. A first workflow for preparation of the sample can comprise securing and sectioning at least a portion of a fixed tissue (e.g., a formalin-fixed paraffin embedded tissue sample). The tissue can be sectioned into one or more 10 to 50 micrometer scrolls, which can then be placed into a sample tube. To the one or more scrolls, 3 milliliters (mL) of a non-polar solvent (e.g., xylene, neo-clear, orange oil, etc.) can be added such that the one or more scrolls are completely immersed and left for 5 minutes. The non-polar solvent can then be removed and discarded, and the process repeated two more times. Subsequent to the addition of the non-polar solvent, 3 mL of 100% ethanol can be added to the sample tube and incubated with the one or more scrolls for 30 seconds at ambient temperatures. The ethanol can be aspirated using a Pasteur pipette and discarded. This process can be repeated with 1 mL of 70% ethanol, 1 mL of 50% ethanol, and 1 mL of double distilled water.

Subsequently, 1 mL of phosphate buffered saline (PBS) can be added to the sample tube at ambient temperature, and subsequently removed without disturbing the one or more scrolls. Optionally, 1 mL of citrate pH 8.0 crosslinking buffer can be added to the sample tube. If the optional citrate buffer is added, the sample tube can be incubated for 30 minutes to 1 hour at 70 degrees Celsius. The sample can then be centrifuged at 850-2000 relative centrifugal force (rcf).

Whether or not the optional addition of citrate is performed, a dissociation solution comprising, for example, liberase with low thermolysis (TL), liberase with medium thermolysis (TM), liberase with high thermolysis (TH), collagenases, or the like, or any combination thereof, can be heated at 37 degrees Celsius for 10 minutes. 2 mL of the pre-warmed dissociation solution can be added to the sample and incubated for 20 minutes to 1 hour at 37 degrees Celsius while shaking the sample tube intermittently. Then, using a silanized glass pipette, the scrolls can be triturated 15 to 20 times (e.g., until the solution begins to turn cloudy) to obtain a cell suspension.

The dissociated tissue can be passed through a 70 micrometer filter, and any tissue pieces can be pushed through the filter with the back of a syringe plunger to maximize cell yields and remove debris and undissociated tissue pieces. An additional wash of the 70 micrometer filter can be performed by adding 2 mL of PBS to the filter. The filtrate from the additional wash can be added to the filtrate from the first filtering operation. The combined filtrates can be centrifuged at 850-2000 rcf for 5 minutes, the supernatant can be removed without disturbing the pellet formed by centrifugation, and the pellet can be resuspended in 1 mL of chilled PBS.

The cell concentration of the resuspended solution can then be determined using a Countess II FL Automated Cell Counter, a Cellaca MX High-Throughput Automated Cell Counter, or the like using a fluorescent dye (e.g., ethidium homodimer-1, ect.) or AO/PI staining solution, or the like. The resuspended solution may then be used as a sample for the methods and systems described elsewhere herein (e.g., RNA profiling, etc.).

A second workflow may comprise securing and sectioning at least a portion of a fixed tissue (e.g., a formalin-fixed paraffin embedded tissue sample). The tissue can be sectioned into one or more 10 to 50 micrometer scrolls, which can then be placed onto a slide. To the one or more scrolls, 1 milliliter (mL) of a non-polar solvent (e.g., xylene, neoclear, orange oil, etc.) can be added such that the one or more scrolls are completely immersed and left for 5 minutes. The non-polar solvent can then be removed and discarded, and the process repeated two more times. Subsequent to the additions and removals of the non-polar solvent, 1 mL of 100% ethanol can be added to the slide and incubated with the one or more scrolls for 30 seconds at ambient temperatures. The ethanol can be aspirated using a Pasteur pipette and discarded. The ethanol additions may be configured as an ethanol hydration (e.g., the amount of water mixed with the ethanol can increase with each addition. This process can be repeated with 1 mL of 70% ethanol, 1 mL of 50% ethanol, and 1 mL of double distilled water.

Subsequently, 1 mL of phosphate buffered saline (PBS) can be added to the sample tube at ambient temperature, and subsequently removed without disturbing the one or more scrolls. Subsequently, the one or more tissue scrolls can be chopped finely on the slide and placed into a sample tube. A dissociation solution comprising, for example, liberase with low thermolysis (TL), liberase with medium thermolysis (TM), liberase with high thermolysis (TH), collagenases, or the like, or any combination thereof, can be heated at 37 degrees Celsius for 10 minutes. 2 mL of the pre-warmed dissociation solution can be added to the sample and incubated for 20 minutes to 1 hour at 37 degrees Celsius while shaking the sample tube intermittently. Then, using a silanized glass pipette, the scrolls can be triturated 15 to 20 times (e.g., until the solution begins to turn cloudy) to obtain a cell suspension.

The dissociated tissue can be passed through a 70 micrometer filter, and any tissue pieces can be pushed through the filter with the back of a syringe plunger to maximize cell yields and remove debris and undissociated tissue pieces. An additional wash of the 70 micrometer filter can be performed by adding 2 mL of PBS to the filter. The filtrate from the additional wash can be added to the filtrate from the first filtering operation. The combined filtrates can be centrifuged at 850-2000 rcf for 5 minutes, the supernatant can be removed without disturbing the pellet formed by centrifugation, and the pellet can be resuspended in 1 mL of chilled PBS.

The cell concentration of the resuspended solution can then be determined using a Countess II FL Automated Cell Counter, a Cellaca MX High-Throughput Automated Cell Counter, or the like using a fluorescent dye (e.g., ethidium homodimer-1, ect.) or AO/PI staining solution, or the like. The resuspended solution may then be used as a sample for the methods and systems described elsewhere herein (e.g., RNA profiling, etc.).

Example 12—Time Series Analysis of T-Cell Response

T-cell stimulation with anti-CD3 and anti-CD28 may be used to study antigen specific T-cell response. The use of single-cell transcriptomics may uncover gene-level drives of activation and/or associations with cell surface protein activation markers. Measuring single-cell gene expression on a minute scale time frame, such as that of T-cell stimulation, may be difficult due to the logistics of sampling, counting, and processing cells. Use of fixatives to freeze samples at short time scales may enable single-cell level analysis of these fast processes.

Figure 39A:
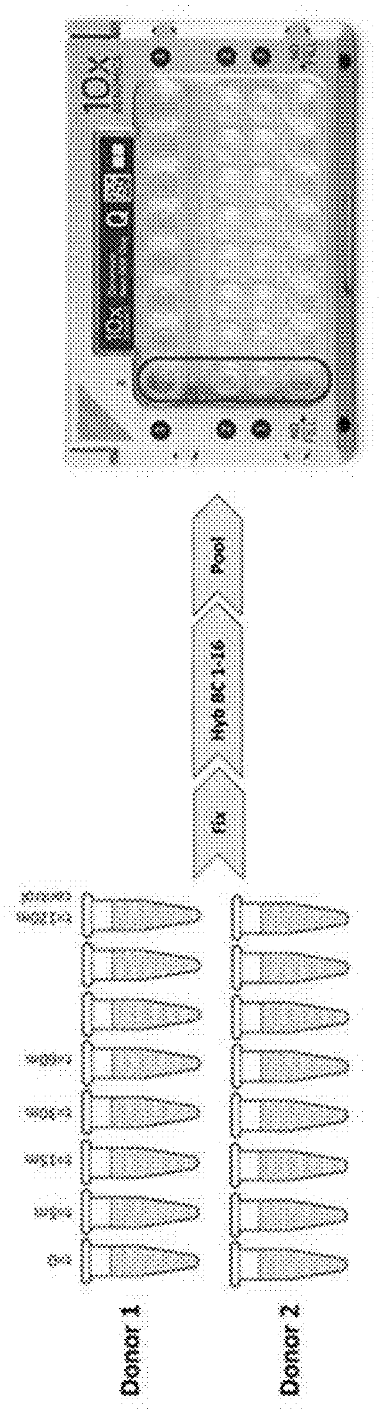
FIGS. 39A-39E are an example of time series data for fixed samples.
Figure 39B:
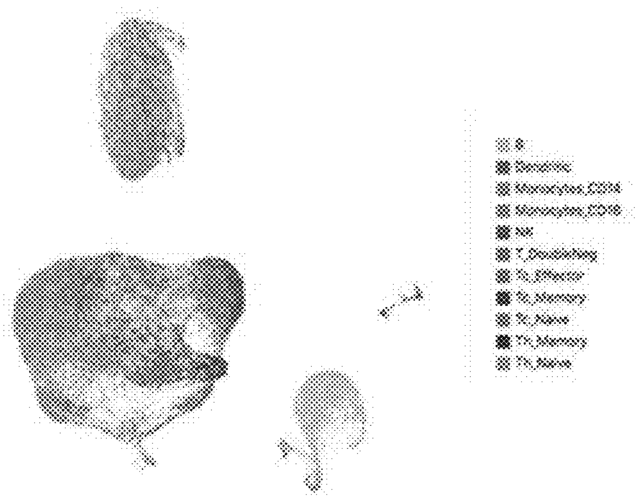
Figure 39C:
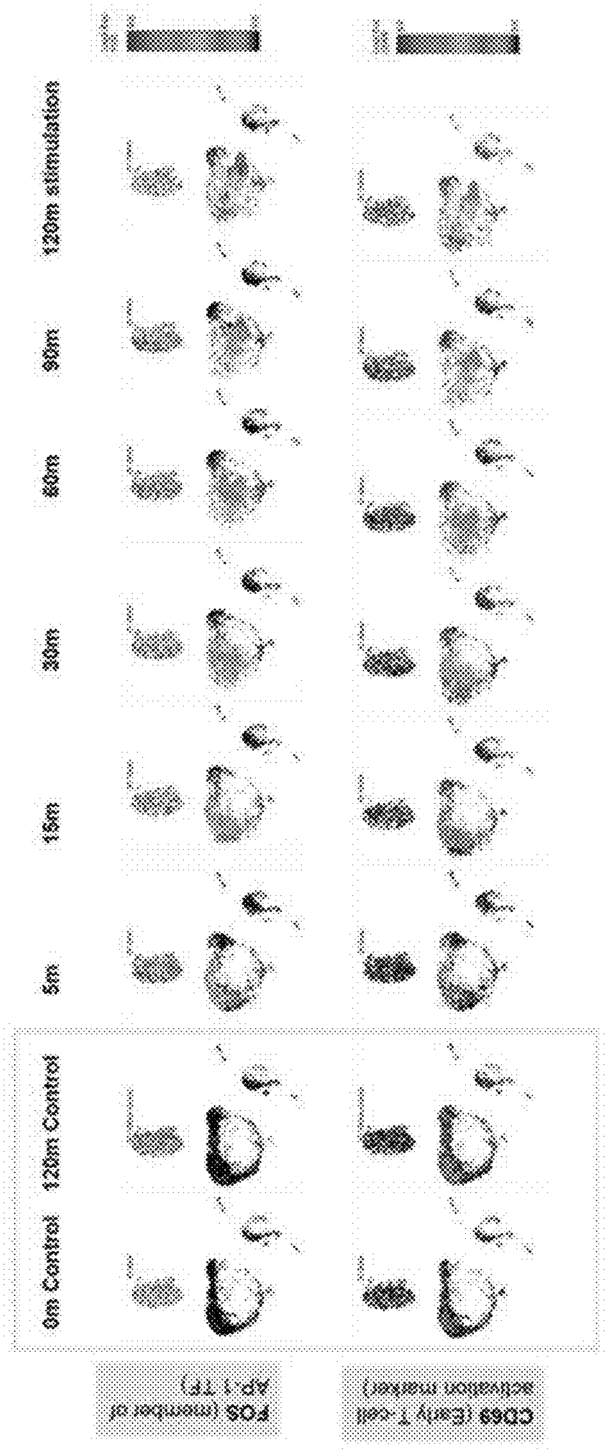
Figure 39D:
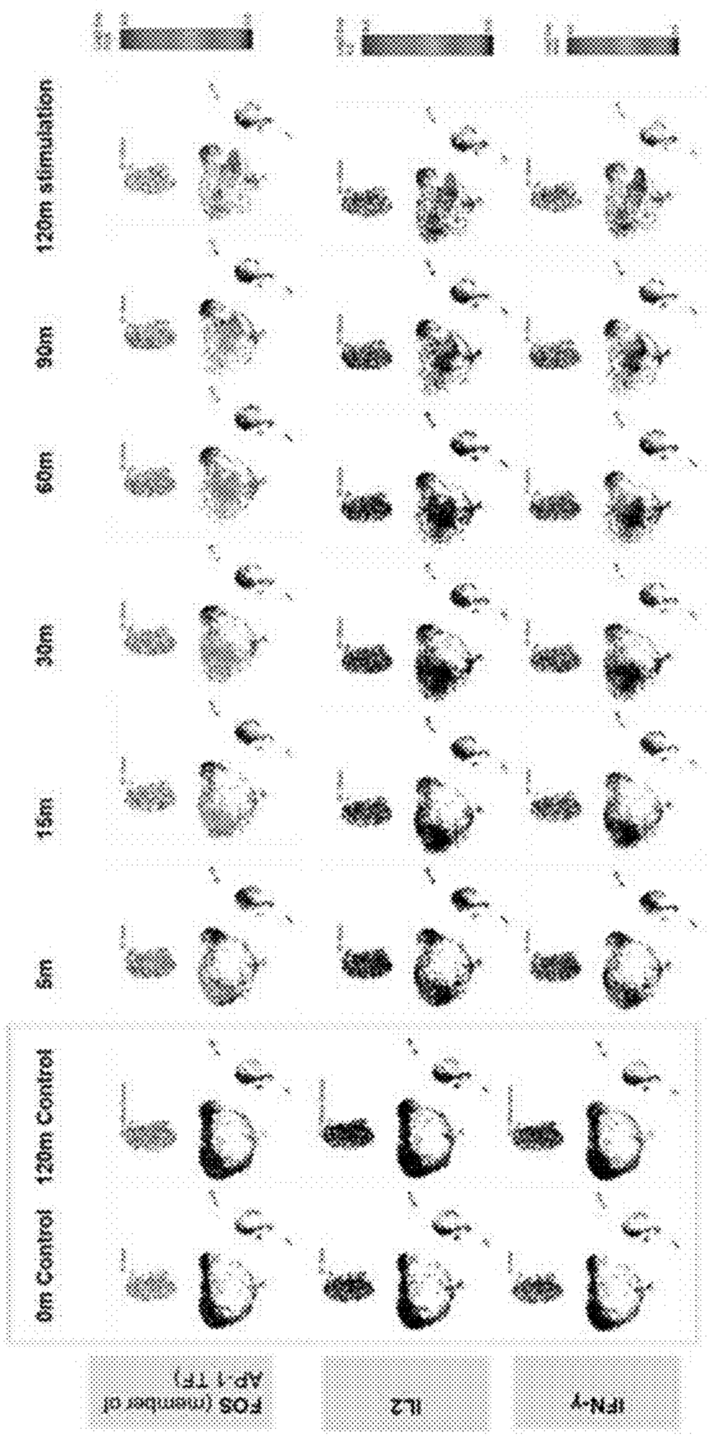
Figure 39E:
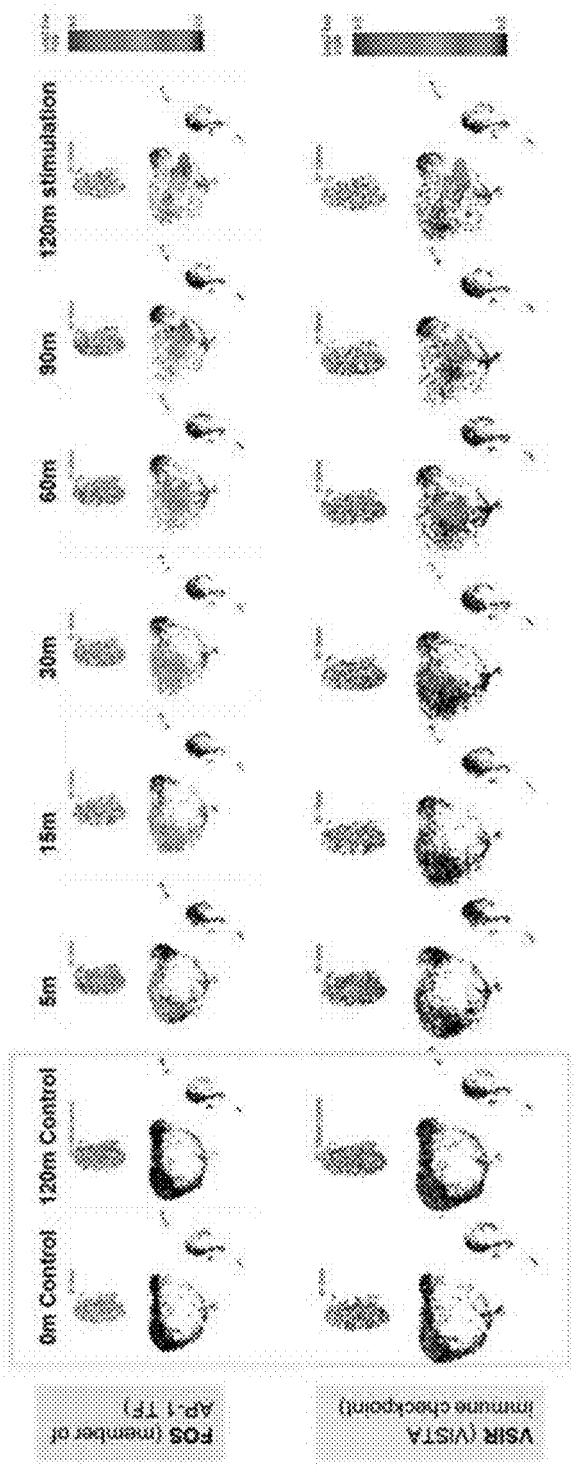

For example, two samples of peripheral blood mononuclear cells can be cultured and stimulated using anti-CD3 and anti-CD28, and the resultant stimulated cells can be sampled at 6 different time scales, as shown in FIG. 39A. The samples can be fixed at the various times to freeze the samples in the state of those time frames, multiplexed into an analysis chip, and sequenced. As seen in FIG. 39B, each fixed time sample can be analyzed, and the cells can be prepared as described elsewhere herein (e.g., Example 11). The overlay of FIG. 39B can show clusters of monocytes, T-cells, and B-cells. FIG. 39C shows that, subsequent to T-cell activation, FOS expression can be broadly observed with the T-cell population. Similarly, CD69 expression can be observed as being upregulated and detected at an RNA level within 15 minutes of stimulation. This may be faster than the protein level detection of CD69, which may take an hour or more for the CD69 to be translated sufficiently for detection. Similarly, in FIG. 39D, the transcripts of Interleukin 2 (IL2) and interferon gamma (IFN-$\gamma$) can be detected at elevated levels subsequent to stimulation. FIG. 39E shows expression of the VISR gene, which can encode the V-domain Ig suppressor of T-cell activation (VISTA) protein. The protein may be produced at high levels in activated T-cells and tumor infiltrating T-cells. The VISR gene may be transcribed in higher levels after an hour or more of activation in the activated T-cells.

Example 13—Sample Fixation and Probe Hybridization

A fixed sample can be generated using 4% formaldehyde as the fixation reagent and a 10× Genomics Fixed RNA Sample Preparation Kit. The sample can be fixed for 1 hour at ambient temperature or 16 to 24 hours at 4 degrees Celsius. For samples fixed at low temperatures (e.g., 4 degrees Celsius), the same fixation time being used can reduce batch effects observed between samples. For example, each sample can be fixed for 16 hours to reduce batch effects between the samples. After the fixation, the samples can be stored at −80 degrees Celsius until further processing is performed. For example, the samples can be maintained at −80 degrees Celsius for years prior to analysis without significantly decreased performance of a nucleic acid sequencing processes performed on the sample.

Example 14—Fixed Tissue Preparation Methods

Figure 44:
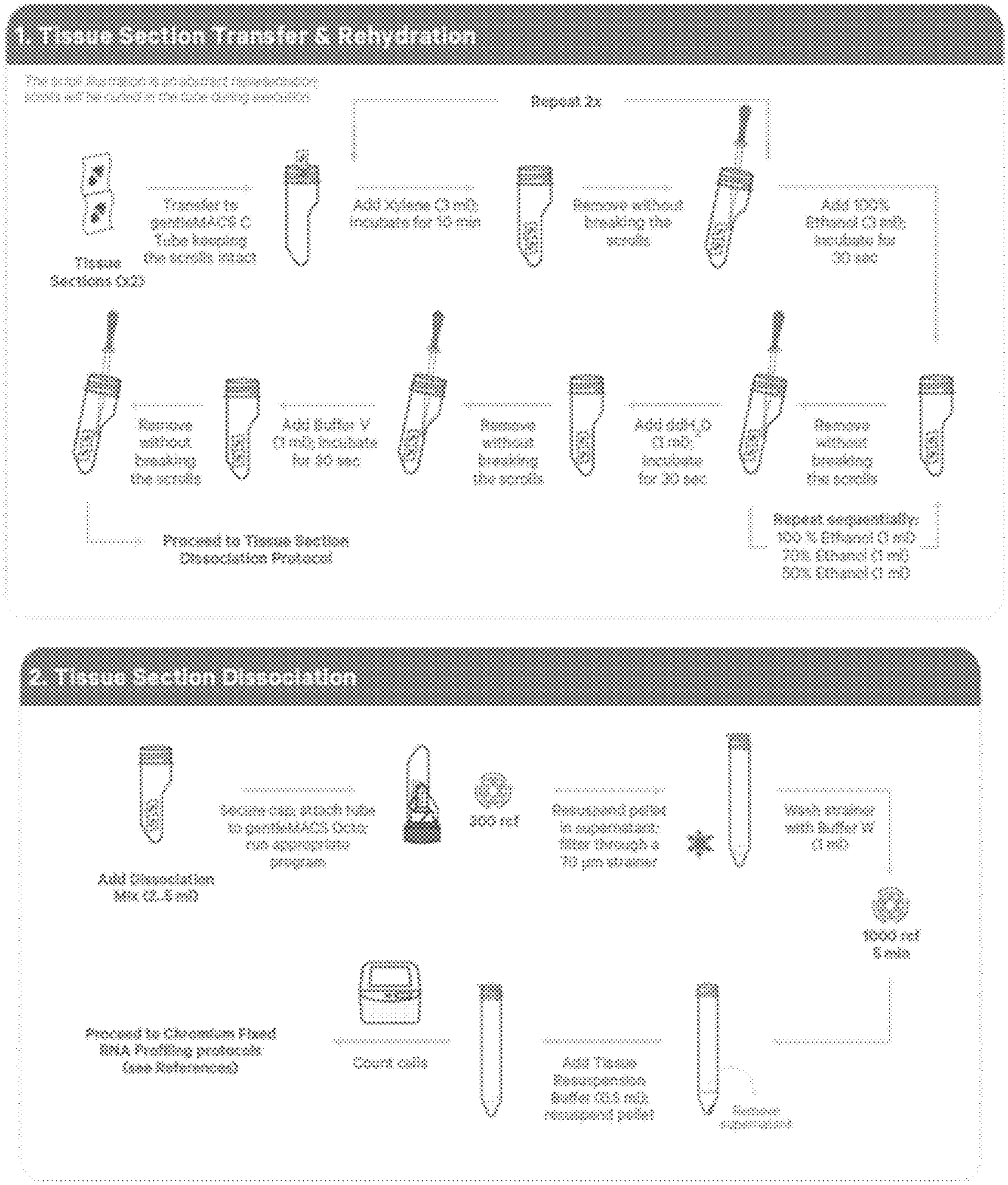
FIGS. 44-46 show examples of methods of preparation for fixed samples, according to some embodiments.
Figure 45:
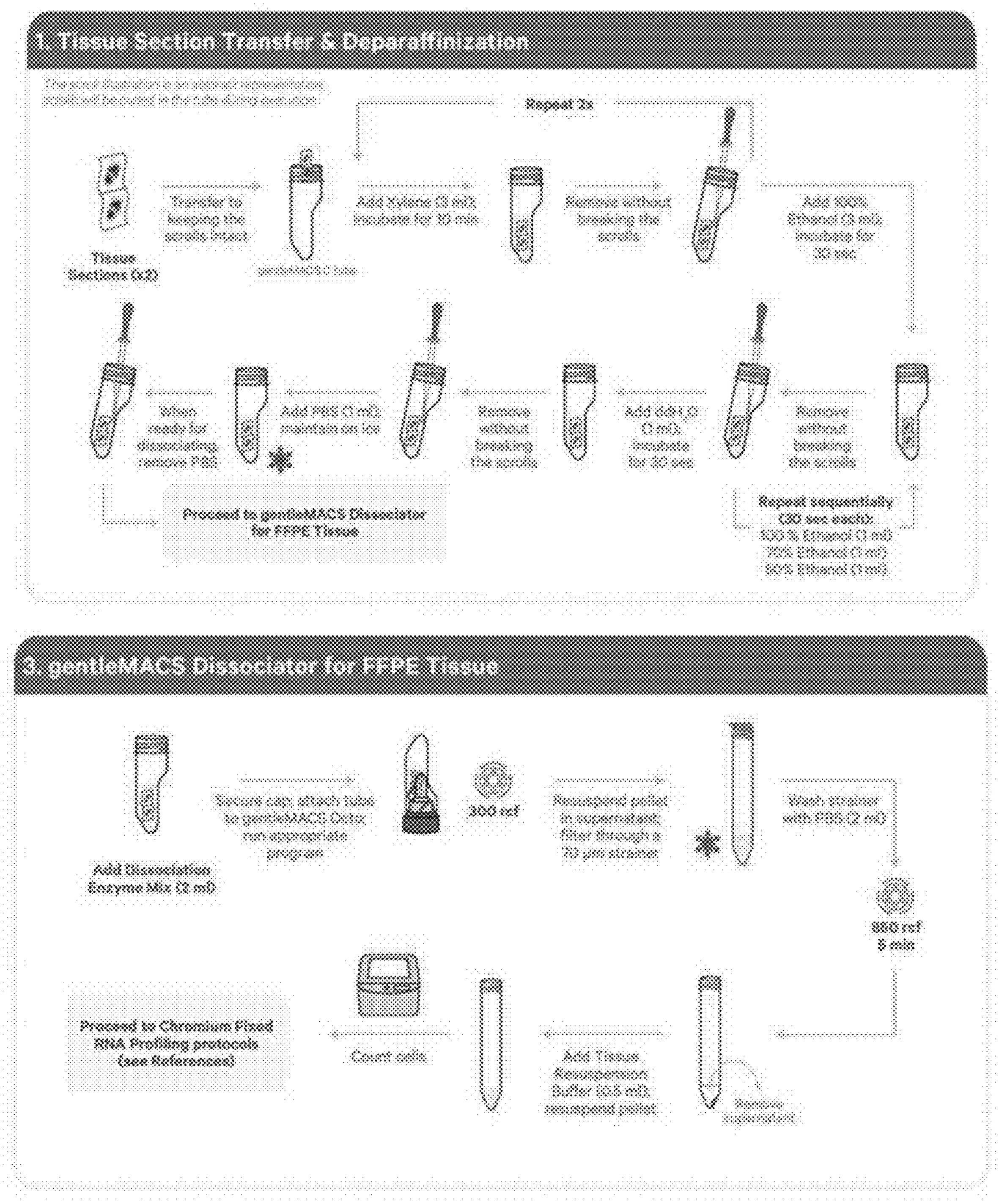
Figure 46:
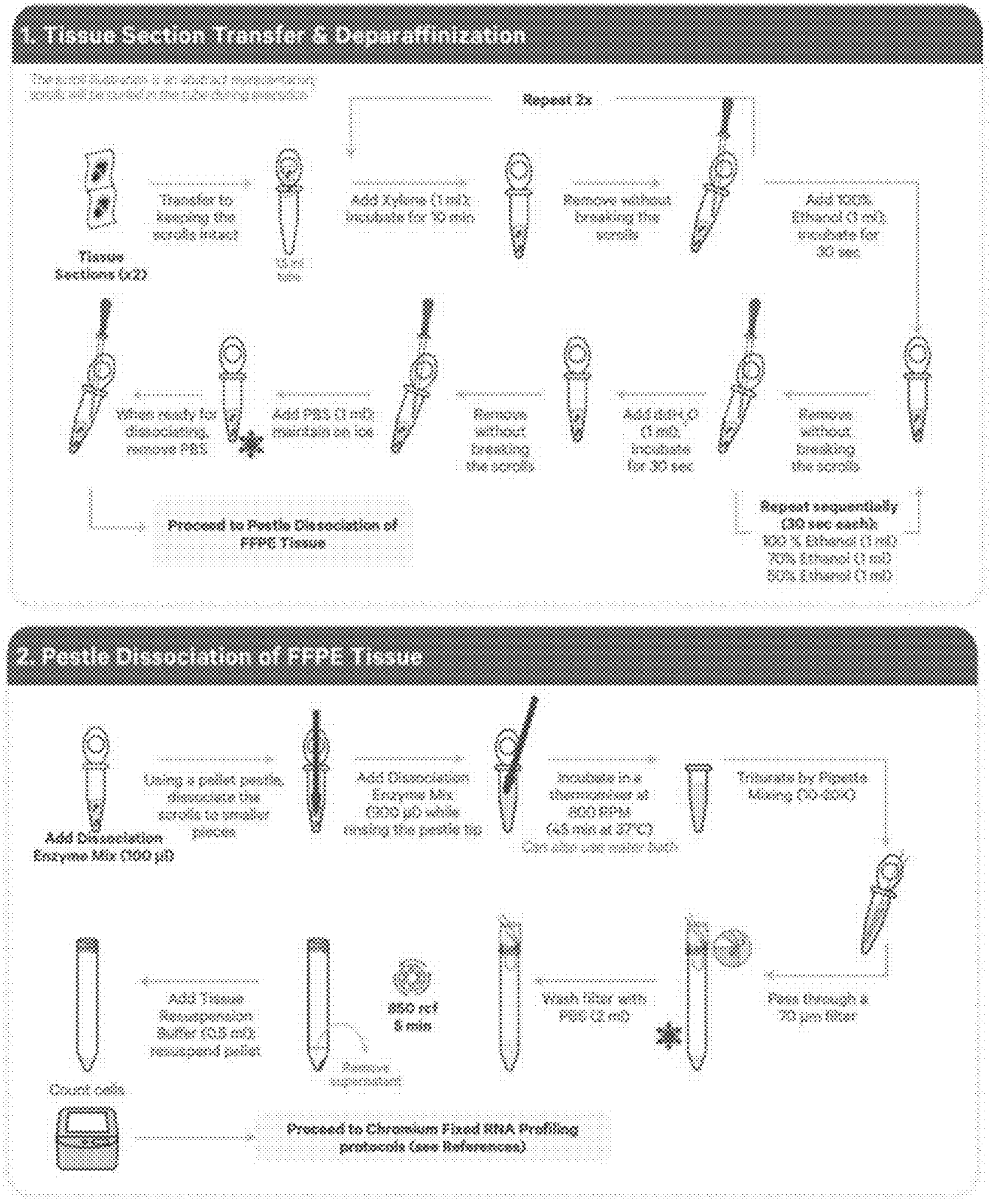

FIGS. 44-46 show examples of methods of preparation for fixed samples, according to some embodiments. The methods of this example can be operated on two 25 micrometer scrolls per sample. In this example, the methods are validated with both expert and novice users.

The tissue section transfer and rehydration portion may be similar for various methods of the present example. In other words, the tissue rehydration process can be agnostic to the dissociation method used on the tissue sample. The tissue rehydration may be as described elsewhere herein, e.g., Example 11. The dissociation can comprise use of an automated dissociator (e.g., gentleMACS octo dissociator) (FIGS. 44-45) or a manual dissociator (FIG. 46). A difference between FIGS. 44 and 45 can be that FIG. 44 uses the Miltenyi FFPE kit while FIG. 45 uses the methods and systems of the present disclosure.

The automated dissociation can comprise addition of 2 mL of a dissociation enzyme mixture (e.g., a 1 milligram/milliliter liberase TH mixture) to a rehydrated sample rehydrated as described elsewhere herein held in a dissociation tube. Once the tube is sealed with a cap, the sample can be dissociated using the automated dissociator and subsequently centrifuged at 300 rcf. Subsequent to the dissociation, the pellet can be resuspended in a supernatant as described elsewhere herein and filtered through a 70 micrometer strainer. The strainer can be washed with phosphate buffered saline (PBS) to enhance yield before an additional centrifugation at 850 rcf for 5 minutes. The supernatant can be removed from the resultant pellet, and the pellet can be resuspended in 0.5 mL of tissue resuspension buffer. The sample can be counted and analyzed as described elsewhere herein.

The manual dissociation can comprise adding 100 microliters of a liberase TH 1 mg/mL and using the manual dissociation pestle to dissociate the scrolls. 900 microliters of dissociation enzyme mix can be used to clean the tip of the pestle. The full 1 mL of solution can be incubated for 45 minutes at 37 degrees Celsius (e.g., in a water bath, in a thermomixer at 800 rpm, etc.). Subsequent to the incubation, the sample can be triturated by pipette mixing ten to twenty times before being passed through a 70 micrometer filter. The filter can be washed with 2 mL of buffer to enhance yields before the filtered solution is centrifuged at 850 rcf for five minutes, the supernatant is discarded, 0.5 mL of resuspension buffer is added and the sample is ready for further analysis.

In these examples, validation provided a fraction of usable reads of at least about 40%, a fraction of reads mapped to the filtered probe set of at least about 80%, a fraction of reads in cells on high quality preparations of at least about 60%, and at least about 90% valid barcodes. The yield of the examples was at least about 400,000 cells per sample for the 2 25 micrometer sections, with an observed cells to expected cells recovered of at least about 50%. Additionally, the pseudobulk gene expression versus cytassist assay ratio was at least about 0.7, and the observed targeted gene cell-UMI recovery median was at least about 0.8.

Figure 48:
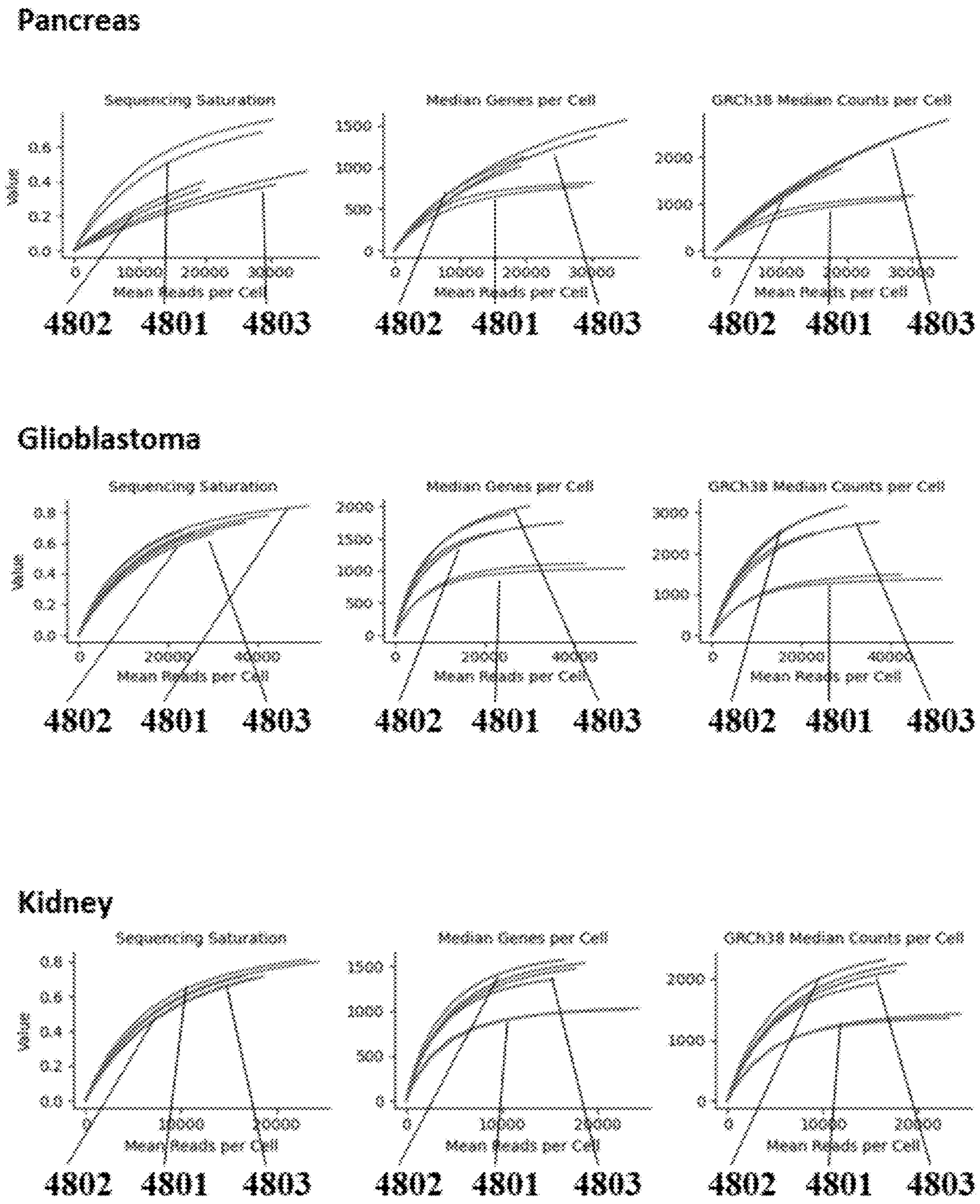
FIG. 48, shows examples of various tissues processed by the workflows of FIGS. 44-46, according to some embodiments.

FIG. 47 provides a table of the pass percentages and other properties for the various procedures of the present example, according to some embodiments. The table shows the enhanced performance of the methods of the present disclosure versus other sample preparation methods, and this data is further seen in FIG. 48, which shows examples of various tissues processed by the workflows of FIGS. 44-46 (labeled as 4801, 4802, and 4803, respectively), according to some embodiments. The table shown in FIG. 47 provides a design input requirement (DIR) which may correspond to a success threshold or validation threshold for an assay. For example, the validation threshold for cell yield from two scrolls may be greater than or equal to 400,000 cells.

Example 14—Single Cell Whole Transcriptome Profiling

Formalin fixed, paraffin embedded (FFPE) tissue samples may be a large repository of human tumor specimens. Gene expression profiling of FFPE samples may provide insights into disease etiology. The methods described herein may be useful for profiling gene expression in FFPE samples without RNA degradation or with significantly reduced RNA degradation at single cell resolution. The methods described herein may permit single cell FFPE sequencing for detection of whole transcriptome gene expression in dissociated FFPE tissues via in situ hybridization, ligation, and barcoding of RNA-specific probe pairs.

FFPE sections from nine different human cancer tissue blocks may be profiled using the methods described herein. FFPE sectioned tissue samples (e.g., scrolls) of each cancer block may be dissociated into a single cell suspension using a combination of enzymatic digestion and mechanical dissociation. The dissociated cells may be processed using the workflow described elsewhere herein, for example, as shown in FIG. 42. Genes and UMIs per cell may demonstrate sensitive of the single cell assay on FFPE tissues at single cell resolution. Cell numbers post dissociation from two 25 μm sectioning of each tissue type may be sufficient for hybridization and partitioning, for example, partitioning into droplets. Table 3 shows example gene expression metrics for the profiled tissues. Gene and UMI metrics may be measured at 10,000 raw reads per cell. Post dissociation cell yields of tissue sections may be listed along with the tissue cross section dimensions.

TABLE 3

Gene expression metrics for each of the tissues profiled.

| Tissue Type | Cell Yield: 2 × 25 μm sections | Tissue cross section (x * y * mm) | Median Genes per Cell | Median UMIs per Cell | Fraction of Reads in Cells |
|---|---|---|---|---|---|
| Prostate Cancer | $1.60 \times 10^6$ | 9 × 9 mm | 906 | 1,292 | 78.1% |
| Glioblastoma | $0.76 \times 10^6$ | 10 × 13 mm | 1,474 | 2,107 | 81.8% |
| Breast Cancer | $1.72 \times 10^6$ | 13 × 7 mm | 921 | 1,245 | 80.7% |
| Melanoma | $0.23 \times 10^6$ | 4 × 4 mm | 2,028 | 2,934 | 76.0% |
| Ovarian Cancer | $1.92 \times 10^6$ | 10 × 18 mm | 1,071 | 1,613 | 90.4% |

TABLE 3-continued

Gene expression metrics for each of the tissues profiled.

| Tissue Type | Cell Yield: 2 × 25 μm sections | Tissue cross section (x * y * mm) | Median Genes per Cell | Median UMIs per Cell | Fraction of Reads in Cells |
|---|---|---|---|---|---|
| Colorectal Cancer | $0.88 \times 10^6$ | 10 × 9 mm | 912 | 1,342 | 85.7% |
| Endocervical Cancer | $1.69 \times 10^6$ | 10 × 7 mm | 635 | 959 | 77.3% |
| Liver Cancer | $0.67 \times 10^6$ | 5 × 9 mm | 646 | 1,196 | 53.8% |
| Lung Cancer | $0.74 \times 10^6$ | 9 × 8 mm | 1,299 | 2,036 | 89.9% |

Figure 49A:
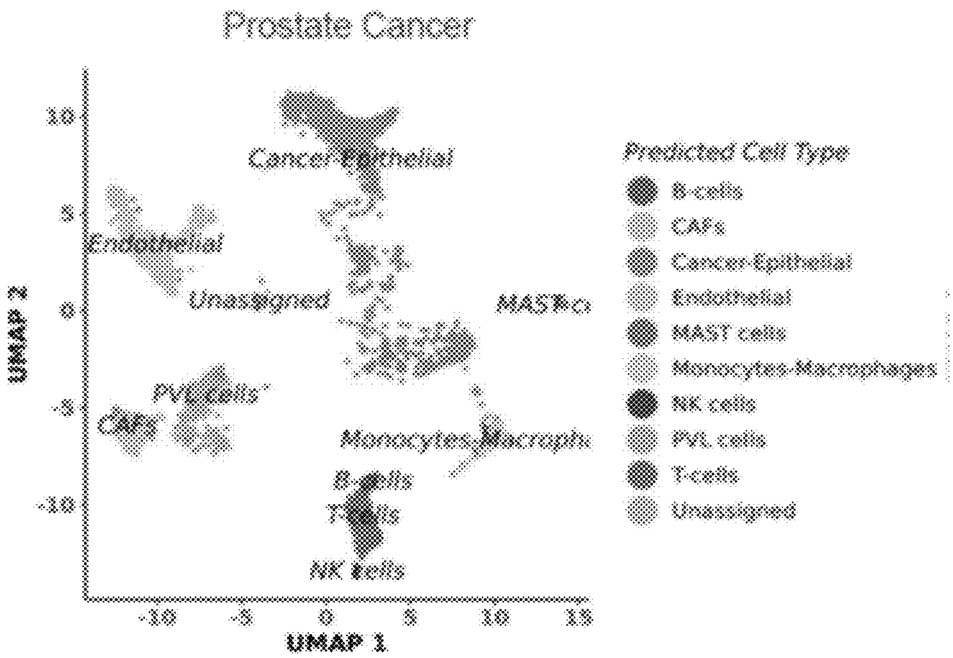
FIGS. 49A-49D show example cell type clustering for single cell cancer fixed tissues.
Figure 49B:
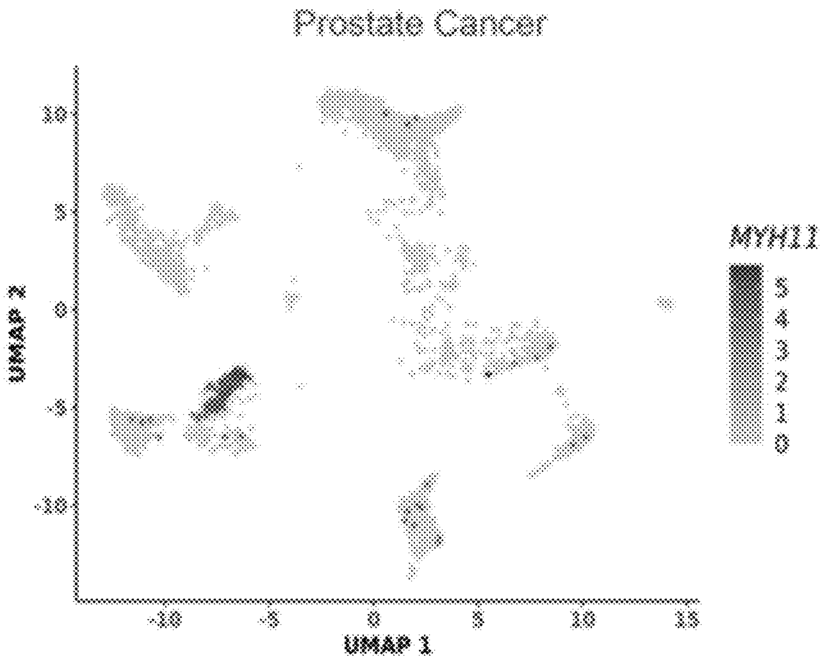
Figure 49C:
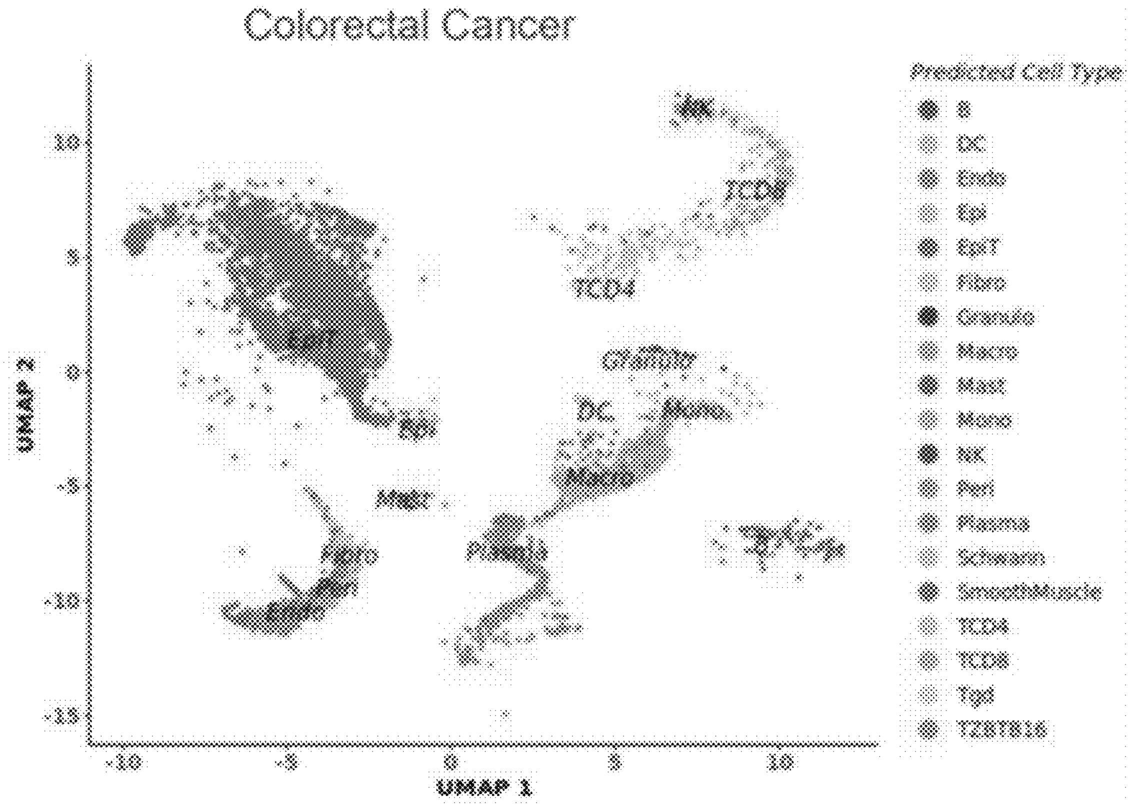
Figure 49D:
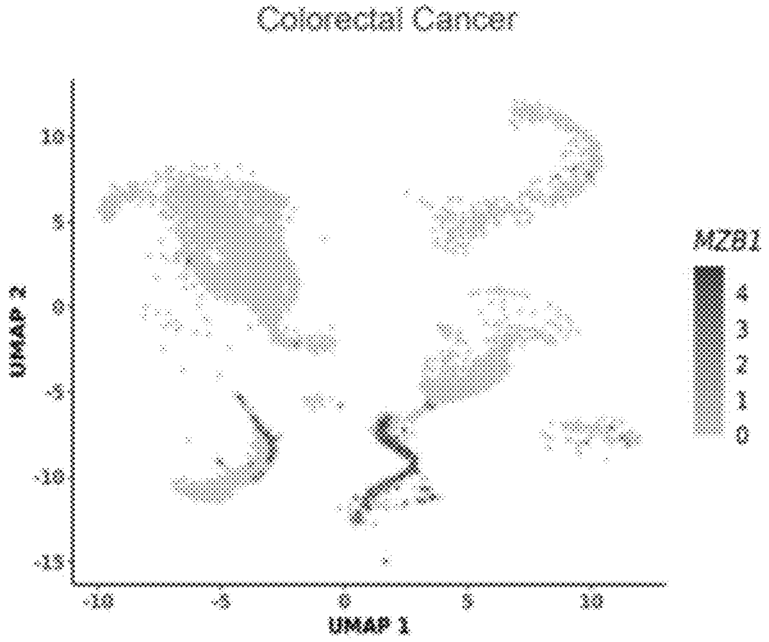

FIGS. 49A-49D show example cell type clustering in single cell FFPE. FIG. 49A shows an example uniform manifold approximation and projection (UMAP) projection of single cells taken from prostate cancer FFPE. Cell types may be manually annotated. FIG. 49B show MYH11 gene expression showing higher expression in the perivascular-like (PVL) cell cluster. FIG. 49C shows an example UMAP projection of single cells taken from colorectal cancer FFPE. FIG. 49D shows MZB1 gene expression showing higher expression in the plasma cell cluster.

Example 15—Isolation of Cells from FFPE Tissue Sections

Cells may be isolated from formaldehyde fixed & paraffin embedded (FFPE) tissue sections for use with the methods described elsewhere herein. Cell isolation may include deparaffinizing and rehydrating fixed tissue sections. The deparaffinized and rehydrated tissue sections may be dissociated using a dissociation enzyme mix and a pellet pestle or a gentleMACS Octo Dissociator. The dissociated cells may be resuspended in a tissue resuspension buffer or quenching buffer prior to cell counting. At least 400,000 cells may be used for singleplex cell analysis. At least 100,000 cells may be used for multiplex cell analysis. Prior to a large multiplex study, a pilot multiplex assay may be run using 10,000 cells per probe barcode for a singleplex assay or a four sample multiplex assay. For multiplexing sixteen samples, 8,000 cells may be loaded per probe barcode. Cell isolation may be demonstrated using FFPE tissue samples ranging from one to ten years in age. Each tissue sample may yield different amounts of material and data quality depending on age, tissue type, pre-fixation tissue quality, tissue density, and size and area of tissue in the scrolls.

Cell isolation may be demonstrated using two or more 25 micrometer (μm) or 50 μm tissue sections from a diverse spectrum of tissue types. For human tissue, two or more 25 μm sections may be used. For mouse tissue, two or more 50 μm sections may be used. Some tissue types may use more than two sections to yield sufficient cells for further processing. FFPE block properties may also impact yields. In some cases, a single 25 μm or 50 μm tissue section may yield sufficient cells for further processing.

Tissue may be sectioned and dissociated using pestle dissociation or gentleMACS Octo Dissociator protocols. For pestle dissociation, tissue sections (e.g., scrolls) may be transferred to a 1.5 milliliter (mL) tube for deparaffinization. The deparaffinized sample may be dissociated using pestle dissociation. Alternatively, the tissue sections (e.g., scrolls) may be transferred to a gentleMACS C tube for deparaffinization. The deparaffinized sample may then be processed by the Octo Dissociator.

Prior to cell isolation, the FFPE block may be inspected for extend of dehydration. The Tissue black may be faced to remove a portion of the paraffin and expose the tissue. The faced tissue block may be placed for a sufficient time in an ice water back with the block facing the water to rehydrate of the tissue block. Using a microtome, the first 5 μm of the tissue may be removed and disposed. The microtome may be used to section the fixed tissue into 25 μm or 50 μm sections (e.g., scrolls). After discarding the first section, additional section(s) from the rehydrated FFPE block may be transferred into a 1.5 mL tube or gentleMACS C tube while maintaining the scrolls intact. The scrolls may be stored at 4° C. for up to one week. One mL of xylene may be added to the 1.5 mL tube or 3 mL of xylene to the gentleMACS tube. The tubes may be incubated for 10 minutes at room temperature. Using a Pasteur pipette, the liquid may be removed from the tubes without braking or otherwise damaging the scrolls. The xylene wash may be repeated for a total of three washes. One mL of 100% ethanol may be added to the 1.5 mL tube or 3 mL of 100% ethanol may be added to the gentleMACS C tube. The tubes may be incubated at room temperature for 30 seconds. The liquid may be removed from the tube using a Pasteur pipette. One mL of 70% ethanol may be added to the 1.5 mL tube or 3 mL of 70% ethanol may be added to the gentleMACS C tube. The tubes may be incubated at room temperature for 30 seconds. The liquid may be removed from the tube using a Pasteur pipette without breaking or damaging the scrolls. One mL of 50% ethanol may be added to the 1.5 mL tube or 3 mL of 50% ethanol may be added to the gentleMACS C tube. The tubes may be incubated at room temperature for 30 seconds. The liquid may be removed from the tube using a Pasteur pipette without breaking or damaging the scrolls. One mL of nuclease-free water may be added to the tube. The tube may be incubated for 30 seconds at room temperature. One mL of phosphate buffered saline (PBS) may be added to the tube and the tube may be maintained on ice. The sample may then be subjected to pellet pestle dissociation or dissociation via a gentleMACS Octo Dissociator.

Example 16—Pestle Dissociation of FFPE Tissue

Figure 50A:
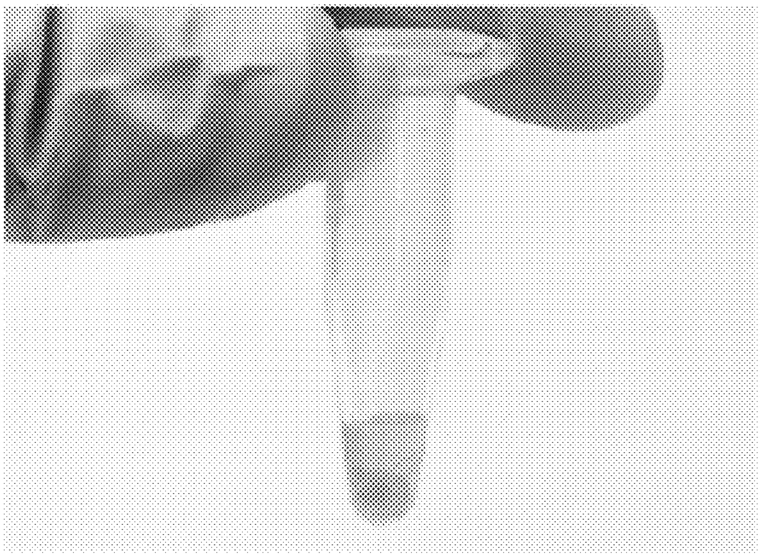
FIGS. 50A and 50B show example tissue dissociation using pestle dissociation.
Figure 50B:
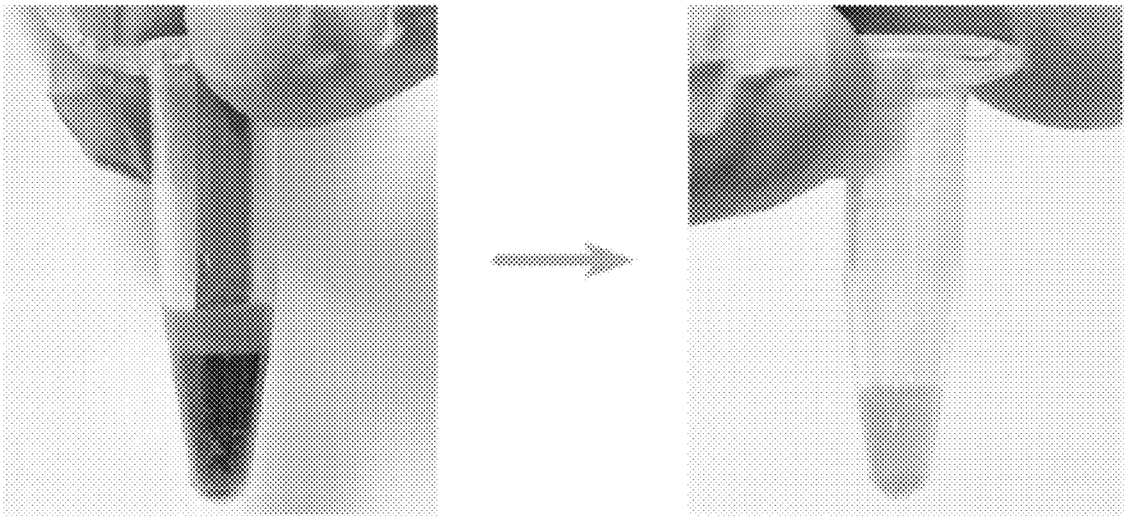

The PBS buffer may be removed from the 1.5 mL tube using a Pasteur pipette without breaking the scrolls. 100 μL of dissociation enzyme mix may be added to the tube, as shown in FIG. 50A. The tissue scrolls may be dissociated using a 1.5 mL pellet pestle to break the scrolls into smaller pieces, as shown in FIG. 50B. 900 μL of dissociation enzyme mix may be added to the tube while rinsing the pestle tip into the tube to collect any additional tissue pieces sticking to the pestle. The tissue pieces may be mixed with the dissociation enzyme mix using a pipette. The tube may be incubated for 45 minutes at 37° C. in a thermomixer at 800 rpm. Alternatively, the tube may be incubated at 37° C. for 45 minutes. The sample may be mixed at 15 minute intervals via inversion. Using a 1,000 μL pipette, the tissue pieces may be triturated by pipetting 10 to 20 times. Optionally, the sample may be aspirated by pushing the tissue pieces and solution through a 23-gauge needle five or more times to improve cell recovery. The suspension may be passed through a pre-separation filter (30 μm) placed on a 5- or 15-mL tube placed on ice. The original tube and filter may each be rinsed with 1 mL chilled PBS to minimize cell loss. The filtrate may be collected in the 5- or 15-mL tube. The tube comprising the cell suspension may be centrifuged at 850 rcf at 4° C. for 5 minutes. The supernatant may be removed without disturbing the pellet. The pellet may be resuspended in 0.5 mL chilled tissue resuspension buffer or quenching buffer. The mixture may be pipetted five or more times to mix and maintained on ice. The cell concentration of the fixed tissue sample may be determined using an automated cell counter (e.g., Countess II or Cellaca MX) or hemocytometer. The sample may immediately be used for analysis described elsewhere herein.

Example 17—GentleMACS Octo Dissociator for FFPE Tissue

The PBS may be removed from the gentleMACS C tube without breaking the scrolls. Two mL of dissociation enzyme mix may be added to the tube and it may be closed securely. The tube may be placed in the gentleMACS Octo Dissociator, applying Heting Units and running the gentleMACS Program 37C_FFPE_1, as shown in FIG. 51. The program may be run for about 48 minutes. At the end of the program, the tube may be detached from the gentleMACS Octo Dissociator and visually inspected to ensure the scrolls have been dissociated. The tube may be centrifuged at about 300 rcf for 1 min and the resultant pellet may be resuspended in the supernatant. The suspension may be passed through a pre-separation filter (30 μm) placed on a 15-mL tube on ice. The original gentleMACS tube and filter may be rinsed with 2 mL of chilled PBS to minimize cell loss. The filtrate may be collected in the tube. The cell suspension may be centrifuged at 850 rcf at 4° C. for 5 min. The supernatant may be removed without disturbing the pellet. The pellet may be resuspended in 0.5 mL chilled tissue resuspension buffer or quenching buffer. The pellet may be mixed with the buffer by pipetting the mixture five or more time while on ice. The cell concentration of the fixed tissue sample may be determined using an automated cell counter (e.g., Countess II or Cellaca MX) or hemocytometer. The sample may immediately be used for analysis described elsewhere herein.

Example 18—Counting Using Ethidium Homodimer-1

Samples may be counted using Ethidium Homodimer-1 and the Countess II FL Automated Cell Counter (with red fluorescent protein (RFP) light cube) to permit accurate quantification even in the presence of sub-cellular debris. Cell concentration for the Countess may be between 1,000 and 4,000 cells per μL. The sample may be vortexed, centrifuged briefly, and diluted approximately 1:100. 10 μL of Ethidium Homodimer-1 may be aliquoted to a tube. The sample may be gently mixed and 10 μL may be added to the tube comprising the Ethidium Homodimer-1. 10 μL of the sample may be transferred to the Countess II Cell Counting Slide chamber. The slide may be inserted into the Countess II FL Cell counter. The sample may be images using the RFP setting of fluorescent illumination and filtering. The absence of large clumps may be confirmed using bright-field mode. The RFP-positive concentration may be measured and cell concentration may be determined by multiplying the measured concentration by two. Alternatively, samples stained with Ethidium Homodimer-1 may be counted using a Cellaca Counter.

Example 19—Counting Cells Using Propidium Iodide (PI) Staining Solution

Figure 52A:
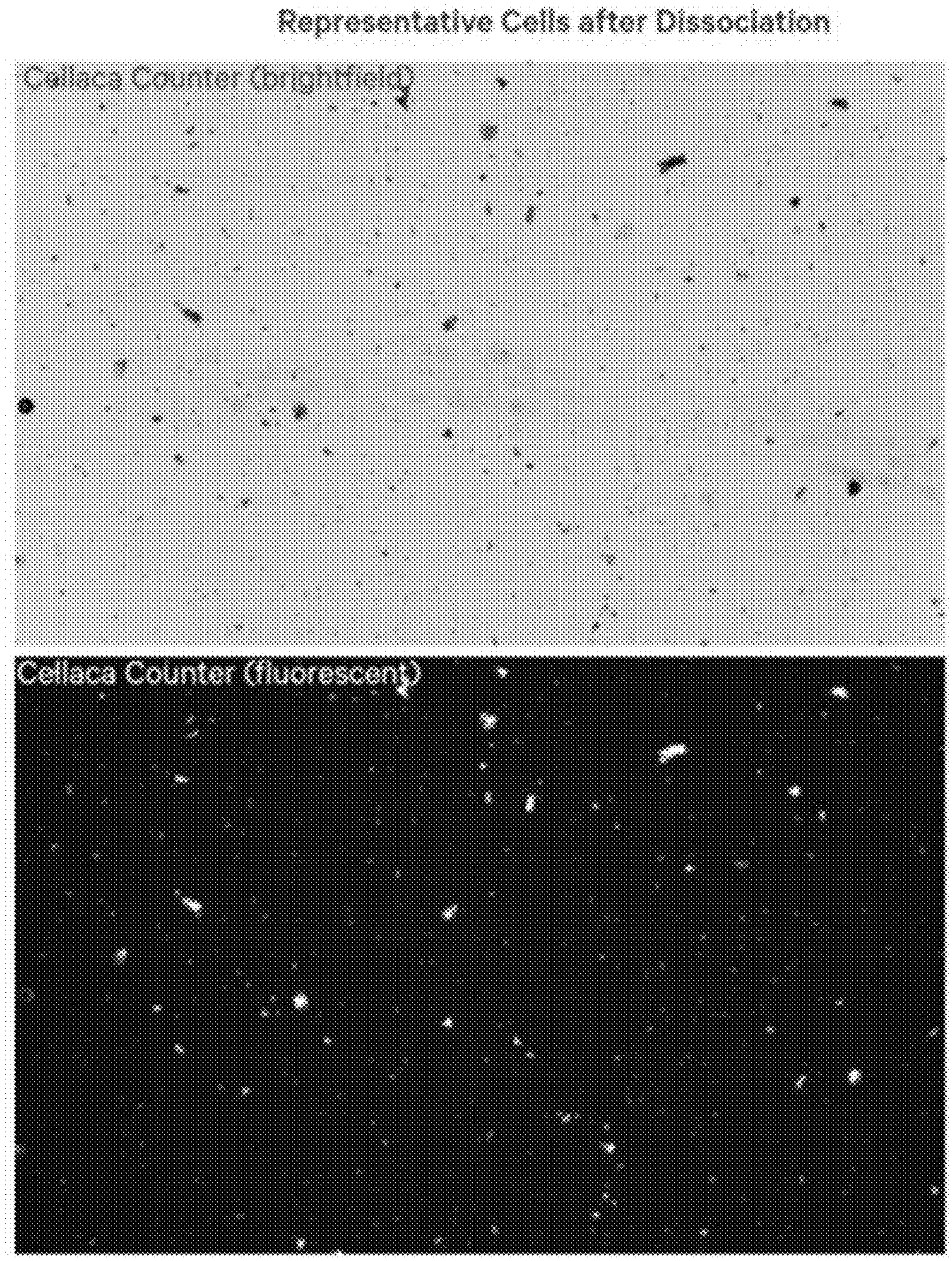
FIG. 52A shows an example of representative cells after dissociation.
Figure 52B:
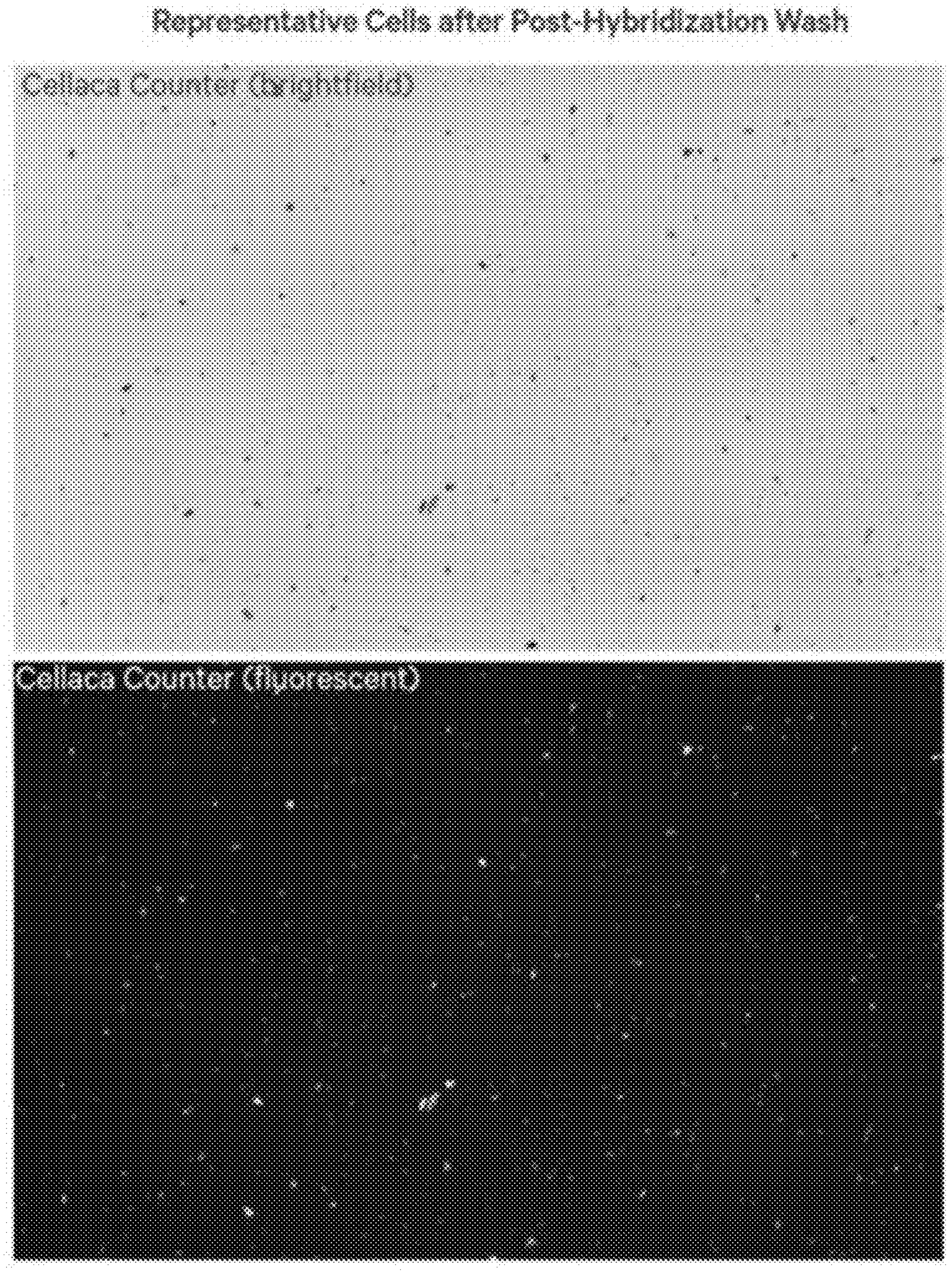
FIG. 52B shows an example of representative cells after post-hybridization wash.

Propidium Iodide (PI) may be used with the Cellaca Counter to count cells in a fixed tissue sample in the presence of sub-cellular debris. Cell concentration for the Cellaca Counter may be 100 to 10,000 cells per μL. 25 μL of PI staining solution may be added to the mixing row of the Cellaca Plate. The fixed tissue sample may be gently mixed. Depending on concentration, the sample may be diluted 1:1 using PBS by, for example, adding 15 μL of PBS to 15 μL of sample. 25 μL of sample may be added to the mixing row of the place containing the PI staining solution. The staining solution and sample may be gently mixed 8 or more times. The stained sample may be transferred to the loading row of the Cellaca plate. The PI channel may be used to count number of cells. Alternatively, samples stained with PI may be counted using the Countess II FL Automated Cell Counter. FIG. 52A shows example images of cells after dissociation. After dissociation, the cell sample may include some debris. Further processing, for example post-hybridization washing, may reduce debris, as shown in FIG. 52B.

FIG. 53 shows example cell yield data for various samples processed using pestle dissociation and samples processed using gentleMACS Octo Dissociator.

Example 20—Fixed Sample Storage

Fixed samples, for example, dissociated cells resuspended in quenching buffer or in tissue resuspension buffer, may be stored for short or long term. Short-term storage may include storage at 4° C. Frozen enhancer may be thawed for 10 minutes at 65° C. The thawed enhancer may be vortexed and centrifuged briefly. Enhancer may be added to the fixed sample at a 1:10 dilution factor, for example, by adding 50 μL of enhancer to 500 μL fixed sample in quenching buffer or tissue resuspension buffer. The sample may be stored at 4° C. for up to one week.

For long term storage, the enhancer may be added to the sample at the same 1:10 dilution factor. 50% glycerol may be added to the sample for a final glycerol concentration of 10%. For example, 137.5 μL 50% glycerol may be added to 550 μL fixed sample in quenching buffer or in tissue resuspension buffer with enhancer. The sample may be stored at −80° C. for up to six months.

Samples may undergo a color change during storage (e.g., black, light gray, or green). Samples stored at −80° C. may be thawed at room temperature until no ice is present. The thawed sample may be centrifuged at 850 rcf for 5 minutes at room temperature. The supernatant may be removed without disturbing the pellet. The cell pellet may be resuspended in 0.5 mL 0.5×PBS with 0.02% bovine serum albumin (BSA). In an example, 0.2 U/μL RNase inhibitor may be used. The sample may be kept on ice. The cell concentration of the fixed sample may be determined as described elsewhere herein and the sample may be immediately used for analysis as described elsewhere herein.

The methods described herein may be useful in analyzing single cell FFPE gene expression to probe biology preserved in achieved FFPE tumor samples. The methods may serve to facilitate discoveries in disease progression and therapeutic target development. For example, the sample preparation described herein may yield dissociated cells that may be sufficient for assaying at least the transcriptome rom tissues that have been preserved as FFPE tissues, thus permitting analysis of preserved tissues.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:

(a) processing a sample comprising:

a fixed tissue embedded in a solid medium, wherein the fixed tissue comprises a cell comprising a nucleic acid molecule, and wherein the processing removes a portion of the solid medium from the fixed tissue, thereby obtaining a processed tissue;

(b) dissociating the processed tissue into a plurality of cells, wherein the plurality of cells comprises the cell comprising the nucleic acid molecule;

(c) after (b), contacting the cell with a probe, wherein the probe hybridizes to the nucleic acid molecule;

(d) after (c), partitioning the plurality of cells into a plurality of partitions, wherein the cell comprising the nucleic acid molecule is co-partitioned with a barcode molecule comprising a barcode sequence in a partition of the plurality of partitions; and (e) generating a barcoded nucleic acid molecule using the nucleic acid molecule and the barcode molecule, wherein the barcoded nucleic acid molecule comprises (i) a sequence corresponding to the nucleic acid molecule and (ii) the barcode sequence or reverse complement thereof.

2. The method of claim 1, wherein (a) further comprises contacting the sample with a solvent to dissolve the portion of the solid medium, thereby generating a dissolved medium in the solvent.

3. The method of claim 2, wherein the solvent is non-polar.

4. The method of claim 2, wherein the solvent comprises xylene.

5. The method of claim 2, wherein (a) further comprises removing the solvent and the dissolved medium in the solvent from the fixed tissue.

6. The method of claim 5, further comprising contacting the processed tissue with an additional solvent.

7. The method of claim 6, wherein the additional solvent is polar.

8. The method of claim 6, wherein the additional solvent comprises ethanol.

9. The method of claim 6, further comprising removing the additional solvent from the fixed tissue.

10. The method of claim 5, further comprising contacting the processed tissue with a hydration agent comprising water.

11. The method of claim 10, further comprising removing the hydration agent from the processed tissue.

12. The method of claim 5, further comprising contacting the processed tissue with a buffer.

13. The method of claim 12, further comprising removing the buffer from the processed tissue.

14. The method of claim 5, further comprising resuspending the processed tissue in a supernatant.

15. The method of claim 14, further comprising filtering the processed tissue after resuspending the processed tissue in the supernatant.

16. The method of claim 15, further comprising washing the processed tissue after filtering the processed tissue.

17. The method of claim 16, further comprising resuspending the processed tissue in additional supernatant after washing the processed tissue.

18. The method of claim 1, wherein (b) yields at least about $1\times10^5$ cells per two 25 micrometer sections of the processed tissue.

19. The method of claim 1, wherein the fixed tissue comprises fixed human tissue.

20. The method of claim 1, wherein the fixed tissue is fixed at least about 1 year prior to (a).

21. The method of claim 20, wherein the fixed tissue is fixed at least about 5 years prior to (a).

22. The method of claim 1, wherein (e) comprises performing a nucleic acid extension reaction to generate the barcoded nucleic acid molecule.

23. The method of claim 1, wherein (e) comprises performing a ligation reaction to generate the barcoded nucleic acid molecule.

24. The method of claim 1, wherein the sample comprises a formalin fixed, paraffin-embedded tissue.

25. The method of claim 1, wherein the probe comprises a probe barcode sequence.

26. The method of claim 25, wherein the probe barcode sequence identifies the sample.

27. The method of claim 1, wherein the probe comprises a probe region and an overhang region, and wherein (e) further comprises barcoding the overhang region of the probe or a derivative thereof.

28. The method of claim 1, wherein, in (c), the probe hybridizes to a first target region of the nucleic acid molecule, and wherein (c) further comprises:

(I) contacting the cell with an additional probe, wherein the additional probe hybridizes to a second target region of the nucleic acid molecule, and (II) generating a probe-linked molecule comprising the probe and the additional probe via a ligation reaction.

29. A method comprising:

(a) processing a sample comprising:

a fixed tissue embedded in a solid medium, wherein the fixed tissue comprises a cell comprising a nucleic acid molecule, and wherein the processing removes a portion of the solid medium from the fixed tissue, thereby obtaining a processed tissue;

(b) dissociating the processed tissue into a plurality of cells, wherein the plurality of cells comprises the cell comprising the nucleic acid molecule;

(c) contacting the cell with a probe comprising a probe region and an overhang region, wherein the probe region of the probe hybridizes to a region of the nucleic acid molecule;

(d) after (c), partitioning the plurality of cells into a plurality of partitions, wherein the cell comprising the nucleic acid molecule is co-partitioned with a barcode molecule comprising a barcode sequence in a partition of the plurality of partitions; and (e) barcoding the overhang region of the probe or a derivative thereof using the barcode molecule, thereby generating a barcoded nucleic acid molecule, wherein the barcoded nucleic acid molecule comprises (i) a sequence corresponding to the probe and (ii) the barcode sequence or reverse complement thereof.

* * * * *